US010294493B2

(12) United States Patent
Wang et al.

(10) Patent No.: US 10,294,493 B2
(45) Date of Patent: May 21, 2019

(54) SUBGROUP B RECOMBINANT HUMAN ADENOVIRUS VECTOR, AND METHODS FOR CONSTRUCTING AND FOR USING THE SAME

(71) Applicant: Beijing Bio-Targeting Therapeutics Technology Inc., Beijing (CN)

(72) Inventors: Yaohe Wang, Zhengzhou (CN); Guozhong Jiang, Zhengzhou (CN); Hanshi Wong, Zhengzhou (CN); Fengyu Cao, Zhengzhou (CN); Nick Lemoine, London (GB)

(73) Assignee: BEIJING BIO-TARGETING THERAPEUTICS TECHNOLOGY INC., Beijing (CN)

( * ) Notice: Subject to any disclaimer, the term of this patent is extended or adjusted under 35 U.S.C. 154(b) by 0 days.

(21) Appl. No.: 15/904,408

(22) Filed: Feb. 25, 2018

(65) Prior Publication Data

US 2018/0187214 A1 Jul. 5, 2018

Related U.S. Application Data

(60) Division of application No. 15/098,342, filed on Apr. 14, 2016, now Pat. No. 9,932,606, which is a division of application No. 14/093,078, filed on Nov. 29, 2013, now Pat. No. 9,315,827, which is a continuation-in-part of application No. PCT/CN2012/071757, filed on Feb. 29, 2012.

(30) Foreign Application Priority Data

May 31, 2011 (CN) .......................... 2011 1 0143385

(51) Int. Cl.
*A61K 35/761* (2015.01)
*C12N 15/86* (2006.01)
*C12N 15/861* (2006.01)
*C12N 7/00* (2006.01)

(52) U.S. Cl.
CPC ............ *C12N 15/86* (2013.01); *A61K 35/761* (2013.01); *C12N 7/00* (2013.01); *C12N 2710/10321* (2013.01); *C12N 2710/10332* (2013.01); *C12N 2710/10343* (2013.01)

(58) Field of Classification Search
CPC .................. A61K 35/761; C12N 15/86; C12N 2710/10332; C12N 2710/10343
USPC ............... 435/6.1, 91.1, 91.31, 91.41, 320.1; 514/44; 536/23.1, 24.5
See application file for complete search history.

*Primary Examiner* — Jane J Zara
(74) *Attorney, Agent, or Firm* — Matthias Scholl P.C.; Matthias Scholl

(57) ABSTRACT

A subgroup B recombinant human adenovirus vector Ad11-5EP (SEQ ID NO: 1), which is constructed by a method including: substituting a 365 bp fragment containing an enhancer and a promoter of an upstream coding sequence of Ad5 E1A (SEQ ID NO: 2) for a corresponding region of a serotype Ad11 (SEQ ID NO: 3) of a subgroup B human adenovirus vector by homologous recombination to construct the subgroup B recombinant human adenovirus vector Ad11-5EP (SEQ ID NO: 1).

2 Claims, 9 Drawing Sheets

Specification includes a Sequence Listing.

0 tumor cell 10 tumor cells 100 tumor cells 1000 tumor cells

SUBGROUP B RECOMBINANT HUMAN ADENOVIRUS VECTOR, AND METHODS FOR CONSTRUCTING AND FOR USING THE SAME

CROSS-REFERENCE TO RELAYED APPLICATIONS

This application is a divisional of U.S. application Ser. No. 15/098,342, filed Apr. 14, 2016, which is a divisional of U.S. application Ser. No. 14/093,078, filed on Nov. 29, 2013, issued as U.S. Pat. No. 9,315,827 on Apr. 19, 2016, which is a continuation-in-part of International Patent Application No. PCT/CN2012/071757 with an international filing date of Feb. 29, 2012, designating the United States, now pending, and further claims priority benefits to Chinese Patent Application No. 201110143385.3 filed May 31, 2011. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND OF THE INVENTION

Field of the Invention

The invention relates to a subgroup B recombinant human adenovirus vectors Ad11-5EP and Ad11-5ETel-GFP and methods for constructing and for using the same.

Description of the Related Art

Adenovirus 11 (Ad11) is a serotype of the subgroup B human adenovirus and is obviously superior to Ad 5 in oncolytic virotherapy. Ad11 is able to combine other cell surface receptor X besides the CD46 receptor. Tuve has reported that Ad11 is the only virus in the B subgroup adenovirus that is able to combine CD46 as well as the surface receptor X, which indicated that Ad11 is capable of infecting a much wider spectrum of tumor cells, thereby solving the problem of low infection rate in the application of Ad5 due to downregulation of virus acceptor. Ad11 is also superior to Ad5 in that the content of neutralizing antibodies of Ad11 is relatively low, being 10-31%, compared with 45-90% of that of Ad5, and the neutralizing antibodies of Ad11 have no cross-reactivity. When Ad11 is intravenously injected to transgenic mice expressing CD46, no obvious intrahepatic transduction or hepatotoxicity occurs. Furthermore, Ad11 is able to effectively transduce dendritic cells, allows tumor-specific antigens to express, and enhances the immune response to benefit the cancer therapy.

Studies on other adenovirus serotypes except Ad5 used as a vaccine or gene conversion vector have been reported, but the use of the adenovirus serotype used as an oncolytic virus has been rarely conducted. In vitro and in vivo studies from Sandberg indicated that transduction, replication, and lysis of Ad11 effectively undergo in prostate cancer cell line PC-3, but the comparison between Ad5 was not conducted by Sandberg. Shashakova et al. have compared oncolytic efficacy among Ad5, Ad6, Ad11, and Ad35 based on in vitro studies on human tumor cell lines and in vivo studies on human prostate cancer cell lines DC145, and found that Ad5, Ad6, and Ad11 have similar antitumoral efficacy whereas Ad35 has no antitumoral efficacy. The most important is that only Ad5 has hepatotoxicity. After that, chimeric oncolytic Ad5 (by substituting cilium of Ad5 by that of the B subgroup adenovirus) was constructed for allowing the chimeric oncolytic Ad5 to combine with membrane receptor CD46 to improve the antitumoral efficacy. However, compared with a whole B subgroup adenovirus, this method is not able to overcome the neutralizing ability of hexon antigen of Ad5.

The number of circulating tumor cells (CTCs) is in relation to the clinical stage, treatment effect, and short survival rate. CTCs level in peripheral blood in tumor patient is taken as the basis for monitoring, adjusting the treatment, and anticipating the results. Thus, a specific and sensitive method for detecting these cells is necessitated. In recent years, immune cells counting analysis and quantitative PCR have been applied by which a small amount of CTCs were detected, however, the application of these methods were restricted because of a high testing cost and the lack of specific biological markers.

Replication-selective oncolytic adenovirus is a new kind of medicine for treating tumors. To be noted, it has been reported recently that the replication-selective oncolytic adenovirus expressing GFP has been used to detect CTCs among more than hundred million of peripheral blood cells. However, genetic variation of tumor cells is a very important factor affecting the infection ability of adenovirus. A low expression of CAR in tumor cells significantly decreases the infection ability of Ad5, which further influences the positive rate of tumor cells. Besides the known influence mechanism of the low expression of CAR, it has also been found that other tumor related genes like CEACAM6 influences Ad5 from entering the nuclear, thereby decreasing the infection ability of Ad5 on tumor cells. These data indicate that methods for testing CTCs using Ad5 have a low sensitivity in some tumor cells.

SUMMARY OF THE INVENTION

In view of the above-described problems, it is one objective of the invention to provide an adenovirus vector Ad11-5EP that is more effective in cancer therapy, and to provide a subgroup B recombinant human adenovirus vector Ad11-5ETel-GFP for treating tumor or detecting tumor cells in circulating blood.

Inventors have first compared the anti-tumor potencies of Ad11 and Ad5 in human cancer cell lines in vitro, and found that only 9 among 25 cell lines being tested are Ad11-sensitive, in which, PC-3 is insensitive to Ad5 and sensitive to Ad11. Compared with Ad5, Ad11 obviously inhibits the growth of subcutaneous tumors of PC-3 cells in vivo, and further improves the survival of tumor-bearing animals. When the above experiment is conducted on Ad5-sensitive and Ad11-insensitive MIAPaCa-2 cell line, the antitumoral efficacy of Ad11 is obviously reduced.

Although Ad11 receptors are often highly expressed within human tumor cells, the wild-type Ad11 is not able to effectively kill the tumor cells. The inventors have conducted extensive studies and proved that more Ad11 than Ad5 are attached to the membrane of tumor cells by using two different methods. The attached Ad11 virus particles are capable of entering the nucleus, which means a relatively high level of Ad11 exists in the nucleus in early stage of the virus infection compared with Ad5. The inventors have studied expressions of two viruses in early stage of tumor cells infection, and levels of mRNA of E1A are tested by using specific primers for quantitative PCR. After 2 hours of virus infection in all cell lines, it was found that in cell lines that had a high level of Ad11, E1AmRNA was highly expressed. Expression of E1AmRNA of Ad11 in Ad11-insensitive cell lines (MIAPaCa-2 and LNCaP) after 2 hours of the infection is obviously decreased. Ad11-sensitive Capan-2 and PC-3 cells have a high level of Ad11E1AmRNA. Ad11E1AmRNA directly influences the replication of virus, so that the decrease of the level of Ad11E1AmRNA in MIAPaCa-2 and LNCaP cell lines will decrease the replication level of the virus, and correspondingly decrease the synthesis of hexon protein. Such result is in accordance with the production of low level of Ad11 virus particles and the cytotoxicity from the initial observation. These results indicate that the replication and cell killing of Ad11 have no relationship with its infectivity, but are associated with the activity of the enhancer and the promoter of early gene E1A.

To solve the above problem, one objective of the invention is to construct a tumor targeting adenoviral vector (Ad11-5EP) where the original enhancer and promoter of Ad11 E1A gene was replaced by the counterpart of Ad5. Experiments indicate that Ad11-5EP is a very useful backbone vector capable of developing replication-selective oncolytic adenovirus for treating a wider spectrum of human cancers.

To explore the application of the new adenovirus vector and improve the sensitivity to detect circulating tumor cells in the blood using replication-selective adenovirus, the Ad5 promoter of Ad11-5EP is substituted by a promoter of human telomerase gene, a reporter gene GFP was inserted into E3gp18.5 K of Ad11, and a replication-selective adenovirus (Ad11-5ETel-GFP) capable of expressing reporter genes was created by homologous recombination. As telomerase is highly expressed in 95% of human tumor cells, Ad11-5ETel-GFP selectively replicates and expresses GFP in tumor cells but has no activity in normal epithelial cells.

To achieve the above objective, in accordance with one embodiment of the invention, there is provided a method for constructing a subgroup B recombinant human adenovirus vector Ad11-5EP (SEQ ID NO: 1), comprises substituting a 365 bp fragment comprising an enhancer and a promoter of an upstream coding sequence of Ad5 E1A (SEQ ID NO: 2) for a corresponding region of a serotype Ad11 (SEQ ID NO: 3) of a subgroup B human adenovirus vector by homologous recombination to construct the subgroup B recombinant human adenovirus vector Ad11-5EP In a class of this embodiment, the homologous recombination comprises: amplifying a 329 bp fragment in the front of the Ad11 genome as a left arm sequence, providing a fragment formed by ligating a 195-559 bp fragment of Ad5 E1A comprising the enhancer and the promoter and a 568-1125 bp fragment of Ad11 E1A (SEQ ID NO: 4) as a right arm sequence, and ligating the left arm sequence and the right arm sequence to multi-cloning sites arranged on two sides of pSS-ChI (SEQ ID NO: 12), respectively, to construct a shuttle vector pSS-A1A7 (SEQ ID NO: 5); digesting and purifying the pSS-A1A7 by PmeI while performing homologous recombination between a PmeI digested segment and pAd11 (SEQ ID NO: 6) plasmid within BJ5183 cells, and screening positive clones using agar plates comprising ampicillin and chloramphenicol; and digesting the positive clones by SwaI, and deleting a chloramphenicol-resistance gene expression cassette to yield pAd11-Ad5EP (SEQ ID NO: 7), digesting and linearizing the pAd11-Ad5EP by NotI, and transfecting 293 cells to yield the adenovirus vector Ad11-5EP.

In a class of this embodiment, the concentrations of ampicillin and chloramphenicol are 100 mg/mL and 25 mg/mL, respectively.

A method for reconstructing replication-selective oncolytic adenovirus using the subgroup B recombinant human adenovirus vector Ad11-5EP, the method comprises one of the following steps:

1) deleting E1A CR2 gene (SEQ ID NO: 8) and/or anti-apoptotic gene E1B 21K (SEQ ID NO: 9) that are necessary for viability of the adenovirus in normal cells but not necessary in tumor cells;
2) inserting a tumor-specific promoter to drive the expression of E1A gene;
3) re-directing a cellular tropism of Ad11-5EP according to receptors on a tumor cell surface; or
4) allowing adenovirus to selectively replicate in tumor cells combining with MicroRNA technology.

A method for constructing a subgroup B recombinant human adenovirus vector Ad11-5ETel-GFP (SEQ ID NO: 10), the method comprises:

1) constructing vectors pSS-ChI and pSS-kna (SEQ ID NO: 13) by using two different antibiotics-resistance cassettes, introducing SwaI restriction sites to two flanks of a chloramphenicol-resistance gene sequence cassette, and introducing sbfI restriction sites to two flanks of a kanamycin-resistance gene sequence cassette;
2) cloning an initiation sequence for replication of pBR322 (SEQ ID NO: 14) by pUC18 (SEQ ID NO: 15), ligating a first synthetic nucleotide sequence comprising multi-cloning sites to the chloramphenicol-resistance gene sequence cassette to yield pSS-ChI, homologously recombining an upstream of a left arm sequence and a downstream of a right arm sequence of the chloramphenicol-resistance gene sequence cassette, and inserting the upstream of the left arm sequence of the chloramphenicol-resistance gene sequence cassette and the downstream of the right arm sequence of the chloramphenicol-resistance gene sequence cassette into the multi-cloning sites on two sides of pSS-ChI by blunt end insertion or cohesive end insertion, respectively, to construct a shuttle vector pSSENTel (SEQ ID NO: 16) for recombination;
3) cloning an initiation sequence for replication of pBR322 by pUC18, ligating a second synthetic nucleotide sequence comprising multi-cloning sites to the kanamycin-resistance gene sequence cassette to yield pSS-kna, homologously recombining an upstream of a left arm sequence and a downstream of a right arm sequence of the kanamycin-resistance gene sequence cassette, and inserting the upstream of the left arm sequence of the kanamycin-resistance gene sequence cassette and the downstream of the right arm sequence of the kanamycin-resistance gene sequence cassette into the multi-cloning sites on two sides of pSS-kna by blunt end insertion or cohesive end insertion, respectively, to construct a shuttle vector pSSGFP (SEQ ID NO: 17) for recombination;
4) constructing pSSENTe comprising: amplifying a 329 bp in the front of Ad11 genome as a left arm sequence, providing a fragment formed by ligating 195-378 bp of Ad5 E1A enhancer, -714-0 bp of human TERT promoter, and 568-1125 bp of Ad11 E1A in order as a right arm sequence, introducing two restriction enzyme sites XbaI and NcoI to two sides of the human TERT promoter, and inserting the left arm sequence and the right arm sequence into SnabI and EcoRV arranged on two sides of pSS-ChI, respectively, by blunt end insertion, to yield pSSENTel;

5) constructing pSSGFP comprising: providing a left arm being a product by ligating 27301-27837 bp of DNA segment of Ad11 genome with EGFP gene via NcoI, and introducing a SnaBI site to 3' terminal of EGFP; providing a right arm being 28337-28920 bp of DNA segment of Ad11 genome; and inserting the left arm and the right arm into SnabI and EcoRV sites arranged on two sides of pSS-kna by blunt end insertion, to yield pSSGFP; and 6) digesting and purifying the pSSENTel and pSSGFP by PmeI, to yield two PmeI digested segments, performing homogenous recombination synchronously between the two PmeI digested segments and pAd11 plasmid, respectively, in BJ5183 cells; screening positive clones using agar plates comprising ampicillin, kanamycin, and chloramphenicol; digesting the positive clones by SwaI and SbfI, and deleting chloramphenicol-resistance gene expression cassette and kanamycin-resistance gene expression cassette to yield pAd11-5ETel-GFP (SEQ ID NO: 11); and digesting and linearizing the pAd11-5ETel-GFP by NotI, and transfecting 293 cells to produce adenovirs vector Ad11-5ETel-GFP.

In a class of this embodiment, the concentrations of ampicillin, kanamycin, and chloramphenicol are 100 mg/mL, 50 μg/mL, and 25 mg/mL, respectively.

In a class of this embodiment, Tel sequence of pSSENTel is substitutable by promoters of other tumor specific genes to yield a tumor-specific oncolytic adenovirus; and GFP sequence of pSSGFP is substitutable by a signal gene or therapeutic gene.

In a class of this embodiment, Ad11 18.5 K gene promoter of pSSGFP is substitutable by a tumor-specific promoter.

A method for treatment of tumor comprises applying a subgroup B recombinant human adenovirus vector Ad11-5EP.

A method for treatment of tumor or detection of tumor cells in circulating blood comprises applying a subgroup B adenovirus vector Ad11-5ETel-GFP.

Advantages of the invention are as follows:

1) The tumor targeting adenovirus vector Ad11-5EP is acquired by substituting the enhancer and the promoter of E1A by the enhancer and the promoter of Ad5E1A based on the wild type Ad11. Such a vector has stronger oncolytic efficacy than the wild type Ad11, thereby enhancing the potency on the tumor cells.

2) The tumor targeting adenovirus vector Ad11-5EP has tumor targeting and antitumoral efficacy. Experiments from oncolytic potency have indicated that Ad11-5EP has stronger potency on tumor cells than Ad5 and stronger cell toxicity than Ad11. Measurements of tumor growth and tumor clearance indicate that Ad11-5EP significantly reduces the tumor growth, and the non-tumor ratio of the tumor-bearing mice is significantly better than Ad11.

3) The tumor targeting adenovirus vector Ad11-5EP can be used as a tumor-targeting genetic engineering drug for treating cancer, thereby producing social and economic benefits.

4) The method for constructing subgroup B human recombinant adenovirus vector Ad11-5ETel-GFP of the invention features that homogeneous recombination is performed synchronously between Ad11-5EP genome and shutter vectors of pSSENTel and pSSGFP to produce recombinant virus vector Ad11-5ETel-GFP. Ad11-5ETel-GFP can be used in cancer therapy or detection of cancer cells in circulating blood. Expression tests of GFP of Ad11-5ETel-GFP in human normal epithelial cells and cancer cells and CTCs tests demonstrated that Ad11-5ETel-GFP is very sensitive to cancer cells and is capable of infecting a wide spectrum of cancer cells, thereby being specific, sensitive, and economic to apply in cancer cells detection in circulating blood.

BRIEF DESCRIPTION OF THE DRAWINGS

in FIGS. 2 and 3, white columns represent Ad5, black columns represents Ad11, grid columns represent Ad11-5EP;

in FIGS. 4-5, 1 represents PBS, 2 represents Ad11, 3 represents Ad11-5EP, and 4 represents AdS;

DETAILED DESCRIPTION OF THE EMBODIMENTS

The invention is further described by the following embodiments but not to limit the protection scope of the invention. It will be obvious to those skilled in the art that changes and modifications may be made without departing from the invention in its broader aspects, and therefore, the aim in the appended claims is to cover all such changes and modifications as fall within the true spirit and scope of the invention.

EXAMPLE 1

Method for Constructing a Subgroup B Recombinant Human Adenovirus Vector Ad11-5EP A 365 bp fragment comprising an enhancer and a promoter of an upstream coding sequence of Ad5 E1A was substituted for a corresponding region of a serotype Ad11 of a subgroup B human adenovirus vector by homologous recombination to construct the subgroup B recombinant human adenovirus vector Ad11-5EP.

Figure 1:
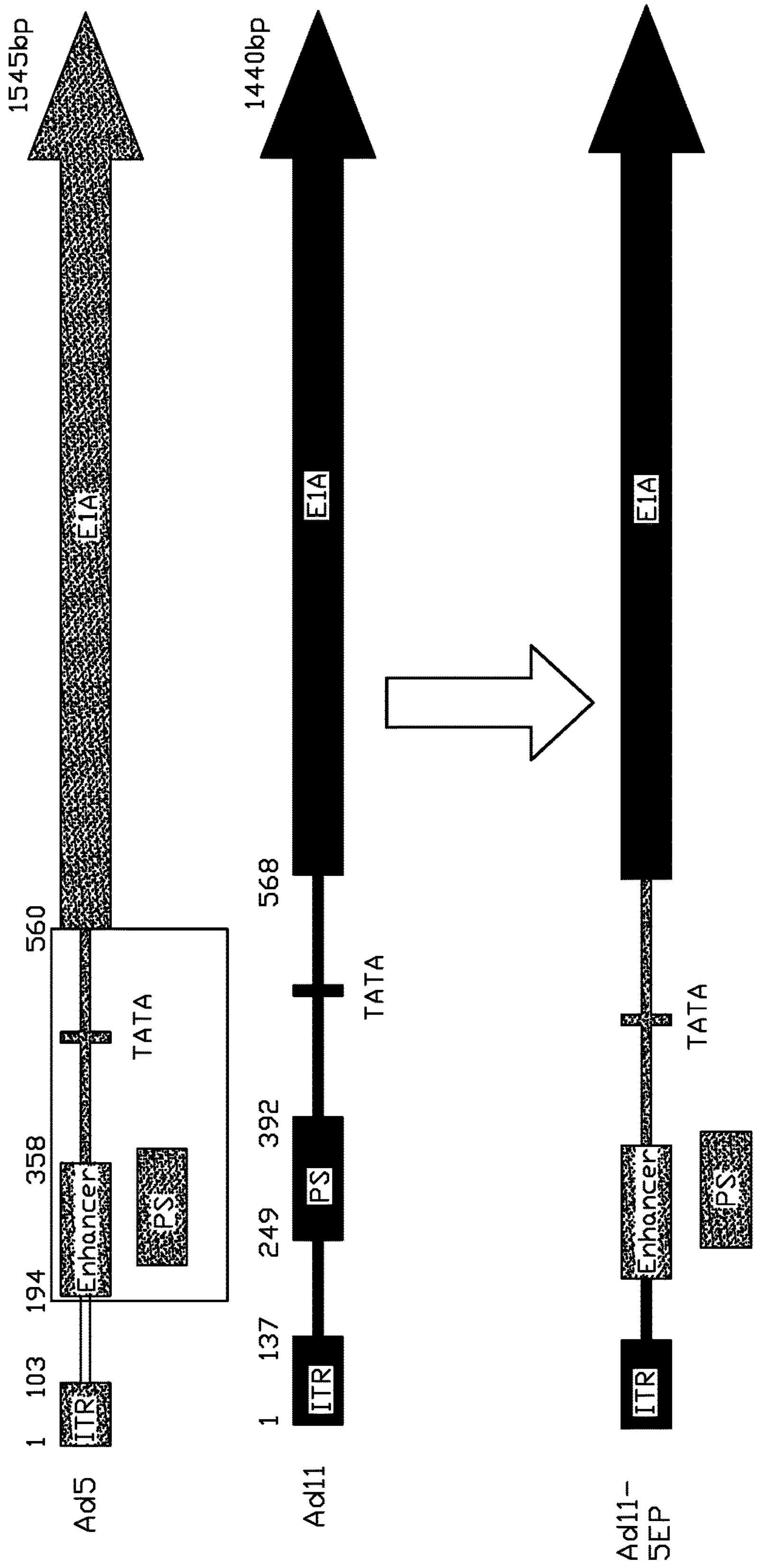
FIG. 1 is a diagram showing a method of construction of a subgroup B recombinant human adenovirus vector Ad11-5EP.

A 329 bp fragment in the front of the Ad11 genome was provided as a left arm sequence, and a fragment formed by ligating a 195-559 bp fragment of Ad5 E1A comprising the enhancer and the promoter and a 568-1125 bp fragment of Ad11 E1A was provided as a right arm sequence. The left arm sequence and the right arm sequence were connected to multi-cloning sites arranged on two sides of pSS-ChI, respectively, to construct a shuttle vector pSS-A1A7. The pSS-A1A7 was digested and purified by PmeI while performing homologous recombination between a PmeI digested segment and pAd11 plasmid within BJ5183 cells. Positive clones were screened using agar plates comprising ampicillin and chloramphenicol. The positive clones were digested by SwaI, and a chloramphenicol-resistance gene expression cassette was deleted to yield pAd11-Ad5EP. The pAd11-Ad5EP was and linearized by NotI, and 293 cells were transfected to yield the adenovirus vector Ad11-5EP (as shown in FIG. 1).

EXAMPLE 2

Oncolytic Potencies of Ad5, Ad11, and Ad11-5EP in Ad11-sensitive and -insensitive Human Cancer Cell Lines Oncolytic potencies of Ad5, Ad11, and Ad11-5EP were tested on Ad11-sensitive human tumor cell lines Capan-2, PaTu8988s, PC-3m MCF7, HT-29 and Ad11-insensitive human tumor cell lines MIAPaCa-2, MDA-MB-231, HCT116, LNCaP, and A549 in vitro. 2% of fetal bovine serum (FBS) medium was employed to prepare cell suspensions of the above 10 cell lines, respectively, and were inoculated to a 96-well plate. After 14-18 h, virus was diluted by a serious dilution. An original concentration was 1×104 pt/cell, and the viral solution was then diluted by a ten-fold series dilution. The diluted solution was added to different cell lines of the 96-well plate at an addition of 10 μl/hole, and the oncolytic potencies of Ad5, Ad11, and Ad11-5EP were tested by MTS on a $6^{th}$ day after the infection.

Figure 2:
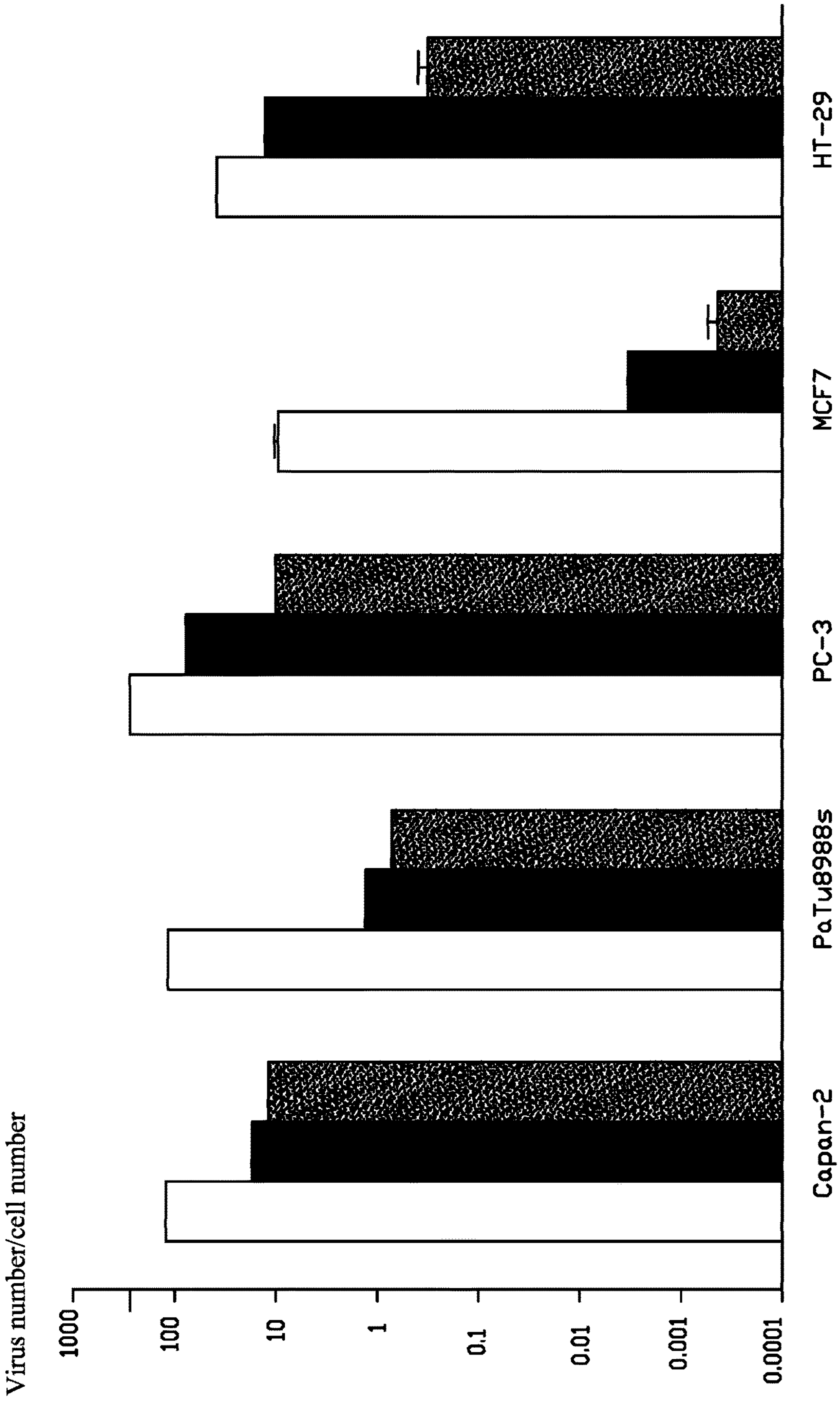
FIG. 2 is a diagram showing oncolytic potency of Ad5, Ad11 and Ad11-5EP in human cancer cells sensitive to Ad11.
Figure 3:
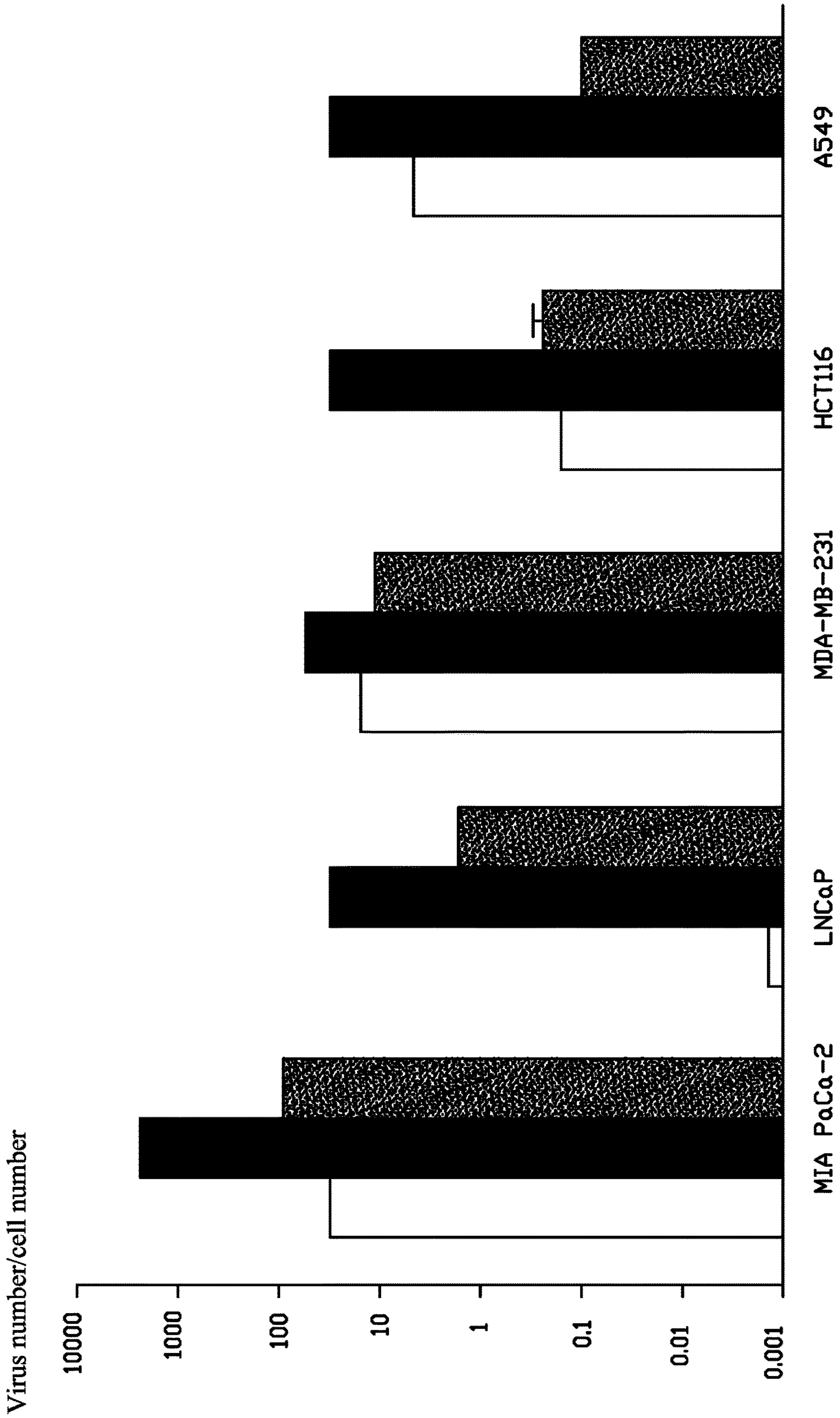
FIG. 3 is a diagram showing oncolytic potency of Ad5, Ad11 and Ad11-5EP in human cancer cells less sensitive to Ad11.

Results showed that: in all Ad11-sensitive cell lines, Ad11-5EP has better oncolytic potency than Ad5, and Ad11 produced stronger cytotoxicity (as shown in FIG. 2) whereas in Ad11-insensitive cell lines, performance of Ad11-5EP was significantly improved (as shown in FIG. 3). Ad11-5EP showed a high sensitivity in 90% (9/10) cell lines, which indicated that Ad5 and Ad11 has better cancer killing efficacy, and Ad11-5EP was capable of killing a wide spectrum of cancer cells.

EXAMPLE 3

Figure 4:
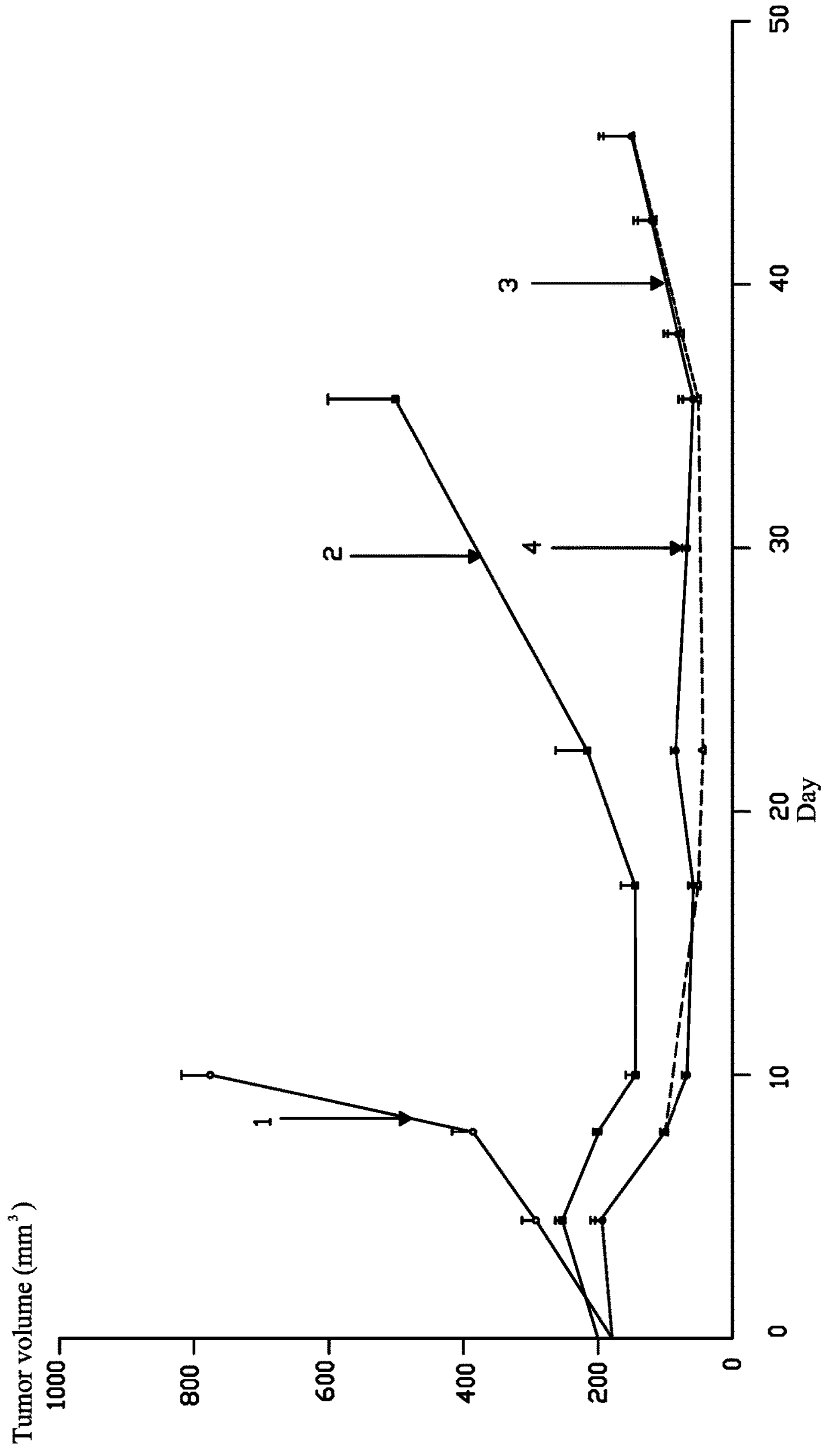
FIG. 4 is a curve chart showing mean tumor volume after treatment of Ad5, Ad11, and Ad11-5EP in MIAPaCa-2 subcutaneous xenograft model.
Figure 5:
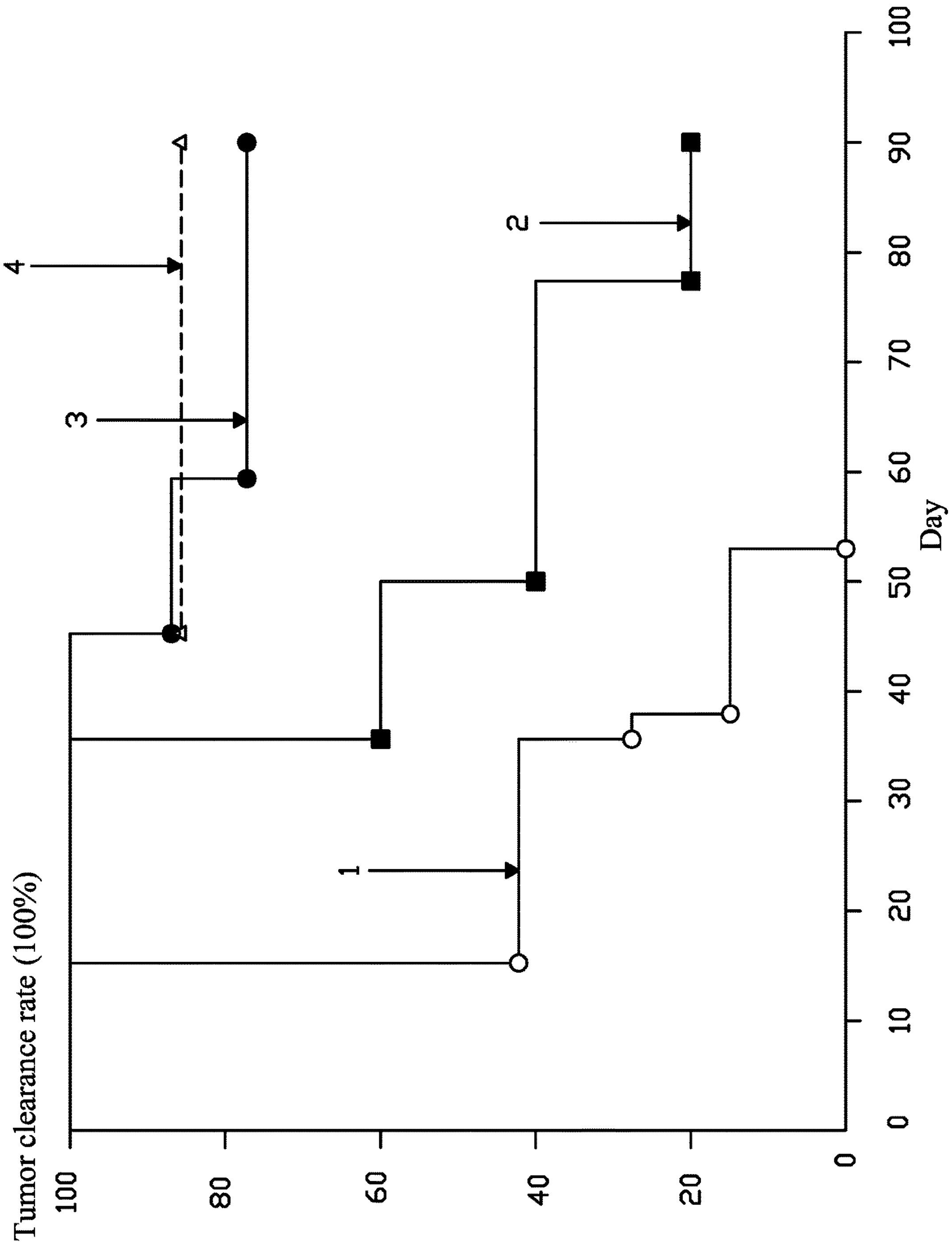
FIG. 5 is a chart showing percentage of progression-free mice after treatment with Ad5, Ad11, and Ad11-5EP in MIAPaCa-2 subcutaneous xenograft model.

Antitumoral Efficacy of Ad5, Ad11, and Ad11-5EP in a MIAPaCa-2 Subcutaneous Xenograft Model MIAPaCa-2 cells (as MIAPaCa-2 is Ad11-insensitive and Ad5-sensitive) were subcutaneously grafted to right backs of BALA/c nude mice (n=8/group), respectively, to construct subcutaneous xenograft models. When a volume of the tumor reached 180 $mm^3$, PBS or viruses (Ad5, Ad11, and Ad11-5EP, 1×1010 viral particles/injection) were injected at a $1^{st}$, $3^{rd}$ and $5^{th}$ days, tumor growth and tumor clearance rate were observed. Results showed that Ad11-5EP was as effective as Ad5 in reducing tumor growth (as shown in FIG. 4), and non-tumor ratio of tumor-bearing mice was significantly better than Ad11-treated group (as shown in FIG. 5).

EXAMPLE 4

Method for Constructing a Subgroup B Recombinant Human Adenovirus Vector Ad11-5ETel-GFP 1) Vectors pSS-ChI and pSS-kna were constructed by using two different antibiotics-resistance cassettes, SwaI restriction sites were introduced to two flanks of a chloramphenicol-resistance gene sequence cassette, and sbfI restriction sites were introduced to two flanks of a kanamycin-resistance gene sequence cassette.

2) An initiation sequence for replication of pBR32 was cloned by pUC18, and a first synthetic nucleotide sequence comprising multi-cloning sites was connected to the chloramphenicol-resistance gene sequence cassette to yield pSS-ChI. Homologously recombination between an upstream of a left arm sequence and a downstream of a right arm sequence of the chloramphenicol-resistance gene sequence cassette was performed, and the upstream of the left arm sequence of the chloramphenicol-resistance gene sequence cassette and the downstream of the right arm sequence of the chloramphenicol-resistance gene sequence cassette were inserted into the multi-cloning sites on two sides of pSS-ChI by blunt end insertion or cohesive end insertion, respectively, to construct a shuttle vector pSSEN-Tel for recombination.

3) An initiation sequence for replication of pBR32 was cloned by pUC18, and a second synthetic nucleotide sequence comprising multi-cloning sites was connected to the kanamycin-resistance gene sequence cassette to yield pSS-kna. Homologously recombination was performed between an upstream of a left arm sequence and a downstream of a right arm sequence of the kanamycin-resistance gene sequence cassette, and the upstream of the left arm sequence of the kanamycin-resistance gene sequence cassette and the downstream of the right arm sequence of the kanamycin-resistance gene sequence cassette were inserted into the multi-cloning sites on two sides of pSS-kna by blunt end insertion or cohesive end insertion, respectively, to construct a shuttle vector pSSGFP for recombination.

4) pSSENTe was constructed, and the construction of pSSENTe comprised: amplifying a 329 bp in the front of Ad11 genome as a left arm sequence, providing a fragment formed by ligating 195-378 bp of Ad5 E1A enhancer, -714-0 bp of human TERT promoter, and 568-1125 bp of Ad11 E1A in order as a right arm sequence, introducing two restriction enzyme sites XbaI and NcoI to two sides of the human TERT promoter, and inserting the left arm sequence and the right arm sequence into SnabI and EcoRV arranged on two sides of pSS-ChI, respectively, by blunt end insertion, to yield pSSENTel.

5) pSSGFP was constructed and the construction of pSSGFP comprised: providing a left arm being a product by ligating 27301-27837 bp of DNA segment of Ad11 genome with EGFP gene via NcoI, and introducing a SnaBI site to 3' terminal of EGFP; providing a right arm being 28337-28920 bp of DNA segment of Ad11 genome; and inserting the left arm and the right arm into SnabI and EcoRV sites arranged on two sides of pSS-kna by blunt end insertion, to yield pSSGFP.

Figure 6:
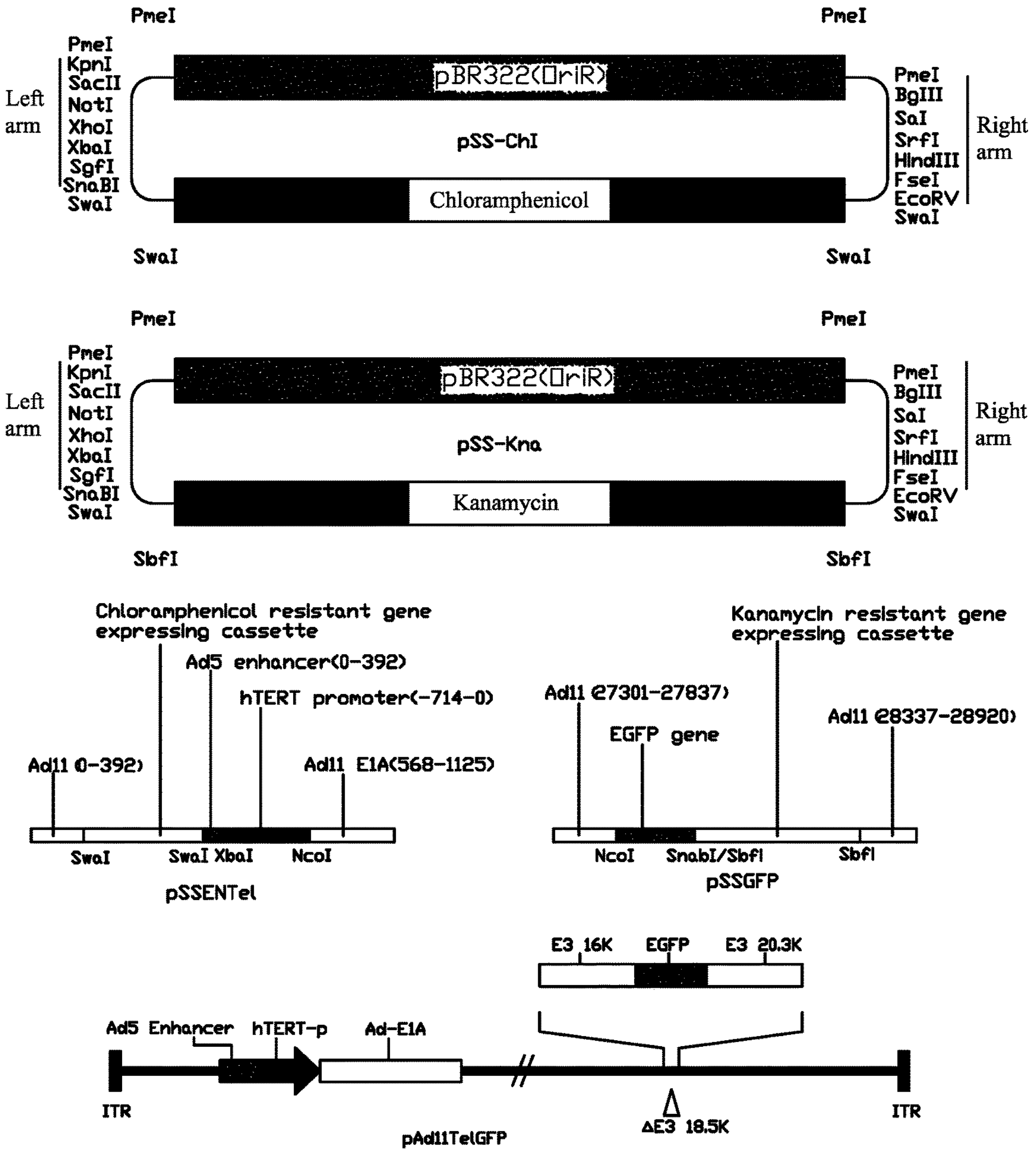
FIG. 6 is a procedure diagram of construction of shutter vectors pSSENTel and pSSGFP and replication-selective oncolytic adenovirus plasmid pAd11-5ETel-GFP.

6) pSSENTel and pSSGFP were digested and purified by PmeI to yield two PmeI digested segments, homogenous recombination was synchronously performed between the two PmeI digested segments and pAd11 plasmid, respectively, in BJ5183 cells. Positive clones were screened using agar plates comprising ampicillin, kanamycin, and chloramphenicol. The positive clones were digested by SwaI and SbfI, and chloramphenicol-resistance gene expression cassette and kanamycin-resistance gene expression cassette were deleted to yield pAd11-5ETel-GFP (as shown in FIG. 6).

The pAd11-5ETel-GFP was and linearized by NotI, and 293 cells were transfected to produce adenovirus vector Ad11-5ETel-GFP.

EXAMPLE 5

Figure 7:
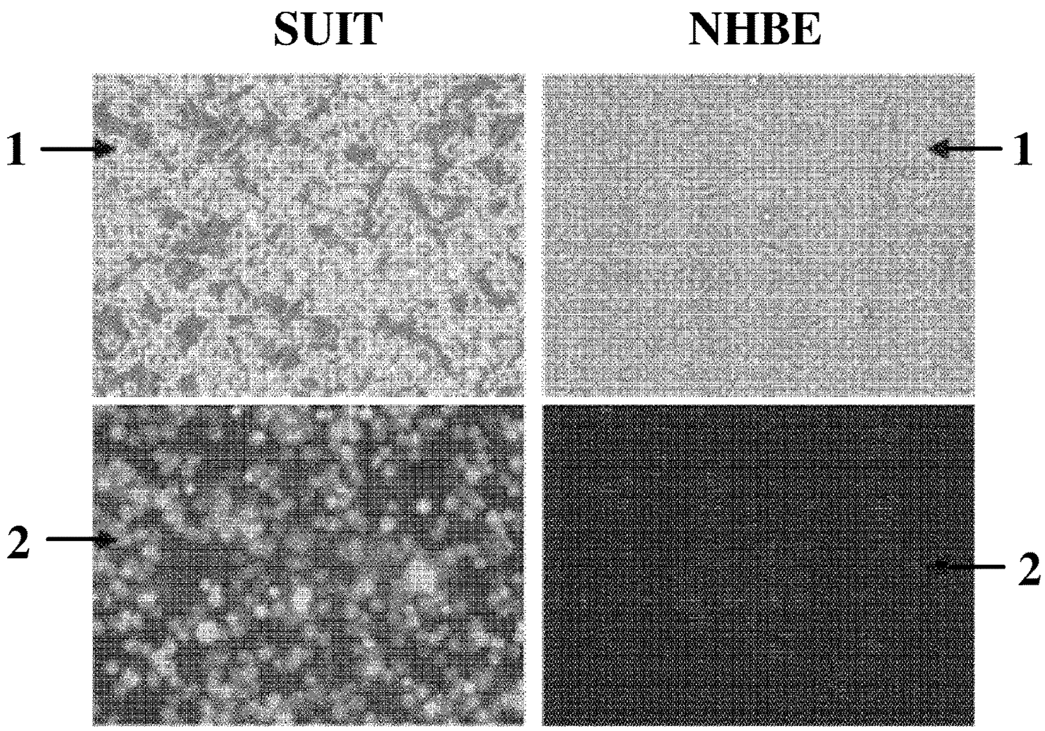
FIG. 7 is a comparison chart of GFP expression after Ad11-5ETel-GFP infection in human normal epithelial cells and cancer cells.

Expression of GFP of Ad11-5ETel-GFP in Human Normal Epithelial Cells and Cancer Cells Ad11-5ETel-GFP was used to infect human pancreatic cancer cell line SUIT-2 and human normal bronchial epithelial cell line NHBE (an infection concentration of 100 pfu/cell), expression of GFP was observed under immunofluorescence microscope after 24 h. It has been found that GFP had a high expression in cancer cell line SUIT-2, and relatively low expression in normal cells NHBE (as shown in FIG. 7), which indicated that the cancer cell line SUIT-2 is Ad11-5ETel-GFP-sensitive.

EXAMPLE 6

Figure 8:
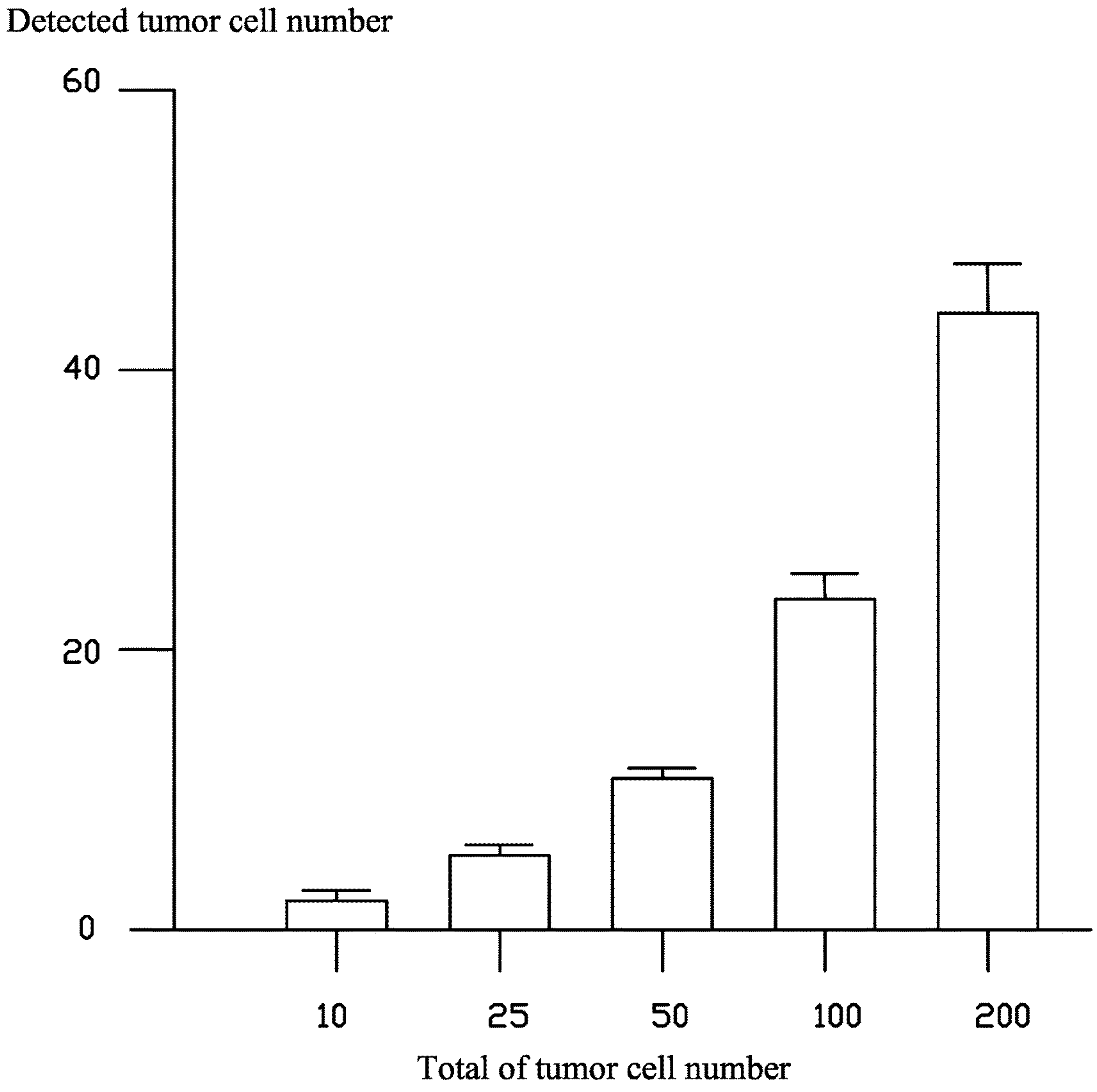
FIG. 8 is a histogram of detected tumor cells in blood by Ad11-5ETel-GFP in number.
Figure 9:
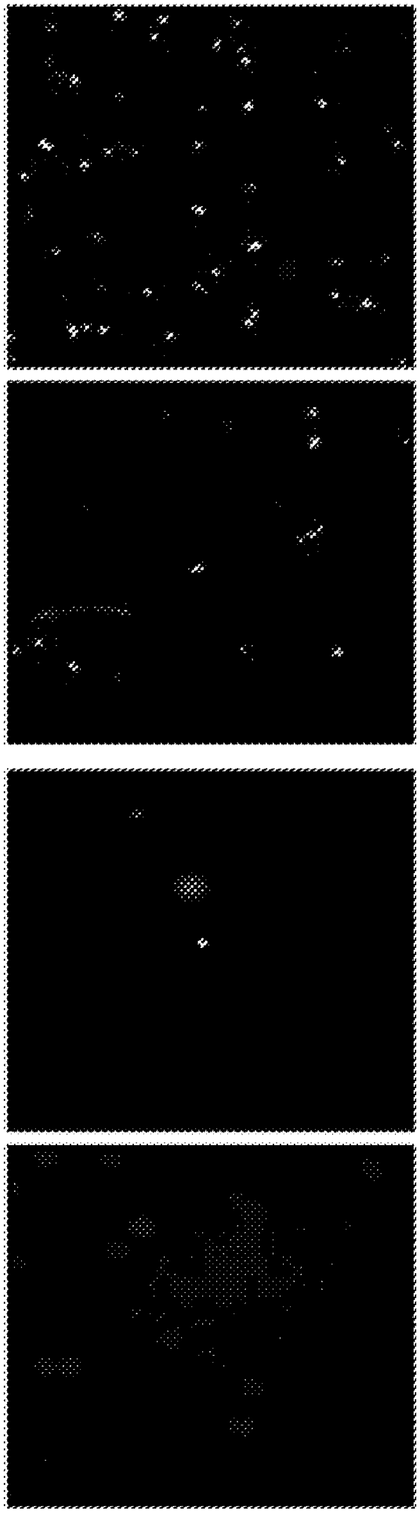
FIG. 9 is a fluorescent image showing detected tumor cells in blood by Ad11-5ETel-GFP in fluorescent image.

Circulation Tumor Cells (CTCs) Detection Using Ad11-5ETel-GFP 10, 25, 50, 100, and 200 human pancreatic cancer cell line SUIT-2 were respectively mixed with 3 mL of blood, nucleated cells were collected by centrifugation after red blood cells were lysised. Thereafter, the nucleated cells were resuspended in 900 μL of DMEM medium, added with 1×104 pfu of Ad11-5ETel-GFP, and cultured for 24 h. GFP positive cells were counted under an immunofluorescence microscope (as shown in FIG. 8). Peripheral blood cells were mixed with 0, 10, 100, and 1000 human pancreatic cancer cell line SUIT-2, respectively (an infection concentration of 100 pfu/cell). The samples were processed as described above. GFP positive cells were observed under the immunofluorescence microscope after 24 h of culturing and it demonstrated that the cancer cell line SUIT-2 is Ad11-5ETel-GFP-sensitive. The GFP-positive cells were correlated to the number of tumor cells mixed with the blood cells.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A subgroup B recombinant human adenovirus vector Ad11-5EP (SEQ ID NO: 1), wherein the subgroup B recombinant human adenovirus vector Ad11-5EP (SEQ ID NO: 1) is constructed by a method comprising substituting a 365 bp fragment comprising an enhancer and a promoter of an upstream coding sequence of Ad5 E1A (SEQ ID NO: 2) for a corresponding region of a serotype Ad11 (SEQ ID NO: 3) of a subgroup B human adenovirus vector by homologous recombination to construct the subgroup B recombinant human adenovirus vector Ad11-5EP (SEQ ID NO: 1).

2. A method for treatment of tumor, the method comprising applying a subgroup B recombinant human adenovirus vector Ad11-5EP (SEQ ID NO: 1).

* * * * *

SEQUENCE LISTING

<160> NUMBER OF SEQ ID NOS: 17

<210> SEQ ID NO 1
<211> LENGTH: 34801
<212> TYPE: DNA
<213> ORGANISM: Artificial Sequence
<220> FEATURE:
<223> OTHER INFORMATION: Fully synthetic

<400> SEQUENCE: 1

```
catcatcaat aatatacctt atagatggaa tggtgccaat atgtaaatga ggtgatttta      60

aaaagtgtgg atcgtgtggt gattggctgt ggggttaacg gctaaaaggg gcggtgcgac     120

cgtgggaaaa tgacgttttg tgggggtgga gtttttttgc aagttgtcgc gggaaatgtg     180

acgcataaaa aggctacaca ggaagtgaca attttcgcgc ggttttaggc ggatgttgta     240

gtaaatttgg gcgtaaccga gtaagatttg gccattttcg cgggaaaact gaataagagg     300

aagtgaaatc tgaataattt tgtgttactc atagcgcgta atatttgtct agggccgcgg     360

ggactttgac cgtttacgtg gagactcgcc caggtgtttt tctcaggtgt tttccgcgtt     420

cgggtcaaag ttggcgtttt attattatag tcagctgacg tgtagtgtat ttatacccgg     480

tgagttcctc aagaggccac tcttgagtgc cagcgagtag agttttctcc tccgagccgc     540

tccgacaccg ggactgaaaa atgagagatt tgcgatttct gcctcaggaa ataatctctg     600

ctgagactgg aaatgaaata ttggagcttg tggtgcacgc cctgatggga gacgatccgg     660

agccacctgt gcagcttttt gagcctccta cgcttcagga actgtatgat ttagaggtag     720

agggatcgga ggattctaat gaggaagctg taaatggctt ttttaccgat tctatgcttt     780

tagctgctaa tgaagggtta gaattagatc cgcctttgga cacttttgat actccagggg     840

taattgtgga aagcggtaca ggtgtaagaa aattacctga tttgagttcc gtggactgtg     900

atttgcactg ctatgaagac gggtttcctc cgagtgatga ggaggaccat gaaaaggagc     960

agtccatgca gactgcagcg ggtgagggag tgaaggctgc caatgttggt tttcagttgg    1020

attgcccgga gcttcctgga catggctgta agtcttgtga atttcacagg aaaaatactg    1080

gagtaaagga actgttatgt tcgctttgtt atatgagaac gcactgccac tttatttaca    1140

gtaagtgtgt ttaagttaaa atttaaagga atatgctgtt tttcacatgt atattgagtg    1200
```

-continued

```
tgagttttgt gcttcttatt ataggtcctg tgtctgatgc tgatgaatca ccatctcctg   1260
attctactac ctcacctcct gagattcaag cacctgttcc tgtggacgtg cgcaagccca   1320
ttcctgtgaa gcttaagcct gggaaacgtc cagcagtgga aaaacttgag gacttgttac   1380
agggtgggga cggacctttg gacttgagta cacggaaacg tccaagacaa taagtgttcc   1440
atatccgtgt ttacttaagg tgacgtcaat atttgtgtga cagtgcaatg taataaaaat   1500
atgttaactg ttcactggtt tttattgctt tttgggcggg gactcaggta tataagtaga   1560
agcagacctg tgtggttagc tcataggagc tggctttcat ccatggaggt ttgggccatt   1620
ttggaagacc ttaggaagac taggcaactg ttagagaacg cttcggacgg agtctccggt   1680
ttttggagat tctggttcgc tagtgaatta gctagggtag tttttaggat aaaacaggac   1740
tataaacaag aatttgaaaa gttgttggta gattgcccag gactttttga agctcttaat   1800
ttgggccatc aggttcactt taaagaaaaa gttttatcag ttttagactt ttcaacccca   1860
ggtagaactg ctgctgctgt ggcttttctt acttttatat tagataaatg gatcccgcag   1920
actcatttca gcaggggata cgttttggat ttcatagcca cagcattgtg gagaacatgg   1980
aaggttcgca agatgaggac aatcttaggt tactggccag tgcagccttt gggtgtagcg   2040
ggaatcctga ggcatccacc ggtcatgcca gcggttctgg aggaggaaca gcaagaggac   2100
aacccgagag ccggcctgga ccctccagtg gaggaggcgg agtagctgac ttgtctcctg   2160
aactgcaacg ggtgcttact ggatctacgt ccactggacg ggataggggc gttaagaggg   2220
agagggcatc tagtggtact gatgctagat ctgagttggc tttaagttta atgagtcgca   2280
gacgtcctga aaccatttgg tggcatgagg ttcagaaaga gggaagggat gaagtttctg   2340
tattgcagga gaaatattca ctggaacagg tgaaaacatg ttggttggag cctgaggatg   2400
attgggaggt ggccattaaa aattatgcca agatagcttt gaggcctgat aaacagtata   2460
agattactag acggattaat atccggaatg cttgttacat atctggaaat ggggctgagg   2520
tggtaataga tactcaagac aaggcagtta ttagatgctg catgatggat atgtggcctg   2580
gggtagtcgg tatggaagca gtaacttttg taaatgttaa gtttagggga gatggttata   2640
atggaatagt gtttatggcc aataccaaac ttatattgca tggttgtagc ttttttggtt   2700
tcaacaatac ctgtgtagat gcctggggac aggttagtgt acggggatgt agtttctatg   2760
cgtgttggat tgccacagct ggcagaacca agagtcaatt gtctctgaag aaatgcatat   2820
ttcaaagatg taacctgggc attctgaatg aaggcgaagc aagggtccgc cactgcgctt   2880
ctacagatac tggatgtttt attttgatta agggaaatgc cagcgtaaag cataacatga   2940
tttgcggtgc ttccgatgag aggccttatc aaatgctcac ttgtgctggt gggcattgta   3000
atatgctggc tactgtgcat attgtttccc atcaacgcaa aaaatggcct gtttttgatc   3060
acaatgtgat gacgaagtgt accatgcatg caggtgggcg tagaggaatg tttatgcctt   3120
accagtgtaa catgaatcat gtgaaagtgt tgttggaacc agatgccttt tccagaatga   3180
gcctaacagg aatttttgac atgaacatgc aaatctggaa gatcctgagg tatgatgata   3240
cgagatcgag ggtacgcgca tgcgaatgcg gaggcaagca tgccaggttc cagccggtgt   3300
gtgtagatgt gactgaagat ctcagaccgg atcatttggt tattgcccgc actggagcag   3360
agttcggatc cagtggagaa gaaactgact aaggtgagta ttgggaaaac tttggggtgg   3420
gattttcaga tggacagatt gagtaaaaat ttgtttttttc tgtcttgcag ctgtcatgag   3480
tggaaacgct tcttttaagg ggggagtctt cagcccttat ctgacagggc gtctcccatc   3540
```

-continued

```
ctgggcagga gttcgtcaga atgttatggg atctactgtg gatggaagac ccgtccaacc   3600
cgccaattct tcaacgctga cctatgctac tttaagttct tcacctttgg acgcagctgc   3660
agctgccgcc gccgcttctg ttgccgctaa cactgtgctt ggaatgggtt actatggaag   3720
catcatggct aattccactt cctctaataa cccttctacc ctgactcagg acaagttact   3780
tgtccttttg gcccagctgg aggctttgac ccaacgtctg ggtgaacttt ctcagcaggt   3840
ggtcgagttg cgagtacaaa ctgagtctgc tgtcggcacg gcaaagtcta aataaaaaaa   3900
tcccagaatc aatgaataaa taaacaagct tgttgttgat ttaaaatcaa gtgtttttat   3960
ttcatttttc gcgcacggta tgccctagac caccgatctc tatcattgag aactcggtgg   4020
atttttttcca ggatcctata gaggtgggat tgaatgttta gatacatggg cattaggccg   4080
tctttggggt ggagatagct ccattgaagg gattcatgct ccggggtagt gttgtaaatc   4140
acccagtcat aacaaggtcg cagtgcatgg tgttgcacaa tatcttttag aagtaggctg   4200
attgccacag ataagccctt ggtgtaggtg tttacaaacc ggttgagctg ggatgggtgc   4260
attcggggtg aaattatgtg cattttggat tggattttta agttggcaat attgccgcca   4320
agatcccgtc ttgggttcat gttatgaagg accaccaaga cggtgtatcc ggtacattta   4380
ggaaatttat cgtgcagctt ggatggaaaa gcgtggaaaa atttggagac acccttgtgt   4440
cctccaagat tttccatgca ctcatccatg ataatagcaa tggggccgtg ggcagcggcg   4500
cgggcaaaca cgttccgtgg gtctgacaca tcatagttat gttcctgagt taaatcatca   4560
taagccattt taatgaattt ggggcggaga gtaccagatt ggggtatgaa tgttccttcg   4620
ggccccggag catagttccc ctcacagatt tgcatttccc aagctttcag ttccgagggt   4680
ggaatcatgt ccacctgggg ggctatgaaa aacaccgttt ctggggcggg ggtgattaat   4740
tgtgatgata gcaaatttct gagcaattga gatttgccac atccggtggg gccataaatg   4800
attccgatta cgggttgcag gtggtagttt agggaacggc aactgccgtc ttctcgaagc   4860
aagggggcca cctcgttcat catttccctt acatgcatat tttcccgcac caaatccatt   4920
aggaggcgct ctcctcctag tgatagaagt tcttgtagtg aggaaaagtt tttcagcggt   4980
ttcagaccgt cagccatggg cattttggag agagtttgct gcaaaagttc tagtctgttc   5040
cacagttcag tgatgtgttc tatggcatct cgatccagca gacctcctcg tttcgcgggt   5100
ttggacggct cctggaatag ggtatgagac gatgggcgtc cagcgctgcc agggttcggt   5160
ccttccaggg tctcagtgtt cgagtcaggg ttgtttccgt cacagtgaag ggtgtgcgc   5220
ctgcttgggc gcttgccagg gtgcgcttca gactcatcct gctggtcgaa aacttctgtc   5280
gcttggcgcc ctgtatgtcg gccaagtagc agtttaccat gagttcgtag ttgagcgcct   5340
cggctgcgtg gcctttggcg cggagcttac ctttggaagt tttcttgcat accgggcagt   5400
ataggcattt cagcgcatac aacttgggcg caaggaaaac ggattctggg gagtatgcat   5460
ctgcgccgca ggaggcgcaa acagtttcac attccaccag ccaggttaaa tccggttcat   5520
tggggtcaaa aacaagtttt ccgccatatt ttttgatgcg tttcttacct ttggtctcca   5580
tgagttcgtg tcctcgttga gtgacaaaca ggctgtccgt gtccccgtag actgatttta   5640
caggcctctt ctccagtgga gtgcctcggt cttcttcgta caggaactct gaccactctg   5700
atacaaaggc gcgcgtccag gccagcacaa aggaggctat gtgggagggg tagcgatcgt   5760
tgtcaaccag gggtccacc ttttccaaag tatgcaaaca catgtcaccc tcttcaacat   5820
ccaggaatgt gattggcttg taggtgtatt tcacgtgacc tggggtcccc gctgggggg   5880
tataaaaggg ggcggttctt tgctcttcct cactgtcttc cggatcgctg tccaggaacg   5940
```

-continued

```
tcagctgttg gggtaggtat tccctctcga aggcgggcat gacctctgca ctcaggttgt   6000
cagtttctaa gaacgaggag gatttgatat tgacagtgcc ggttgagatg cctttcatga   6060
ggttttcgtc catttggtca gaaaacacaa ttttttttatt gtcaagtttg gtggcaaatg   6120
atccatacag ggcgttggat aaaagtttgg caatggatcg catggtttgg ttcttttcct   6180
tgtccgcgcg ctctttggcg gcgatgttga gttggacata ctcgcgtgcc aggcacttcc   6240
attcggggaa gatagttgtt aattcatctg gcacgattct cacttgccac cctcgattat   6300
gcaaggtaat taaatccaca ctggtggcca cctcgcctcg aaggggttca ttggtccaac   6360
agagcctacc tcctttccta gaacagaaag gggaagtgg gtctagcata agttcatcgg   6420
gagggtctgc atccatggta aagattcccg gaagtaaatc cttatcaaaa tagctgatgg   6480
gagtggggtc atctaaggcc atttgccatt ctcgagctgc cagtgcgcgc tcatatgggt   6540
taaggggact gccccatggc atgggatggg tgagtgcaga ggcatacatg ccacagatgt   6600
catagacgta gatgggatcc tcaaagatgc ctatgtaggt tggatagcat cgccccccctc   6660
tgatacttgc tcgcacatag tcatatagtt catgtgatgg cgctagcagc cccggaccca   6720
agttggtgcg attgggtttt tctgttctgt agacgatctg gcgaaagatg gcgtgagaat   6780
tggaagagat ggtgggtctt tgaaaaatgt tgaaatgggc atgaggtaga cctacagagt   6840
ctctgacaaa gtgggcataa gattcttgaa gcttggttac cagttcggcg gtgacaagta   6900
cgtctagggc gcagtagtca agtgtttctt gaatgatgtc ataacctggt tggtttttct   6960
tttcccacag ttcgcggttg agaaggtatt cttcgcgatc cttccagtac tcttctagcg   7020
gaaacccgtc tttgtctgca cggtaagatc ctagcatgta gaactgatta actgccttgt   7080
aagggcagca gcccttctct acgggtagag agtatgcttg agcagctttt cgtagcgaag   7140
cgtgagtaag ggcaaaggtg tctctgacca tgactttgag aaattggtat ttgaagtcga   7200
tgtcgtcaca ggctccctgt tcccagagtt ggaagtctac ccgtttcttg taggcggggt   7260
tgggcaaagc gaaagtaaca tcattgaaga gaatcttacc ggctctgggc ataaaattgc   7320
gagtgatgcg aaaaggctgt ggtacttccg ctcgattgtt gatcacctgg gcagctagga   7380
cgatctcgtc gaaaccgttg atgttgtgtc ctacgatgta taattctatg aaacgcggcg   7440
tgcctctgac gtgaggtagc ttactgagct catcaaaggt taggtctgtg ggtcagata    7500
aggcgtagtg ttcgagagcc cattcgtgca ggtgaggatt tgcatgtagg aatgatgacc   7560
aaagatctac cgccagtgct gtttgtaact ggtcccgata ctgacgaaaa tgccggccaa   7620
ttgccatttt ttctggagtg acacagtaga aggttctggg gtcttgttgc catcgatccc   7680
acttgagttt aatggctaga tcgtgggcca tgttgacgag acgctcttct cctgagagtt   7740
tcatgaccag catgaaagga actagttgtt tgccaaagga tcccatccag gtgtaagttt   7800
ccacatcgta ggtcaggaag agtctttctg tgcgaggatg agagccgatc gggaagaact   7860
ggatttcctg ccaccagttg gaggattggc tgttgatgtg atggaagtag aagtttctgc   7920
ggcgcgccga gcattcgtgt ttgtgcttgt acagacggcc gcagtagtcg cagcgttgca   7980
cgggttgtat ctcgtgaatg agttgtacct ggcttccctt gacgagaaat ttcagtggga   8040
agccgaggcc tggcgattgt atctcgtgct cttctatatt cgctgtatcg gcctgttcat   8100
cttctgtttc gatggtggtc atgctgacga gcccccgcgg gaggcaagtc cagacctcgg   8160
cgcgggaggg gcggagctga aggacgagag cgcgcaggct ggagctgtcc agagtcctga   8220
gacgctgcgg actcaggtta gtaggtaggg acagaagatt aacttgcatg atcttttcca   8280
```

-continued

```
gggcgtgcgg gaggttcaga tggtacttga tttccacagg ttcgtttgta gagacgtcaa   8340
tggcttgcag ggttccgtgt cctttgggcg ccactaccgt acctttgttt tttcttttga   8400
tcggtggtgg ctctcttgct tcttgcatgc tcagaagcgg tgacggggac gcgcgccggg   8460
cggcagcggt tgttccggac ccgagggcat ggctggtagt ggcacgtcgg cgccgcgcac   8520
gggcaggttc tggtactgcg ctctgagaag acttgcgtgc gccaccacgc gtcgattgac   8580
gtcttgtatc tgacgtctct gggtgaaagc taccggcccc gtgagcttga acctgaaaga   8640
gagttcaaca gaatcaattt cggtatcgtt aacggcagct tgtctcagta tttcttgtac   8700
gtcaccagag ttgtcctggt aggcgatctc cgccatgaac tgctcgattt cttcctcctg   8760
aagatctccg cgacccgctc tttcgacggt ggccgcgagg tcattggaga tacggcccat   8820
gagttgggag aatgcattca tgcccgcctc gttccagacg cggctgtaaa ccacggcccc   8880
ctcggagtct cttgcgcgca tcaccacctg agcgaggtta agctccacgt gtctggtgaa   8940
gaccgcatag ttgcataggc gctgaaaaag gtagttgagt gtggtggcaa tgtgttcggc   9000
gacgaagaaa tacatgatcc atcgtctcag cggcatttcg ctaacatcgc ccagagcttc   9060
caagcgctcc atggcctcgt agaagtccac ggcaaaatta aaaaactggg agtttcgcgc   9120
ggacacggtc aattcctcct cgagaagacg gatgagttcg gctatggtgg cccgtacttc   9180
gcgttcgaag gctcccggga tctcttcttc ctcttctatc tcttcttcca ctaacatctc   9240
ttcttcgtct tcaggcgggg gcggaggggg cacgcggcga cgtcgacggc gcacgggcaa   9300
acggtcgatg aatcgttcaa tgacctctcc gcggcggcgg cgcatggttt cagtgacggc   9360
gcggccgttc tcgcgcggtc gcagagtaaa aacaccgccg cgcatctcct taaagtggtg   9420
actgggaggt tctccgtttg ggagggagag ggcgctgatt atacatttta ttaattggcc   9480
cgtagggact gcacgcagag atctgatcgt gtcaagatcc acgggatctg aaaacctttc   9540
gacgaaagcg tctaaccagt cacagtcaca aggtaggctg agtacggctt cttgtgggcg   9600
ggggtggtta tgtgttcggt ctgggtcttc tgtttcttct tcatctcggg aaggtgagac   9660
gatgctgctg gtgatgaaat taaagtaggc agttctaaga cggcggatgg tggcgaggag   9720
caccaggtct ttgggtccgg cttgctggat acgcaggcga ttggccattc cccaagcatt   9780
atcctgacat ctagcaagat ctttgtagta gtcttgcatg agccgttcta cgggcacttc   9840
ttcctcaccc gttctgccat gcatacgtgt gagtccaaat ccgcgcattg gttgtaccag   9900
tgccaagtca gctacgactc tttcggcgag gatggcttgc tgtacttggg taagggtggc   9960
ttgaaagtca tcaaaatcca caaagcggtg gtaagctcct gtattaatgg tgtaagcaca  10020
gttggccatg actgaccagt taactgtctg gtgaccaggg cgcacgagct cggtgtattt  10080
aaggcgcgaa taggcgcggg tgtcaaagat gtaatcgttg caggtgcgca ccagatactg  10140
gtaccctata agaaaatgcg gcggtggttg gcggtagaga ggccatcgtt ctgtagctgg  10200
agcgccaggg gcgaggtctt ccaacataag gcggtgatag ccgtagatgt acctggacat  10260
ccaggtgatt cctgcggcgg tagtagaagc ccgaggaaac tcgcgtacgc ggttccaaat  10320
gttgcgtagc ggcatgaagt agttcattgt aggcacggtt tgaccagtga ggcgcgcgca  10380
gtcattgatg ctctatagac acggagaaaa tgaaagcgtt cagcgactcg actccgtagc  10440
ctggaggaac gtgaacgggt tgggtcgcgg tgtaccccgg ttcgagactt gtactcgagc  10500
cggccggagc cgcggctaac gtggtattgg cactcccgtc tcgacccagc ctacaaaaat  10560
ccaggatacg gaatcgagtc gttttgctgg tttccgaatg gcagggaagt gagtcctatt  10620
ttttttttt tgccgctcag atgcatcccg tgctgcgaca gatgcgcccc caacaacagc  10680
```

-continued

```
cccccctcgca gcagcagcag cagcaatcac aaaaggctgt ccctgcaact actgcaactg  10740
ccgccgtgag cggtgcggga cagcccgcct atgatctgga cttggaagag ggcgaaggac  10800
tggcacgtct aggtgcgcct tcacccgagc ggcatccgcg agttcaactg aaaaaagatt  10860
ctcgcgaggc gtatgtgccc caacagaacc tatttagaga cagaagcggc gaggagccgg  10920
aggagatgcg agcttcccgc tttaacgcgg gtcgtgagct gcgtcacggt ttggaccgaa  10980
gacgagtgtt gcgggacgag gatttcgaag ttgatgaaat gacagggatc agtcctgcca  11040
gggcacacgt ggctgcagcc aaccttgtat cggcttacga gcagacagta aaggaagagc  11100
gtaacttcca aaagtctttt aataatcatg tgcgaaccct gattgcccgc gaagaagtta  11160
cccttggttt gatgcatttg tgggatttga tggaagctat cattcagaac cctactagca  11220
aacctctgac cgcccagctg tttctggtgg tgcaacacag cagagacaat gaggctttca  11280
gagaggcgct gctgaacatc accgaacccg aggggagatg gttgtatgat cttatcaaca  11340
ttctacagag tatcatagtg caggagcgga gcctgggcct ggccgagaag gtggctgcca  11400
tcaattactc ggttttgagc ttgggaaaat attacgctcg caaaatctac aagactccat  11460
acgttcccat agacaaggag gtgaagatag atgggttcta catgcgcatg acgctcaagg  11520
tcttgaccct gagcgatgat cttggggtgt atcgcaatga cagaatgcat cgcgcggtta  11580
gcgccagcag gaggcgcgag ttaagcgaca gggaactgat gcacagtttg caaagagctc  11640
tgactggagc tggaaccgag ggtgagaatt acttcgacat gggagctgac ttgcagtggc  11700
agcctagtcg cagggctctg agcgccgcga cggcaggatg tgagcttcct tacatagaag  11760
aggcggatga aggcgaggag gaagagggcg agtacttgga agactgatgg cacaacccgt  11820
gtttttgct agatggaaca gcaagcaccg gatcccgcaa tgcgggcggc gctgcagagc  11880
cagccgtccg gcattaactc ctcggacgat tggacccagg ccatgcaacg tatcatggcg  11940
ttgacgactc gcaaccccga agcctttaga cagcaacccc aggccaaccg tctatcggcc  12000
atcatggaag ctgtagtgcc ttcccgctct aatcccactc atgagaaggt cctggccatc  12060
gtgaacgcgt tggtggagaa caaagctatt cgtccagatg aggccggact ggtatacaac  12120
gctctcttag aacgcgtggc tcgctacaac agtagcaatg tgcaaaccaa tttggaccgt  12180
atgataacag atgtacgcga agccgtgtct cagcgcgaaa ggttccagcg tgatgccaac  12240
ctgggttcgc tggtggcgtt aaatgctttc ttgagtactc agcctgctaa tgtgccgcgt  12300
ggtcaacagg attatactaa ctttttaagt gctttgagac tgatggtatc agaagtacct  12360
cagagcgaag tgtatcagtc cggtcctgat tacttctttc agactagcag acagggcttg  12420
cagacggtaa atctgagcca agcttttaaa aaccttaaag gtttgtgggg agtgcatgcc  12480
ccggtaggag aaagagcaac cgtgtctagc ttgttaactc cgaactcccg cctattatta  12540
ctgttggtag ctcctttcac cgacagcggt agcatcgacc gtaattccta tttgggttac  12600
ctactaaacc tgtatcgcga agccataggg caaagtcagg tggacgagca gacctatcaa  12660
gaaattaccc aagtcagtcg cgctttggga caggaagaca ctggcagttt ggaagccact  12720
ctgaacttct tgcttaccaa tcggtctcaa aagatccctc ctcaatatgc tcttactgcg  12780
gaggaggaga ggatccttag atatgtgcag cagagcgtgg gattgtttct gatgcaagag  12840
ggggcaactc cgactgcagc actggacatg acagcgcgaa atatggagcc cagcatgtat  12900
gccagtaacc gacctttcat taacaaactg ctggactact tgcacagagc tgccgctatg  12960
aactctgatt atttcaccaa tgccatctta aacccgcact ggctgccccc acctggtttc  13020
```

-continued

```
tacacgggcg aatatgacat gcccgaccct aatgacggat ttctgtggga cgacgtggac  13080
agcgatgttt tttcacctct ttctgatcat cgcacgtgga aaaaggaagg cggcgataga  13140
atgcattctt ctgcatcgct gtccggggtc atgggtgcta ccgcggctga gcccgagtct  13200
gcaagtcctt ttcctagtct acccttttct ctacacagtg tacgtagcag cgaagtgggt  13260
agaataagtc gcccgagttt aatgggcgaa gaggagtatc taaacgattc cttgctcaga  13320
ccggcaagag aaaaaaattt cccaaacaat ggaatagaaa gtttggtgga taaaatgagt  13380
agatggaaga cttatgctca ggatcacaga gacgagcctg ggatcatggg gattacaagt  13440
agagcgagcc gtagacgcca gcgccatgac agacagaggg gtcttgtgtg ggacgatgag  13500
gattcggccg atgatagcag cgtgctggac ttgggtggga gaggaagggg caacccgttt  13560
gctcatttgc gccctcgctt gggtggtatg ttgtaaaaaa aaataaaaaa aaaactcacc  13620
aaggccatgg cgacgagcgt acgttcgttc ttctttatta tctgtgtcta gtataatgag  13680
gcgagtcgtg ctaggcggag cggtggtgta tccggagggt cctcctcctt cgtacgagag  13740
cgtgatgcag cagcagcagg cgacggcggt gatgcaatcc ccactggagg ctccctttgt  13800
gcctccgcga tacctggcac ctacggaggg cagaaacagc attcgttatt cggaactggc  13860
acctcagtac gataccacca ggttgtatct ggtggacaac aagtcggcgg acattgcttc  13920
tctgaactat cagaatgacc acagcaactt cttgaccacg gtggtgcaaa acaatgactt  13980
tacccctacg gaagccagca cccagaccat taactttgat gaacgatcgc ggtggggcgg  14040
tcagctaaag accatcatgc atactaacat gccaaacgtg aacgagtata tgtttagtaa  14100
caagttcaaa gcgcgtgtga tggtgtccag aaaacctccc gacggtgctg cagttgggga  14160
tacttatgat cacaagcagg atattttgaa atatgagtgg ttcgagttta ctttgccaga  14220
aggcaacttt tcagttacta tgactattga tttgatgaac aatgccatca tagataatta  14280
cttgaaagtg ggtagacaga atggagtgct tgaaagtgac attggtgtta agttcgacac  14340
caggaacttc aagctgggat gggatcccga aaccaagttg atcatgcctg gagtgtatac  14400
gtatgaagcc ttccatcctg acattgtctt actgcctggc tgcggagtgg attttaccga  14460
gagtcgtttg agcaaccttc ttggtatcag aaaaaaacag ccatttcaag agggttttaa  14520
gattttgtat gaagatttag aaggtggtaa tattccggcc ctcttggatg tagatgccta  14580
tgagaacagt aagaaagaac aaaaagccaa aatagaagct gctacagctg ctgcagaagc  14640
taaggcaaac atagttgcca gcgactctac aagggttgct aacgctggag aggtcagagg  14700
agacaatttt gcgccaacac ctgttccgac tgcagaatca ttattggccg atgtgtctga  14760
aggaacggac gtgaaactca ctattcaacc tgtagaaaaa gatagtaaga atagaagcta  14820
taatgtgttg gaagacaaaa tcaacacagc ctatcgcagt tggtatcttt cgtacaatta  14880
tggcgatccc gaaaaaggag tgcgttcctg gacattgctc accacctcag atgtcacctg  14940
cggagcagag caggtctact ggtcgcttcc agacatgatg aaggatcctg tcactttccg  15000
ctccactaga caagtcagta actaccctgt ggtgggtgca gagcttatgc ccgtcttctc  15060
aaagagcttc tacaacgaac aagctgtgta ctcccagcag ctccgccagt ccacctcgct  15120
tacgcacgtc ttcaaccgct ttcctgagaa ccagatttta atccgtccgc cggcgcccac  15180
cattaccacc gtcagtgaaa acgttcctgc tctcacagat cacgggaccc tgccgttgcg  15240
cagcagtatc cggggagtcc aacgtgtgac cgttactgac gccagacgcc gcacctgtcc  15300
ctacgtgtac aaggcactgg gcatagtcgc accgcgcgtc ctttcaagcc gcactttcta  15360
aaaaaaaaaa aaatgtccat tcttatctcg cccagtaata acaccggttg ggtctgcgc   15420
```

-continued

```
gctccaagca agatgtacgg aggcgcacgc aaacgttcta cccaacatcc tgtccgtgtt  15480
cgcggacatt ttcgcgctcc atggggcgcc ctcaagggcc gcactcgcgt tcgaaccacc  15540
gtcgatgatg taatcgatca ggtggttgcc gacgcccgta attatactcc tactgcgcct  15600
acatctactg tggatgcagt tattgacagt gtagtggctg acgctcgcaa ctatgctcga  15660
cgtaagagcc ggcgaaggcg cattgccaga cgccaccgag ctaccactgc catgcgagcc  15720
gcaagagctc tgctacgaag agctagacgc gtggggcgaa gagccatgct tagggcggcc  15780
agacgtgcag cttcgggcgc cagcgccggc aggtcccgca ggcaagcagc cgctttcgca  15840
gcggcgacta ttgccgacat ggcccaatcg cgaagaggca atgtatactg ggtgcgtgac  15900
gctgccaccg gtcaacgtgt acccgtgcgc acccgtcccc ctcgcactta gaagatactg  15960
agcagtctcc gatgttgtgt cccagcggcg aggatgtcca agcgcaaata caaggaagaa  16020
atgctgcagg ttatcgcacc tgaagtctac ggccaaccgt tgaaggatga aaaaaaaccc  16080
cgcaaaatca agcgggttaa aaaggacaaa aaagaagagg aagatggcga tgatgggctg  16140
gcggagtttg tgcgcgagtt tgccccacgg cgacgcgtgc aatggcgtgg gcgcaaagtt  16200
cgacatgtgt tgagacctgg aacttcggtg gtctttacac ccggcgagcg ttcaagcgct  16260
acttttaagc gttcctatga tgaggtgtac ggggatgatg atattcttga gcaggcggct  16320
gaccgattag gcgagtttgc ttatggcaag cgtagtagaa taacttccaa ggatgagaca  16380
gtgtcgatac ccttggatca tggaaatccc accccctagtc ttaaaccggt cactttgcag  16440
caagtgttac ccgtaactcc gcgaacaggt gttaaacgcg aaggtgaaga tttgtatccc  16500
actatgcaac tgatggtacc caaacgccag aagttggagg acgttttgga gaaagtaaaa  16560
gtggatccag atattcaacc tgaggttaaa gtgagaccca ttaagcaggt agcgcctggt  16620
ctgggggtac aaactgtaga cattaagatt cccactgaaa gtatggaagt gcaaactgaa  16680
cccgcaaagc ctactgccac ctccactgaa gtgcaaacgg atccatggat gcccatgcct  16740
attacaactg acgccgccgg tcccactcga agatcccgac gaaagtacgg tccagcaagt  16800
ctgttgatgc ccaattatgt tgtacaccca tctattattc ctactcctgg ttaccgaggc  16860
actcgctact atcgcagccg aaacagtacc tcccgccgtc gccgcaagac acctgcaaat  16920
cgcagtcgtc gccgtagacg cacaagcaaa ccgactcccg gcgccctggt gcggcaagtg  16980
taccgcaatg gtagtgcgga acctttgaca ctgccgcgtg cgcgttacca tccgagtatc  17040
atcacttaat caatgttgcc gctgcctcct tgcagatatg gccctcactt gtcgccttcg  17100
cgttcccatc actggttacc gaggaagaaa ctcgcgccgt agaagaggga tgttgggacg  17160
cggaatgcga cgctacaggc gacggcgtgc tatccgcaag caattgcggg gtggtttttt  17220
accagcctta attccaatta tcgctgctgc aattggcgcg ataccaggca tagcttccgt  17280
ggcggttcag gcctcgcaac gacattgaca ttggaaaaaa acgtataaat aaaaaaaaaa  17340
aaatacaatg gactctgaca ctcctggtcc tgtgactatg ttttcttaga gatggaagac  17400
atcaattttt catccttggc tccgcgacac ggcacgaagc cgtacatggg cacctggagc  17460
gacatcggca cgagccaact gaacgggggc gccttcaatt ggagcagtat ctggagcggg  17520
cttaaaaatt ttggctcaac cataaaaaca tacgggaaca aagcttggaa cagcagtaca  17580
ggacaggcgc ttagaaataa acttaaagac cagaacttcc aacaaaaagt agtcgatggg  17640
atagcttccg gcatcaatgg agtggtagat ttggctaacc aggctgtgca gaaaaagata  17700
aacagtcgtt tggacccgcc gccagcaacc ccaggtgaaa tgcaagtgga ggaagaaatt  17760
```

-continued

```
cctccgccag aaaaacgagg cgacaagcgt ccgcgtcccg atttggaaga gacgctggtg  17820
acgcgcgtag atgaaccgcc ttcttatgag gaagcaacga agcttggaat gcccaccact  17880
agaccgatag ccccaatggc caccggggtg atgaaacctt ctcagttgca tcgacccgtc  17940
accttggatt tgccccctcc ccctgctgct actgctgtac ccgcttctaa gcctgtcgct  18000
gccccgaaac cagtcgccgt agccaggtca cgtcccgggg gcgctcctcg tccaaatgcg  18060
cactggcaaa atactctgaa cagcatcgtg ggtctaggcg tgcaaagtgt aaaacgccgt  18120
cgctgctttt aattaaatat ggagtagcgc ttaacttgcc tatctgtgta tatgtgtcat  18180
tacacgccgt cacagcagca gaggaaaaaa ggaagaggtc gtgcgtcgac gctgagttac  18240
tttcaagatg gccaccccat cgatgctgcc ccaatgggca tacatgcaca tcgccggaca  18300
ggatgcttcg gagtacctga gtccgggtct ggtgcagttc gcccgcgcca cagacaccta  18360
cttcaatctg ggaaataagt ttagaaatcc caccgtagcg ccgacccacg atgtgaccac  18420
cgaccgtagc cagcggctca tgttgcgctt cgtgcccgtt gaccgggagg acaatacata  18480
ctcttacaaa gtgcggtaca ccctggccgt gggcgacaac agagtgctgg atatggccag  18540
cacgttcttt gacattaggg gtgtgttgga cagaggtccc agtttcaaac cctattctgg  18600
tacggcttac aactccctgg ctcctaaagg cgctccaaat acatctcagt ggattgcaga  18660
aggtgtaaaa aatacaactg gtgaggaaca cgtaacagaa gaggaaacca atactactac  18720
ttacactttt ggcaatgctc ctgtaaaagc tgaagctgaa attacaaaag aaggactccc  18780
agtaggtttg gaagtttcag atgaagaaag taaaccgatt tatgctgata aaacatatca  18840
gccagaacct cagctgggag atgaaacttg gactgacctt gatggaaaaa ccgaaaagta  18900
tggaggcagg gctctcaaac ccgatactaa gatgaaacca tgctacgggt cctttgccaa  18960
acctactaat gtgaaaggcg gtcaggcaaa acaaaaaaca acggagcagc caaatcagaa  19020
agtcgaatat gatatcgaca tggagttttt tgatgcggca tcgcagaaaa caaacttaag  19080
tcctaaaatt gtcatgtatg cagaaaatgt aaatttggaa actccagaca ctcatgtagt  19140
gtacaaacct ggaacagaag acacaagttc cgaagctaat ttgggacaac aatctatgcc  19200
caacagaccc aactacattg gcttcagaga taactttatt ggacttatgt actataacag  19260
tactggtaac atgggggtgc tggctggtca agcgtctcag ttaaatgcag tggttgactt  19320
gcaggacaga aacacagaac tttcttacca actcttgctt gactctctgg gcgacagaac  19380
cagatacttt agcatgtgga atcaggctgt ggacagttat gatcctgatg tacgtgttat  19440
tgaaaatcat ggtgtggaag atgaacttcc caactactgt tttccactgg acggcatagg  19500
tgttccaaca accagttaca aatcaatagt tccaaatgga gacaatgcgc ctaattggaa  19560
ggaacctgaa gtaaatggaa caagtgagat cggacagggt aatttgtttg ccatggaaat  19620
taaccttcaa gccaatctat ggcgaagttt cctttattcc aatgtggctc tatatctccc  19680
agactcgtac aaatacaccc cgtccaatgt cactcttcca gaaaacaaaa acacctacga  19740
ctacatgaac gggcgggtgg tgccgccatc tctagtagac acctatgtga acattggtgc  19800
caggtggtct ctggatgcca tggacaatgt caacccattc aaccaccacc gtaacgctgg  19860
cttgcgttac cgatccatgc ttctgggtaa cggacgttat gtgcctttcc acatacaagt  19920
gcctcaaaaa ttcttcgctg ttaaaaacct gctgcttctc ccaggctcct acacttatga  19980
gtggaacttt aggaaggatg tgaacatggt tctacagagt tccctcggta acgacctgcg  20040
ggtagatggc gccagcatca gtttcacgag catcaacctc tatgctactt ttttccccat  20100
ggctcacaac accgcttcca cccttgaagc catgctgcgg aatgacacca atgatcagtc  20160
```

-continued

```
attcaacgac tacctatctg cagctaacat gctctacccc attcctgcca atgcaaccaa  20220
tattcccatt tccattcctt ctcgcaactg ggcggctttc agaggctggt catttaccag  20280
actgaaaacc aaagaaactc cctctttggg gtctggattt gacccctact ttgtctattc  20340
tggttctatt ccctacctgg atggtacctt ctacctgaac cacactttta agaaggtttc  20400
catcatgttt gactcttcag tgagctggcc tggaaatgac aggttactat ctcctaacga  20460
atttgaaata aagcgcactg tggatggcga aggctacaac gtagcccaat gcaacatgac  20520
caaagactgg ttcttggtac agatgctcgc caactacaac atcggctatc agggcttcta  20580
cattccagaa ggatacaaag atcgcatgta ttcatttttc agaaacttcc agcccatgag  20640
caggcaggtg gttgatgagg tcaattacaa agacttcaag gccgtcgcca taccctacca  20700
acacaacaac tctggctttg tgggttacat ggctccgacc atgcgccaag gtcaacccta  20760
tcccgctaac tatccctatc cactcattgg aacaactgcc gtaaatagtg ttacgcagaa  20820
aaagttcttg tgtgacagaa ccatgtggcg cataccgttc tcgagcaact tcatgtctat  20880
gggggccctt acagacttgg gacagaatat gctctatgcc aactcagctc atgctctgga  20940
catgaccttt gaggtggatc ccatggatga gcccaccctg ctttatcttc tcttcgaagt  21000
tttcgacgtg gtcagagtgc atcagccaca ccgcggcatc atcgaggcag tctacctgcg  21060
tacaccgttc tcggccggta acgctaccac gtaagaagct tcttgcttct tgcaaatagc  21120
agctgcaacc atggcctgcg gatcccaaaa cggctccagc gagcaagagc tcagagccat  21180
tgtccaagac ctgggttgcg gaccctattt tttgggaacc tacgataagc gcttcccggg  21240
gttcatggcc cccgataagc tcgcctgtgc cattgtaaat acggccggac gtgagacggg  21300
gggagagcac tggttggctt tcggttggaa cccacgttct aacacctgct accttttga   21360
tccttttgga ttctcggatg atcgtctcaa acagatttac cagtttgaat atgagggtct  21420
cctgcgccgc agcgctcttg ctaccaagga ccgctgtatt acgctggaaa aatctaccca  21480
gaccgtgcag ggtccccgtt ctgccgcctg cggacttttc tgctgcatgt tccttcacgc  21540
ctttgtgcac tggcctgacc gtcccatgga cggaaacccc accatgaaat tgctaactgg  21600
agtgccaaac aacatgcttc attctcctaa agtccagccc accctgtgtg acaatcaaaa  21660
agcactctac cattttctta atacccattc gccttatttt cgctcccatc gtacacacat  21720
cgaaagggcc actgcgttcg accgtatgga tgttcaataa tgactcatgt aaacaacgtg  21780
ttcaataaac atcactttat ttttttacat gtatcaaggc tctgcattac ttatttattt  21840
acaagtcgaa tgggttctga cgagaatcag aatgacccgc aggcagtgat acgttgcgga  21900
actgatactt gggttgccac ttgaattcgg gaatcaccaa cttgggaacc ggtatatcgg  21960
gcaggatgtc actccacagc tttctggtca gctgcaaagc tccaagcagg tcaggagccg  22020
aaatcttgaa atcacaatta ggaccagtgc tttgagcgcg agagttgcgg tacaccggat  22080
tgcagcactg aaacaccatc agcgacggat gtctcacgct tgccagcacg gtgggatctg  22140
caatcatgcc cacatccaga tcttcagcat tggcaatgct gaacggggtc atcttgcagg  22200
tctgcctacc catggcgggc acccaattag gcttgtggtt gcaatcgcag tgcaggggga  22260
tcagtatcat cttggcctga tcctgtctga ttcctggata cacggctctc atgaaagcat  22320
catattgctt gaaagcctgc tgggctttac taccctcggt ataaaacatc ccgcaggacc  22380
tgctcgaaaa ctggttagct gcacagccgg catcattcac acagcagcgg gcgtcattgt  22440
tagctatttg caccacactt ctgccccagc ggttttgggt gattttggtt cgctcgggat  22500
```

-continued

```
tctcctttaa ggctcgttgt ccgttctcgc tggccacatc catctcgata atctgctcct  22560
tctgaatcat aatattgcca tgcaggcact tcagcttgcc ctcataatca ttgcagccat  22620
gaggccacaa cgcacagcct gtacattccc aattatggtg ggcgatctga gaaaaagaat  22680
gtatcattcc ctgcagaaat cttcccatca tcgtgctcag tgtcttgtga ctagtgaaag  22740
ttaactggat gcctcggtgc tcctcgttta cgtactggtg acagatgcgc ttgtattgtt  22800
cgtgttgctc aggcattagt ttaaaagagg ttctaagttc gttatccagc ctgtacttct  22860
ccatcagcag acacatcact tccatgcctt tctcccaagc agacaccagg ggcaagctaa  22920
tcggattctt aacagtgcag gcagcagctc ctttagccag agggtcatct ttagcgatct  22980
tctcaatgct tcttttgcca tccttctcaa cgatgcgcac gggcgggtag ctgaaaccca  23040
ctgctacaag ttgcgcctct tctctttctt cttcgctgtc ttgactgatg tcttgcatgg  23100
ggatatgttt ggtcttcctt ggcttctttt tggggggtat cggaggagga ggactgtcgc  23160
tccgttccgg agacagggag gattgtgacg tttcgctcac cattaccaac tgactgtcgg  23220
tagaagaacc tgaccccaca cggcgacagg tgtttctctt cgggggcaga ggtggaggcg  23280
attgcgaagg gctgcggtcc gacctggaag gcggatgact ggcagaaccc cttccgcgtt  23340
cgggggtgtg ctccctgtgg cggtcgctta actgatttcc ttcgcggctg gccattgtgt  23400
tctcctaggc agagaaacaa cagacatgga aactcagcca ttgctgtcaa catcgccacg  23460
agtgccatca catctcgtcc tcagcgacga ggaaaaggag cagagcttaa gcattccacc  23520
gcccagtcct gccaccacct ctaccctaga agataaggag gtcgacgcat ctcatgacat  23580
gcagaataaa aaagcgaaag agtctgagac agacatcgag caagacccgg gctatgtgac  23640
accggtggaa cacgaggaag agttgaaacg ctttctagag agagaggatg aaaactgccc  23700
aaaacaacga gcagataact atcaccaaga tgctggaaat agggatcaga acaccgacta  23760
cctcataggg cttgacgggg aagacgcgct ccttaaacat ctagcaagac agtcgctcat  23820
agtcaaggat gcattattgg acagaactga agtgcccatc agtgtggaag agctcagccg  23880
cgcctacgag cttaacctct tttcacctcg tactcccccc aaacgtcagc caaacggcac  23940
ctgcgagcca aatcctcgct taaactttta tccagctttt gctgtgccag aagtactggc  24000
tacctatcac atcttttta aaaatcaaaa aattccagtc tcctgccgcg ctaatcgcac  24060
ccgcgccgat gccctactca atctgggacc tggttcacgc ttacctgata tagcttcctt  24120
ggaagaggtt ccaaagatct tcgagggtct gggcaataat gagactcggg ccgcaaatgc  24180
tctgcaaaag ggagaaaatg gcatggatga gcatcacagc gttctggtgg aattggaagg  24240
cgataatgcc agactcgcag tactcaagcg aagcatcgag gtcacacact tcgcatatcc  24300
cgctgtcaac ctgcccccta aagtcatgac ggcggtcatg gaccagttac tcattaagcg  24360
cgcaagtccc ctttcagaag acatgcatga cccagatgcc tgtgatgagg gtaaaccagt  24420
ggtcagtgat gagcagctaa cccgatggct gggcaccgac tctcccaggg atttggaaga  24480
gcgtcgcaag cttatgatgg ccgtggtgct ggttaccgta gaactagagt gtctccgacg  24540
tttctttacc gattcagaaa ccttgcgcaa actcgaagag aatctgcact acactttag  24600
acacggcttt gtgcggcagg catgcaagat atctaacgtg gaactcacca acctggtttc  24660
ctacatgggt attctgcatg agaatcgcct aggacaaagc gtgctgcaca gcaccctgaa  24720
gggggaagcc cgccgtgatt acatccgcga ttgtgtctat ctgtacctgt gccaaacgtg  24780
gcaaaccggc atgggtgtat ggcagcaatg tttagaagaa cagaacttga aagagcttga  24840
caagctctta cagaaatctc ttaaggttct gtggacaggg ttcgacgagc gcaccgtcgc  24900
```

ttccgacctg gcagacctca tcttcccaga gcgtctcagg gttactttgc gaaacggatt 24960
gcctgacttt atgagccaga gcatgcttaa caattttcgc tctttcatcc tggaacgctc 25020
cggtatcctg cccgccacct gctgcgcact gccctccgac tttgtgcctc tcacctaccg 25080
cgagtgcccc ccgccgctat ggagtcactg ctacctgttc cgtctggcca actatctctc 25140
ctaccactcg gatgtgatcg aggatgtgag cggagacggc ttgctggagt gtcactgccg 25200
ctgcaatctg tgcacgcccc accggtccct agcttgcaac ccccagttga tgagcgaaac 25260
ccagataata ggcacctttg aattgcaagg ccccagcagc caaggcgatg ggtcttctcc 25320
tgggcaaagt ttaaaactga ccccgggact gtggacctcc gcctacttgc gcaagtttgc 25380
tccggaagat taccacccct atgaaatcaa gttctatgag gaccaatcac agcctccaaa 25440
ggccgaactt tcggcctgcg tcatcaccca gggggcaatt ctggcccaat tgcaagccat 25500
ccaaaaatcc cgccaagaat ttctactgaa aaagggtaag gggtctacc ttgaccccca 25560
gaccggcgag gaactcaaca caaggttccc tcaggatgtc ccaacgacga gaaaacaaga 25620
agttgaaggt gcagccgccg cccccagaag atatggagga agattgggac agtcaggcag 25680
aggaggcgga ggaggacagt ctggaggaca gtctggagga agacagtttg gaggaggaaa 25740
acgaggaggc agaggaggtg gaagaagtaa ccgccgacaa acagttatcc tcggctgcgg 25800
agacaagcaa cagcgctacc atctccgctc cgagtcgagg aacccggcgg cgtcccagca 25860
gtagatggga cgagaccgga cgcttcccga acccaaccag cgcttccaag accggtaaga 25920
aggatcggca gggatacaag tcctggcggg ggcataagaa tgccatcatc tcctgcttgc 25980
atgagtgcgg gggcaacata tccttcacgc ggcgctactt gctattccac catggggtga 26040
actttccgcg caatgttttg cattactacc gtcacctcca cagcccctac tatagccagc 26100
aaatcccggc agtctcgaca gataaagaca gcggcggcga cctccaacag aaaaccagca 26160
gcggcagtta gaaaatacac aacaagtgca gcaacaggag gattaaagat tacagccaac 26220
gagccagcgc aaacccgaga gttaagaaat cggatctttc caaccctgta tgccatcttc 26280
cagcagagtc ggggtcaaga gcaggaactg aaaataaaaa accgatctct gcgttcgctc 26340
accagaagtt gtttgtatca caagagcgaa gatcaacttc agcgcactct cgaggacgcc 26400
gaggctctct tcaacaagta ctgcgcgctg actcttaaag agtaggcagc gaccgcgctt 26460
attcaaaaaa ggcgggaatt acatcatcct cgacatgagt aaagaaattc ccacgcctta 26520
catgtggagt tatcaacccc aaatgggatt ggcggcaggc gcctcccagg actactccac 26580
ccgcatgaat tggctcagcg ccgggccttc tatgatttct cgagttaatg atatacgcgc 26640
ctaccgaaac caaatacttt tggaacagtc agctcttacc accacgcccc gccaacacct 26700
taatcccaga aattggcccg ccgccctagt gtaccaggaa agtcccgctc ccaccactgt 26760
attacttcct cgagacgccc aggccgaagt ccaaatgact aatgcaggtg cgcagttagc 26820
tggcggctcc accctatgtc gtcacaggcc tcggcataat ataaaacgcc tgatgatcag 26880
aggccgaggt atccagctca acgacgagtc ggtgagctct ccgcttggtc tacgaccaga 26940
cggaatcttt cagattgccg gctgcgggag atcttccttc acccctcgtc aggctgttct 27000
gactttggaa agttcgtctt cgcaaccccg ctcgggcgga atcgggaccg ttcaatttgt 27060
ggaggagttt actccctctg tctacttcaa ccccttctcc ggatctcctg ggcattaccc 27120
ggacgagttc ataccgaact tcgacgcgat tagcgagtca gtggacggct acgattgatg 27180
tctggtgacg cggctgagct atctcggctg cgacatctag accactgccg ccgctttcgc 27240

```
tgctttgccc gggaactcat tgagttcatc tacttcgaac tccccaagga tcaccctcaa  27300
ggtccggccc acggagtgcg gatttctatc gaaggcaaaa tagactctcg cctgcaacga  27360
attttctccc agcggcccgt gctgatcgag cgagaccagg gaaacaccac ggtttccatc  27420
tactgcattt gtaatcaccc cggattgcat gaaagccttt gctgtcttat gtgtactgag  27480
tttaataaaa actgaattaa gactctccta cggactgccg cttcttcaac ccggatttta  27540
caaccagaag aacgaaactt ttcctgtcgt ccaggactct gttaacttca cctttcctac  27600
tcacaaacta gaagctcaac gactacaccg cttttccaga agcattttcc ctactaatac  27660
tactttcaaa accggaggtg agctccaagg tcttcctaca gaaaaccctt gggtggaagc  27720
gggccttgta gtgctaggaa ttcttgcggg tgggcttgtg attattcttt gctacctata  27780
cacaccttgc ttcactttct tagtggtgtt gtggtattgg tttaaaaaat ggggcccata  27840
ctagtcttgc ttgttttact ttcgcttttg gaaccgggtt ctgccaatta cgatccatgt  27900
ctagacttcg acccagaaaa ctgcacactt acttttgcac ccgacacaag ccgcatctgt  27960
ggagttctta ttaagtgcgg atgggaatgc aggtccgttg aaattacaca caataacaaa  28020
acctggaaca ataccttatc caccacatgg gagccaggag ttcccgagtg gtacactgtc  28080
tctgtccgag gtcctgacgg ttccatccgc attagtaaca acactttcat tttttctgaa  28140
atgtgcgatc tggccatgtt catgagcaaa cagtattctc tatggcctcc tagcaaggac  28200
aacatcgtaa cgttctccat tgcttattgc ttgtgcgctt gccttcttac tgctttactg  28260
tgcgtatgca tacacctgct tgtaaccact cgcatcaaaa acgccaataa caaagaaaaa  28320
atgccttaac ctctttctgt ttacctcttt ctgtttacag acatggcttc tcttacatct  28380
ctcatatttg tcagcattgt cactgccgct catggacaaa cagtcgtctc tatccctcta  28440
ggacataatt acactctcat aggaccccca atcacttcag aggtcatctg ggccaaactg  28500
ggaagcgttg attactttga tataatctgc aacaaaacaa aaccaataat agtaacttgc  28560
aacatacaaa atcttacatt gattaatgtt agcaaagttt acagcggtta ctattatggt  28620
tatgacagat acagtagtca atatagaaat tacttggttc gtgttaccca gttgaaaacc  28680
acgaaaatgc caaatatggc aaagattcga tccgatgaca attctctaga aacttttaca  28740
tctcccacca cacccgacga aaaaaacatc ccagattcaa tgattgcaat tgttgcagcg  28800
gtggcagtgg tgatggcact aataataata tgcatgcttt tatatgcttg tcgctacaaa  28860
aagtttcatc ctaaaaaaca agatctccta ctaaggctta acatttaatt tctttttata  28920
cagccatggt ttccactacc acattcctta tgcttactag tctcgcaact ctgacttctg  28980
ctcgctcaca cctcactgta actataggct caaactgcac actaaaagga cctcaaggtg  29040
gtcatgtctt ttggtggaga atatatgaca atggatggtt tacaaaacca tgtgaccaac  29100
ctggtagatt tttctgcaac ggcagagacc taaccattat caacgtgaca gcaaatgaca  29160
aaggcttcta ttatggaacc gactataaaa gtagtttaga ttataacatt attgtactgc  29220
catctaccac tccagcaccc cgcacaacta ctttctctag cagcagtgtc gctaacaata  29280
caatttccaa tccaaccttt gccgcgcttt taaaacgcac tgtgaataat tctacaactt  29340
cacatacaac aatttccact tcaacaatca gcattatcgc tgcagtgaca attggaatat  29400
ctattcttgt ttttaccata acctactacg cctgctgcta tagaaaagac aaacataaag  29460
gtgatccatt acttagattt gatatttaat ttgttctttt ttttttttatt tacagtatgg  29520
tgaacaccaa tcatggtacc tagaaatttc ttcttcacca tactcatttg tgcatttaat  29580
gtttgcgcta ctttcacagc agtagccaca gcaaccccag actgtatagg agcatttgct  29640
```

-continued

```
tcctatgcac tttttgcttt tgttacttgc atctgcgtat gtagcatagt ctgcctggtt  29700
attaattttt tccaacttat agactggatc cttgtgcgaa ttgcctacct gcgccaccat  29760
cccgaatacc gcaaccaaaa tatcgcggca cttcttagac tcatctaaaa ccatgcaggc  29820
tatactacca atatttttgc ttctattgct tccctacgct gtctcaaccc cagctgccta  29880
tagtactcca ccagaacacc ttagaaaatg caaattccaa caaccgtggt catttcttgc  29940
ttgctatcga gaaaaatcag aaattccccc aaatttaata atgattgctg gaataattaa  30000
tataatctgt tgcaccataa tttcattttt gatataccc ctatttgatt ttggctggaa  30060
tgctcccaat gcacatgatc atccacaaga cccagaggaa cacattcccc tacaaaacat  30120
gcaacatcca atagcgctaa tagattacga aagtgaacca caaccccccac tactccctgc  30180
tattagttac ttcaacctaa ccggcggaga tgactgaaac actcaccacc tccaattccg  30240
ccgaggatct gctcgatatg gacggccgcg tctcagaaca gcgactcgcc caactacgca  30300
tccgccagca gcaggaacgc gcggccaaag agctcagaga tgtcatccaa attcaccaat  30360
gcaaaaaagg catattctgt ttggtaaaac aagccaagat atcctacgag atcaccgcta  30420
ctgaccatcg cctctcttac gaacttggcc cccaacgaca aaaatttacc tgcatggtgg  30480
gaatcaaccc catagttatc acccagcaaa gtggagatac taagggttgc attcactgct  30540
cctgcgattc catcgagtgc acctacaccc tgctgaagac cctatgcggc ctaagagacc  30600
tgctaccaat gaattaaaaa atgattaata aaaaatcact tacttgaaat cagcaataag  30660
gtctctgttg aaattttctc ccagcagcac ctcacttccc tcttcccaac tctggtattc  30720
taaaccccgt tcagcggcat actttctcca tactttaaag gggatgtcaa attttagctc  30780
ctctcctgta cccacaatct tcatgtcttt cttcccagat gaccaagaga gtccggctca  30840
gtgactcctt caaccctgtc taccccctatg aagatgaaag cacctcccaa caccccttta  30900
taaacccagg gtttatttcc ccaaatggct tcacacaaag cccaaacgga gttcttactt  30960
taaaatgttt aaccccacta acaaccacag gcggatctct acagctaaaa gtgggagggg  31020
gacttacagt ggatgacacc aacggttttt tgaaagaaaa cataagtgcc accacaccac  31080
tcgttaagac tggtcactct ataggtttac cactaggagc cggattggga acgaatgaaa  31140
ataaactttg tatcaaatta ggacaaggac ttacattcaa ttcaaacaac atttgcattg  31200
atgacaatat taacacctta tggacaggag tcaaccccac cgaagccaac tgtcaaatca  31260
tgaactccag tgaatctaat gattgcaaat taattctaac actagttaaa actggagcac  31320
tagtcactgc atttgtttat gttataggag tatctaacaa ttttaatatg ctaactacac  31380
acagaaatat aaattttact gcagagctgt ttttcgattc tactggtaat ttactaacta  31440
gactctcatc cctcaaaact ccacttaatc ataaatcagg acaaaacatg gctactggtg  31500
ccattactaa tgctaaaggt ttcatgccca gcacgactgc ctatcctttc aatgataatt  31560
ctagagaaaa agaaaactac atttacggaa cttgttacta cacagctagt gatcgcactg  31620
cttttcccat tgacatatct gtcatgctta accgaagagc aataaatgac gagacatcat  31680
attgtattcg tataacttgg tcctggaaca caggagatgc cccagaggtg caaacctctg  31740
ctacaaccct agtcacctcc ccatttacct tttactacat cagagaagac gactgacaaa  31800
taaagtttaa cttgtttatt tgaaaatcaa ttcacaaaat ccgagtagtt attttgcctc  31860
ccccttccca tttaacagaa tacaccaatc tctccccacg cacagcttta aacatttgga  31920
taccattaga tatagacatg gttttagatt ccacattcca aacagtttca gagcgagcca  31980
```

-continued atctggggtc agtgatagat aaaaatccat cgggatagtc ttttaaagcg ctttcacagt 32040
ccaactgctg cggatggact ccggagtctg gatcacggtc atctggaaga agaacgatgg 32100
gaatcataat ccgaaaacgg tatcggacga ttgtgtctca tcaaacccac aagcagccgc 32160
tgtctgcgtc gctccgtgcg actgctgttt atgggatcag ggtccacagt gtcctgaagc 32220
atgattttaa tagcccttaa catcaacttt ctggtgcgat gcgcgcagca acgcattctg 32280
atttcactca aatctttgca gtaggtacaa cacattatta caatattgtt taataaacca 32340
taattaaaag cgctccagcc aaaactcata tctgatataa tcgcccctgc atgaccatca 32400
taccaaagtt taatataaat taaatgacgt tccctcaaaa acacactacc cacatacatg 32460
atctcttttg gcatgtgcat attaacaatc tgtctgtacc atggacaacg ttggttaatc 32520
atgcaaccca atataacctt ccggaaccac actgccaaca ccgctccccc agccatgcat 32580
tgaagtgaac cctgctgatt acaatgacaa tgaagaaccc aattctctcg accgtgaatc 32640
acttgagaat gaaaaatatc tatagtggca caacatagac ataaatgcat gcatcttctc 32700
ataattttta actcctcagg atttagaaac atatcccagg gaataggaag ctcttgcaga 32760
acagtaaagc tggcagaaca aggaagacca cgaacacaac ttacactatg catagtcata 32820
gtatcacaat ctggcaacag cgggtggtct tcagtcatag aagctcgggt ttcattttcc 32880
tcacaacgtg gtaactgggc tctggtgtaa gggtgatgtc tggcgcatga tgtcgagcgt 32940
gcgcgcaacc ttgtcataat ggagttgctt cctgacattc tcgtattttg tatagcaaaa 33000
cgcggccctg gcagaacaca ctcttcttcg ccttctatcc tgccgcttag cgtgttccgt 33060
gtgatagttc aagtacaacc acactcttaa gttggtcaaa agaatgctgg cttcagttgt 33120
aatcaaaact ccatcgcatc taatcgttct gaggaaatca tccacggtag catatgcaaa 33180
tcccaaccaa gcaatgcaac tggattgtgt ttcaagcagg agaggagagg gaagagacgg 33240
aagaaccatg ttaattttta ttccaaacga tctcgcagta cttcaaattg tagatcgcgc 33300
agatggcatc tctcgccccc actgtgttgg tgaaaaagca cagctagatc aaaagaaatg 33360
cgattttcaa ggtgctcaac ggtggcttcc agcaaagcct ccacgcgcac atccaagaac 33420
aaaagaatac caaaagaagg agcattttct aactcctcaa tcatcatatt acattcctgc 33480
accattccca gataattttc agctttccag ccttgaatta ttcgtgtcag ttcttgtggt 33540
aaatccaatc cacacattac aaacaggtcc cggagggcgc cctccaccac cattcttaaa 33600
cacaccctca taatgacaaa atatcttgct cctgtgtcac ctgtagcgaa ttgagaatgg 33660
caacatcaat tgacatgccc ttggctctaa gttcttcttt aagttctagt tgtaaaaact 33720
ctctcatatt atcaccaaac tgcttagcca gaagcccccc gggaacaaga gcaggggacg 33780
ctacagtgca gtacaagcgc agacctcccc aattggctcc agcaaaaaca agattggaat 33840
aagcatattg ggaaccgcca gtaatatcat cgaagttgct ggaaatataa tcaggcagag 33900
tttcttgtaa aaattgaata aaagaaaaat ttgccaaaaa aacattcaaa acctctggga 33960
tgcaaatgca ataggttacc gcgctgcgct ccaacattgt tagttttgaa ttagtctgca 34020
aaaataaaaa aaaaaacaag cgtcatatca tagtagcctg acgaacagat ggataaatca 34080
gtctttccat cacaagacaa gccacagggt ctccagctcg accctcgtaa aacctgtcat 34140
catgattaaa caacagcacc gaaagttcct cgcggtgacc agcatgaata attcttgatg 34200
aagcatacaa tccagacatg ttagcatcag ttaacgagaa aaaacagcca acatagcctt 34260
tgggtataat tatgcttaat cgtaagtata gcaaagccac ccctcgcgga tacaaagtaa 34320
aaggcacagg agaataaaaa atataattat ttctctgctg ctgttcaggc aacgtcgccc 34380

```
ccggtccctc taaatacaca tacaaagcct catcagccat ggcttaccag acaaagtaca  34440

gcgggcacac aaagcacaag ctctaaagtg actctccaac ctctccacaa tatatatata  34500

cacaagccct aaactgacgt aatgggagta aagtgtaaaa aatcccgcca aacccaacac  34560

acaccccgaa actgcgtcac cagggaaaag tacagtttca cttccgcaat cccaacaggc  34620

gtaacttcct ctttctcacg gtacgtgata tcccactaac ttgcaacgtc attttcccac  34680

ggtcgcaccg ccccttttag ccgttaaccc cacagccaat caccacacga tccacacttt  34740

ttaaaatcac ctcatttaca tattggcacc attccatcta taaggtatat tattgatgat  34800

g                                                                  34801
```

<210> SEQ ID NO 2
<211> LENGTH: 1545
<212> TYPE: DNA
<213> ORGANISM: Artificial Sequence
<220> FEATURE:
<223> OTHER INFORMATION: Fully synthetic

<400> SEQUENCE: 2

```
catcatcaat aatatacctt attttggatt gaagccaata tgataatgag ggggtggagt     60

ttgtgacgtg gcgcggggcg tgggaacggg gcgggtgacg tagtagtgtg gcggaagtgt    120

gatgttgcaa gtgtggcgga acacatgtaa gcgacggatg tggcaaaagt gacgtttttg    180

gtgtgcgccg gtgtacacag gaagtgacaa ttttcgcgcg gttttaggcg gatgttgtag    240

taaatttggg cgtaaccgag taagatttgg ccattttcgc gggaaaactg aataagagga    300

agtgaaatct gaataatttt gtgttactca tagcgcgtaa tatttgtcta gggccgcggg    360

gactttgacc gtttacgtgg agactcgccc aggtgttttt ctcaggtgtt ttccgcgttc    420

cgggtcaaag ttggcgtttt attattatag tcagctgacg tgtagtgtat ttatacccgg    480

tgagttcctc aagaggccac tcttgagtgc cagcgagtag agttttctcc tccgagccgc    540

tccgacaccg ggactgaaaa tgagacatat tatctgccac ggaggtgtta ttaccgaaga    600

aatggccgcc agtcttttgg accagctgat cgaagaggta ctggctgata atcttccacc    660

tcctagccat tttgaaccac ctacccttca cgaactgtat gatttagacg tgacggcccc    720

cgaagatccc aacgaggagg cggtttcgca gatttttccc gactctgtaa tgttggcggt    780

gcaggaaggg attgacttac tcacttttcc gccggcgccc ggttctccgg agccgcctca    840

cctttcccgg cagcccgagc agccggagca gagagccttg ggtccggttt ctatgccaaa    900

ccttgtaccg gaggtgatcg atcttacctg ccacgaggct ggctttccac ccagtgacga    960

cgaggatgaa gagggtgagg agtttgtgtt agattatgtg gagcaccccg ggcacggttg   1020

caggtcttgt cattatcacc ggaggaatac gggggaccca gatattatgt gttcgctttg   1080

ctatatgagg acctgtggca tgtttgtcta cagtaagtga aaattatggg cagtgggtga   1140

tagagtggtg ggtttggtgt ggtaattttt tttttaattt ttacagtttt gtggtttaaa   1200

gaattttgta ttgtgatttt tttaaaaggt cctgtgtctg aacctgagcc tgagcccgag   1260

ccagaaccgg agcctgcaag acctacccgc cgtcctaaaa tggcgcctgc tatcctgaga   1320

cgcccgacat cacctgtgtc tagagaatgc aatagtagta cggatagctg tgactccggt   1380

ccttctaaca cacctcctga gatacacccg gtggtcccgc tgtgccccat taaaccagtt   1440

gccgtgagag ttggtgggcg tcgccaggct gtggaatgta tcgaggactt gcttaacgag   1500

cctgggcaac ctttggactt gagctgtaaa cgccccaggc cataa                   1545
```

<210> SEQ ID NO 3
<211> LENGTH: 34793
<212> TYPE: DNA
<213> ORGANISM: Artificial Sequence
<220> FEATURE:
<223> OTHER INFORMATION: Fully synthetic

<400> SEQUENCE: 3
catcatcaat aatatacctt atagatggaa tggtgccaat atgtaaatga ggtgatttta 60
aaaagtgtgg atcgtgtggt gattggctgt ggggttaacg gctaaaaggg gcggtgcgac 120
cgtgggaaaa tgacgttttg tgggggtgga gtttttttgc aagttgtcgc gggaaatgtg 180
acgcataaaa aggctttttt ctcacggaac tacttagttt tcccacggta tttaacagga 240
aatgaggtag ttttgaccgg atgcaagtga aaattgttga ttttcgcgcg aaaactgaat 300
gaggaagtgt ttttctgaat aatgtggtat ttatggcagg gtggagtatt tgttcagggc 360
caggtagact ttgacccatt acgtggaggt ttcgattacc gtgtttttta cctgaatttc 420
cgcgtaccgt gtcaaagtct tctgttttta cgtaggtgtc agctgatcgc tagggtattt 480
atacctcagg gtttgtgtca agaggccact cttgagtgcc agcgagaaga gttttctcct 540
ctgcgccggc agtttaataa taaaaaaatg agagatttgc gatttctgcc tcaggaaata 600
atctctgctg agactggaaa tgaaatattg gagcttgtgg tgcacgccct gatgggagac 660
gatccggagc cacctgtgca gctttttgag cctcctacgc ttcaggaact gtatgattta 720
gaggtagagg gatcggagga ttctaatgag gaagctgtaa atggcttttt taccgattct 780
atgcttttag ctgctaatga agggttagaa ttagatccgc ctttggacac ttttgatact 840
ccaggggtaa ttgtggaaag cggtacaggt gtaagaaaat tacctgattt gagttccgtg 900
gactgtgatt tgcactgcta tgaagacggg tttcctccga gtgatgagga ggaccatgaa 960
aaggagcagt ccatgcagac tgcagcgggt gagggagtga aggctgccaa tgttggtttt 1020
cagttggatt gcccggagct tcctggacat ggctgtaagt cttgtgaatt tcacaggaaa 1080
aatactggag taaaggaact gttatgttcg ctttgttata tgagaacgca ctgccacttt 1140
atttacagta agtgtgttta agttaaaatt taaaggaata tgctgttttt cacatgtata 1200
ttgagtgtga gttttgtgct tcttattata ggtcctgtgt ctgatgctga tgaatcacca 1260
tctcctgatt ctactacctc acctcctgag attcaagcac ctgttcctgt ggacgtgcgc 1320
aagcccattc ctgtgaagct taagcctggg aaacgtccag cagtggaaaa acttgaggac 1380
ttgttacagg gtggggacgg acctttggac ttgagtacac ggaaacgtcc aagacaataa 1440
gtgttccata tccgtgttta cttaaggtga cgtcaatatt tgtgtgacag tgcaatgtaa 1500
taaaaatatg ttaactgttc actggttttt attgcttttt gggcggggac tcaggtatat 1560
aagtagaagc agacctgtgt ggttagctca taggagctgg ctttcatcca tggaggtttg 1620
ggccattttg gaagacctta ggaagactag gcaactgtta gagaacgctt cggacggagt 1680
ctccggtttt tggagattct ggttcgctag tgaattagct agggtagttt ttaggataaa 1740
acaggactat aaacaagaat ttgaaaagtt gttggtagat tgcccaggac tttttgaagc 1800
tcttaatttg ggccatcagg ttcactttaa agaaaaagtt ttatcagttt tagacttttc 1860
aaccccaggt agaactgctg ctgctgtggc ttttcttact tttatattag ataaatggat 1920
cccgcagact catttcagca ggggatacgt tttggatttc atagccacag cattgtggag 1980
aacatggaag gttcgcaaga tgaggacaat cttaggttac tggccagtgc agcctttggg 2040
tgtagcggga atcctgaggc atccaccggt catgccagcg gttctggagg aggaacagca 2100

-continued

```
agaggacaac ccgagagccg gcctggaccc tccagtggag gaggcggagt agctgacttg   2160
tctcctgaac tgcaacgggt gcttactgga tctacgtcca ctggacggga taggggcgtt   2220
aagagggaga gggcatctag tggtactgat gctagatctg agttggcttt aagtttaatg   2280
agtcgcagac gtcctgaaac catttggtgg catgaggttc agaaagaggg aagggatgaa   2340
gtttctgtat tgcaggagaa atattcactg gaacaggtga aaacatgttg gttggagcct   2400
gaggatgatt gggaggtggc cattaaaaat tatgccaaga tagctttgag gcctgataaa   2460
cagtataaga ttactagacg gattaatatc cggaatgctt gttacatatc tggaaatggg   2520
gctgaggtgg taatagatac tcaagacaag gcagttatta gatgctgcat gatggatatg   2580
tggcctgggg tagtcggtat ggaagcagta acttttgtaa atgttaagtt taggggagat   2640
ggttataatg gaatagtgtt tatggccaat accaaactta tattgcatgg ttgtagcttt   2700
tttggtttca acaatacctg tgtagatgcc tggggacagg ttagtgtacg gggatgtagt   2760
ttctatgcgt gttggattgc cacagctggc agaaccaaga gtcaattgtc tctgaagaaa   2820
tgcatatttc aaagatgtaa cctgggcatt ctgaatgaag gcgaagcaag ggtccgccac   2880
tgcgcttcta cagatactgg atgttttatt ttgattaagg gaaatgccag cgtaaagcat   2940
aacatgattt gcggtgcttc cgatgagagg ccttatcaaa tgctcacttg tgctggtggg   3000
cattgtaata tgctggctac tgtgcatatt gtttcccatc aacgcaaaaa atggcctgtt   3060
tttgatcaca atgtgatgac gaagtgtacc atgcatgcag gtgggcgtag aggaatgttt   3120
atgccttacc agtgtaacat gaatcatgtg aaagtgttgt tggaaccaga tgccttttcc   3180
agaatgagcc taacaggaat ttttgacatg aacatgcaaa tctggaagat cctgaggtat   3240
gatgatacga gatcgagggt acgcgcatgc gaatgcggag gcaagcatgc caggttccag   3300
ccggtgtgtg tagatgtgac tgaagatctc agaccggatc atttggttat tgcccgcact   3360
ggagcagagt tcggatccag tggagaagaa actgactaag gtgagtattg ggaaaacttt   3420
ggggtgggat tttcagatgg acagattgag taaaaatttg tttttctgt cttgcagctg   3480
tcatgagtgg aaacgcttct tttaaggggg gagtcttcag cccttatctg acagggcgtc   3540
tcccatcctg ggcaggagtt cgtcagaatg ttatgggatc tactgtggat ggaagacccg   3600
tccaacccgc caattcttca acgctgacct atgctacttt aagttcttca cctttggacg   3660
cagctgcagc tgccgccgcc gcttctgttg ccgctaacac tgtgcttgga atgggttact   3720
atggaagcat catggctaat tccacttcct ctaataaccc ttctaccctg actcaggaca   3780
agttacttgt ccttttggcc cagctggagg ctttgaccca acgtctgggt gaactttctc   3840
agcaggtggt cgagttgcga gtacaaactg agtctgctgt cggcacggca aagtctaaat   3900
aaaaaaatcc cagaatcaat gaataaataa acaagcttgt tgttgattta aaatcaagtg   3960
tttttatttc atttttcgcg cacggtatgc cctagaccac cgatctctat cattgagaac   4020
tcggtggatt ttttccagga tcctatagag gtgggattga atgtttagat acatgggcat   4080
taggccgtct ttggggtgga gatagctcca ttgaagggat tcatgctccg gggtagtgtt   4140
gtaaatcacc cagtcataac aaggtcgcag tgcatggtgt tgcacaatat cttttagaag   4200
taggctgatt gccacagata agcccttggt gtaggtgttt acaaaccggt tgagctggga   4260
tgggtgcatt cggggtgaaa ttatgtgcat tttggattgg atttttaagt tggcaatatt   4320
gccgccaaga tcccgtcttg ggttcatgtt atgaaggacc accaagacgg tgtatccggt   4380
acatttagga aatttatcgt gcagcttgga tggaaaagcg tggaaaaatt tggagacacc   4440
```

-continued

```
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccattttaa tgaatttggg gcggagagta ccagattggg gtatgaatgt   4620
tccttcgggc cccggagcat agttcccctc acagatttgc atttcccaag ctttcagttc   4680
cgagggtgga atcatgtcca cctggggggc tatgaaaaac accgtttctg ggcgggggt    4740
gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag gggccacct cgttcatcat ttcccttaca tgcatatttt cccgcaccaa    4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
tctgttccac agttcagtga tgtgttctat ggcatctcga tccagcagac ctcctcgttt   5100
cgcgggtttg gacggctcct ggaatagggt atgagacgat gggcgtccag cgctgccagg   5160
gttcggtcct tccagggtct cagtgttcga gtcagggttg tttccgtcac agtgaagggg   5220
tgtgcgcctg cttgggcgct tgccagggtg cgcttcagac tcatcctgct ggtcgaaaac   5280
ttctgtcgct tggcgccctg tatgtcggcc aagtagcagt ttaccatgag ttcgtagttg   5340
agcgcctcgg ctgcgtggcc tttggcgcgg agcttacctt tggaagtttt cttgcatacc   5400
gggcagtata ggcatttcag cgcatacaac ttgggcgcaa ggaaaacgga ttctggggag   5460
tatgcatctg cgccgcagga ggcgcaaaca gtttcacatt ccaccagcca ggttaaatcc   5520
ggttcattgg ggtcaaaaac aagttttccg ccatattttt tgatgcgttt cttacctttg   5580
gtctccatga gttcgtgtcc tcgttgagtg acaaacaggc tgtccgtgtc cccgtagact   5640
gattttacag gcctcttctc cagtggagtg cctcggtctt cttcgtacag gaactctgac   5700
cactctgata caaaggcgcg cgtccaggcc agcacaaagg aggctatgtg ggaggggtag   5760
cgatcgttgt caaccagggg gtccaccttt tccaaagtat gcaaacacat gtcaccctct   5820
tcaacatcca ggaatgtgat tggcttgtag gtgtatttca cgtgacctgg ggtccccgct   5880
gggggggtat aaaagggggc ggttctttgc tcttcctcac tgtcttccgg atcgctgtcc   5940
aggaacgtca gctgttgggg taggtattcc ctctcgaagg cgggcatgac ctctgcactc   6000
aggttgtcag tttctaagaa cgaggaggat ttgatattga cagtgccggt tgagatgcct   6060
ttcatgaggt tttcgtccat ttggtcagaa aacacaattt ttttattgtc aagtttggtg   6120
gcaaatgatc catacagggc gttggataaa agtttggcaa tggatcgcat ggtttggttc   6180
ttttccttgt ccgcgcgctc tttggcggcg atgttgagtt ggacatactc gcgtgccagg   6240
cacttccatt cggggaagat agttgttaat tcatctggca cgattctcac ttgccaccct   6300
cgattatgca aggtaattaa atccacactg gtggccacct cgcctcgaag ggggttcattg  6360
gtccaacaga gcctacctcc tttcctagaa cagaaagggg gaagtgggtc tagcataagt   6420
tcatcgggag ggtctgcatc catggtaaag attcccggaa gtaaatcctt atcaaaatag   6480
ctgatgggag tggggtcatc taaggccatt tgccattctc gagctgccag tgcgcgctca   6540
tatgggttaa ggggactgcc ccatggcatg ggatgggtga gtgcagaggc atacatgcca   6600
cagatgtcat agacgtagat gggatcctca aagatgccta tgtaggttgg atagcatcgc   6660
ccccctctga tacttgctcg cacatagtca tatagttcat gtgatggcgc tagcagcccc   6720
ggacccaagt tggtgcgatt gggtttttct gttctgtaga cgatctggcg aaagatggcg   6780
tgagaattgg aagagatggt gggtctttga aaaatgttga aatgggcatg aggtagacct   6840
```

-continued acagagtctc tgacaaagtg ggcataagat tcttgaagct tggttaccag ttcggcggtg 6900
acaagtacgt ctagggcgca gtagtcaagt gtttcttgaa tgatgtcata acctggttgg 6960
tttttctttt cccacagttc gcggttgaga aggtattctt cgcgatcctt ccagtactct 7020
tctagcggaa acccgtcttt gtctgcacgg taagatccta gcatgtagaa ctgattaact 7080
gccttgtaag ggcagcagcc cttctctacg ggtagagagt atgcttgagc agcttttcgt 7140
agcgaagcgt gagtaagggc aaaggtgtct ctgaccatga ctttgagaaa ttggtatttg 7200
aagtcgatgt cgtcacaggc tccctgttcc cagagttgga agtctacccg tttcttgtag 7260
gcggggttgg gcaaagcgaa agtaacatca ttgaagagaa tcttaccggc tctgggcata 7320
aaattgcgag tgatgcgaaa aggctgtggt acttccgctc gattgttgat cacctgggca 7380
gctaggacga tctcgtcgaa accgttgatg ttgtgtccta cgatgtataa ttctatgaaa 7440
cgcggcgtgc ctctgacgtg aggtagctta ctgagctcat caaaggttag gtctgtgggg 7500
tcagataagg cgtagtgttc gagagcccat tcgtgcaggt gaggatttgc atgtaggaat 7560
gatgaccaaa gatctaccgc cagtgctgtt tgtaactggt cccgatactg acgaaaatgc 7620
cggccaattg ccatttttttc tggagtgaca cagtagaagg ttctggggtc ttgttgccat 7680
cgatcccact tgagtttaat ggctagatcg tgggccatgt tgacgagacg ctcttctcct 7740
gagagtttca tgaccagcat gaaaggaact agttgtttgc caaaggatcc catccaggtg 7800
taagtttcca catcgtaggt caggaagagt ctttctgtgc gaggatgaga gccgatcggg 7860
aagaactgga tttcctgcca ccagttggag gattggctgt tgatgtgatg gaagtagaag 7920
tttctgcggc gcgccgagca ttcgtgtttg tgcttgtaca gacggccgca gtagtcgcag 7980
cgttgcacgg gttgtatctc gtgaatgagt tgtacctggc ttcccttgac gagaaatttc 8040
agtgggaagc cgaggcctgg cgattgtatc tcgtgctctt ctatattcgc tgtatcggcc 8100
tgttcatctt ctgtttcgat ggtggtcatg ctgacgagcc cccgcgggag gcaagtccag 8160
acctcggcgc gggaggggcg gagctgaagg acgagagcgc gcaggctgga gctgtccaga 8220
gtcctgagac gctgcggact caggttagta ggtagggaca gaagattaac ttgcatgatc 8280
ttttccaggg cgtgcgggag gttcagatgg tacttgattt ccacaggttc gtttgtagag 8340
acgtcaatgg cttgcagggt tccgtgtcct ttgggcgcca ctaccgtacc tttgtttttt 8400
cttttgatcg gtggtggctc tcttgcttct tgcatgctca gaagcggtga cggggacgcg 8460
cgccgggcgg cagcggttgt tccggacccg agggcatggc tggtagtggc acgtcggcgc 8520
cgcgcacggg caggttctgg tactgcgctc tgagaagact tgcgtgcgcc accacgcgtc 8580
gattgacgtc ttgtatctga cgtctctggg tgaaagctac cggccccgtg agcttgaacc 8640
tgaaagagag ttcaacagaa tcaatttcgg tatcgttaac ggcagcttgt ctcagtattt 8700
cttgtacgtc accagagttg tcctggtagg cgatctccgc catgaactgc tcgatttctt 8760
cctcctgaag atctccgcga cccgctcttt cgacggtggc cgcgaggtca ttggagatac 8820
ggcccatgag ttgggagaat gcattcatgc ccgcctcgtt ccagacgcgg ctgtaaacca 8880
cggccccctc ggagtctctt gcgcgcatca ccacctgagc gaggttaagc tccacgtgtc 8940
tggtgaagac cgcatagttg cataggcgct gaaaaaggta gttgagtgtg gtggcaatgt 9000
gttcggcgac gaagaaatac atgatccatc gtctcagcgg catttcgcta acatcgccca 9060
gagcttccaa gcgctccatg gcctcgtaga agtccacggc aaaattaaaa aactgggagt 9120
ttcgcgcgga cacggtcaat tcctcctcga gaagacggat gagttcggct atggtggccc 9180

-continued

```
gtacttcgcg ttcgaaggct cccgggatct cttcttcctc ttctatctct tcttccacta   9240
acatctcttc ttcgtcttca ggcgggggcg gagggggcac gcggcgacgt cgacggcgca   9300
cgggcaaacg gtcgatgaat cgttcaatga cctctccgcg gcggcggcgc atggtttcag   9360
tgacggcgcg gccgttctcg cgcggtcgca gagtaaaaac accgccgcgc atctccttaa   9420
agtggtgact gggaggttct ccgtttggga gggagagggc gctgattata cattttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
ctcaaggtct tgaccctgag cgatgatctt ggggtgtatc gcaatgacag aatgcatcgc  11580
```

-continued

```
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
```

-continued

```
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tttcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
aagcgctact tttaagcgtt cctatgatga ggtgtacggg gatgatgata ttcttgagca  16320
```

```
ggcggctgac cgattaggcg agtttgctta tggcaagcgt agtagaataa cttccaagga  16380
tgagacagtg tcgataccct tggatcatgg aaatcccacc cctagtctta aaccggtcac  16440
tttgcagcaa gtgttacccg taactccgcg aacaggtgtt aaacgcgaag gtgaagattt  16500
gtatcccact atgcaactga tggtacccaa acgccagaag ttggaggacg ttttggagaa  16560
agtaaaagtg gatccagata ttcaacctga ggttaaagtg agacccatta agcaggtagc  16620
gcctggtctg gggtacaaa ctgtagacat taagattccc actgaaagta tggaagtgca  16680
aactgaaccc gcaaagccta ctgccacctc cactgaagtg caaacggatc catggatgcc  16740
catgcctatt acaactgacg ccgccggtcc cactcgaaga tcccgacgaa agtacggtcc  16800
agcaagtctg ttgatgccca attatgttgt acacccatct attattccta ctcctggtta  16860
ccgaggcact cgctactatc gcagccgaaa cagtacctcc cgccgtcgcc gcaagacacc  16920
tgcaaatcgc agtcgtcgcc gtagacgcac aagcaaaccg actcccggcg ccctggtgcg  16980
gcaagtgtac cgcaatggta gtgcggaacc tttgacactg ccgcgtgcgc gttaccatcc  17040
gagtatcatc acttaatcaa tgttgccgct gcctccttgc agatatggcc ctcacttgtc  17100
gccttcgcgt tcccatcact ggttaccgag gaagaaactc gcgccgtaga agagggatgt  17160
tgggacgcgg aatgcgacgc tacaggcgac ggcgtgctat ccgcaagcaa ttgcggggtg  17220
gtttttacc agccttaatt ccaattatcg ctgctgcaat tggcgcgata ccaggcatag  17280
cttccgtggc ggttcaggcc tcgcaacgac attgacattg gaaaaaaacg tataaataaa  17340
aaaaaaaaaa tacaatggac tctgacactc ctggtcctgt gactatgttt tcttagagat  17400
ggaagacatc aatttttcat ccttggctcc gcgacacggc acgaagccgt acatgggcac  17460
ctggagcgac atcggcacga gccaactgaa cgggggcgcc ttcaattgga gcagtatctg  17520
gagcgggctt aaaaatttg gctcaaccat aaaaacatac gggaacaaag cttggaacag  17580
cagtacagga caggcgctta gaaataaact taaagaccag aacttccaac aaaaagtagt  17640
cgatgggata gcttccggca tcaatggagt ggtagatttg gctaaccagg ctgtgcagaa  17700
aaagataaac agtcgtttgg acccgccgcc agcaacccca ggtgaaatgc aagtggagga  17760
agaaattcct ccgccagaaa aacgaggcga caagcgtccg cgtcccgatt tggaagagac  17820
gctggtgacg cgcgtagatg aaccgccttc ttatgaggaa gcaacgaagc ttggaatgcc  17880
caccactaga ccgatagccc caatggccac cggggtgatg aaaccttctc agttgcatcg  17940
acccgtcacc ttggatttgc cccctccccc tgctgctact gctgtacccg cttctaagcc  18000
tgtcgctgcc ccgaaaccag tcgccgtagc caggtcacgt cccgggggcg ctcctcgtcc  18060
aaatgcgcac tggcaaaata ctctgaacag catcgtgggt ctaggcgtgc aaagtgtaaa  18120
acgccgtcgc tgcttttaat taaatatgga gtagcgctta acttgcctat ctgtgtatat  18180
gtgtcattac acgccgtcac agcagcagag gaaaaaagga agaggtcgtg cgtcgacgct  18240
gagttacttt caagatggcc accccatcga tgctgcccca atgggcatac atgcacatcg  18300
ccggacagga tgcttcggag tacctgagtc cgggtctggt gcagttcgcc cgcgccacag  18360
acacctactt caatctggga aataagttta gaaatcccac cgtagcgccg acccacgatg  18420
tgaccaccga ccgtagccag cggctcatgt tgcgcttcgt gcccgttgac cgggaggaca  18480
atacatactc ttacaaagtg cggtacaccc tggccgtggg cgacaacaga gtgctggata  18540
tggccagcac gttctttgac attaggggtg tgttggacag aggtcccagt ttcaaaccct  18600
attctggtac ggcttacaac tccctggctc ctaaaggcgc tccaaataca tctcagtgga  18660
```

-continued

```
ttgcagaagg tgtaaaaaat acaactggtg aggaacacgt aacagaagag gaaaccaata  18720
ctactactta cacttttggc aatgctcctg taaaagctga agctgaaatt acaaaagaag  18780
gactcccagt aggtttggaa gtttcagatg aagaaagtaa accgatttat gctgataaaa  18840
catatcagcc agaacctcag ctgggagatg aaacttggac tgaccttgat ggaaaaaccg  18900
aaaagtatgg aggcagggct ctcaaacccg atactaagat gaaaccatgc tacgggtcct  18960
ttgccaaacc tactaatgtg aaaggcggtc aggcaaaaca aaaaacaacg gagcagccaa  19020
atcagaaagt cgaatatgat atcgacatgg agtttttga tgcggcatcg cagaaaacaa  19080
acttaagtcc taaaattgtc atgtatgcag aaaatgtaaa tttggaaact ccagacactc  19140
atgtagtgta caaacctgga acagaagaca caagttccga agctaatttg ggacaacaat  19200
ctatgcccaa cagacccaac tacattggct tcagagataa ctttattgga cttatgtact  19260
ataacagtac tggtaacatg gggggtgctgg ctggtcaagc gtctcagtta aatgcagtgg  19320
ttgacttgca ggacagaaac acagaacttt cttaccaact cttgcttgac tctctgggcg  19380
acagaaccag atactttagc atgtggaatc aggctgtgga cagttatgat cctgatgtac  19440
gtgttattga aaatcatggt gtggaagatg aacttcccaa ctactgtttt ccactggacg  19500
gcataggtgt tccaacaacc agttacaaat caatagttcc aaatggagac aatgcgccta  19560
attggaagga acctgaagta aatggaacaa gtgagatcgg acagggtaat ttgtttgcca  19620
tggaaattaa ccttcaagcc aatctatggc gaagtttcct ttattccaat gtggctctat  19680
atctcccaga ctcgtacaaa tacaccccgt ccaatgtcac tcttccagaa aacaaaaaca  19740
cctacgacta catgaacggg cgggtggtgc cgccatctct agtagacacc tatgtgaaca  19800
ttggtgccag gtggtctctg gatgccatgg acaatgtcaa cccattcaac caccaccgta  19860
acgctggctt gcgttaccga tccatgcttc tgggtaacgg acgttatgtg cctttccaca  19920
tacaagtgcc tcaaaaattc ttcgctgtta aaaacctgct gcttctccca ggctcctaca  19980
cttatgagtg gaactttagg aaggatgtga acatggttct acagagttcc ctcggtaacg  20040
acctgcgggt agatggcgcc agcatcagtt tcacgagcat caacctctat gctacttttt  20100
tccccatggc tcacaacacc gcttccaccc ttgaagccat gctgcggaat gacaccaatg  20160
atcagtcatt caacgactac ctatctgcag ctaacatgct ctaccccatt cctgccaatg  20220
caaccaatat tcccatttcc attccttctc gcaactgggc ggctttcaga ggctggtcat  20280
ttaccagact gaaaaccaaa gaaactccct ctttggggtc tggatttgac ccctactttg  20340
tctattctgg ttctattccc tacctggatg gtaccttcta cctgaaccac acttttaaga  20400
aggtttccat catgtttgac tcttcagtga gctggcctgg aaatgacagg ttactatctc  20460
ctaacgaatt tgaaataaag cgcactgtgg atggcgaagg ctacaacgta gcccaatgca  20520
acatgaccaa agactggttc ttggtacaga tgctcgccaa ctacaacatc ggctatcagg  20580
gcttctacat tccagaagga tacaaagatc gcatgtattc atttttcaga aacttccagc  20640
ccatgagcag gcaggtggtt gatgaggtca attacaaaga cttcaaggcc gtcgccatac  20700
cctaccaaca caacaactct ggctttgtgg gttacatggc tccgaccatg cgccaaggtc  20760
aaccctatcc cgctaactat ccctatccac tcattggaac aactgccgta aatagtgtta  20820
cgcagaaaaa gttcttgtgt gacagaacca tgtggcgcat accgttctcg agcaacttca  20880
tgtctatggg ggcccttaca gacttgggac agaatatgct ctatgccaac tcagctcatg  20940
ctctggacat gacctttgag gtggatccca tggatgagcc caccctgctt tatcttctct  21000
tcgaagtttt cgacgtggtc agagtgcatc agccacaccg cggcatcatc gaggcagtct  21060
```

acctgcgtac accgttctcg gccggtaacg ctaccacgta agaagcttct tgcttcttgc 21120
aaatagcagc tgcaaccatg gcctgcggat cccaaaacgg ctccagcgag caagagctca 21180
gagccattgt ccaagacctg ggttgcggac cctatttttt gggaacctac gataagcgct 21240
tcccggggtt catggccccc gataagctcg cctgtgccat tgtaaatacg gccggacgtg 21300
agacgggggg agagcactgg ttggctttcg gttggaaccc acgttctaac acctgctacc 21360
tttttgatcc ttttggattc tcggatgatc gtctcaaaca gatttaccag tttgaatatg 21420
agggtctcct gcgccgcagc gctcttgcta ccaaggaccg ctgtattacg ctggaaaaat 21480
ctacccagac cgtgcagggt ccccgttctg ccgcctgcgg acttttctgc tgcatgttcc 21540
ttcacgcctt tgtgcactgg cctgaccgtc ccatggacgg aaaccccacc atgaaattgc 21600
taactggagt gccaaacaac atgcttcatt ctcctaaagt ccagcccacc ctgtgtgaca 21660
atcaaaaagc actctaccat tttcttaata cccattcgcc ttattttcgc tcccatcgta 21720
cacacatcga aagggccact gcgttcgacc gtatggatgt tcaataatga ctcatgtaaa 21780
caacgtgttc aataaacatc actttatttt tttacatgta tcaaggctct gcattactta 21840
tttatttaca agtcgaatgg gttctgacga gaatcagaat gacccgcagg cagtgatacg 21900
ttgcggaact gatacttggg ttgccacttg aattcgggaa tcaccaactt gggaaccggt 21960
atatcgggca ggatgtcact ccacagcttt ctggtcagct gcaaagctcc aagcaggtca 22020
ggagccgaaa tcttgaaatc acaattagga ccagtgcttt gagcgcgaga gttgcggtac 22080
accggattgc agcactgaaa caccatcagc gacggatgtc tcacgcttgc cagcacggtg 22140
ggatctgcaa tcatgcccac atccagatct tcagcattgg caatgctgaa cggggtcatc 22200
ttgcaggtct gcctacccat ggcgggcacc caattaggct tgtggttgca atcgcagtgc 22260
agggggatca gtatcatctt ggcctgatcc tgtctgattc ctggatacac ggctctcatg 22320
aaagcatcat attgcttgaa agcctgctgg gctttactac cctcggtata aaacatcccg 22380
caggacctgc tcgaaaactg gttagctgca cagccggcat cattcacaca gcagcgggcg 22440
tcattgttag ctatttgcac cacacttctg ccccagcggt tttgggtgat tttggttcgc 22500
tcgggattct cctttaaggc tcgttgtccg ttctcgctgg ccacatccat ctcgataatc 22560
tgctccttct gaatcataat attgccatgc aggcacttca gcttgccctc ataatcattg 22620
cagccatgag gccacaacgc acagcctgta cattcccaat tatggtgggc gatctgagaa 22680
aaagaatgta tcattccctg cagaaatctt cccatcatcg tgctcagtgt cttgtgacta 22740
gtgaaagtta actggatgcc tcggtgctcc tcgtttacgt actggtgaca gatgcgcttg 22800
tattgttcgt gttgctcagg cattagttta aaagaggttc taagttcgtt atccagcctg 22860
tacttctcca tcagcagaca catcacttcc atgcctttct cccaagcaga caccaggggc 22920
aagctaatcg gattcttaac agtgcaggca gcagctcctt tagccagagg gtcatcttta 22980
gcgatcttct caatgcttct tttgccatcc ttctcaacga tgcgcacggg cgggtagctg 23040
aaacccactg ctacaagttg cgcctcttct ctttcttctt cgctgtcttg actgatgtct 23100
tgcatgggga tatgtttggt cttccttggc ttctttttgg ggggtatcgg aggaggagga 23160
ctgtcgctcc gttccggaga cagggaggat tgtgacgttt cgctcaccat taccaactga 23220
ctgtcggtag aagaacctga ccccacacgg cgacaggtgt ttctcttcgg gggcagaggt 23280
ggaggcgatt gcgaagggct gcggtccgac ctggaaggcg gatgactggc agaacccctt 23340
ccgcgttcgg gggtgtgctc cctgtggcgg tcgcttaact gatttccttc gcggctggcc 23400

-continued

```
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
aaacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac caccccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
gaggaaaacg aggaggcaga ggaggtggaa gaagtaaccg ccgacaaaca gttatcctcg  25800
```

gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
gttagctggc ggctccaccc tatgtcgtca caggcctcgg cataatataa aacgcctgat 26880
gatcagaggc cgaggtatcc agctcaacga cgagtcggtg agctctccgc ttggtctacg 26940
accagacgga atctttcaga ttgccggctg cgggagatct tccttcaccc ctcgtcaggc 27000
tgttctgact ttggaaagtt cgtcttcgca accccgctcg ggcggaatcg ggaccgttca 27060
atttgtggag gagtttactc cctctgtcta cttcaacccc ttctccggat ctcctgggca 27120
ttacccggac gagttcatac cgaacttcga cgcgattagc gagtcagtgg acggctacga 27180
ttgatgtctg gtgacgcggc tgagctatct cggctgcgac atctagacca ctgccgccgc 27240
tttcgctgct ttgcccggga actcattgag ttcatctact tcgaactccc caaggatcac 27300
cctcaaggtc cggcccacgg agtgcggatt tctatcgaag gcaaaataga ctctcgcctg 27360
caacgaattt tctcccagcg gcccgtgctg atcgagcgag accagggaaa caccacggtt 27420
tccatctact gcatttgtaa tcaccccgga ttgcatgaaa gcctttgctg tcttatgtgt 27480
actgagttta ataaaaactg aattaagact ctcctacgga ctgccgcttc ttcaacccgg 27540
attttacaac cagaagaacg aaacttttcc tgtcgtccag gactctgtta acttcacctt 27600
tcctactcac aaactagaag ctcaacgact acaccgcttt tccagaagca ttttccctac 27660
taatactact ttcaaaaccg gaggtgagct ccaaggtctt cctacagaaa acccttgggt 27720
ggaagcgggc cttgtagtgc taggaattct tgcgggtggg cttgtgatta ttctttgcta 27780
cctatacaca ccttgcttca ctttcttagt ggtgttgtgg tattggttta aaaaatgggg 27840
cccatactag tcttgcttgt tttactttcg cttttggaac cgggttctgc caattacgat 27900
ccatgtctag acttcgaccc agaaaactgc acacttactt ttgcacccga cacaagccgc 27960
atctgtggag ttcttattaa gtgcggatgg gaatgcaggt ccgttgaaat tacacacaat 28020
aacaaaacct ggaacaatac cttatccacc acatgggagc caggagttcc cgagtggtac 28080
actgtctctg tccgaggtcc tgacggttcc atccgcatta gtaacaacac tttcattttt 28140

```
tctgaaatgt gcgatctggc catgttcatg agcaaacagt attctctatg gcctcctagc  28200
aaggacaaca tcgtaacgtt ctccattgct tattgcttgt gcgcttgcct tcttactgct  28260
ttactgtgcg tatgcataca cctgcttgta accactcgca tcaaaaacgc caataacaaa  28320
gaaaaaatgc cttaacctct ttctgtttac agacatggct tctcttacat ctctcatatt  28380
tgtcagcatt gtcactgccg ctcatggaca aacagtcgtc tctatccctc taggacataa  28440
ttacactctc ataggacccc caatcacttc agaggtcatc tgggccaaac tgggaagcgt  28500
tgattacttt gatataatct gcaacaaaac aaaaccaata atagtaactt gcaacataca  28560
aaatcttaca ttgattaatg ttagcaaagt ttacagcggt tactattatg gttatgacag  28620
atacagtagt caatatagaa attacttggt tcgtgttacc cagttgaaaa ccacgaaaat  28680
gccaaatatg gcaaagattc gatccgatga caattctcta gaaactttta catctcccac  28740
cacacccgac gaaaaaaaca tcccagattc aatgattgca attgttgcag cggtggcagt  28800
ggtgatggca ctaataataa tatgcatgct tttatatgct tgtcgctaca aaaagtttca  28860
tcctaaaaaa caagatctcc tactaaggct taacatttaa tttcttttta tacagccatg  28920
gtttccacta ccacattcct tatgcttact agtctcgcaa ctctgacttc tgctcgctca  28980
cacctcactg taactatagg ctcaaactgc acactaaaag gacctcaagg tggtcatgtc  29040
ttttggtgga gaatatatga caatggatgg tttacaaaac catgtgacca acctggtaga  29100
tttttctgca acggcagaga cctaaccatt atcaacgtga cagcaaatga caaaggcttc  29160
tattatggaa ccgactataa aagtagttta gattataaca ttattgtact gccatctacc  29220
actccagcac cccgcacaac tactttctct agcagcagtg tcgctaacaa tacaatttcc  29280
aatccaacct ttgccgcgct tttaaaacgc actgtgaata attctacaac ttcacataca  29340
acaatttcca cttcaacaat cagcattatc gctgcagtga caattggaat atctattctt  29400
gtttttacca taacctacta cgcctgctgc tatagaaaag acaaacataa aggtgatcca  29460
ttacttagat ttgatattta atttgttctt tttttttta tttacagtat ggtgaacacc  29520
aatcatggta cctagaaatt tcttcttcac catactcatt tgtgcattta atgtttgcgc  29580
tactttcaca gcagtagcca cagcaacccc agactgtata ggagcatttg cttcctatgc  29640
actttttgct tttgttactt gcatctgcgt atgtagcata gtctgcctgg ttattaattt  29700
tttccaactt atagactgga tccttgtgcg aattgcctac ctgcgccacc atcccgaata  29760
ccgcaaccaa aatatcgcgg cacttcttag actcatctaa aaccatgcag gctatactac  29820
caatattttt gcttctattg cttccctacg ctgtctcaac cccagctgcc tatagtactc  29880
caccagaaca ccttagaaaa tgcaaattcc aacaaccgtg gtcatttctt gcttgctatc  29940
gagaaaaatc agaaattccc ccaaatttaa taatgattgc tggaataatt aatataatct  30000
gttgcaccat aatttcattt ttgatatacc ccctatttga ttttggctgg aatgctccca  30060
atgcacatga tcatccacaa gacccagagg aacacattcc cctacaaaac atgcaacatc  30120
caatagcgct aatagattac gaaagtgaac cacaaccccc actactccct gctattagtt  30180
acttcaacct aaccggcgga gatgactgaa acactcacca cctccaattc cgccgaggat  30240
ctgctcgata tggacggccg cgtctcagaa cagcgactcg cccaactacg catccgccag  30300
cagcaggaac gcgcggccaa agagctcaga gatgtcatcc aaattcacca atgcaaaaaa  30360
ggcatattct gtttggtaaa acaagccaag atatcctacg agatcaccgc tactgaccat  30420
cgcctctctt acgaacttgg cccccaacga caaaaattta cctgcatggt gggaatcaac  30480
cccatagtta tcacccagca aagtggagat actaagggtt gcattcactg ctcctgcgat  30540
```

```
tccatcgagt gcacctacac cctgctgaag accctatgcg gcctaagaga cctgctacca  30600
atgaattaaa aaatgattaa taaaaaatca cttacttgaa atcagcaata aggtctctgt  30660
tgaaattttc tcccagcagc acctcacttc cctcttccca actctggtat tctaaacccc  30720
gttcagcggc atactttctc catactttaa aggggatgtc aaattttagc tcctctcctg  30780
tacccacaat cttcatgtct ttcttcccag atgaccaaga gagtccggct cagtgactcc  30840
ttcaaccctg tctaccccta tgaagatgaa agcacctccc aacacccctt tataaaccca  30900
gggtttattt ccccaaatgg cttcacacaa agcccaaacg gagttcttac tttaaaatgt  30960
ttaaccccac taacaaccac aggcggatct ctacagctaa aagtgggagg gggacttaca  31020
gtggatgaca ccaacggttt tttgaaagaa aacataagtg ccaccacacc actcgttaag  31080
actggtcact ctataggttt accactagga gccggattgg gaacgaatga aaataaactt  31140
tgtatcaaat taggacaagg acttacattc aattcaaaca acatttgcat tgatgacaat  31200
attaacacct tatggacagg agtcaacccc accgaagcca actgtcaaat catgaactcc  31260
agtgaatcta atgattgcaa attaattcta acactagtta aaactggagc actagtcact  31320
gcatttgttt atgttatagg agtatctaac aattttaata tgctaactac acacagaaat  31380
ataaatttta ctgcagagct gtttttcgat tctactggta atttactaac tagactctca  31440
tccctcaaaa ctccacttaa tcataaatca ggacaaaaca tggctactgg tgccattact  31500
aatgctaaag gtttcatgcc cagcacgact gcctatcctt tcaatgataa ttctagagaa  31560
aaagaaaact acatttacgg aacttgttac tacacagcta gtgatcgcac tgcttttccc  31620
attgacatat ctgtcatgct taaccgaaga gcaataaatg acgagacatc atattgtatt  31680
cgtataactt ggtcctggaa cacaggagat gccccagagg tgcaaacctc tgctacaacc  31740
ctagtcacct ccccatttac cttttactac atcagagaag acgactgaca aataaagttt  31800
aacttgttta tttgaaaatc aattcacaaa atccgagtag ttattttgcc tcccccttcc  31860
catttaacag aatacaccaa tctctcccca cgcacagctt taaacatttg gataccatta  31920
gatatagaca tggttttaga ttccacattc caaacagttt cagagcgagc caatctgggg  31980
tcagtgatag ataaaaatcc atcgggatag tcttttaaag cgctttcaca gtccaactgc  32040
tgcggatgga ctccggagtc tggatcacgg tcatctggaa gaagaacgat gggaatcata  32100
atccgaaaac ggtatcggac gattgtgtct catcaaaccc acaagcagcc gctgtctgcg  32160
tcgctccgtg cgactgctgt ttatgggatc agggtccaca gtgtcctgaa gcatgatttt  32220
aatagccctt aacatcaact ttctggtgcg atgcgcgcag caacgcattc tgatttcact  32280
caaatctttg cagtaggtac aacacattat tacaatattg tttaataaac cataattaaa  32340
agcgctccag ccaaaactca tatctgatat aatcgcccct gcatgaccat cataccaaag  32400
tttaatataa attaaatgac gttccctcaa aaacacacta cccacataca tgatctcttt  32460
tggcatgtgc atattaacaa tctgtctgta ccatggacaa cgttggttaa tcatgcaacc  32520
caatataacc ttccggaacc acactgccaa caccgctccc ccagccatgc attgaagtga  32580
accctgctga ttacaatgac aatgaagaac ccaattctct cgaccgtgaa tcacttgaga  32640
atgaaaaata tctatagtgg cacaacatag acataaatgc atgcatcttc tcataatttt  32700
taactcctca ggatttagaa acatatccca gggaatagga agctcttgca gaacagtaaa  32760
gctggcagaa caaggaagac cacgaacaca acttacacta tgcatagtca tagtatcaca  32820
atctggcaac agcgggtggt cttcagtcat agaagctcgg gtttcatttt cctcacaacg  32880
```

```
tggtaactgg gctctggtgt aagggtgatg tctggcgcat gatgtcgagc gtgcgcgcaa  32940

ccttgtcata atggagttgc ttcctgacat tctcgtattt tgtatagcaa aacgcggccc  33000

tggcagaaca cactcttctt cgccttctat cctgccgctt agcgtgttcc gtgtgatagt  33060

tcaagtacaa ccacactctt aagttggtca aaagaatgct ggcttcagtt gtaatcaaaa  33120

ctccatcgca tctaatcgtt ctgaggaaat catccacggt agcatatgca aatcccaacc  33180

aagcaatgca actggattgt gtttcaagca ggagaggaga gggaagagac ggaagaacca  33240

tgttaatttt tattccaaac gatctcgcag tacttcaaat tgtagatcgc gcagatggca  33300

tctctcgccc ccactgtgtt ggtgaaaaag cacagctaga tcaaaagaaa tgcgattttc  33360

aaggtgctca acggtggctt ccagcaaagc ctccacgcgc acatccaaga acaaaagaat  33420

accaaaagaa ggagcatttt ctaactcctc aatcatcata ttacattcct gcaccattcc  33480

cagataattt tcagctttcc agccttgaat tattcgtgtc agttcttgtg gtaaatccaa  33540

tccacacatt acaaacaggt cccggagggc gccctccacc accattctta aacacaccct  33600

cataatgaca aaatatcttg ctcctgtgtc acctgtagcg aattgagaat ggcaacatca  33660

attgacatgc ccttggctct aagttcttct ttaagttcta gttgtaaaaa ctctctcata  33720

ttatcaccaa actgcttagc cagaagcccc ccgggaacaa gagcagggga cgctacagtg  33780

cagtacaagc gcagacctcc ccaattggct ccagcaaaaa caagattgga ataagcatat  33840

tgggaaccgc cagtaatatc atcgaagttg ctggaaatat aatcaggcag agtttcttgt  33900

aaaaattgaa taaaagaaaa atttgccaaa aaaacattca aaacctctgg gatgcaaatg  33960

caataggtta ccgcgctgcg ctccaacatt gttagttttg aattagtctg caaaaataaa  34020

aaaaaaaaca agcgtcatat catagtagcc tgacgaacag atggataaat cagtctttcc  34080

atcacaagac aagccacagg gtctccagct cgaccctcgt aaaacctgtc atcatgatta  34140

aacaacagca ccgaaagttc ctcgcggtga ccagcatgaa taattcttga tgaagcatac  34200

aatccagaca tgttagcatc agttaacgag aaaaaaacagc caacatagcc tttgggtata  34260

attatgctta atcgtaagta tagcaaagcc acccctcgcg gatacaaagt aaaaggcaca  34320

ggagaataaa aaatataatt atttctctgc tgctgttcag gcaacgtcgc ccccggtccc  34380

tctaaataca catacaaagc ctcatcagcc atggcttacc agacaaagta cagcgggcac  34440

acaaagcaca agctctaaag tgactctcca acctctccac aatatatata tacacaagcc  34500

ctaaactgac gtaatgggag taaagtgtaa aaaatcccgc caaacccaac acacaccccg  34560

aaactgcgtc accagggaaa agtacagttt cacttccgca atcccaacag gcgtaacttc  34620

ctctttctca cggtacgtga tatcccacta acttgcaacg tcattttccc acggtcgcac  34680

cgccccttttt agccgttaac cccacagcca atcaccacac gatccacact ttttaaaatc  34740

acctcattta catattggca ccattccatc tataaggtat attattgatg atg         34793
```

<210> SEQ ID NO 4
<211> LENGTH: 1440
<212> TYPE: DNA
<213> ORGANISM: Artificial Sequence
<220> FEATURE:
<223> OTHER INFORMATION: Fully synthetic

<400> SEQUENCE: 4

```
catcatcaat aatatacctt atagatggaa tggtgccaat atgtaaatga ggtgatttta     60

aaaagtgtgg atcgtgtggt gattggctgt ggggttaacg gctaaaaggg gcggtgcgac    120

cgtgggaaaa tgacgttttg tgggggtgga gttttttttgc aagttgtcgc gggaaatgtg    180
```

acgcataaaa aggctttttt ctcacggaac tacttagttt tcccacggta tttaacagga 240
aatgaggtag ttttgaccgg atgcaagtga aaattgttga ttttcgcgcg aaaactgaat 300
gaggaagtgt ttttctgaat aatgtggtat ttatggcagg gtggagtatt tgttcagggc 360
caggtagact ttgacccatt acgtggaggt ttcgattacc gtgtttttta cctgaatttc 420
cgcgtaccgt gtcaaagtct tctgttttta cgtaggtgtc agctgatcgc tagggtattt 480
atacctcagg gtttgtgtca agaggccact cttgagtgcc agcgagaaga gttttctcct 540
ctgcgccggc agtttaataa taaaaaaatg agagatttgc gatttctgcc tcaggaaata 600
atctctgctg agactggaaa tgaaatattg gagcttgtgg tgcacgccct gatgggagac 660
gatccggagc cacctgtgca gctttttgag cctcctacgc ttcaggaact gtatgattta 720
gaggtagagg gatcggagga ttctaatgag gaagctgtaa atggcttttt taccgattct 780
atgcttttag ctgctaatga agggttagaa ttagatccgc ctttggacac ttttgatact 840
ccaggggtaa ttgtggaaag cggtacaggt gtaagaaaat tacctgattt gagttccgtg 900
gactgtgatt tgcactgcta tgaagacggg tttcctccga gtgatgagga ggaccatgaa 960
aaggagcagt ccatgcagac tgcagcgggt gagggagtga aggctgccaa tgttggtttt 1020
cagttggatt gcccggagct tcctggacat ggctgtaagt cttgtgaatt tcacaggaaa 1080
aatactggag taaaggaact gttatgttcg ctttgttata tgagaacgca ctgccacttt 1140
atttacagta agtgtgttta agttaaaatt taaaggaata tgctgttttt cacatgtata 1200
ttgagtgtga gttttgtgct tcttattata ggtcctgtgt ctgatgctga tgaatcacca 1260
tctcctgatt ctactacctc acctcctgag attcaagcac ctgttcctgt ggacgtgcgc 1320
aagcccattc ctgtgaagct taagcctggg aaacgtccag cagtggaaaa acttgaggac 1380
ttgttacagg gtggggacgg acctttggac ttgagtacac ggaaacgtcc aagacaataa 1440

<210> SEQ ID NO 5
<211> LENGTH: 3153
<212> TYPE: DNA
<213> ORGANISM: Artificial Sequence
<220> FEATURE:
<223> OTHER INFORMATION: Fully synthetic

<400> SEQUENCE: 5
atacctgtga cggaagatca cttcgcagaa taaataaatc ctggtgtccc tgttgatacc 60
gggaagccct gggccaactt ttggcgaaaa tgagacgttg atcggcacgt aagaggttcc 120
aactttcacc ataatgaaat aagatcacta ccgggcgtat tttttgagtt atcgagattt 180
tcaggagcta aggaagctaa aatggagaaa aaaatcactg gatataccac cgttgatata 240
tcccaatggc atcgtaaaga acattttgag gcatttcagt cagttgctca atgtacctat 300
aaccagaccg ttcagctgga tattacggcc tttttaaaga ccgtaaagaa aaataagcac 360
aagttttatc cggcctttat tcacattctt gcccgcctga tgaatgctca tccggaattc 420
cgtatggcaa tgaaagacgg tgagctggtg atatgggata gtgttcaccc ttgttacacc 480
gttttccatg agcaaactga aacgttttca tcgctctgga gtgaatacca cgacgatttc 540
cggcagtttc tacacatata ttcgcaagat gtggcgtgtt acggtgaaaa cctggcctat 600
ttccctaaag ggtttattga gaatatgttt ttcgtctcag ccaatccctg ggtgagtttc 660
accagttttg atttaaacgt ggccaatatg gacaacttct tcgcccccgt tttcaccatg 720
ggcaaatatt atacgcaagg cgacaaggtg ctgatgccgc tggcgattca ggttcatcat 780

-continued

```
gccgtctgtg atggcttcca tgtcggcaga atgcttaatg aattacaaca gtactgcgat    840
gagtggcagg gcggggcgta atttttttaa ggcagttatt ggtgccttta aacgcctatt    900
taaattacgt cattttccca cggtcgcacc gcccctttta gccgttaacc ccacagccaa    960
tcaccacacg atccacactt tttaaaatca cctcatttac atattggcac cattccatct   1020
ataaggtata ttattgatga tgcatcatca ataatatacc ttatagatgg aatggtgcca   1080
atatgtaaat gaggtgattt taaaaagtgt ggatcgtgtg gtgattggct gtggggttaa   1140
cggctaaaag gggcggtgcg accgtgggaa aatgacgttt tgtgggggtg gagttttttt   1200
gcaagttgtc gcgggaaatg tgacgcataa aaaggctgta gcgatcgctt agactcgagc   1260
ggccgcggtc cgtttaaact gtcagaccaa gtttactcat atatacttta gattgattta   1320
aaacttcatt tttaatttaa aaggatctag gtgaagatcc tttttgataa tctcatgacc   1380
aaaatccctt aacgtgagtt ttcgttccac tgagcgtcag accccgtaga aaagaccaaa   1440
ggatcttctt gagatccttt ttttctgcgc gtaatctgct gcttgcaaac aaaaaaacca   1500
ccgctaccag cggtggtttg tttgccggat caagagctac caactctttt tccgaaggta   1560
actggcttca gcagagcgca gataccaaat actgtccttc tagtgtagcc gtagttgggc   1620
caccacttca agaactctgt agcaccgcct acatacctcg ctctgctaat cctgttacca   1680
gtggctgctg ccagtggcga taagtcgtgt cttaccgggt tggactcaag acgatagtta   1740
ccggataagg cgcagcggtc gggctgaacg gggggttcgt gcacacagcc cagcttggag   1800
cgaacgacct acaccgaact gagataccta cagcgtgagc tatgagaaag cgccacgctt   1860
cccgaaggga gaaaggcgga caggtatccg gtaagcggca gggtcggaac aggagagcgc   1920
acgaaggagc ttccaggggg aaacgcctgg tatctttata gtcctgtcgg gtttcgccac   1980
ctctgacttg agcgtcgatt tttgtgatgc tcgtcagggg ggcggagcct atggaaaaac   2040
gccagcaacg cggccttttt acggttcctg gccttttgct ggccttttgc tcacatgttc   2100
cttcctgcgt tatcccctga ttctgtggat aaccgtatta ccgcctttga gtgagctgat   2160
accgctcgcc gcaggtttaa acagatctgt cgacgcccgg gcaagctggc cggccgatac   2220
acaggaagtg acaattttcg cgcggtttta ggcggatgtt gtagtaaatt tgggcgtaac   2280
cgagtaagat ttggccattt tcgcgggaaa actgaataag aggaagtgaa atctgaataa   2340
ttttgtgtta ctcatagcgc gtaatatttg tctagggccg cggggacttt gaccgtttac   2400
gtggagactc gcccaggtgt ttttctcagg tgttttccgc gttccgggtc aaagttggcg   2460
ttttattatt atagtcagct gacgtgtagt gtatttatac ccggtgagtt cctcaagagg   2520
ccactcttga gtgccagcga gtagagtttt ctcctccgag ccgctccgac accgggactg   2580
aaaaatgaga gatttgcgat ttctgcctca ggaaataatc tctgctgaga ctggaaatga   2640
aatattggag cttgtggtgc acgccctgat gggagacgat ccggagccac ctgtgcagct   2700
ttttgagcct cctacgcttc aggaactgta tgatttagag gtagagggat cggaggattc   2760
taatgaggaa gctgtaaatg gctttttttac cgattctatg cttttagctg ctaatgaagg   2820
gttagaatta gatccgcctt tggacacttt tgatactcca ggggtaattg tggaaagcgg   2880
tacaggtgta agaaaattac ctgatttgag ttccgtggac tgtgatttgc actgctatga   2940
agacgggttt cctccgagtg atgaggagga ccatgaaaag gagcagtcca tgcagactgc   3000
agcgggtgag ggagtgaagg ctgccaatgt tggttttcag ttggattgcc cggagcttcc   3060
tggacatggc tgtaagtctt gtgaatttca caggaaaaat actggagtaa aggaactgtt   3120
atgttcgctt tgttatatga gaatcattta aat                                3153
```

<210> SEQ ID NO 6
<211> LENGTH: 34793
<212> TYPE: DNA
<213> ORGANISM: Artificial Sequence
<220> FEATURE:
<223> OTHER INFORMATION: Fully synthetic

<400> SEQUENCE: 6
catcatcaat aatatacctt atagatggaa tggtgccaat atgtaaatga ggtgatttta 60
aaaagtgtgg atcgtgtggt gattggctgt ggggttaacg gctaaaaggg gcggtgcgac 120
cgtgggaaaa tgacgttttg tgggggtgga gtttttttgc aagttgtcgc gggaaatgtg 180
acgcataaaa aggctttttt ctcacggaac tacttagttt tcccacggta tttaacagga 240
aatgaggtag ttttgaccgg atgcaagtga aaattgttga ttttcgcgcg aaaactgaat 300
gaggaagtgt ttttctgaat aatgtggtat ttatggcagg gtggagtatt tgttcagggc 360
caggtagact ttgacccatt acgtggaggt ttcgattacc gtgtttttta cctgaatttc 420
cgcgtaccgt gtcaaagtct tctgttttta cgtaggtgtc agctgatcgc tagggtattt 480
atacctcagg gtttgtgtca agaggccact cttgagtgcc agcgagaaga gttttctcct 540
ctgcgccggc agtttaataa taaaaaaatg agagatttgc gatttctgcc tcaggaaata 600
atctctgctg agactggaaa tgaaatattg gagcttgtgg tgcacgccct gatgggagac 660
gatccggagc cacctgtgca gctttttgag cctcctacgc ttcaggaact gtatgattta 720
gaggtagagg gatcggagga ttctaatgag gaagctgtaa atggcttttt taccgattct 780
atgcttttag ctgctaatga agggttagaa ttagatccgc ctttggacac ttttgatact 840
ccaggggtaa ttgtggaaag cggtacaggt gtaagaaaat tacctgattt gagttccgtg 900
gactgtgatt tgcactgcta tgaagacggg tttcctccga gtgatgagga ggaccatgaa 960
aaggagcagt ccatgcagac tgcagcgggt gagggagtga aggctgccaa tgttggtttt 1020
cagttggatt gcccggagct tcctggacat ggctgtaagt cttgtgaatt tcacaggaaa 1080
aatactggag taaaggaact gttatgttcg ctttgttata tgagaacgca ctgccacttt 1140
atttacagta agtgtgttta agttaaaatt taaaggaata tgctgttttt cacatgtata 1200
ttgagtgtga gttttgtgct tcttattata ggtcctgtgt ctgatgctga tgaatcacca 1260
tctcctgatt ctactacctc acctcctgag attcaagcac ctgttcctgt ggacgtgcgc 1320
aagcccattc ctgtgaagct taagcctggg aaacgtccag cagtggaaaa acttgaggac 1380
ttgttacagg gtggggacgg acctttggac ttgagtacac ggaaacgtcc aagacaataa 1440
gtgttccata tccgtgttta cttaaggtga cgtcaatatt tgtgtgacag tgcaatgtaa 1500
taaaaatatg ttaactgttc actggttttt attgcttttt gggcggggac tcaggtatat 1560
aagtagaagc agacctgtgt ggttagctca taggagctgg ctttcatcca tggaggtttg 1620
ggccattttg gaagacctta ggaagactag gcaactgtta gagaacgctt cggacggagt 1680
ctccggtttt tggagattct ggttcgctag tgaattagct agggtagttt ttaggataaa 1740
acaggactat aaacaagaat ttgaaaagtt gttggtagat tgcccaggac tttttgaagc 1800
tcttaatttg ggccatcagg ttcactttaa agaaaaagtt ttatcagttt tagacttttc 1860
aaccccaggt agaactgctg ctgctgtggc ttttcttact tttatattag ataaatggat 1920
cccgcagact catttcagca ggggatacgt tttggatttc atagccacag cattgtggag 1980
aacatggaag gttcgcaaga tgaggacaat cttaggttac tggccagtgc agcctttggg 2040

-continued tgtagcggga atcctgaggc atccaccggt catgccagcg gttctggagg aggaacagca 2100
agaggacaac ccgagagccg gcctggaccc tccagtggag gaggcggagt agctgacttg 2160
tctcctgaac tgcaacgggt gcttactgga tctacgtcca ctggacggga taggggcgtt 2220
aagagggaga gggcatctag tggtactgat gctagatctg agttggcttt aagtttaatg 2280
agtcgcagac gtcctgaaac catttggtgg catgaggttc agaaagaggg aagggatgaa 2340
gtttctgtat tgcaggagaa atattcactg gaacaggtga aacatgttg gttggagcct 2400
gaggatgatt gggaggtggc cattaaaaat tatgccaaga tagctttgag gcctgataaa 2460
cagtataaga ttactagacg gattaatatc cggaatgctt gttacatatc tggaaatggg 2520
gctgaggtgg taatagatac tcaagacaag gcagttatta gatgctgcat gatggatatg 2580
tggcctgggg tagtcggtat ggaagcagta acttttgtaa atgttaagtt taggggagat 2640
ggttataatg gaatagtgtt tatggccaat accaaactta tattgcatgg ttgtagcttt 2700
tttggtttca acaatacctg tgtagatgcc tggggacagg ttagtgtacg gggatgtagt 2760
ttctatgcgt gttggattgc cacagctggc agaaccaaga gtcaattgtc tctgaagaaa 2820
tgcatatttc aaagatgtaa cctgggcatt ctgaatgaag gcgaagcaag ggtccgccac 2880
tgcgcttcta cagatactgg atgttttatt ttgattaagg gaaatgccag cgtaaagcat 2940
aacatgattt gcggtgcttc cgatgagagg ccttatcaaa tgctcacttg tgctggtggg 3000
cattgtaata tgctggctac tgtgcatatt gtttcccatc aacgcaaaaa atggcctgtt 3060
tttgatcaca atgtgatgac gaagtgtacc atgcatgcag gtgggcgtag aggaatgttt 3120
atgccttacc agtgtaacat gaatcatgtg aaagtgttgt tggaaccaga tgccttttcc 3180
agaatgagcc taacaggaat ttttgacatg aacatgcaaa tctggaagat cctgaggtat 3240
gatgatacga gatcgagggt acgcgcatgc gaatgcggag gcaagcatgc caggttccag 3300
ccggtgtgtg tagatgtgac tgaagatctc agaccggatc atttggttat tgcccgcact 3360
ggagcagagt tcggatccag tggagaagaa actgactaag gtgagtattg ggaaaacttt 3420
ggggtgggat tttcagatgg acagattgag taaaaatttg tttttctgt cttgcagctg 3480
tcatgagtgg aaacgcttct tttaaggggg gagtcttcag cccttatctg acagggcgtc 3540
tcccatcctg ggcaggagtt cgtcagaatg ttatgggatc tactgtggat ggaagacccg 3600
tccaacccgc caattcttca acgctgacct atgctacttt aagttcttca cctttggacg 3660
cagctgcagc tgccgccgcc gcttctgttg ccgctaacac tgtgcttgga atgggttact 3720
atggaagcat catggctaat tccacttcct ctaataaccc ttctaccctg actcaggaca 3780
agttacttgt ccttttggcc cagctggagg ctttgaccca acgtctgggt gaactttctc 3840
agcaggtggt cgagttgcga gtacaaactg agtctgctgt cggcacggca aagtctaaat 3900
aaaaaaatcc cagaatcaat gaataaataa acaagcttgt tgttgattta aaatcaagtg 3960
tttttatttc atttttcgcg cacggtatgc cctagaccac cgatctctat cattgagaac 4020
tcggtggatt ttttccagga tcctatagag gtgggattga atgtttagat acatgggcat 4080
taggccgtct ttggggtgga gatagctcca ttgaagggat tcatgctccg gggtagtgtt 4140
gtaaatcacc cagtcataac aaggtcgcag tgcatggtgt tgcacaatat cttttagaag 4200
taggctgatt gccacagata agcccttggt gtaggtgttt acaaaccggt tgagctggga 4260
tgggtgcatt cggggtgaaa ttatgtgcat tttggattgg atttttaagt tggcaatatt 4320
gccgccaaga tcccgtcttg ggttcatgtt atgaaggacc accaagacgg tgtatccggt 4380
acatttagga aatttatcgt gcagcttgga tggaaaagcg tggaaaaatt tggagacacc 4440

-continued

```
cttgtgtcct ccaagatttt ccatgcactc atccatgata atagcaatgg ggccgtgggc   4500
agcggcgcgg gcaaacacgt tccgtgggtc tgacacatca tagttatgtt cctgagttaa   4560
atcatcataa gccattttaa tgaatttggg gcggagagta ccagattggg gtatgaatgt   4620
tccttcgggc cccggagcat agttcccctc acagatttgc atttcccaag ctttcagttc   4680
cgagggtgga atcatgtcca cctgggggc tatgaaaaac accgtttctg ggcgggggt    4740
gattaattgt gatgatagca aatttctgag caattgagat ttgccacatc cggtggggcc   4800
ataaatgatt ccgattacgg gttgcaggtg gtagtttagg gaacggcaac tgccgtcttc   4860
tcgaagcaag gggccacct cgttcatcat ttcccttaca tgcatatttt cccgcaccaa    4920
atccattagg aggcgctctc ctcctagtga tagaagttct tgtagtgagg aaaagttttt   4980
cagcggtttc agaccgtcag ccatgggcat tttggagaga gtttgctgca aaagttctag   5040
tctgttccac agttcagtga tgtgttctat ggcatctcga tccagcagac ctcctcgttt   5100
cgcgggtttg gacggctcct ggaatagggt atgagacgat gggcgtccag cgctgccagg   5160
gttcggtcct tccagggtct cagtgttcga gtcagggttg tttccgtcac agtgaagggg   5220
tgtgcgcctg cttgggcgct tgccagggtg cgcttcagac tcatcctgct ggtcgaaaac   5280
ttctgtcgct tggcgccctg tatgtcggcc aagtagcagt ttaccatgag ttcgtagttg   5340
agcgcctcgg ctgcgtggcc tttggcgcgg agcttacctt tggaagtttt cttgcatacc   5400
gggcagtata ggcatttcag cgcatacaac ttgggcgcaa ggaaaacgga ttctggggag   5460
tatgcatctg cgccgcagga ggcgcaaaca gtttcacatt ccaccagcca ggttaaatcc   5520
ggttcattgg ggtcaaaaac aagttttccg ccatattttt tgatgcgttt cttacctttg   5580
gtctccatga gttcgtgtcc tcgttgagtg acaaacaggc tgtccgtgtc cccgtagact   5640
gattttacag gcctcttctc cagtggagtg cctcggtctt cttcgtacag gaactctgac   5700
cactctgata caaaggcgcg cgtccaggcc agcacaaagg aggctatgtg ggaggggtag   5760
cgatcgttgt caaccagggg gtccaccttt tccaaagtat gcaaacacat gtcaccctct   5820
tcaacatcca ggaatgtgat tggcttgtag gtgtatttca cgtgacctgg ggtccccgct   5880
gggggggtat aaaagggggc ggttctttgc tcttcctcac tgtcttccgg atcgctgtcc   5940
aggaacgtca gctgttgggg taggtattcc ctctcgaagg cgggcatgac ctctgcactc   6000
aggttgtcag tttctaagaa cgaggaggat ttgatattga cagtgccggt tgagatgcct   6060
ttcatgaggt tttcgtccat ttggtcagaa aacacaattt ttttattgtc aagtttggtg   6120
gcaaatgatc catacagggc gttggataaa agtttggcaa tggatcgcat ggtttggttc   6180
ttttccttgt ccgcgcgctc tttggcggcg atgttgagtt ggacatactc gcgtgccagg   6240
cacttccatt cggggaagat agttgttaat tcatctggca cgattctcac ttgccaccct   6300
cgattatgca aggtaattaa atccacactg gtggccacct cgcctcgaag ggggttcattg  6360
gtccaacaga gcctacctcc tttcctagaa cagaaagggg gaagtgggtc tagcataagt   6420
tcatcgggag ggtctgcatc catggtaaag attcccggaa gtaaatcctt atcaaaatag   6480
ctgatgggag tggggtcatc taaggccatt tgccattctc gagctgccag tgcgcgctca   6540
tatgggttaa ggggactgcc ccatggcatg ggatgggtga gtgcagaggc atacatgcca   6600
cagatgtcat agacgtagat gggatcctca aagatgccta tgtaggttgg atagcatcgc   6660
ccccctctga tacttgctcg cacatagtca tatagttcat gtgatggcgc tagcagcccc   6720
ggacccaagt tggtgcgatt gggtttttct gttctgtaga cgatctggcg aaagatggcg   6780
```

-continued

```
tgagaattgg aagagatggt gggtctttga aaaatgttga aatgggcatg aggtagacct   6840
acagagtctc tgacaaagtg ggcataagat tcttgaagct tggttaccag ttcggcggtg   6900
acaagtacgt ctagggcgca gtagtcaagt gtttcttgaa tgatgtcata acctggttgg   6960
tttttctttt cccacagttc gcggttgaga aggtattctt cgcgatcctt ccagtactct   7020
tctagcggaa acccgtcttt gtctgcacgg taagatccta gcatgtagaa ctgattaact   7080
gccttgtaag ggcagcagcc cttctctacg ggtagagagt atgcttgagc agcttttcgt   7140
agcgaagcgt gagtaagggc aaaggtgtct ctgaccatga ctttgagaaa ttggtatttg   7200
aagtcgatgt cgtcacaggc tccctgttcc cagagttgga agtctacccg tttcttgtag   7260
gcggggttgg gcaaagcgaa agtaacatca ttgaagagaa tcttaccggc tctgggcata   7320
aaattgcgag tgatgcgaaa aggctgtggt acttccgctc gattgttgat cacctgggca   7380
gctaggacga tctcgtcgaa accgttgatg ttgtgtccta cgatgtataa ttctatgaaa   7440
cgcggcgtgc ctctgacgtg aggtagctta ctgagctcat caaaggttag gtctgtgggg   7500
tcagataagg cgtagtgttc gagagcccat tcgtgcaggt gaggatttgc atgtaggaat   7560
gatgaccaaa gatctaccgc cagtgctgtt tgtaactggt cccgatactg acgaaaatgc   7620
cggccaattg ccatttttc tggagtgaca cagtagaagg ttctggggtc ttgttgccat   7680
cgatcccact tgagtttaat ggctagatcg tgggccatgt tgacgagacg ctcttctcct   7740
gagagtttca tgaccagcat gaaaggaact agttgtttgc caaaggatcc catccaggtg   7800
taagtttcca catcgtaggt caggaagagt ctttctgtgc gaggatgaga gccgatcggg   7860
aagaactgga tttcctgcca ccagttggag gattggctgt tgatgtgatg gaagtagaag   7920
tttctgcggc gcgccgagca ttcgtgtttg tgcttgtaca gacggccgca gtagtcgcag   7980
cgttgcacgg gttgtatctc gtgaatgagt tgtacctggc ttcccttgac gagaaatttc   8040
agtgggaagc cgaggcctgg cgattgtatc tcgtgctctt ctatattcgc tgtatcggcc   8100
tgttcatctt ctgtttcgat ggtggtcatg ctgacgagcc cccgcgggag gcaagtccag   8160
acctcggcgc gggaggggcg gagctgaagg acgagagcgc gcaggctgga gctgtccaga   8220
gtcctgagac gctgcggact caggttagta ggtagggaca gaagattaac ttgcatgatc   8280
ttttccaggg cgtgcgggag gttcagatgg tacttgattt ccacaggttc gtttgtagag   8340
acgtcaatgg cttgcagggt tccgtgtcct ttgggcgcca ctaccgtacc tttgtttttt   8400
cttttgatcg gtggtggctc tcttgcttct tgcatgctca gaagcggtga cggggacgcg   8460
cgccgggcgg cagcggttgt tccggacccg agggcatggc tggtagtggc acgtcggcgc   8520
cgcgcacggg caggttctgg tactgcgctc tgagaagact tgcgtgcgcc accacgcgtc   8580
gattgacgtc ttgtatctga cgtctctggg tgaaagctac cggccccgtg agcttgaacc   8640
tgaaagagag ttcaacagaa tcaatttcgg tatcgttaac ggcagcttgt ctcagtattt   8700
cttgtacgtc accagagttg tcctggtagg cgatctccgc catgaactgc tcgatttctt   8760
cctcctgaag atctccgcga cccgctcttt cgacggtggc cgcgaggtca ttggagatac   8820
ggcccatgag ttgggagaat gcattcatgc ccgcctcgtt ccagacgcgg ctgtaaacca   8880
cggccccctc ggagtctctt gcgcgcatca ccacctgagc gaggttaagc tccacgtgtc   8940
tggtgaagac cgcatagttg cataggcgct gaaaaaggta gttgagtgtg gtggcaatgt   9000
gttcggcgac gaagaaatac atgatccatc gtctcagcgg catttcgcta acatcgccca   9060
gagcttccaa gcgctccatg gcctcgtaga agtccacggc aaaattaaaa aactgggagt   9120
ttcgcgcgga cacggtcaat tcctcctcga gaagacggat gagttcggct atggtggccc   9180
```

```
gtacttcgcg ttcgaaggct cccgggatct cttcttcctc ttctatctct tcttccacta   9240
acatctcttc ttcgtcttca ggcgggggcg gagggggcac gcggcgacgt cgacggcgca   9300
cgggcaaacg gtcgatgaat cgttcaatga cctctccgcg gcggcggcgc atggtttcag   9360
tgacggcgcg gccgttctcg cgcggtcgca gagtaaaaac accgccgcgc atctccttaa   9420
agtggtgact gggaggttct ccgtttggga gggagagggc gctgattata cattttatta   9480
attggcccgt agggactgca cgcagagatc tgatcgtgtc aagatccacg ggatctgaaa   9540
acctttcgac gaaagcgtct aaccagtcac agtcacaagg taggctgagt acggcttctt   9600
gtgggcgggg gtggttatgt gttcggtctg ggtcttctgt ttcttcttca tctcgggaag   9660
gtgagacgat gctgctggtg atgaaattaa agtaggcagt tctaagacgg cggatggtgg   9720
cgaggagcac caggtctttg ggtccggctt gctggatacg caggcgattg gccattcccc   9780
aagcattatc ctgacatcta gcaagatctt tgtagtagtc ttgcatgagc cgttctacgg   9840
gcacttcttc ctcacccgtt ctgccatgca tacgtgtgag tccaaatccg cgcattggtt   9900
gtaccagtgc caagtcagct acgactcttt cggcgaggat ggcttgctgt acttgggtaa   9960
gggtggcttg aaagtcatca aaatccacaa agcggtggta agctcctgta ttaatggtgt  10020
aagcacagtt ggccatgact gaccagttaa ctgtctggtg accagggcgc acgagctcgg  10080
tgtatttaag gcgcgaatag gcgcgggtgt caaagatgta atcgttgcag gtgcgcacca  10140
gatactggta ccctataaga aaatgcggcg gtggttggcg gtagagaggc catcgttctg  10200
tagctggagc gccaggggcg aggtcttcca acataaggcg gtgatagccg tagatgtacc  10260
tggacatcca ggtgattcct gcggcggtag tagaagcccg aggaaactcg cgtacgcggt  10320
tccaaatgtt gcgtagcggc atgaagtagt tcattgtagg cacggtttga ccagtgaggc  10380
gcgcgcagtc attgatgctc tatagacacg gagaaaatga aagcgttcag cgactcgact  10440
ccgtagcctg gaggaacgtg aacgggttgg gtcgcggtgt accccggttc gagacttgta  10500
ctcgagccgg ccggagccgc ggctaacgtg gtattggcac tcccgtctcg acccagccta  10560
caaaaatcca ggatacggaa tcgagtcgtt ttgctggttt ccgaatggca gggaagtgag  10620
tcctattttt tttttttgc cgctcagatg catcccgtgc tgcgacagat gcgcccccaa  10680
caacagcccc cctcgcagca gcagcagcag caatcacaaa aggctgtccc tgcaactact  10740
gcaactgccg ccgtgagcgg tgcgggacag cccgcctatg atctggactt ggaagagggc  10800
gaaggactgg cacgtctagg tgcgccttca cccgagcggc atccgcgagt tcaactgaaa  10860
aaagattctc gcgaggcgta tgtgccccaa cagaacctat ttagagacag aagcggcgag  10920
gagccggagg agatgcgagc ttcccgcttt aacgcgggtc gtgagctgcg tcacggtttg  10980
gaccgaagac gagtgttgcg ggacgaggat ttcgaagttg atgaaatgac agggatcagt  11040
cctgccaggg cacacgtggc tgcagccaac cttgtatcgg cttacgagca gacagtaaag  11100
gaagagcgta acttccaaaa gtcttttaat aatcatgtgc gaaccctgat tgcccgcgaa  11160
gaagttaccc ttggtttgat gcatttgtgg gatttgatgg aagctatcat tcagaaccct  11220
actagcaaac ctctgaccgc ccagctgttt ctggtggtgc aacacagcag agacaatgag  11280
gctttcagag aggcgctgct gaacatcacc gaacccgagg ggagatggtt gtatgatctt  11340
atcaacattc tacagagtat catagtgcag gagcggagcc tgggcctggc cgagaaggtg  11400
gctgccatca attactcggt tttgagcttg ggaaaatatt acgctcgcaa aatctacaag  11460
actccatacg ttcccataga caaggaggtg aagatagatg ggttctacat gcgcatgacg  11520
```

-continued

```
ctcaaggtct tgaccctgag cgatgatctt ggggtgtatc gcaatgacag aatgcatcgc  11580
gcggttagcg ccagcaggag gcgcgagtta agcgacaggg aactgatgca cagtttgcaa  11640
agagctctga ctggagctgg aaccgagggt gagaattact tcgacatggg agctgacttg  11700
cagtggcagc ctagtcgcag ggctctgagc gccgcgacgg caggatgtga gcttccttac  11760
atagaagagg cggatgaagg cgaggaggaa gagggcgagt acttggaaga ctgatggcac  11820
aacccgtgtt ttttgctaga tggaacagca agcaccggat cccgcaatgc gggcggcgct  11880
gcagagccag ccgtccggca ttaactcctc ggacgattgg acccaggcca tgcaacgtat  11940
catggcgttg acgactcgca accccgaagc ctttagacag caaccccagg ccaaccgtct  12000
atcggccatc atggaagctg tagtgccttc ccgctctaat cccactcatg agaaggtcct  12060
ggccatcgtg aacgcgttgg tggagaacaa agctattcgt ccagatgagg ccggactggt  12120
atacaacgct ctcttagaac gcgtggctcg ctacaacagt agcaatgtgc aaaccaattt  12180
ggaccgtatg ataacagatg tacgcgaagc cgtgtctcag cgcgaaaggt tccagcgtga  12240
tgccaacctg ggttcgctgg tggcgttaaa tgctttcttg agtactcagc ctgctaatgt  12300
gccgcgtggt caacaggatt atactaactt tttaagtgct ttgagactga tggtatcaga  12360
agtacctcag agcgaagtgt atcagtccgg tcctgattac ttctttcaga ctagcagaca  12420
gggcttgcag acggtaaatc tgagccaagc ttttaaaaac cttaaaggtt tgtggggagt  12480
gcatgccccg gtaggagaaa gagcaaccgt gtctagcttg ttaactccga actcccgcct  12540
attattactg ttggtagctc ctttcaccga cagcggtagc atcgaccgta attcctattt  12600
gggttaccta ctaaacctgt atcgcgaagc catagggcaa agtcaggtgg acgagcagac  12660
ctatcaagaa attacccaag tcagtcgcgc tttgggacag gaagacactg gcagtttgga  12720
agccactctg aacttcttgc ttaccaatcg gtctcaaaag atccctcctc aatatgctct  12780
tactgcggag gaggagagga tccttagata tgtgcagcag agcgtgggat tgtttctgat  12840
gcaagagggg gcaactccga ctgcagcact ggacatgaca gcgcgaaata tggagcccag  12900
catgtatgcc agtaaccgac ctttcattaa caaactgctg gactacttgc acagagctgc  12960
cgctatgaac tctgattatt tcaccaatgc catcttaaac ccgcactggc tgcccccacc  13020
tggtttctac acgggcgaat atgacatgcc cgaccctaat gacggatttc tgtgggacga  13080
cgtggacagc gatgtttttt cacctctttc tgatcatcgc acgtggaaaa aggaaggcgg  13140
cgatagaatg cattcttctg catcgctgtc cggggtcatg ggtgctaccg cggctgagcc  13200
cgagtctgca agtccttttc ctagtctacc cttttctcta cacagtgtac gtagcagcga  13260
agtgggtaga ataagtcgcc cgagtttaat gggcgaagag gagtatctaa acgattcctt  13320
gctcagaccg gcaagagaaa aaaatttccc aaacaatgga atagaaagtt tggtggataa  13380
aatgagtaga tggaagactt atgctcagga tcacagagac gagcctggga tcatggggat  13440
tacaagtaga gcgagccgta gacgccagcg ccatgacaga cagaggggtc ttgtgtggga  13500
cgatgaggat tcggccgatg atagcagcgt gctggacttg ggtgggagag gaaggggcaa  13560
cccgtttgct catttgcgcc ctcgcttggg tggtatgttg taaaaaaaaa taaaaaaaaa  13620
actcaccaag gccatggcga cgagcgtacg ttcgttcttc tttattatct gtgtctagta  13680
taatgaggcg agtcgtgcta ggcggagcgg tggtgtatcc ggagggtcct cctccttcgt  13740
acgagagcgt gatgcagcag cagcaggcga cggcggtgat gcaatcccca ctggaggctc  13800
cctttgtgcc tccgcgatac ctggcaccta cggagggcag aaacagcatt cgttattcgg  13860
aactggcacc tcagtacgat accaccaggt tgtatctggt ggacaacaag tcggcggaca  13920
```

```
ttgcttctct gaactatcag aatgaccaca gcaacttctt gaccacggtg gtgcaaaaca  13980
atgactttac ccctacggaa gccagcaccc agaccattaa ctttgatgaa cgatcgcggt  14040
ggggcggtca gctaaagacc atcatgcata ctaacatgcc aaacgtgaac gagtatatgt  14100
ttagtaacaa gttcaaagcg cgtgtgatgg tgtccagaaa acctcccgac ggtgctgcag  14160
ttggggatac ttatgatcac aagcaggata ttttgaaata tgagtggttc gagtttactt  14220
tgccagaagg caacttttca gttactatga ctattgattt gatgaacaat gccatcatag  14280
ataattactt gaaagtgggt agacagaatg gagtgcttga aagtgacatt ggtgttaagt  14340
tcgacaccag gaacttcaag ctgggatggg atcccgaaac caagttgatc atgcctggag  14400
tgtatacgta tgaagccttc catcctgaca ttgtcttact gcctggctgc ggagtggatt  14460
ttaccgagag tcgtttgagc aaccttcttg gtatcagaaa aaaacagcca tttcaagagg  14520
gttttaagat tttgtatgaa gatttagaag gtggtaatat tccggccctc ttggatgtag  14580
atgcctatga gaacagtaag aaagaacaaa aagccaaaat agaagctgct acagctgctg  14640
cagaagctaa ggcaaacata gttgccagcg actctacaag ggttgctaac gctggagagg  14700
tcagaggaga caattttgcg ccaacacctg ttccgactgc agaatcatta ttggccgatg  14760
tgtctgaagg aacggacgtg aaactcacta ttcaacctgt agaaaaagat agtaagaata  14820
gaagctataa tgtgttggaa gacaaaatca acacagccta tcgcagttgg tatctttcgt  14880
acaattatgg cgatcccgaa aaaggagtgc gttcctggac attgctcacc acctcagatg  14940
tcacctgcgg agcagagcag gtctactggt cgcttccaga catgatgaag gatcctgtca  15000
ctttccgctc cactagacaa gtcagtaact accctgtggt gggtgcagag cttatgcccg  15060
tcttctcaaa gagcttctac aacgaacaag ctgtgtactc ccagcagctc cgccagtcca  15120
cctcgcttac gcacgtcttc aaccgctttc ctgagaacca gattttaatc cgtccgccgg  15180
cgcccaccat taccaccgtc agtgaaaacg ttcctgctct cacagatcac gggaccctgc  15240
cgttgcgcag cagtatccgg ggagtccaac gtgtgaccgt tactgacgcc agacgccgca  15300
cctgtcccta cgtgtacaag gcactgggca tagtcgcacc gcgcgtcctt tcaagccgca  15360
ctttctaaaa aaaaaaaaaa tgtccattct tatctcgccc agtaataaca ccggttgggg  15420
tctgcgcgct ccaagcaaga tgtacggagg cgcacgcaaa cgttctaccc aacatcctgt  15480
ccgtgttcgc ggacattttc gcgctccatg ggcgccctc aagggccgca ctcgcgttcg  15540
aaccaccgtc gatgatgtaa tcgatcaggt ggttgccgac gcccgtaatt atactcctac  15600
tgcgcctaca tctactgtgg atgcagttat tgacagtgta gtggctgacg ctcgcaacta  15660
tgctcgacgt aagagccggc gaaggcgcat tgccagacgc caccgagcta ccactgccat  15720
gcgagccgca agagctctgc tacgaagagc tagacgcgtg gggcgaagag ccatgcttag  15780
ggcggccaga cgtgcagctt cgggcgccag cgccggcagg tcccgcaggc aagcagccgc  15840
tttcgcagcg gcgactattg ccgacatggc ccaatcgcga agaggcaatg tatactgggt  15900
gcgtgacgct gccaccggtc aacgtgtacc cgtgcgcacc cgtccccctc gcacttagaa  15960
gatactgagc agtctccgat gttgtgtccc agcggcgagg atgtccaagc gcaaatacaa  16020
ggaagaaatg ctgcaggtta tcgcacctga agtctacggc caaccgttga aggatgaaaa  16080
aaaaccccgc aaaatcaagc gggttaaaaa ggacaaaaaa gaagaggaag atggcgatga  16140
tgggctggcg gagtttgtgc gcgagtttgc cccacggcga cgcgtgcaat ggcgtgggcg  16200
caaagttcga catgtgttga gacctggaac ttcggtggtc tttacacccg gcgagcgttc  16260
```

aagcgctact tttaagcgtt cctatgatga ggtgtacggg gatgatgata ttcttgagca 16320
ggcggctgac cgattaggcg agtttgctta tggcaagcgt agtagaataa cttccaagga 16380
tgagacagtg tcgataccct tggatcatgg aaatcccacc cctagtctta aaccggtcac 16440
tttgcagcaa gtgttacccg taactccgcg aacaggtgtt aaacgcgaag gtgaagattt 16500
gtatcccact atgcaactga tggtacccaa acgccagaag ttggaggacg ttttggagaa 16560
agtaaaagtg gatccagata ttcaacctga ggttaaagtg agacccatta agcaggtagc 16620
gcctggtctg gggtacaaa ctgtagacat taagattccc actgaaagta tggaagtgca 16680
aactgaaccc gcaaagccta ctgccacctc cactgaagtg caaacggatc catggatgcc 16740
catgcctatt acaactgacg ccgccggtcc cactcgaaga tcccgacgaa agtacggtcc 16800
agcaagtctg ttgatgccca attatgttgt acacccatct attattccta ctcctggtta 16860
ccgaggcact cgctactatc gcagccgaaa cagtacctcc cgccgtcgcc gcaagacacc 16920
tgcaaatcgc agtcgtcgcc gtagacgcac aagcaaaccg actcccggcg ccctggtgcg 16980
gcaagtgtac cgcaatggta gtgcggaacc tttgacactg ccgcgtgcgc gttaccatcc 17040
gagtatcatc acttaatcaa tgttgccgct gcctccttgc agatatggcc ctcacttgtc 17100
gccttcgcgt tcccatcact ggttaccgag gaagaaactc gcgccgtaga agagggatgt 17160
tgggacgcgg aatgcgacgc tacaggcgac ggcgtgctat ccgcaagcaa ttgcggggtg 17220
gtttttacc agccttaatt ccaattatcg ctgctgcaat tggcgcgata ccaggcatag 17280
cttccgtggc ggttcaggcc tcgcaacgac attgacattg gaaaaaaacg tataaataaa 17340
aaaaaaaaaa tacaatggac tctgacactc ctggtcctgt gactatgttt tcttagagat 17400
ggaagacatc aatttttcat ccttggctcc gcgacacggc acgaagccgt acatgggcac 17460
ctggagcgac atcggcacga gccaactgaa cgggggcgcc ttcaattgga gcagtatctg 17520
gagcgggctt aaaaattttg gctcaaccat aaaaacatac gggaacaaag cttggaacag 17580
cagtacagga caggcgctta gaaataaact taaagaccag aacttccaac aaaaagtagt 17640
cgatgggata gcttccggca tcaatggagt ggtagatttg gctaaccagg ctgtgcagaa 17700
aaagataaac agtcgtttgg acccgccgcc agcaacccca ggtgaaatgc aagtggagga 17760
agaaattcct ccgccagaaa aacgaggcga caagcgtccg cgtcccgatt tggaagagac 17820
gctggtgacg cgcgtagatg aaccgccttc ttatgaggaa gcaacgaagc ttggaatgcc 17880
caccactaga ccgatagccc caatggccac cggggtgatg aaaccttctc agttgcatcg 17940
acccgtcacc ttggatttgc cccctccccc tgctgctact gctgtacccg cttctaagcc 18000
tgtcgctgcc ccgaaaccag tcgccgtagc caggtcacgt cccgggggcg ctcctcgtcc 18060
aaatgcgcac tggcaaaata ctctgaacag catcgtgggt ctaggcgtgc aaagtgtaaa 18120
acgccgtcgc tgcttttaat taaatatgga gtagcgctta acttgcctat ctgtgtatat 18180
gtgtcattac acgccgtcac agcagcagag gaaaaaagga agaggtcgtg cgtcgacgct 18240
gagttacttt caagatggcc accccatcga tgctgcccca atgggcatac atgcacatcg 18300
ccggacagga tgcttcggag tacctgagtc cgggtctggt gcagttcgcc cgcgccacag 18360
acacctactt caatctggga aataagttta gaaatcccac cgtagcgccg acccacgatg 18420
tgaccaccga ccgtagccag cggctcatgt tgcgcttcgt gcccgttgac cgggaggaca 18480
atacatactc ttacaaagtg cggtacaccc tggccgtggg cgacaacaga gtgctggata 18540
tggccagcac gttctttgac attaggggtg tgttggacag aggtcccagt ttcaaaccct 18600
attctggtac ggcttacaac tccctggctc ctaaaggcgc tccaaataca tctcagtgga 18660
ttgcagaagg tgtaaaaaat acaactggtg aggaacacgt aacagaagag gaaaccaata 18720
ctactactta cacttttggc aatgctcctg taaaagctga agctgaaatt acaaaagaag 18780
gactcccagt aggtttggaa gtttcagatg aagaaagtaa accgatttat gctgataaaa 18840
catatcagcc agaacctcag ctgggagatg aaacttggac tgaccttgat ggaaaaaccg 18900
aaaagtatgg aggcagggct ctcaaacccg atactaagat gaaaccatgc tacgggtcct 18960
ttgccaaacc tactaatgtg aaaggcggtc aggcaaaaca aaaaacaacg gagcagccaa 19020
atcagaaagt cgaatatgat atcgacatgg agtttttga tgcggcatcg cagaaaacaa 19080
acttaagtcc taaaattgtc atgtatgcag aaaatgtaaa tttggaaact ccagacactc 19140
atgtagtgta caaacctgga acagaagaca caagttccga agctaatttg ggacaacaat 19200
ctatgcccaa cagacccaac tacattggct tcagagataa ctttattgga cttatgtact 19260
ataacagtac tggtaacatg gggtgctgg ctggtcaagc gtctcagtta aatgcagtgg 19320
ttgacttgca ggacagaaac acagaacttt cttaccaact cttgcttgac tctctgggcg 19380
acagaaccag atactttagc atgtggaatc aggctgtgga cagttatgat cctgatgtac 19440
gtgttattga aaatcatggt gtggaagatg aacttcccaa ctactgtttt ccactggacg 19500
gcataggtgt tccaacaacc agttacaaat caatagttcc aaatggagac aatgcgccta 19560
attggaagga acctgaagta aatggaacaa gtgagatcgg acagggtaat ttgtttgcca 19620
tggaaattaa ccttcaagcc aatctatggc gaagtttcct ttattccaat gtggctctat 19680
atctcccaga ctcgtacaaa tacaccccgt ccaatgtcac tcttccagaa aacaaaaaca 19740
cctacgacta catgaacggg cgggtggtgc cgccatctct agtagacacc tatgtgaaca 19800
ttggtgccag gtggtctctg gatgccatgg acaatgtcaa cccattcaac caccaccgta 19860
acgctggctt gcgttaccga tccatgcttc tgggtaacgg acgttatgtg cctttccaca 19920
tacaagtgcc tcaaaaattc ttcgctgtta aaaacctgct gcttctccca ggctcctaca 19980
cttatgagtg gaactttagg aaggatgtga acatggttct acagagttcc ctcggtaacg 20040
acctgcgggt agatggcgcc agcatcagtt tcacgagcat caacctctat gctacttttt 20100
tccccatggc tcacaacacc gcttccaccc ttgaagccat gctgcggaat gacaccaatg 20160
atcagtcatt caacgactac ctatctgcag ctaacatgct ctaccccatt cctgccaatg 20220
caaccaatat tcccatttcc attccttctc gcaactgggc ggctttcaga ggctggtcat 20280
ttaccagact gaaaaccaaa gaaactccct ctttggggtc tggatttgac cctactttg 20340 tctattctgg ttctattccc tacctggatg gtaccttcta cctgaaccac acttttaaga 20400
aggtttccat catgtttgac tcttcagtga gctggcctgg aaatgacagg ttactatctc 20460
ctaacgaatt tgaaataaag cgcactgtgg atggcgaagg ctacaacgta gcccaatgca 20520
acatgaccaa agactggttc ttggtacaga tgctcgccaa ctacaacatc ggctatcagg 20580
gcttctacat tccagaagga tacaaagatc gcatgtattc atttttcaga aacttccagc 20640
ccatgagcag gcaggtggtt gatgaggtca attacaaaga cttcaaggcc gtcgccatac 20700
cctaccaaca caacaactct ggctttgtgg gttacatggc tccgaccatg cgccaaggtc 20760
aaccctatcc cgctaactat ccctatccac tcattggaac aactgccgta aatagtgtta 20820
cgcagaaaaa gttcttgtgt gacagaacca tgtggcgcat accgttctcg agcaacttca 20880
tgtctatggg ggcccttaca gacttgggac agaatatgct ctatgccaac tcagctcatg 20940
ctctggacat gacctttgag gtggatccca tggatgagcc caccctgctt tatcttctct 21000

-continued

```
tcgaagtttt cgacgtggtc agagtgcatc agccacaccg cggcatcatc gaggcagtct  21060
acctgcgtac accgttctcg gccggtaacg ctaccacgta agaagcttct tgcttcttgc  21120
aaatagcagc tgcaaccatg gcctgcggat cccaaaacgg ctccagcgag caagagctca  21180
gagccattgt ccaagacctg ggttgcggac cctatttttt gggaacctac gataagcgct  21240
tcccggggtt catggccccc gataagctcg cctgtgccat tgtaaatacg gccggacgtg  21300
agacgggggg agagcactgg ttggctttcg gttggaaccc acgttctaac acctgctacc  21360
tttttgatcc ttttggattc tcggatgatc gtctcaaaca gatttaccag tttgaatatg  21420
agggtctcct gcgccgcagc gctcttgcta ccaaggaccg ctgtattacg ctggaaaaat  21480
ctacccagac cgtgcagggt ccccgttctg ccgcctgcgg acttttctgc tgcatgttcc  21540
ttcacgcctt tgtgcactgg cctgaccgtc ccatggacgg aaaccccacc atgaaattgc  21600
taactggagt gccaaacaac atgcttcatt ctcctaaagt ccagcccacc ctgtgtgaca  21660
atcaaaaagc actctaccat tttcttaata cccattcgcc ttattttcgc tcccatcgta  21720
cacacatcga aagggccact gcgttcgacc gtatggatgt tcaataatga ctcatgtaaa  21780
caacgtgttc aataaacatc actttatttt tttacatgta tcaaggctct gcattactta  21840
tttatttaca agtcgaatgg gttctgacga gaatcagaat gacccgcagg cagtgatacg  21900
ttgcggaact gatacttggg ttgccacttg aattcgggaa tcaccaactt gggaaccggt  21960
atatcgggca ggatgtcact ccacagcttt ctggtcagct gcaaagctcc aagcaggtca  22020
ggagccgaaa tcttgaaatc acaattagga ccagtgcttt gagcgcgaga gttgcggtac  22080
accggattgc agcactgaaa caccatcagc gacggatgtc tcacgcttgc cagcacggtg  22140
ggatctgcaa tcatgcccac atccagatct tcagcattgg caatgctgaa cggggtcatc  22200
ttgcaggtct gcctacccat ggcgggcacc caattaggct tgtggttgca atcgcagtgc  22260
agggggatca gtatcatctt ggcctgatcc tgtctgattc ctggatacac ggctctcatg  22320
aaagcatcat attgcttgaa agcctgctgg gctttactac cctcggtata aaacatcccg  22380
caggacctgc tcgaaaactg gttagctgca cagccggcat cattcacaca gcagcgggcg  22440
tcattgttag ctatttgcac cacacttctg ccccagcggt tttgggtgat tttggttcgc  22500
tcgggattct cctttaaggc tcgttgtccg ttctcgctgg ccacatccat ctcgataatc  22560
tgctccttct gaatcataat attgccatgc aggcacttca gcttgccctc ataatcattg  22620
cagccatgag gccacaacgc acagcctgta cattcccaat tatggtgggc gatctgagaa  22680
aaagaatgta tcattccctg cagaaatctt cccatcatcg tgctcagtgt cttgtgacta  22740
gtgaaagtta actggatgcc tcggtgctcc tcgtttacgt actggtgaca gatgcgcttg  22800
tattgttcgt gttgctcagg cattagttta aaagaggttc taagttcgtt atccagcctg  22860
tacttctcca tcagcagaca catcacttcc atgcctttct cccaagcaga caccaggggc  22920
aagctaatcg gattcttaac agtgcaggca gcagctcctt tagccagagg gtcatcttta  22980
gcgatcttct caatgcttct tttgccatcc ttctcaacga tgcgcacggg cgggtagctg  23040
aaacccactg ctacaagttg cgcctcttct ctttcttctt cgctgtcttg actgatgtct  23100
tgcatgggga tatgtttggt cttccttggc ttctttttgg ggggtatcgg aggaggagga  23160
ctgtcgctcc gttccggaga cagggaggat tgtgacgttt cgctcaccat taccaactga  23220
ctgtcggtag aagaacctga ccccacacgg cgacaggtgt ttctcttcgg gggcagaggt  23280
ggaggcgatt gcgaagggct gcggtccgac ctggaaggcg gatgactggc agaacccctt  23340
ccgcgttcgg gggtgtgctc cctgtggcgg tcgcttaact gatttccttc gcggctggcc  23400
```

-continued

```
attgtgttct cctaggcaga gaaacaacag acatggaaac tcagccattg ctgtcaacat  23460
cgccacgagt gccatcacat ctcgtcctca gcgacgagga aaaggagcag agcttaagca  23520
ttccaccgcc cagtcctgcc accacctcta ccctagaaga taaggaggtc gacgcatctc  23580
atgacatgca gaataaaaaa gcgaaagagt ctgagacaga catcgagcaa gacccgggct  23640
atgtgacacc ggtggaacac gaggaagagt tgaaacgctt tctagagaga gaggatgaaa  23700
actgcccaaa acaacgagca gataactatc accaagatgc tggaaatagg gatcagaaca  23760
ccgactacct catagggctt gacggggaag acgcgctcct taaacatcta gcaagacagt  23820
cgctcatagt caaggatgca ttattggaca gaactgaagt gcccatcagt gtggaagagc  23880
tcagccgcgc ctacgagctt aacctctttt cacctcgtac tccccccaaa cgtcagccaa  23940
acggcacctg cgagccaaat cctcgcttaa acttttatcc agcttttgct gtgccagaag  24000
tactggctac ctatcacatc ttttttaaaa atcaaaaaat tccagtctcc tgccgcgcta  24060
atcgcacccg cgccgatgcc ctactcaatc tgggacctgg ttcacgctta cctgatatag  24120
cttccttgga agaggttcca aagatcttcg agggtctggg caataatgag actcgggccg  24180
caaatgctct gcaaaaggga gaaaatggca tggatgagca tcacagcgtt ctggtggaat  24240
tggaaggcga taatgccaga ctcgcagtac tcaagcgaag catcgaggtc acacacttcg  24300
catatcccgc tgtcaacctg ccccctaaag tcatgacggc ggtcatggac cagttactca  24360
ttaagcgcgc aagtcccctt tcagaagaca tgcatgaccc agatgcctgt gatgagggta  24420
aaccagtggt cagtgatgag cagctaaccc gatggctggg caccgactct cccagggatt  24480
tggaagagcg tcgcaagctt atgatggccg tggtgctggt taccgtagaa ctagagtgtc  24540
tccgacgttt ctttaccgat tcagaaacct tgcgcaaact cgaagagaat ctgcactaca  24600
cttttagaca cggctttgtg cggcaggcat gcaagatatc taacgtggaa ctcaccaacc  24660
tggtttccta catgggtatt ctgcatgaga atcgcctagg acaaagcgtg ctgcacagca  24720
ccctgaaggg ggaagcccgc cgtgattaca tccgcgattg tgtctatctg tacctgtgcc  24780
aaacgtggca aaccggcatg ggtgtatggc agcaatgttt agaagaacag aacttgaaag  24840
agcttgacaa gctcttacag aaatctctta aggttctgtg gacagggttc gacgagcgca  24900
ccgtcgcttc cgacctggca gacctcatct tcccagagcg tctcagggtt actttgcgaa  24960
acggattgcc tgactttatg agccagagca tgcttaacaa ttttcgctct ttcatcctgg  25020
aacgctccgg tatcctgccc gccacctgct gcgcactgcc ctccgacttt gtgcctctca  25080
cctaccgcga gtgccccccg ccgctatgga gtcactgcta cctgttccgt ctggccaact  25140
atctctccta ccactcggat gtgatcgagg atgtgagcgg agacggcttg ctggagtgtc  25200
actgccgctg caatctgtgc acgccccacc ggtccctagc ttgcaacccc cagttgatga  25260
gcgaaaccca gataataggc acctttgaat tgcaaggccc cagcagccaa ggcgatgggt  25320
cttctcctgg gcaaagttta aaactgaccc cgggactgtg gacctccgcc tacttgcgca  25380
agtttgctcc ggaagattac cacccctatg aaatcaagtt ctatgaggac caatcacagc  25440
ctccaaaggc cgaactttcg gcctgcgtca tcacccaggg ggcaattctg gcccaattgc  25500
aagccatcca aaaatcccgc caagaatttc tactgaaaaa gggtaagggg gtctaccttg  25560
acccccagac cggcgaggaa ctcaacacaa ggttccctca ggatgtccca acgacgagaa  25620
aacaagaagt tgaaggtgca gccgccgccc ccagaagata tggaggaaga ttgggacagt  25680
caggcagagg aggcggagga ggacagtctg gaggacagtc tggaggaaga cagtttggag  25740
```

-continued gaggaaaacg aggaggcaga ggaggtggaa gaagtaaccg ccgacaaaca gttatcctcg 25800
gctgcggaga caagcaacag cgctaccatc tccgctccga gtcgaggaac ccggcggcgt 25860
cccagcagta gatgggacga gaccggacgc ttcccgaacc caaccagcgc ttccaagacc 25920
ggtaagaagg atcggcaggg atacaagtcc tggcgggggc ataagaatgc catcatctcc 25980
tgcttgcatg agtgcggggg caacatatcc ttcacgcggc gctacttgct attccaccat 26040
ggggtgaact ttccgcgcaa tgttttgcat tactaccgtc acctccacag cccctactat 26100
agccagcaaa tcccggcagt ctcgacagat aaagacagcg gcggcgacct ccaacagaaa 26160
accagcagcg gcagttagaa aatacacaac aagtgcagca acaggaggat taaagattac 26220
agccaacgag ccagcgcaaa cccgagagtt aagaaatcgg atctttccaa ccctgtatgc 26280
catcttccag cagagtcggg gtcaagagca ggaactgaaa ataaaaaacc gatctctgcg 26340
ttcgctcacc agaagttgtt tgtatcacaa gagcgaagat caacttcagc gcactctcga 26400
ggacgccgag gctctcttca acaagtactg cgcgctgact cttaaagagt aggcagcgac 26460
cgcgcttatt caaaaaaggc gggaattaca tcatcctcga catgagtaaa gaaattccca 26520
cgccttacat gtggagttat caaccccaaa tgggattggc ggcaggcgcc tcccaggact 26580
actccacccg catgaattgg ctcagcgccg ggccttctat gatttctcga gttaatgata 26640
tacgcgccta ccgaaaccaa atacttttgg aacagtcagc tcttaccacc acgccccgcc 26700
aacaccttaa tcccagaaat tggcccgccg ccctagtgta ccaggaaagt cccgctccca 26760
ccactgtatt acttcctcga gacgcccagg ccgaagtcca aatgactaat gcaggtgcgc 26820
gttagctggc ggctccaccc tatgtcgtca caggcctcgg cataatataa aacgcctgat 26880
gatcagaggc cgaggtatcc agctcaacga cgagtcggtg agctctccgc ttggtctacg 26940
accagacgga atctttcaga ttgccggctg cgggagatct tccttcaccc ctcgtcaggc 27000
tgttctgact ttggaaagtt cgtcttcgca accccgctcg ggcggaatcg ggaccgttca 27060
atttgtggag gagtttactc cctctgtcta cttcaacccc ttctccggat ctcctgggca 27120
ttacccggac gagttcatac cgaacttcga cgcgattagc gagtcagtgg acggctacga 27180
ttgatgtctg gtgacgcggc tgagctatct cggctgcgac atctagacca ctgccgccgc 27240
tttcgctgct ttgcccggga actcattgag ttcatctact tcgaactccc caaggatcac 27300
cctcaaggtc cggcccacgg agtgcggatt tctatcgaag gcaaaataga ctctcgcctg 27360
caacgaattt tctcccagcg gcccgtgctg atcgagcgag accagggaaa caccacggtt 27420
tccatctact gcatttgtaa tcaccccgga ttgcatgaaa gcctttgctg tcttatgtgt 27480
actgagttta ataaaaactg aattaagact ctcctacgga ctgccgcttc ttcaacccgg 27540
attttacaac cagaagaacg aaacttttcc tgtcgtccag gactctgtta acttcacctt 27600
tcctactcac aaactagaag ctcaacgact acaccgcttt tccagaagca ttttccctac 27660
taatactact ttcaaaaccg gaggtgagct ccaaggtctt cctacagaaa acccttgggt 27720
ggaagcgggc cttgtagtgc taggaattct tgcgggtggg cttgtgatta ttctttgcta 27780
cctatacaca ccttgcttca ctttcttagt ggtgttgtgg tattggttta aaaaatgggg 27840
cccatactag tcttgcttgt tttactttcg cttttggaac cgggttctgc caattacgat 27900
ccatgtctag acttcgaccc agaaaactgc acacttactt ttgcacccga cacaagccgc 27960
atctgtggag ttcttattaa gtgcggatgg gaatgcaggt ccgttgaaat tacacacaat 28020
aacaaaacct ggaacaatac cttatccacc acatgggagc caggagttcc cgagtggtac 28080
actgtctctg tccgaggtcc tgacggttcc atccgcatta gtaacaacac tttcattttt 28140
tctgaaatgt gcgatctggc catgttcatg agcaaacagt attctctatg gcctcctagc 28200
aaggacaaca tcgtaacgtt ctccattgct tattgcttgt gcgcttgcct tcttactgct 28260
ttactgtgcg tatgcataca cctgcttgta accactcgca tcaaaaacgc caataacaaa 28320
gaaaaaatgc cttaacctct ttctgtttac agacatggct tctcttacat ctctcatatt 28380
tgtcagcatt gtcactgccg ctcatggaca aacagtcgtc tctatccctc taggacataa 28440
ttacactctc ataggacccc caatcacttc agaggtcatc tgggccaaac tgggaagcgt 28500
tgattacttt gatataatct gcaacaaaac aaaaccaata atagtaactt gcaacataca 28560
aaatcttaca ttgattaatg ttagcaaagt ttacagcggt tactattatg gttatgacag 28620
atacagtagt caatatagaa attacttggt tcgtgttacc cagttgaaaa ccacgaaaat 28680
gccaaatatg gcaaagattc gatccgatga caattctcta gaaactttta catctcccac 28740
cacacccgac gaaaaaaaca tcccagattc aatgattgca attgttgcag cggtggcagt 28800
ggtgatggca ctaataataa tatgcatgct tttatatgct tgtcgctaca aaaagtttca 28860
tcctaaaaaa caagatctcc tactaaggct taacatttaa tttcttttta tacagccatg 28920
gtttccacta ccacattcct tatgcttact agtctcgcaa ctctgacttc tgctcgctca 28980
cacctcactg taactatagg ctcaaactgc acactaaaag gacctcaagg tggtcatgtc 29040
ttttggtgga gaatatatga caatggatgg tttacaaaac catgtgacca acctggtaga 29100
tttttctgca acggcagaga cctaaccatt atcaacgtga cagcaaatga caaaggcttc 29160
tattatggaa ccgactataa aagtagttta gattataaca ttattgtact gccatctacc 29220
actccagcac cccgcacaac tactttctct agcagcagtg tcgctaacaa tacaatttcc 29280
aatccaacct ttgccgcgct tttaaaacgc actgtgaata attctacaac ttcacataca 29340
acaatttcca cttcaacaat cagcattatc gctgcagtga caattggaat atctattctt 29400
gtttttacca taacctacta cgcctgctgc tatagaaaag acaaacataa aggtgatcca 29460
ttacttagat ttgatattta atttgttctt ttttttttta tttacagtat ggtgaacacc 29520
aatcatggta cctagaaatt tcttcttcac catactcatt tgtgcattta atgtttgcgc 29580
tactttcaca gcagtagcca cagcaacccc agactgtata ggagcatttg cttcctatgc 29640
actttttgct tttgttactt gcatctgcgt atgtagcata gtctgcctgg ttattaattt 29700
tttccaactt atagactgga tccttgtgcg aattgcctac ctgcgccacc atcccgaata 29760
ccgcaaccaa aatatcgcgg cacttcttag actcatctaa aaccatgcag gctatactac 29820
caatattttt gcttctattg cttccctacg ctgtctcaac cccagctgcc tatagtactc 29880
caccagaaca ccttagaaaa tgcaaattcc aacaaccgtg gtcatttctt gcttgctatc 29940
gagaaaaatc agaaattccc ccaaatttaa taatgattgc tggaataatt aatataatct 30000
gttgcaccat aatttcattt ttgatatacc ccctatttga ttttggctgg aatgctccca 30060
atgcacatga tcatccacaa gacccagagg aacacattcc cctacaaaac atgcaacatc 30120
caatagcgct aatagattac gaaagtgaac cacaaccccc actactccct gctattagtt 30180
acttcaacct aaccggcgga gatgactgaa acactcacca cctccaattc cgccgaggat 30240
ctgctcgata tggacggccg cgtctcagaa cagcgactcg cccaactacg catccgccag 30300
cagcaggaac gcgcggccaa agagctcaga gatgtcatcc aaattcacca atgcaaaaaa 30360
ggcatattct gtttggtaaa acaagccaag atatcctacg agatcaccgc tactgaccat 30420
cgcctctctt acgaacttgg cccccaacga caaaaattta cctgcatggt gggaatcaac 30480

-continued

```
cccatagtta tcacccagca aagtggagat actaagggtt gcattcactg ctcctgcgat  30540
tccatcgagt gcacctacac cctgctgaag accctatgcg gcctaagaga cctgctacca  30600
atgaattaaa aaatgattaa taaaaaatca cttacttgaa atcagcaata aggtctctgt  30660
tgaaattttc tcccagcagc acctcacttc cctcttccca actctggtat tctaaacccc  30720
gttcagcggc atactttctc catactttaa aggggatgtc aaattttagc tcctctcctg  30780
tacccacaat cttcatgtct ttcttcccag atgaccaaga gagtccggct cagtgactcc  30840
ttcaaccctg tctaccccta tgaagatgaa agcacctccc aacacccctt tataaaccca  30900
gggtttattt ccccaaatgg cttcacacaa agcccaaacg gagttcttac tttaaaatgt  30960
ttaaccccac taacaaccac aggcggatct ctacagctaa aagtgggagg gggacttaca  31020
gtggatgaca ccaacggttt tttgaaagaa aacataagtg ccaccacacc actcgttaag  31080
actggtcact ctataggttt accactagga gccggattgg gaacgaatga aaataaactt  31140
tgtatcaaat taggacaagg acttacattc aattcaaaca acatttgcat tgatgacaat  31200
attaacacct tatggacagg agtcaacccc accgaagcca actgtcaaat catgaactcc  31260
agtgaatcta atgattgcaa attaattcta acactagtta aaactggagc actagtcact  31320
gcatttgttt atgttatagg agtatctaac aattttaata tgctaactac acacagaaat  31380
ataaatttta ctgcagagct gtttttcgat tctactggta atttactaac tagactctca  31440
tccctcaaaa ctccacttaa tcataaatca ggacaaaaca tggctactgg tgccattact  31500
aatgctaaag gtttcatgcc cagcacgact gcctatcctt tcaatgataa ttctagagaa  31560
aaagaaaact acatttacgg aacttgttac tacacagcta gtgatcgcac tgcttttccc  31620
attgacatat ctgtcatgct taaccgaaga gcaataaatg acgagacatc atattgtatt  31680
cgtataactt ggtcctggaa cacaggagat gccccagagg tgcaaacctc tgctacaacc  31740
ctagtcacct ccccatttac cttttactac atcagagaag acgactgaca aataaagttt  31800
aacttgttta tttgaaaatc aattcacaaa atccgagtag ttattttgcc tccccccttcc  31860
catttaacag aatacaccaa tctctcccca cgcacagctt taaacatttg gataccatta  31920
gatatagaca tggttttaga ttccacattc caaacagttt cagagcgagc caatctgggg  31980
tcagtgatag ataaaaaatcc atcgggatag tcttttaaag cgctttcaca gtccaactgc  32040
tgcggatgga ctccggagtc tggatcacgg tcatctggaa gaagaacgat gggaatcata  32100
atccgaaaac ggtatcggac gattgtgtct catcaaaccc acaagcagcc gctgtctgcg  32160
tcgctccgtg cgactgctgt ttatgggatc agggtccaca gtgtcctgaa gcatgatttt  32220
aatagccctt aacatcaact ttctggtgcg atgcgcgcag caacgcattc tgatttcact  32280
caaatctttg cagtaggtac aacacattat tacaatattg tttaataaac cataattaaa  32340
agcgctccag ccaaaactca tatctgatat aatcgcccct gcatgaccat cataccaaag  32400
tttaatataa attaaatgac gttccctcaa aaacacacta cccacataca tgatctcttt  32460
tggcatgtgc atattaacaa tctgtctgta ccatggacaa cgttggttaa tcatgcaacc  32520
caatataacc ttccggaacc acactgccaa caccgctccc ccagccatgc attgaagtga  32580
accctgctga ttacaatgac aatgaagaac ccaattctct cgaccgtgaa tcacttgaga  32640
atgaaaaata tctatagtgg cacaacatag acataaatgc atgcatcttc tcataatttt  32700
taactcctca ggatttagaa acatatccca gggaatagga agctcttgca gaacagtaaa  32760
gctggcagaa caaggaagac cacgaacaca acttacacta tgcatagtca tagtatcaca  32820
atctggcaac agcgggtggt cttcagtcat agaagctcgg gtttcatttt cctcacaacg  32880
```

```
tggtaactgg gctctggtgt aagggtgatg tctggcgcat gatgtcgagc gtgcgcgcaa  32940

ccttgtcata atggagttgc ttcctgacat tctcgtattt tgtatagcaa aacgcggccc  33000

tggcagaaca cactcttctt cgccttctat cctgccgctt agcgtgttcc gtgtgatagt  33060

tcaagtacaa ccacactctt aagttggtca aaagaatgct ggcttcagtt gtaatcaaaa  33120

ctccatcgca tctaatcgtt ctgaggaaat catccacggt agcatatgca aatcccaacc  33180

aagcaatgca actggattgt gtttcaagca ggagaggaga gggaagagac ggaagaacca  33240

tgttaatttt tattccaaac gatctcgcag tacttcaaat tgtagatcgc gcagatggca  33300

tctctcgccc ccactgtgtt ggtgaaaaag cacagctaga tcaaaagaaa tgcgattttc  33360

aaggtgctca acggtggctt ccagcaaagc ctccacgcgc acatccaaga acaaaagaat  33420

accaaaagaa ggagcatttt ctaactcctc aatcatcata ttacattcct gcaccattcc  33480

cagataattt tcagctttcc agccttgaat tattcgtgtc agttcttgtg gtaaatccaa  33540

tccacacatt acaaacaggt cccggagggc gccctccacc accattctta aacacaccct  33600

cataatgaca aaatatcttg ctcctgtgtc acctgtagcg aattgagaat ggcaacatca  33660

attgacatgc ccttggctct aagttcttct ttaagttcta gttgtaaaaa ctctctcata  33720

ttatcaccaa actgcttagc cagaagcccc ccgggaacaa gagcagggga cgctacagtg  33780

cagtacaagc gcagacctcc ccaattggct ccagcaaaaa caagattgga ataagcatat  33840

tgggaaccgc cagtaatatc atcgaagttg ctggaaatat aatcaggcag agtttcttgt  33900

aaaaattgaa taaaagaaaa atttgccaaa aaaacattca aaacctctgg gatgcaaatg  33960

caataggtta ccgcgctgcg ctccaacatt gttagttttg aattagtctg caaaaataaa  34020

aaaaaaaaca agcgtcatat catagtagcc tgacgaacag atggataaat cagtctttcc  34080

atcacaagac aagccacagg gtctccagct cgaccctcgt aaaacctgtc atcatgatta  34140

aacaacagca ccgaaagttc ctcgcggtga ccagcatgaa taattcttga tgaagcatac  34200

aatccagaca tgttagcatc agttaacgag aaaaaaacagc caacatagcc tttgggtata  34260

attatgctta atcgtaagta tagcaaagcc accccctcgcg gatacaaagt aaaaggcaca  34320

ggagaataaa aaatataatt atttctctgc tgctgttcag gcaacgtcgc ccccggtccc  34380

tctaaataca catacaaagc ctcatcagcc atggcttacc agacaaagta cagcgggcac  34440

acaaagcaca agctctaaag tgactctcca acctctccac aatatatata tacacaagcc  34500

ctaaactgac gtaatgggag taaagtgtaa aaaatcccgc caaacccaac acacaccccg  34560

aaactgcgtc accagggaaa agtacagttt cacttccgca atcccaacag gcgtaacttc  34620

ctctttctca cggtacgtga tatcccacta acttgcaacg tcattttccc acggtcgcac  34680

cgccccctttt agccgttaac cccacagcca atcaccacac gatccacact ttttaaaatc  34740

acctcattta catattggca ccattccatc tataaggtat attattgatg atg         34793
```

<210> SEQ ID NO 7
<211> LENGTH: 34801
<212> TYPE: DNA
<213> ORGANISM: Artificial Sequence
<220> FEATURE:
<223> OTHER INFORMATION: Fully synthetic

<400> SEQUENCE: 7

```
catcatcaat aatatacctt atagatggaa tggtgccaat atgtaaatga ggtgatttta     60

aaaagtgtgg atcgtgtggt gattggctgt ggggttaacg gctaaaaggg gcggtgcgac    120
```

-continued

```
cgtgggaaaa tgacgttttg tgggggtgga gtttttttgc aagttgtcgc gggaaatgtg    180
acgcataaaa aggctacaca ggaagtgaca attttcgcgc ggttttaggc ggatgttgta    240
gtaaatttgg gcgtaaccga gtaagatttg gccattttcg cgggaaaact gaataagagg    300
aagtgaaatc tgaataattt tgtgttactc atagcgcgta atatttgtct agggccgcgg    360
ggactttgac cgtttacgtg gagactcgcc caggtgtttt tctcaggtgt tttccgcgtt    420
cgggtcaaag ttggcgtttt attattatag tcagctgacg tgtagtgtat ttatacccgg    480
tgagttcctc aagaggccac tcttgagtgc cagcgagtag agttttctcc tccgagccgc    540
tccgacaccg ggactgaaaa atgagagatt tgcgatttct gcctcaggaa ataatctctg    600
ctgagactgg aaatgaaata ttggagcttg tggtgcacgc cctgatggga gacgatccgg    660
agccacctgt gcagcttttt gagcctccta cgcttcagga actgtatgat ttagaggtag    720
agggatcgga ggattctaat gaggaagctg taaatggctt ttttaccgat tctatgcttt    780
tagctgctaa tgaagggtta gaattagatc cgcctttgga cacttttgat actccagggg    840
taattgtgga aagcggtaca ggtgtaagaa aattacctga tttgagttcc gtggactgtg    900
atttgcactg ctatgaagac gggtttcctc cgagtgatga ggaggaccat gaaaaggagc    960
agtccatgca gactgcagcg ggtgagggag tgaaggctgc caatgttggt tttcagttgg   1020
attgcccgga gcttcctgga catggctgta agtcttgtga atttcacagg aaaaatactg   1080
gagtaaagga actgttatgt tcgctttgtt atatgagaac gcactgccac tttatttaca   1140
gtaagtgtgt ttaagttaaa atttaaagga atatgctgtt tttcacatgt atattgagtg   1200
tgagttttgt gcttcttatt ataggtcctg tgtctgatgc tgatgaatca ccatctcctg   1260
attctactac ctcacctcct gagattcaag cacctgttcc tgtggacgtg cgcaagccca   1320
ttcctgtgaa gcttaagcct gggaaacgtc cagcagtgga aaaacttgag gacttgttac   1380
agggtgggga cggacctttg gacttgagta cacggaaacg tccaagacaa taagtgttcc   1440
atatccgtgt ttacttaagg tgacgtcaat atttgtgtga cagtgcaatg taataaaaat   1500
atgttaactg ttcactggtt tttattgctt tttgggcggg gactcaggta tataagtaga   1560
agcagacctg tgtggttagc tcataggagc tggctttcat ccatggaggt ttgggccatt   1620
ttggaagacc ttaggaagac taggcaactg ttagagaacg cttcggacgg agtctccggt   1680
ttttggagat tctggttcgc tagtgaatta gctagggtag tttttaggat aaaacaggac   1740
tataaacaag aatttgaaaa gttgttggta gattgcccag gactttttga agctcttaat   1800
ttgggccatc aggttcactt taaagaaaaa gttttatcag ttttagactt ttcaacccca   1860
ggtagaactg ctgctgctgt ggcttttctt acttttatat tagataaatg gatcccgcag   1920
actcatttca gcaggggata cgttttggat ttcatagcca cagcattgtg gagaacatgg   1980
aaggttcgca agatgaggac aatcttaggt tactggccag tgcagccttt gggtgtagcg   2040
ggaatcctga ggcatccacc ggtcatgcca gcggttctgg aggaggaaca gcaagaggac   2100
aacccgagag ccggcctgga ccctccagtg gaggaggcgg agtagctgac ttgtctcctg   2160
aactgcaacg ggtgcttact ggatctacgt ccactggacg ggataggggc gttaagaggg   2220
agagggcatc tagtggtact gatgctagat ctgagttggc tttaagttta atgagtcgca   2280
gacgtcctga aaccatttgg tggcatgagg ttcagaaaga gggaagggat gaagtttctg   2340
tattgcagga gaaatattca ctggaacagg tgaaaacatg ttggttggag cctgaggatg   2400
attgggaggt ggccattaaa aattatgcca agatagcttt gaggcctgat aaacagtata   2460
agattactag acggattaat atccggaatg cttgttacat atctggaaat ggggctgagg   2520
```

-continued

```
tggtaataga tactcaagac aaggcagtta ttagatgctg catgatggat atgtggcctg   2580
gggtagtcgg tatggaagca gtaacttttg taaatgttaa gtttagggga gatggttata   2640
atggaatagt gtttatggcc aataccaaac ttatattgca tggttgtagc ttttttggtt   2700
tcaacaatac ctgtgtagat gcctggggac aggttagtgt acggggatgt agtttctatg   2760
cgtgttggat tgccacagct ggcagaacca agagtcaatt gtctctgaag aaatgcatat   2820
ttcaaagatg taacctgggc attctgaatg aaggcgaagc aagggtccgc cactgcgctt   2880
ctacagatac tggatgtttt attttgatta agggaaatgc cagcgtaaag cataacatga   2940
tttgcggtgc ttccgatgag aggccttatc aaatgctcac ttgtgctggt gggcattgta   3000
atatgctggc tactgtgcat attgtttccc atcaacgcaa aaaatggcct gtttttgatc   3060
acaatgtgat gacgaagtgt accatgcatg caggtgggcg tagaggaatg tttatgcctt   3120
accagtgtaa catgaatcat gtgaaagtgt tgttggaacc agatgccttt tccagaatga   3180
gcctaacagg aatttttgac atgaacatgc aaatctggaa gatcctgagg tatgatgata   3240
cgagatcgag ggtacgcgca tgcgaatgcg gaggcaagca tgccaggttc cagccggtgt   3300
gtgtagatgt gactgaagat ctcagaccgg atcatttggt tattgcccgc actggagcag   3360
agttcggatc cagtggagaa gaaactgact aaggtgagta ttgggaaaac tttggggtgg   3420
gattttcaga tggacagatt gagtaaaaat ttgttttttc tgtcttgcag ctgtcatgag   3480
tggaaacgct tcttttaagg ggggagtctt cagcccttat ctgacagggc gtctcccatc   3540
ctgggcagga gttcgtcaga atgttatggg atctactgtg gatggaagac ccgtccaacc   3600
cgccaattct tcaacgctga cctatgctac tttaagttct tcacctttgg acgcagctgc   3660
agctgccgcc gccgcttctg ttgccgctaa cactgtgctt ggaatgggtt actatggaag   3720
catcatggct aattccactt cctctaataa cccttctacc ctgactcagg acaagttact   3780
tgtccttttg gcccagctgg aggctttgac ccaacgtctg ggtgaacttt ctcagcaggt   3840
ggtcgagttg cgagtacaaa ctgagtctgc tgtcggcacg gcaaagtcta aataaaaaaa   3900
tcccagaatc aatgaataaa taaacaagct tgttgttgat ttaaaatcaa gtgtttttat   3960
ttcatttttc gcgcacggta tgccctagac caccgatctc tatcattgag aactcggtgg   4020
atttttttcca ggatcctata gaggtgggat tgaatgttta gatacatggg cattaggccg   4080
tctttggggt ggagatagct ccattgaagg gattcatgct ccggggtagt gttgtaaatc   4140
acccagtcat aacaaggtcg cagtgcatgg tgttgcacaa tatcttttag aagtaggctg   4200
attgccacag ataagccctt ggtgtaggtg tttacaaacc ggttgagctg ggatgggtgc   4260
attcggggtg aaattatgtg cattttggat tggattttta agttggcaat attgccgcca   4320
agatcccgtc ttgggttcat gttatgaagg accaccaaga cggtgtatcc ggtacattta   4380
ggaaatttat cgtgcagctt ggatggaaaa gcgtggaaaa atttggagac acccttgtgt   4440
cctccaagat tttccatgca ctcatccatg ataatagcaa tggggccgtg ggcagcggcg   4500
cgggcaaaca cgttccgtgg gtctgacaca tcatagttat gttcctgagt taaatcatca   4560
taagccattt taatgaattt ggggcggaga gtaccagatt ggggtatgaa tgttccttcg   4620
ggccccggag catagttccc ctcacagatt tgcatttccc aagctttcag ttccgagggt   4680
ggaatcatgt ccacctgggg ggctatgaaa aacaccgttt ctggggcggg ggtgattaat   4740
tgtgatgata gcaaatttct gagcaattga gatttgccac atccggtggg gccataaatg   4800
attccgatta cgggttgcag gtggtagttt agggaacggc aactgccgtc ttctcgaagc   4860
```

-continued aagggggcca cctcgttcat catttccctt acatgcatat tttcccgcac caaatccatt 4920
aggaggcgct ctcctcctag tgatagaagt tcttgtagtg aggaaaagtt tttcagcggt 4980
ttcagaccgt cagccatggg cattttggag agagtttgct gcaaaagttc tagtctgttc 5040
cacagttcag tgatgtgttc tatggcatct cgatccagca gacctcctcg tttcgcgggt 5100
ttggacggct cctggaatag ggtatgagac gatgggcgtc cagcgctgcc agggttcggt 5160
ccttccaggg tctcagtgtt cgagtcaggg ttgtttccgt cacagtgaag ggtgtgcgc 5220
ctgcttgggc gcttgccagg gtgcgcttca gactcatcct gctggtcgaa aacttctgtc 5280
gcttggcgcc ctgtatgtcg gccaagtagc agtttaccat gagttcgtag ttgagcgcct 5340
cggctgcgtg gcctttggcg cggagcttac ctttggaagt tttcttgcat accgggcagt 5400
ataggcattt cagcgcatac aacttgggcg caaggaaaac ggattctggg gagtatgcat 5460
ctgcgccgca ggaggcgcaa acagtttcac attccaccag ccaggttaaa tccggttcat 5520
tggggtcaaa aacaagtttt ccgccatatt ttttgatgcg tttcttacct ttggtctcca 5580
tgagttcgtg tcctcgttga gtgacaaaca ggctgtccgt gtccccgtag actgatttta 5640
caggcctctt ctccagtgga gtgcctcggt cttcttcgta caggaactct gaccactctg 5700
atacaaaggc gcgcgtccag gccagcacaa aggaggctat gtgggagggg tagcgatcgt 5760
tgtcaaccag ggggtccacc ttttccaaag tatgcaaaca catgtcaccc tcttcaacat 5820
ccaggaatgt gattggcttg taggtgtatt tcacgtgacc tggggtcccc gctggggggg 5880
tataaaaggg ggcggttctt tgctcttcct cactgtcttc cggatcgctg tccaggaacg 5940
tcagctgttg gggtaggtat tccctctcga aggcgggcat gacctctgca ctcaggttgt 6000
cagtttctaa gaacgaggag gatttgatat tgacagtgcc ggttgagatg cctttcatga 6060
ggttttcgtc catttggtca gaaaacacaa tttttttatt gtcaagtttg gtggcaaatg 6120
atccatacag ggcgttggat aaaagtttgg caatggatcg catggtttgg ttcttttcct 6180
tgtccgcgcg ctctttggcg gcgatgttga gttggacata ctcgcgtgcc aggcacttcc 6240
attcggggaa gatagttgtt aattcatctg gcacgattct cacttgccac cctcgattat 6300
gcaaggtaat taaatccaca ctggtggcca cctcgcctcg aaggggttca ttggtccaac 6360
agagcctacc tcctttccta gaacagaaag gggaagtggg gtctagcata agttcatcgg 6420
gagggtctgc atccatggta aagattcccg gaagtaaatc cttatcaaaa tagctgatgg 6480
gagtggggtc atctaaggcc atttgccatt ctcgagctgc cagtgcgcgc tcatatgggt 6540
taaggggact gccccatggc atgggatggg tgagtgcaga ggcatacatg ccacagatgt 6600
catagacgta gatgggatcc tcaaagatgc ctatgtaggt tggatagcat cgcccccctc 6660
tgatacttgc tcgcacatag tcatatagtt catgtgatgg cgctagcagc cccggaccca 6720
agttggtgcg attgggtttt tctgttctgt agacgatctg gcgaaagatg gcgtgagaat 6780
tggaagagat ggtgggtctt tgaaaaatgt tgaaatgggc atgaggtaga cctacagagt 6840
ctctgacaaa gtgggcataa gattcttgaa gcttggttac cagttcggcg gtgacaagta 6900
cgtctagggc gcagtagtca agtgtttctt gaatgatgtc ataacctggt tggtttttct 6960
tttcccacag ttcgcggttg agaaggtatt cttcgcgatc cttccagtac tcttctagcg 7020
gaaacccgtc tttgtctgca cggtaagatc ctagcatgta gaactgatta actgccttgt 7080
aagggcagca gcccttctct acgggtagag agtatgcttg agcagctttt cgtagcgaag 7140
cgtgagtaag ggcaaaggtg tctctgacca tgactttgag aaattggtat ttgaagtcga 7200
tgtcgtcaca ggctccctgt tcccagagtt ggaagtctac ccgtttcttg taggcggggt 7260

-continued

```
tgggcaaagc gaaagtaaca tcattgaaga gaatcttacc ggctctgggc ataaaattgc   7320
gagtgatgcg aaaaggctgt ggtacttccg ctcgattgtt gatcacctgg gcagctagga   7380
cgatctcgtc gaaaccgttg atgttgtgtc ctacgatgta taattctatg aaacgcggcg   7440
tgcctctgac gtgaggtagc ttactgagct catcaaaggt taggtctgtg gggtcagata   7500
aggcgtagtg ttcgagagcc cattcgtgca ggtgaggatt tgcatgtagg aatgatgacc   7560
aaagatctac cgccagtgct gtttgtaact ggtcccgata ctgacgaaaa tgccggccaa   7620
ttgccatttt ttctggagtg acacagtaga aggttctggg gtcttgttgc catcgatccc   7680
acttgagttt aatggctaga tcgtgggcca tgttgacgag acgctcttct cctgagagtt   7740
tcatgaccag catgaaagga actagttgtt tgccaaagga tcccatccag gtgtaagttt   7800
ccacatcgta ggtcaggaag agtctttctg tgcgaggatg agagccgatc gggaagaact   7860
ggatttcctg ccaccagttg gaggattggc tgttgatgtg atggaagtag aagtttctgc   7920
ggcgcgccga gcattcgtgt ttgtgcttgt acagacggcc gcagtagtcg cagcgttgca   7980
cgggttgtat ctcgtgaatg agttgtacct ggcttccctt gacgagaaat ttcagtggga   8040
agccgaggcc tggcgattgt atctcgtgct cttctatatt cgctgtatcg gcctgttcat   8100
cttctgtttc gatggtggtc atgctgacga gcccccgcgg gaggcaagtc cagacctcgg   8160
cgcgggaggg gcggagctga aggacgagag cgcgcaggct ggagctgtcc agagtcctga   8220
gacgctgcgg actcaggtta gtaggtaggg acagaagatt aacttgcatg atcttttcca   8280
gggcgtgcgg gaggttcaga tggtacttga tttccacagg ttcgtttgta gagacgtcaa   8340
tggcttgcag ggttccgtgt cctttgggcg ccactaccgt acctttgttt tttcttttga   8400
tcggtggtgg ctctcttgct tcttgcatgc tcagaagcgg tgacggggac gcgcgccggg   8460
cggcagcggt tgttccggac ccgagggcat ggctggtagt ggcacgtcgg cgccgcgcac   8520
gggcaggttc tggtactgcg ctctgagaag acttgcgtgc gccaccacgc gtcgattgac   8580
gtcttgtatc tgacgtctct gggtgaaagc taccggcccc gtgagcttga acctgaaaga   8640
gagttcaaca gaatcaattt cggtatcgtt aacggcagct tgtctcagta tttcttgtac   8700
gtcaccagag ttgtcctggt aggcgatctc cgccatgaac tgctcgattt cttcctcctg   8760
aagatctccg cgacccgctc tttcgacggt ggccgcgagg tcattggaga tacggcccat   8820
gagttgggag aatgcattca tgcccgcctc gttccagacg cggctgtaaa ccacggcccc   8880
ctcggagtct cttgcgcgca tcaccacctg agcgaggtta agctccacgt gtctggtgaa   8940
gaccgcatag ttgcataggc gctgaaaaag gtagttgagt gtggtggcaa tgtgttcggc   9000
gacgaagaaa tacatgatcc atcgtctcag cggcatttcg ctaacatcgc ccagagcttc   9060
caagcgctcc atggcctcgt agaagtccac ggcaaaatta aaaaactggg agtttcgcgc   9120
ggacacggtc aattcctcct cgagaagacg gatgagttcg gctatggtgg cccgtacttc   9180
gcgttcgaag gctcccggga tctcttcttc ctcttctatc tcttcttcca ctaacatctc   9240
ttcttcgtct tcaggcgggg gcggaggggg cacgcggcga cgtcgacggc gcacgggcaa   9300
acggtcgatg aatcgttcaa tgacctctcc gcggcggcgg cgcatggttt cagtgacggc   9360
gcggccgttc tcgcgcggtc gcagagtaaa aacaccgccg cgcatctcct taaagtggtg   9420
actgggaggt tctccgtttg ggagggagag ggcgctgatt atacatttta ttaattggcc   9480
cgtagggact gcacgcagag atctgatcgt gtcaagatcc acgggatctg aaaacctttc   9540
gacgaaagcg tctaaccagt cacagtcaca aggtaggctg agtacggctt cttgtgggcg   9600
```

-continued

```
ggggtggtta tgtgttcggt ctgggtcttc tgtttcttct tcatctcggg aaggtgagac   9660
gatgctgctg gtgatgaaat taaagtaggc agttctaaga cggcggatgg tggcgaggag   9720
caccaggtct ttgggtccgg cttgctggat acgcaggcga ttggccattc cccaagcatt   9780
atcctgacat ctagcaagat ctttgtagta gtcttgcatg agccgttcta cgggcacttc   9840
ttcctcaccc gttctgccat gcatacgtgt gagtccaaat ccgcgcattg gttgtaccag   9900
tgccaagtca gctacgactc tttcggcgag gatggcttgc tgtacttggg taagggtggc   9960
ttgaaagtca tcaaaatcca caaagcggtg gtaagctcct gtattaatgg tgtaagcaca  10020
gttggccatg actgaccagt taactgtctg gtgaccaggg cgcacgagct cggtgtattt  10080
aaggcgcgaa taggcgcggg tgtcaaagat gtaatcgttg caggtgcgca ccagatactg  10140
gtaccctata agaaaatgcg gcggtggttg gcggtagaga ggccatcgtt ctgtagctgg  10200
agcgccaggg gcgaggtctt ccaacataag gcggtgatag ccgtagatgt acctggacat  10260
ccaggtgatt cctgcggcgg tagtagaagc ccgaggaaac tcgcgtacgc ggttccaaat  10320
gttgcgtagc ggcatgaagt agttcattgt aggcacggtt tgaccagtga ggcgcgcgca  10380
gtcattgatg ctctatagac acggagaaaa tgaaagcgtt cagcgactcg actccgtagc  10440
ctggaggaac gtgaacgggt tgggtcgcgg tgtaccccgg ttcgagactt gtactcgagc  10500
cggccggagc cgcggctaac gtggtattgg cactcccgtc tcgacccagc ctacaaaaat  10560
ccaggatacg gaatcgagtc gttttgctgg tttccgaatg gcagggaagt gagtcctatt  10620
ttttttttt tgccgctcag atgcatcccg tgctgcgaca gatgcgcccc caacaacagc  10680
ccccctcgca gcagcagcag cagcaatcac aaaaggctgt ccctgcaact actgcaactg  10740
ccgccgtgag cggtgcggga cagcccgcct atgatctgga cttggaagag ggcgaaggac  10800
tggcacgtct aggtgcgcct tcacccgagc ggcatccgcg agttcaactg aaaaaagatt  10860
ctcgcgaggc gtatgtgccc caacagaacc tatttagaga cagaagcggc gaggagccgg  10920
aggagatgcg agcttcccgc tttaacgcgg gtcgtgagct gcgtcacggt ttggaccgaa  10980
gacgagtgtt gcgggacgag gatttcgaag ttgatgaaat gacagggatc agtcctgcca  11040
gggcacacgt ggctgcagcc aaccttgtat cggcttacga gcagacagta aaggaagagc  11100
gtaacttcca aaagtctttt aataatcatg tgcgaaccct gattgcccgc gaagaagtta  11160
cccttggttt gatgcatttg tgggatttga tggaagctat cattcagaac cctactagca  11220
aacctctgac cgcccagctg tttctggtgg tgcaacacag cagagacaat gaggctttca  11280
gagaggcgct gctgaacatc accgaacccg aggggagatg gttgtatgat cttatcaaca  11340
ttctacagag tatcatagtg caggagcgga gcctgggcct ggccgagaag gtggctgcca  11400
tcaattactc ggttttgagc ttgggaaaat attacgctcg caaaatctac aagactccat  11460
acgttcccat agacaaggag gtgaagatag atgggttcta catgcgcatg acgctcaagg  11520
tcttgaccct gagcgatgat cttggggtgt atcgcaatga cagaatgcat cgcgcggtta  11580
gcgccagcag gaggcgcgag ttaagcgaca gggaactgat gcacagtttg caaagagctc  11640
tgactggagc tggaaccgag ggtgagaatt acttcgacat gggagctgac ttgcagtggc  11700
agcctagtcg cagggctctg agcgccgcga cggcaggatg tgagcttcct tacatagaag  11760
aggcggatga aggcgaggag gaagagggcg agtacttgga agactgatgg cacaacccgt  11820
gtttttttgct agatggaaca gcaagcaccg gatcccgcaa tgcgggcggc gctgcagagc  11880
cagccgtccg gcattaactc ctcggacgat tggacccagg ccatgcaacg tatcatggcg  11940
ttgacgactc gcaaccccga agcctttaga cagcaacccc aggccaaccg tctatcggcc  12000
```

-continued

```
atcatggaag ctgtagtgcc ttcccgctct aatcccactc atgagaaggt cctggccatc  12060
gtgaacgcgt tggtggagaa caaagctatt cgtccagatg aggccggact ggtatacaac  12120
gctctcttag aacgcgtggc tcgctacaac agtagcaatg tgcaaaccaa tttggaccgt  12180
atgataacag atgtacgcga agccgtgtct cagcgcgaaa ggttccagcg tgatgccaac  12240
ctgggttcgc tggtggcgtt aaatgctttc ttgagtactc agcctgctaa tgtgccgcgt  12300
ggtcaacagg attatactaa ctttttaagt gctttgagac tgatggtatc agaagtacct  12360
cagagcgaag tgtatcagtc cggtcctgat tacttctttc agactagcag acagggcttg  12420
cagacggtaa atctgagcca agcttttaaa aaccttaaag gtttgtgggg agtgcatgcc  12480
ccggtaggag aaagagcaac cgtgtctagc ttgttaactc cgaactcccg cctattatta  12540
ctgttggtag ctcctttcac cgacagcggt agcatcgacc gtaattccta tttgggttac  12600
ctactaaacc tgtatcgcga agccataggg caaagtcagg tggacgagca gacctatcaa  12660
gaaattaccc aagtcagtcg cgctttggga caggaagaca ctggcagttt ggaagccact  12720
ctgaacttct tgcttaccaa tcggtctcaa aagatccctc ctcaatatgc tcttactgcg  12780
gaggaggaga ggatccttag atatgtgcag cagagcgtgg gattgtttct gatgcaagag  12840
ggggcaactc cgactgcagc actggacatg acagcgcgaa atatggagcc cagcatgtat  12900
gccagtaacc gacctttcat taacaaactg ctggactact tgcacagagc tgccgctatg  12960
aactctgatt atttcaccaa tgccatctta aacccgcact ggctgccccc acctggtttc  13020
tacacgggcg aatatgacat gcccgaccct aatgacggat ttctgtggga cgacgtggac  13080
agcgatgttt tttcacctct ttctgatcat cgcacgtgga aaaaggaagg cggcgataga  13140
atgcattctt ctgcatcgct gtccggggtc atgggtgcta ccgcggctga gcccgagtct  13200
gcaagtcctt ttcctagtct acccttttct ctacacagtg tacgtagcag cgaagtgggt  13260
agaataagtc gcccgagttt aatgggcgaa gaggagtatc taaacgattc cttgctcaga  13320
ccggcaagag aaaaaaattt cccaaacaat ggaatagaaa gtttggtgga taaaatgagt  13380
agatggaaga cttatgctca ggatcacaga gacgagcctg ggatcatggg gattacaagt  13440
agagcgagcc gtagacgcca gcgccatgac agacagaggg gtcttgtgtg ggacgatgag  13500
gattcggccg atgatagcag cgtgctggac ttgggtggga gaggaagggg caacccgttt  13560
gctcatttgc gccctcgctt gggtggtatg ttgtaaaaaa aaataaaaaa aaaactcacc  13620
aaggccatgg cgacgagcgt acgttcgttc ttctttatta tctgtgtcta gtataatgag  13680
gcgagtcgtg ctaggcggag cggtggtgta tccggagggt cctcctcctt cgtacgagag  13740
cgtgatgcag cagcagcagg cgacggcggt gatgcaatcc ccactggagg ctccctttgt  13800
gcctccgcga tacctggcac ctacggaggg cagaaacagc attcgttatt cggaactggc  13860
acctcagtac gataccacca ggttgtatct ggtggacaac aagtcggcgg acattgcttc  13920
tctgaactat cagaatgacc acagcaactt cttgaccacg gtggtgcaaa acaatgactt  13980
tacccctacg gaagccagca cccagaccat taactttgat gaacgatcgc ggtggggcgg  14040
tcagctaaag accatcatgc atactaacat gccaaacgtg aacgagtata tgtttagtaa  14100
caagttcaaa gcgcgtgtga tggtgtccag aaaacctccc gacggtgctg cagttgggga  14160
tacttatgat cacaagcagg atattttgaa atatgagtgg ttcgagttta ctttgccaga  14220
aggcaacttt tcagttacta tgactattga tttgatgaac aatgccatca tagataatta  14280
cttgaaagtg ggtagacaga atggagtgct tgaaagtgac attggtgtta agttcgacac  14340
```

-continued caggaacttc aagctgggat gggatcccga aaccaagttg atcatgcctg gagtgtatac 14400
gtatgaagcc ttccatcctg acattgtctt actgcctggc tgcggagtgg attttaccga 14460
gagtcgtttg agcaaccttc ttggtatcag aaaaaaacag ccatttcaag agggttttaa 14520
gattttgtat gaagatttag aaggtggtaa tattccggcc ctcttggatg tagatgccta 14580
tgagaacagt aagaaagaac aaaaagccaa aatagaagct gctacagctg ctgcagaagc 14640
taaggcaaac atagttgcca gcgactctac aagggttgct aacgctggag aggtcagagg 14700
agacaatttt gcgccaacac ctgttccgac tgcagaatca ttattggccg atgtgtctga 14760
aggaacggac gtgaaactca ctattcaacc tgtagaaaaa gatagtaaga atagaagcta 14820
taatgtgttg gaagacaaaa tcaacacagc ctatcgcagt tggtatcttt cgtacaatta 14880
tggcgatccc gaaaaaggag tgcgttcctg gacattgctc accacctcag atgtcacctg 14940
cggagcagag caggtctact ggtcgcttcc agacatgatg aaggatcctg tcactttccg 15000
ctccactaga caagtcagta actaccctgt ggtgggtgca gagcttatgc ccgtcttctc 15060
aaagagcttc tacaacgaac aagctgtgta ctcccagcag ctccgccagt ccacctcgct 15120
tacgcacgtc ttcaaccgct ttcctgagaa ccagatttta atccgtccgc cggcgcccac 15180
cattaccacc gtcagtgaaa acgttcctgc tctcacagat cacgggaccc tgccgttgcg 15240
cagcagtatc cggggagtcc aacgtgtgac cgttactgac gccagacgcc gcacctgtcc 15300
ctacgtgtac aaggcactgg gcatagtcgc accgcgcgtc ctttcaagcc gcactttcta 15360
aaaaaaaaaa aaatgtccat tcttatctcg cccagtaata acaccggttg gggtctgcgc 15420
gctccaagca agatgtacgg aggcgcacgc aaacgttcta cccaacatcc tgtccgtgtt 15480
cgcggacatt ttcgcgctcc atggggcgcc ctcaagggcc gcactcgcgt tcgaaccacc 15540
gtcgatgatg taatcgatca ggtggttgcc gacgcccgta attatactcc tactgcgcct 15600
acatctactg tggatgcagt tattgacagt gtagtggctg acgctcgcaa ctatgctcga 15660
cgtaagagcc ggcgaaggcg cattgccaga cgccaccgag ctaccactgc catgcgagcc 15720
gcaagagctc tgctacgaag agctagacgc gtggggcgaa gagccatgct tagggcggcc 15780
agacgtgcag cttcgggcgc cagcgccggc aggtcccgca ggcaagcagc cgctttcgca 15840
gcggcgacta ttgccgacat ggcccaatcg cgaagaggca atgtatactg ggtgcgtgac 15900
gctgccaccg gtcaacgtgt acccgtgcgc acccgtcccc ctcgcactta gaagatactg 15960
agcagtctcc gatgttgtgt cccagcggcg aggatgtcca agcgcaaata caaggaagaa 16020
atgctgcagg ttatcgcacc tgaagtctac ggccaaccgt tgaaggatga aaaaaaaccc 16080
cgcaaaatca agcgggttaa aaaggacaaa aaagaagagg aagatggcga tgatgggctg 16140
gcggagtttg tgcgcgagtt tgccccacgg cgacgcgtgc aatggcgtgg gcgcaaagtt 16200
cgacatgtgt tgagacctgg aacttcggtg gtctttacac ccggcgagcg ttcaagcgct 16260
acttttaagc gttcctatga tgaggtgtac ggggatgatg atattcttga gcaggcggct 16320
gaccgattag gcgagtttgc ttatggcaag cgtagtagaa taacttccaa ggatgagaca 16380
gtgtcgatac ccttggatca tggaaatccc acccctagtc ttaaaccggt cactttgcag 16440
caagtgttac ccgtaactcc gcgaacaggt gttaaacgcg aaggtgaaga tttgtatccc 16500
actatgcaac tgatggtacc caaacgccag aagttggagg acgttttgga gaaagtaaaa 16560
gtggatccag atattcaacc tgaggttaaa gtgagaccca ttaagcaggt agcgcctggt 16620
ctgggggtac aaactgtaga cattaagatt cccactgaaa gtatggaagt gcaaactgaa 16680
cccgcaaagc ctactgccac ctccactgaa gtgcaaacgg atccatggat gcccatgcct 16740
attacaactg acgccgccgg tcccactcga agatcccgac gaaagtacgg tccagcaagt 16800
ctgttgatgc ccaattatgt tgtacaccca tctattattc ctactcctgg ttaccgaggc 16860
actcgctact atcgcagccg aaacagtacc tcccgccgtc gccgcaagac acctgcaaat 16920
cgcagtcgtc gccgtagacg cacaagcaaa ccgactcccg gcgccctggt gcggcaagtg 16980
taccgcaatg gtagtgcgga acctttgaca ctgccgcgtg cgcgttacca tccgagtatc 17040
atcacttaat caatgttgcc gctgcctcct tgcagatatg gccctcactt gtcgccttcg 17100
cgttcccatc actggttacc gaggaagaaa ctcgcgccgt agaagaggga tgttgggacg 17160
cggaatgcga cgctacaggc gacggcgtgc tatccgcaag caattgcggg gtggtttttt 17220
accagcctta attccaatta tcgctgctgc aattggcgcg ataccaggca tagcttccgt 17280
ggcggttcag gcctcgcaac gacattgaca ttggaaaaaa acgtataaat aaaaaaaaaa 17340
aaatacaatg gactctgaca ctcctggtcc tgtgactatg ttttcttaga gatggaagac 17400
atcaattttt catccttggc tccgcgacac ggcacgaagc cgtacatggg cacctggagc 17460
gacatcggca cgagccaact gaacgggggc gccttcaatt ggagcagtat ctggagcggg 17520
cttaaaaatt ttggctcaac cataaaaaca tacgggaaca aagcttggaa cagcagtaca 17580
ggacaggcgc ttagaaataa acttaaagac cagaacttcc aacaaaaagt agtcgatggg 17640
atagcttccg gcatcaatgg agtggtagat ttggctaacc aggctgtgca gaaaaagata 17700
aacagtcgtt tggacccgcc gccagcaacc ccaggtgaaa tgcaagtgga ggaagaaatt 17760
cctccgccag aaaaacgagg cgacaagcgt ccgcgtcccg atttggaaga gacgctggtg 17820
acgcgcgtag atgaaccgcc ttcttatgag gaagcaacga agcttggaat gcccaccact 17880
agaccgatag ccccaatggc caccggggtg atgaaacctt ctcagttgca tcgacccgtc 17940
accttggatt tgccccctcc ccctgctgct actgctgtac ccgcttctaa gcctgtcgct 18000
gccccgaaac cagtcgccgt agccaggtca cgtcccgggg gcgctcctcg tccaaatgcg 18060
cactggcaaa atactctgaa cagcatcgtg ggtctaggcg tgcaaagtgt aaaacgccgt 18120
cgctgctttt aattaaatat ggagtagcgc ttaacttgcc tatctgtgta tatgtgtcat 18180
tacacgccgt cacagcagca gaggaaaaaa ggaagaggtc gtgcgtcgac gctgagttac 18240
tttcaagatg gccaccccat cgatgctgcc ccaatgggca tacatgcaca tcgccggaca 18300
ggatgcttcg gagtacctga gtccgggtct ggtgcagttc gcccgcgcca cagacaccta 18360
cttcaatctg ggaaataagt ttagaaatcc caccgtagcg ccgacccacg atgtgaccac 18420
cgaccgtagc cagcggctca tgttgcgctt cgtgcccgtt gaccgggagg acaatacata 18480
ctcttacaaa gtgcggtaca ccctggccgt gggcgacaac agagtgctgg atatggccag 18540
cacgttcttt gacattaggg gtgtgttgga cagaggtccc agtttcaaac cctattctgg 18600
tacggcttac aactccctgg ctcctaaagg cgctccaaat acatctcagt ggattgcaga 18660
aggtgtaaaa aatacaactg gtgaggaaca cgtaacagaa gaggaaacca atactactac 18720
ttacactttt ggcaatgctc ctgtaaaagc tgaagctgaa attacaaaag aaggactccc 18780
agtaggtttg gaagtttcag atgaagaaag taaaccgatt tatgctgata aaacatatca 18840
gccagaacct cagctgggag atgaaacttg gactgacctt gatggaaaaa ccgaaaagta 18900
tggaggcagg gctctcaaac ccgatactaa gatgaaacca tgctacgggt cctttgccaa 18960
acctactaat gtgaaaggcg gtcaggcaaa acaaaaaaca acggagcagc caaatcagaa 19020
agtcgaatat gatatcgaca tggagttttt tgatgcggca tcgcagaaaa caaacttaag 19080

-continued

```
tcctaaaatt gtcatgtatg cagaaaatgt aaatttggaa actccagaca ctcatgtagt  19140
gtacaaacct ggaacagaag acacaagttc cgaagctaat ttgggacaac aatctatgcc  19200
caacagaccc aactacattg gcttcagaga taactttatt ggacttatgt actataacag  19260
tactggtaac atgggggtgc tggctggtca agcgtctcag ttaaatgcag tggttgactt  19320
gcaggacaga aacacagaac tttcttacca actcttgctt gactctctgg gcgacagaac  19380
cagatacttt agcatgtgga atcaggctgt ggacagttat gatcctgatg tacgtgttat  19440
tgaaaatcat ggtgtggaag atgaacttcc caactactgt tttccactgg acggcatagg  19500
tgttccaaca accagttaca aatcaatagt tccaaatgga gacaatgcgc ctaattggaa  19560
ggaacctgaa gtaaatggaa caagtgagat cggacagggt aatttgtttg ccatggaaat  19620
taaccttcaa gccaatctat ggcgaagttt cctttattcc aatgtggctc tatatctccc  19680
agactcgtac aaatacaccc cgtccaatgt cactcttcca gaaaacaaaa acacctacga  19740
ctacatgaac gggcgggtgg tgccgccatc tctagtagac acctatgtga acattggtgc  19800
caggtggtct ctggatgcca tggacaatgt caacccattc aaccaccacc gtaacgctgg  19860
cttgcgttac cgatccatgc ttctgggtaa cggacgttat gtgcctttcc acatacaagt  19920
gcctcaaaaa ttcttcgctg ttaaaaacct gctgcttctc ccaggctcct acacttatga  19980
gtggaacttt aggaaggatg tgaacatggt tctacagagt tccctcggta acgacctgcg  20040
ggtagatggc gccagcatca gtttcacgag catcaacctc tatgctactt ttttccccat  20100
ggctcacaac accgcttcca cccttgaagc catgctgcgg aatgacacca atgatcagtc  20160
attcaacgac tacctatctg cagctaacat gctctacccc attcctgcca atgcaaccaa  20220
tattcccatt tccattcctt ctcgcaactg ggcggctttc agaggctggt catttaccag  20280
actgaaaacc aaagaaactc cctctttggg gtctggattt gacccctact ttgtctattc  20340
tggttctatt ccctacctgg atggtacctt ctacctgaac cacactttta agaaggtttc  20400
catcatgttt gactcttcag tgagctggcc tggaaatgac aggttactat ctcctaacga  20460
atttgaaata aagcgcactg tggatggcga aggctacaac gtagcccaat gcaacatgac  20520
caaagactgg ttcttggtac agatgctcgc caactacaac atcggctatc agggcttcta  20580
cattccagaa ggatacaaag atcgcatgta ttcatttttc agaaacttcc agcccatgag  20640
caggcaggtg gttgatgagg tcaattacaa agacttcaag gccgtcgcca taccctacca  20700
acacaacaac tctggctttg tgggttacat ggctccgacc atgcgccaag gtcaacccta  20760
tcccgctaac tatccctatc cactcattgg aacaactgcc gtaaatagtg ttacgcagaa  20820
aaagttcttg tgtgacagaa ccatgtggcg cataccgttc tcgagcaact tcatgtctat  20880
gggggccctt acagacttgg gacagaatat gctctatgcc aactcagctc atgctctgga  20940
catgaccttt gaggtggatc ccatggatga gcccaccctg ctttatcttc tcttcgaagt  21000
tttcgacgtg gtcagagtgc atcagccaca ccgcggcatc atcgaggcag tctacctgcg  21060
tacaccgttc tcggccggta acgctaccac gtaagaagct tcttgcttct tgcaaatagc  21120
agctgcaacc atggcctgcg gatcccaaaa cggctccagc gagcaagagc tcagagccat  21180
tgtccaagac ctgggttgcg gaccctattt tttgggaacc tacgataagc gcttcccggg  21240
gttcatggcc cccgataagc tcgcctgtgc cattgtaaat acggccggac gtgagacggg  21300
gggagagcac tggttggctt tcggttggaa cccacgttct aacacctgct accttttga  21360
tccttttgga ttctcggatg atcgtctcaa acagatttac cagtttgaat atgagggtct  21420
cctgcgccgc agcgctcttg ctaccaagga ccgctgtatt acgctggaaa aatctaccca  21480
```

gaccgtgcag ggtccccgtt ctgccgcctg cggacttttc tgctgcatgt tccttcacgc 21540
ctttgtgcac tggcctgacc gtcccatgga cggaaacccc accatgaaat tgctaactgg 21600
agtgccaaac aacatgcttc attctcctaa agtccagccc accctgtgtg acaatcaaaa 21660
agcactctac cattttctta atacccattc gccttatttt cgctcccatc gtacacacat 21720
cgaaagggcc actgcgttcg accgtatgga tgttcaataa tgactcatgt aaacaacgtg 21780
ttcaataaac atcactttat ttttttacat gtatcaaggc tctgcattac ttatttattt 21840
acaagtcgaa tgggttctga cgagaatcag aatgacccgc aggcagtgat acgttgcgga 21900
actgatactt gggttgccac ttgaattcgg gaatcaccaa cttgggaacc ggtatatcgg 21960
gcaggatgtc actccacagc tttctggtca gctgcaaagc tccaagcagg tcaggagccg 22020
aaatcttgaa atcacaatta ggaccagtgc tttgagcgcg agagttgcgg tacaccggat 22080
tgcagcactg aaacaccatc agcgacggat gtctcacgct tgccagcacg gtgggatctg 22140
caatcatgcc cacatccaga tcttcagcat tggcaatgct gaacggggtc atcttgcagg 22200
tctgcctacc catggcgggc acccaattag gcttgtggtt gcaatcgcag tgcaggggga 22260
tcagtatcat cttggcctga tcctgtctga ttcctggata cacggctctc atgaaagcat 22320
catattgctt gaaagcctgc tgggctttac taccctcggt ataaaacatc ccgcaggacc 22380
tgctcgaaaa ctggttagct gcacagccgg catcattcac acagcagcgg gcgtcattgt 22440
tagctatttg caccacactt ctgccccagc ggttttgggt gattttggtt cgctcgggat 22500
tctcctttaa ggctcgttgt ccgttctcgc tggccacatc catctcgata atctgctcct 22560
tctgaatcat aatattgcca tgcaggcact tcagcttgcc ctcataatca ttgcagccat 22620
gaggccacaa cgcacagcct gtacattccc aattatggtg ggcgatctga gaaaaagaat 22680
gtatcattcc ctgcagaaat cttcccatca tcgtgctcag tgtcttgtga ctagtgaaag 22740
ttaactggat gcctcggtgc tcctcgttta cgtactggtg acagatgcgc ttgtattgtt 22800
cgtgttgctc aggcattagt ttaaaagagg ttctaagttc gttatccagc ctgtacttct 22860
ccatcagcag acacatcact tccatgcctt tctcccaagc agacaccagg ggcaagctaa 22920
tcggattctt aacagtgcag gcagcagctc ctttagccag agggtcatct ttagcgatct 22980
tctcaatgct tcttttgcca tccttctcaa cgatgcgcac gggcgggtag ctgaaaccca 23040
ctgctacaag ttgcgcctct tctctttctt cttcgctgtc ttgactgatg tcttgcatgg 23100
ggatatgttt ggtcttcctt ggcttctttt tgggggggtat cggaggagga ggactgtcgc 23160
tccgttccgg agacagggag gattgtgacg tttcgctcac cattaccaac tgactgtcgg 23220
tagaagaacc tgaccccaca cggcgacagg tgtttctctt cgggggcaga ggtggaggcg 23280
attgcgaagg gctgcggtcc gacctggaag gcggatgact ggcagaaccc cttccgcgtt 23340
cgggggtgtg ctccctgtgg cggtcgctta actgatttcc ttcgcggctg gccattgtgt 23400
tctcctaggc agagaaacaa cagacatgga aactcagcca ttgctgtcaa catcgccacg 23460
agtgccatca catctcgtcc tcagcgacga ggaaaaggag cagagcttaa gcattccacc 23520
gcccagtcct gccaccacct ctaccctaga agataaggag gtcgacgcat ctcatgacat 23580
gcagaataaa aaagcgaaag agtctgagac agacatcgag caagacccgg gctatgtgac 23640
accggtggaa cacgaggaag agttgaaacg ctttctagag agagaggatg aaaactgccc 23700
aaaacaacga gcagataact atcaccaaga tgctggaaat agggatcaga acaccgacta 23760
cctcataggg cttgacgggg aagacgcgct ccttaaacat ctagcaagac agtcgctcat 23820

```
agtcaaggat gcattattgg acagaactga agtgcccatc agtgtggaag agctcagccg  23880
cgcctacgag cttaacctct tttcacctcg tactcccccc aaacgtcagc caaacggcac  23940
ctgcgagcca aatcctcgct taaactttta tccagctttt gctgtgccag aagtactggc  24000
tacctatcac atcttttttta aaaatcaaaa aattccagtc tcctgccgcg ctaatcgcac  24060
ccgcgccgat gccctactca atctgggacc tggttcacgc ttacctgata tagcttcctt  24120
ggaagaggtt ccaaagatct tcgagggtct gggcaataat gagactcggg ccgcaaatgc  24180
tctgcaaaag ggagaaaatg gcatggatga gcatcacagc gttctggtgg aattggaagg  24240
cgataatgcc agactcgcag tactcaagcg aagcatcgag gtcacacact tcgcatatcc  24300
cgctgtcaac ctgcccccta aagtcatgac ggcggtcatg gaccagttac tcattaagcg  24360
cgcaagtccc ctttcagaag acatgcatga cccagatgcc tgtgatgagg gtaaaccagt  24420
ggtcagtgat gagcagctaa cccgatggct gggcaccgac tctcccaggg atttggaaga  24480
gcgtcgcaag cttatgatgg ccgtggtgct ggttaccgta gaactagagt gtctccgacg  24540
tttctttacc gattcagaaa ccttgcgcaa actcgaagag aatctgcact acactttttag  24600
acacggcttt gtgcggcagg catgcaagat atctaacgtg gaactcacca acctggtttc  24660
ctacatgggt attctgcatg agaatcgcct aggacaaagc gtgctgcaca gcaccctgaa  24720
gggggaagcc cgccgtgatt acatccgcga ttgtgtctat ctgtacctgt gccaaacgtg  24780
gcaaaccggc atgggtgtat ggcagcaatg tttagaagaa cagaacttga aagagcttga  24840
caagctctta cagaaatctc ttaaggttct gtggacaggg ttcgacgagc gcaccgtcgc  24900
ttccgacctg gcagacctca tcttcccaga gcgtctcagg gttactttgc gaaacggatt  24960
gcctgacttt atgagccaga gcatgcttaa caattttcgc tctttcatcc tggaacgctc  25020
cggtatcctg cccgccacct gctgcgcact gccctccgac tttgtgcctc tcacctaccg  25080
cgagtgcccc ccgccgctat ggagtcactg ctacctgttc cgtctggcca actatctctc  25140
ctaccactcg gatgtgatcg aggatgtgag cggagacggc ttgctggagt gtcactgccg  25200
ctgcaatctg tgcacgcccc accggtccct agcttgcaac ccccagttga tgagcgaaac  25260
ccagataata ggcacctttg aattgcaagg ccccagcagc caaggcgatg ggtcttctcc  25320
tgggcaaagt ttaaaactga ccccgggact gtggacctcc gcctacttgc gcaagtttgc  25380
tccggaagat taccacccct atgaaatcaa gttctatgag gaccaatcac agcctccaaa  25440
ggccgaactt tcggcctgcg tcatcaccca gggggcaatt ctggcccaat tgcaagccat  25500
ccaaaaatcc cgccaagaat ttctactgaa aaagggtaag gggtctacc ttgaccccca  25560
gaccggcgag gaactcaaca caaggttccc tcaggatgtc ccaacgacga gaaaacaaga  25620
agttgaaggt gcagccgccg cccccagaag atatggagga agattgggac agtcaggcag  25680
aggaggcgga ggaggacagt ctggaggaca gtctggagga agacagtttg gaggaggaaa  25740
acgaggaggc agaggaggtg gaagaagtaa ccgccgacaa acagttatcc tcggctgcgg  25800
agacaagcaa cagcgctacc atctccgctc cgagtcgagg aacccggcgg cgtcccagca  25860
gtagatggga cgagaccgga cgcttcccga acccaaccag cgcttccaag accggtaaga  25920
aggatcggca gggatacaag tcctggcggg ggcataagaa tgccatcatc tcctgcttgc  25980
atgagtgcgg gggcaacata tccttcacgc ggcgctactt gctattccac catggggtga  26040
actttccgcg caatgttttg cattactacc gtcacctcca cagcccctac tatagccagc  26100
aaatcccggc agtctcgaca gataaagaca gcggcggcga cctccaacag aaaaccagca  26160
gcggcagtta gaaaatacac aacaagtgca gcaacaggag gattaaagat tacagccaac  26220
```

-continued

```
gagccagcgc aaacccgaga gttaagaaat cggatctttc caaccctgta tgccatcttc  26280
cagcagagtc ggggtcaaga gcaggaactg aaaataaaaa accgatctct gcgttcgctc  26340
accagaagtt gtttgtatca caagagcgaa gatcaacttc agcgcactct cgaggacgcc  26400
gaggctctct tcaacaagta ctgcgcgctg actcttaaag agtaggcagc gaccgcgctt  26460
attcaaaaaa ggcgggaatt acatcatcct cgacatgagt aaagaaattc ccacgcctta  26520
catgtggagt tatcaacccc aaatgggatt ggcggcaggc gcctcccagg actactccac  26580
ccgcatgaat tggctcagcg ccgggccttc tatgatttct cgagttaatg atatacgcgc  26640
ctaccgaaac caaatacttt tggaacagtc agctcttacc accacgcccc gccaacacct  26700
taatcccaga aattggcccg ccgccctagt gtaccaggaa agtcccgctc ccaccactgt  26760
attacttcct cgagacgccc aggccgaagt ccaaatgact aatgcaggtg cgcagttagc  26820
tggcggctcc accctatgtc gtcacaggcc tcggcataat ataaaacgcc tgatgatcag  26880
aggccgaggt atccagctca acgacgagtc ggtgagctct ccgcttggtc tacgaccaga  26940
cggaatcttt cagattgccg gctgcgggag atcttccttc acccctcgtc aggctgttct  27000
gactttggaa agttcgtctt cgcaaccccg ctcgggcgga atcgggaccg ttcaatttgt  27060
ggaggagttt actccctctg tctacttcaa ccccttctcc ggatctcctg ggcattaccc  27120
ggacgagttc ataccgaact tcgacgcgat tagcgagtca gtggacggct acgattgatg  27180
tctggtgacg cggctgagct atctcggctg cgacatctag accactgccg ccgctttcgc  27240
tgctttgccc gggaactcat tgagttcatc tacttcgaac tccccaagga tcaccctcaa  27300
ggtccggccc acggagtgcg gatttctatc gaaggcaaaa tagactctcg cctgcaacga  27360
attttctccc agcggcccgt gctgatcgag cgagaccagg gaaacaccac ggtttccatc  27420
tactgcattt gtaatcaccc cggattgcat gaaagccttt gctgtcttat gtgtactgag  27480
tttaataaaa actgaattaa gactctccta cggactgccg cttcttcaac ccggatttta  27540
caaccagaag aacgaaactt ttcctgtcgt ccaggactct gttaacttca cctttcctac  27600
tcacaaacta gaagctcaac gactacaccg cttttccaga agcattttcc ctactaatac  27660
tactttcaaa accggaggtg agctccaagg tcttcctaca gaaaaccctt gggtggaagc  27720
gggccttgta gtgctaggaa ttcttgcggg tgggcttgtg attattcttt gctacctata  27780
cacaccttgc ttcactttct tagtggtgtt gtggtattgg tttaaaaaat ggggcccata  27840
ctagtcttgc ttgttttact ttcgcttttg gaaccgggtt ctgccaatta cgatccatgt  27900
ctagacttcg acccagaaaa ctgcacactt actttgcac ccgacacaag ccgcatctgt  27960
ggagttctta ttaagtgcgg atgggaatgc aggtccgttg aaattacaca caataacaaa  28020
acctggaaca ataccttatc caccacatgg gagccaggag ttcccgagtg gtacactgtc  28080
tctgtccgag gtcctgacgg ttccatccgc attagtaaca acactttcat tttttctgaa  28140
atgtgcgatc tggccatgtt catgagcaaa cagtattctc tatggcctcc tagcaaggac  28200
aacatcgtaa cgttctccat tgcttattgc ttgtgcgctt gccttcttac tgctttactg  28260
tgcgtatgca tacacctgct tgtaaccact cgcatcaaaa acgccaataa caaagaaaaa  28320
atgccttaac ctctttctgt ttacctcttt ctgtttacag acatggcttc tcttacatct  28380
ctcatatttg tcagcattgt cactgccgct catggacaaa cagtcgtctc tatccctcta  28440
ggacataatt acactctcat aggaccccca atcacttcag aggtcatctg ggccaaactg  28500
ggaagcgttg attactttga tataatctgc aacaaaacaa aaccaataat agtaacttgc  28560
```

```
aacatacaaa atcttacatt gattaatgtt agcaaagttt acagcggtta ctattatggt  28620
tatgacagat acagtagtca atatagaaat tacttggttc gtgttaccca gttgaaaacc  28680
acgaaaatgc caaatatggc aaagattcga tccgatgaca attctctaga aacttttaca  28740
tctcccacca cacccgacga aaaaaacatc ccagattcaa tgattgcaat tgttgcagcg  28800
gtggcagtgg tgatggcact aataataata tgcatgcttt tatatgcttg tcgctacaaa  28860
aagtttcatc ctaaaaaaca agatctccta ctaaggctta acatttaatt tctttttata  28920
cagccatggt ttccactacc acattcctta tgcttactag tctcgcaact ctgacttctg  28980
ctcgctcaca cctcactgta actataggct caaactgcac actaaaagga cctcaaggtg  29040
gtcatgtctt ttggtggaga atatatgaca atggatggtt tacaaaacca tgtgaccaac  29100
ctggtagatt tttctgcaac ggcagagacc taaccattat caacgtgaca gcaaatgaca  29160
aaggcttcta ttatggaacc gactataaaa gtagtttaga ttataacatt attgtactgc  29220
catctaccac tccagcaccc cgcacaacta ctttctctag cagcagtgtc gctaacaata  29280
caatttccaa tccaaccttt gccgcgcttt taaaacgcac tgtgaataat tctacaactt  29340
cacatacaac aatttccact tcaacaatca gcattatcgc tgcagtgaca attggaatat  29400
ctattcttgt ttttaccata acctactacg cctgctgcta tagaaaagac aaacataaag  29460
gtgatccatt acttagattt gatatttaat ttgttctttt ttttttatt tacagtatgg  29520
tgaacaccaa tcatggtacc tagaaatttc ttcttcacca tactcatttg tgcatttaat  29580
gtttgcgcta ctttcacagc agtagccaca gcaaccccag actgtatagg agcatttgct  29640
tcctatgcac tttttgcttt tgttacttgc atctgcgtat gtagcatagt ctgcctggtt  29700
attaattttt tccaacttat agactggatc cttgtgcgaa ttgcctacct gcgccaccat  29760
cccgaatacc gcaaccaaaa tatcgcggca cttcttagac tcatctaaaa ccatgcaggc  29820
tatactacca atatttttgc ttctattgct tccctacgct gtctcaaccc cagctgccta  29880
tagtactcca ccagaacacc ttagaaaatg caaattccaa caaccgtggt catttcttgc  29940
ttgctatcga gaaaaatcag aaattccccc aaatttaata atgattgctg gaataattaa  30000
tataatctgt tgcaccataa tttcattttt gatatacccc ctatttgatt ttggctggaa  30060
tgctcccaat gcacatgatc atccacaaga cccagaggaa cacattcccc tacaaaacat  30120
gcaacatcca atagcgctaa tagattacga aagtgaacca caacccccac tactccctgc  30180
tattagttac ttcaacctaa ccggcggaga tgactgaaac actcaccacc tccaattccg  30240
ccgaggatct gctcgatatg gacggccgcg tctcagaaca gcgactcgcc caactacgca  30300
tccgccagca gcaggaacgc gcggccaaag agctcagaga tgtcatccaa attcaccaat  30360
gcaaaaaagg catattctgt ttggtaaaac aagccaagat atcctacgag atcaccgcta  30420
ctgaccatcg cctctcttac gaacttggcc cccaacgaca aaaatttacc tgcatggtgg  30480
gaatcaaccc catagttatc acccagcaaa gtggagatac taagggttgc attcactgct  30540
cctgcgattc catcgagtgc acctacaccc tgctgaagac cctatgcggc ctaagagacc  30600
tgctaccaat gaattaaaaa atgattaata aaaaatcact tacttgaaat cagcaataag  30660
gtctctgttg aaattttctc ccagcagcac ctcacttccc tcttcccaac tctggtattc  30720
taaaccccgt tcagcggcat actttctcca tactttaaag gggatgtcaa attttagctc  30780
ctctcctgta cccacaatct tcatgtcttt cttcccagat gaccaagaga gtccggctca  30840
gtgactcctt caaccctgtc taccccctatg aagatgaaag cacctcccaa cacccctta  30900
taaacccagg gtttatttcc ccaaatggct tcacacaaag cccaaacgga gttcttactt  30960
```

-continued

```
taaaatgttt aaccccacta acaaccacag gcggatctct acagctaaaa gtgggagggg  31020
gacttacagt ggatgacacc aacggttttt tgaaagaaaa cataagtgcc accacaccac  31080
tcgttaagac tggtcactct ataggtttac cactaggagc cggattggga acgaatgaaa  31140
ataaactttg tatcaaatta ggacaaggac ttacattcaa ttcaaacaac atttgcattg  31200
atgacaatat taacacctta tggacaggag tcaaccccac cgaagccaac tgtcaaatca  31260
tgaactccag tgaatctaat gattgcaaat taattctaac actagttaaa actggagcac  31320
tagtcactgc atttgtttat gttataggag tatctaacaa ttttaatatg ctaactacac  31380
acagaaatat aaattttact gcagagctgt ttttcgattc tactggtaat ttactaacta  31440
gactctcatc cctcaaaact ccacttaatc ataaatcagg acaaaacatg gctactggtg  31500
ccattactaa tgctaaaggt ttcatgccca gcacgactgc ctatcctttc aatgataatt  31560
ctagagaaaa agaaaactac atttacggaa cttgttacta cacagctagt gatcgcactg  31620
cttttcccat tgacatatct gtcatgctta accgaagagc aataaatgac gagacatcat  31680
attgtattcg tataacttgg tcctggaaca caggagatgc cccagaggtg caaacctctg  31740
ctacaaccct agtcacctcc ccatttacct tttactacat cagagaagac gactgacaaa  31800
taaagtttaa cttgtttatt tgaaaatcaa ttcacaaaat ccgagtagtt attttgcctc  31860
ccccttccca tttaacagaa tacaccaatc tctccccacg cacagcttta aacatttgga  31920
taccattaga tatagacatg gttttagatt ccacattcca aacagtttca gagcgagcca  31980
atctggggtc agtgatagat aaaaatccat cgggatagtc ttttaaagcg ctttcacagt  32040
ccaactgctg cggatggact ccggagtctg gatcacggtc atctggaaga agaacgatgg  32100
gaatcataat ccgaaaacgg tatcggacga ttgtgtctca tcaaacccac aagcagccgc  32160
tgtctgcgtc gctccgtgcg actgctgttt atgggatcag ggtccacagt gtcctgaagc  32220
atgattttaa tagcccttaa catcaacttt ctggtgcgat gcgcgcagca acgcattctg  32280
atttcactca aatctttgca gtaggtacaa cacattatta caatattgtt taataaacca  32340
taattaaaag cgctccagcc aaaactcata tctgatataa tcgcccctgc atgaccatca  32400
taccaaagtt taatataaat taaatgacgt tccctcaaaa acacactacc cacatacatg  32460
atctcttttg gcatgtgcat attaacaatc tgtctgtacc atggacaacg ttggttaatc  32520
atgcaaccca atataacctt ccggaaccac actgccaaca ccgctccccc agccatgcat  32580
tgaagtgaac cctgctgatt acaatgacaa tgaagaaccc aattctctcg accgtgaatc  32640
acttgagaat gaaaaatatc tatagtggca caacatagac ataaatgcat gcatcttctc  32700
ataattttta actcctcagg atttagaaac atatcccagg gaataggaag ctcttgcaga  32760
acagtaaagc tggcagaaca aggaagacca cgaacacaac ttacactatg catagtcata  32820
gtatcacaat ctggcaacag cgggtggtct tcagtcatag aagctcgggt ttcattttcc  32880
tcacaacgtg gtaactgggc tctggtgtaa gggtgatgtc tggcgcatga tgtcgagcgt  32940
gcgcgcaacc ttgtcataat ggagttgctt cctgacattc tcgtattttg tatagcaaaa  33000
cgcggccctg gcagaacaca ctcttcttcg ccttctatcc tgccgcttag cgtgttccgt  33060
gtgatagttc aagtacaacc acactcttaa gttggtcaaa agaatgctgg cttcagttgt  33120
aatcaaaact ccatcgcatc taatcgttct gaggaaatca tccacggtag catatgcaaa  33180
tcccaaccaa gcaatgcaac tggattgtgt ttcaagcagg agaggagagg gaagagacgg  33240
aagaaccatg ttaattttta ttccaaacga tctcgcagta cttcaaattg tagatcgcgc  33300
```

agatggcatc tctcgccccc actgtgttgg tgaaaaagca cagctagatc aaaagaaatg 33360
cgattttcaa ggtgctcaac ggtggcttcc agcaaagcct ccacgcgcac atccaagaac 33420
aaaagaatac caaaagaagg agcattttct aactcctcaa tcatcatatt acattcctgc 33480
accattccca gataattttc agctttccag ccttgaatta ttcgtgtcag ttcttgtggt 33540
aaatccaatc cacacattac aaacaggtcc cggagggcgc cctccaccac cattcttaaa 33600
cacaccctca taatgacaaa atatcttgct cctgtgtcac ctgtagcgaa ttgagaatgg 33660
caacatcaat tgacatgccc ttggctctaa gttcttcttt aagttctagt tgtaaaaact 33720
ctctcatatt atcaccaaac tgcttagcca gaagcccccc gggaacaaga gcaggggacg 33780
ctacagtgca gtacaagcgc agacctcccc aattggctcc agcaaaaaca agattggaat 33840
aagcatattg ggaaccgcca gtaatatcat cgaagttgct ggaaatataa tcaggcagag 33900
tttcttgtaa aaattgaata aaagaaaaat ttgccaaaaa aacattcaaa acctctggga 33960
tgcaaatgca ataggttacc gcgctgcgct ccaacattgt tagttttgaa ttagtctgca 34020
aaaataaaaa aaaaaacaag cgtcatatca tagtagcctg acgaacagat ggataaatca 34080
gtctttccat cacaagacaa gccacagggt ctccagctcg accctcgtaa aacctgtcat 34140
catgattaaa caacagcacc gaaagttcct cgcggtgacc agcatgaata attcttgatg 34200
aagcatacaa tccagacatg ttagcatcag ttaacgagaa aaaacagcca acatagcctt 34260
tgggtataat tatgcttaat cgtaagtata gcaaagccac ccctcgcgga tacaaagtaa 34320
aaggcacagg agaataaaaa atataattat ttctctgctg ctgttcaggc aacgtcgccc 34380
ccggtccctc taaatacaca tacaaagcct catcagccat ggcttaccag acaaagtaca 34440
gcgggcacac aaagcacaag ctctaaagtg actctccaac ctctccacaa tatatatata 34500
cacaagccct aaactgacgt aatgggagta aagtgtaaaa aatcccgcca aacccaacac 34560
acaccccgaa actgcgtcac cagggaaaag tacagtttca cttccgcaat cccaacaggc 34620
gtaacttcct ctttctcacg gtacgtgata tcccactaac ttgcaacgtc attttcccac 34680
ggtcgcaccg ccccttttag ccgttaaccc cacagccaat caccacacga tccacacttt 34740
ttaaaatcac ctcatttaca tattggcacc attccatcta taaggtatat tattgatgat 34800
g 34801

<210> SEQ ID NO 8
<211> LENGTH: 873
<212> TYPE: DNA
<213> ORGANISM: Artificial Sequence
<220> FEATURE:
<223> OTHER INFORMATION: Fully synthetic

<400> SEQUENCE: 8
atgagagatt tgcgatttct gcctcaggaa ataatctctg ctgagactgg aaatgaaata 60
ttggagcttg tggtgcacgc cctgatggga gacgatccgg agccacctgt gcagcttttt 120
gagcctccta cgcttcagga actgtatgat ttagaggtag agggatcgga ggattctaat 180
gaggaagctg taaatggctt ttttaccgat tctatgcttt tagctgctaa tgaagggtta 240
gaattagatc cgcctttgga cacttttgat actccagggg taattgtgga aagcggtaca 300
ggtgtaagaa aattacctga tttgagttcc gtggactgtg atttgcactg ctatgaagac 360
gggtttcctc cgagtgatga ggaggaccat gaaaaggagc agtccatgca gactgcagcg 420
ggtgagggag tgaaggctgc caatgttggt tttcagttgg attgcccgga gcttcctgga 480
catggctgta agtcttgtga atttcacagg aaaaatactg gagtaaagga actgttatgt 540

```
tcgctttgtt atatgagaac gcactgccac tttatttaca gtaagtgtgt ttaagttaaa    600

atttaaagga atatgctgtt tttcacatgt atattgagtg tgagttttgt gcttcttatt    660

ataggtcctg tgtctgatgc tgatgaatca ccatctcctg attctactac ctcacctcct    720

gagattcaag cacctgttcc tgtggacgtg cgcaagccca ttcctgtgaa gcttaagcct    780

gggaaacgtc cagcagtgga aaaacttgag gacttgttac agggtgggga cggacctttg    840

gacttgagta cacggaaacg tccaagacaa taa                                 873
```

<210> SEQ ID NO 9
<211> LENGTH: 543
<212> TYPE: DNA
<213> ORGANISM: Artificial Sequence
<220> FEATURE:
<223> OTHER INFORMATION: Fully synthetic

<400> SEQUENCE: 9

```
atggaggttt gggccatttt ggaagacctt aggaagacta ggcaactgtt agagaacgct     60

tcggacggag tctccggttt ttggagattc tggttcgcta gtgaattagc tagggtagtt    120

tttaggataa aacaggacta taaacaagaa tttgaaaagt tgttggtaga ttgcccagga    180

ctttttgaag ctcttaattt gggccatcag gttcacttta aagaaaaagt tttatcagtt    240

ttagactttt caaccccagg tagaactgct gctgctgtgg cttttcttac ttttatatta    300

gataaatgga tcccgcagac tcatttcagc aggggatacg ttttggattt catagccaca    360

gcattgtgga gaacatggaa ggttcgcaag atgaggacaa tcttaggtta ctggccagtg    420

cagcctttgg gtgtagcggg aatcctgagg catccaccgg tcatgccagc ggttctggag    480

gaggaacagc aagaggacaa cccgagagcc ggcctggacc ctccagtgga ggaggcggag    540

tag                                                                  543
```

<210> SEQ ID NO 10
<211> LENGTH: 35541
<212> TYPE: DNA
<213> ORGANISM: Artificial Sequence
<220> FEATURE:
<223> OTHER INFORMATION: Fully synthetic

<400> SEQUENCE: 10

```
catcatcaat aatatacctt atagatggaa tggtgccaat atgtaaatga ggtgatttta     60

aaaagtgtgg atcgtgtggt gattggctgt ggggttaacg gctaaaaggg gcggtgcgac    120

cgtgggaaaa tgacgttttg tgggggtgga gtttttttgc aagttgtcgc gggaaatgtg    180

acgcataaaa aggctacaca ggaagtgaca attttcgcgc ggttttaggc ggatgttgta    240

gtaaatttgg gcgtaaccga gtaagatttg gccattttcg cgggaaaact gaataagagg    300

aagtgaaatc tgaataattt tgtgttactc atagcgcgta atatttgtct agggccgcgg    360

ggactttgac cgtttacgtg tgtcaaggag cccaagtcgc ggggaagtgt tgcagggagg    420

cactccggga ggtcccgcgt gcccgtccag ggagcaatgc gtcctcgggt tcgtccccag    480

ccgcgtctac gcgcctccgt cctccccttc acgtccggca ttcgtggtgc ccggagcccg    540

acgccccgcg tccggacctg gaggcagccc tgggtctccg gatcaggcca gcggccaaag    600

ggtcgccgca cgcacctgtt cccagggcct ccacatcatg gcccctccct cgggttaccc    660

cacagcttag gccgattcga cctctctccg ctggggccct cgctggcgtc cctgcaccct    720

gggagcgcga gcggcgcgcg ggcggggaag cgcggcccag acccccgggt ccgcccggag    780
```

-continued

```
cagctgcgct gtcggggcca ggccgggctc ccagtggatt cgcgggcaca gacgcccagg     840
accgcgcttc ccacgtggcg gagggactgg ggacccgggc acccgtcctg ccccttcacc     900
ttccagctcc gcctcctccg cgcggacccc gccccgtccc gacccctccc gggtccccgg     960
cccagccccc tccgggccct cccagcccct cccctccctt tccgcggccc cgccctctcc    1020
tcgcggcgcg agtttcaggc agcgctgcgt cctgctgcgc acgtgggaag ccctggcccc    1080
ggccaccccc gcgatgagag atttgcgatt tctgcctcag gaaataatct ctgctgagac    1140
tggaaatgaa atattggagc ttgtggtgca cgccctgatg ggagacgatc cggagccacc    1200
tgtgcagctt tttgagcctc ctacgcttca ggaactgtat gatttagagg tagagggatc    1260
ggaggattct aatgaggaag ctgtaaatgg ctttttttacc gattctatgc ttttagctgc    1320
taatgaaggg ttagaattag atccgccttt ggacactttt gatactccag ggtaattgt    1380
ggaaagcggt acaggtgtaa gaaaattacc tgatttgagt tccgtggact gtgatttgca    1440
ctgctatgaa gacgggtttc ctccgagtga tgaggaggac catgaaaagg agcagtccat    1500
gcagactgca gcgggtgagg gagtgaaggc tgccaatgtt ggttttcagt tggattgccc    1560
ggagcttcct ggacatggct gtaagtcttg tgaatttcac aggaaaaata ctggagtaaa    1620
ggaactgtta tgttcgcttt gttatatgag aacgcactgc cactttattt acagtaagtg    1680
tgtttaagtt aaaatttaaa ggaatatgct gtttttcaca tgtatattga gtgtgagttt    1740
tgtgcttctt attataggtc ctgtgtctga tgctgatgaa tcaccatctc ctgattctac    1800
tacctcacct cctgagattc aagcacctgt tcctgtggac gtgcgcaagc ccattcctgt    1860
gaagcttaag cctgggaaac gtccagcagt ggaaaaactt gaggacttgt tacagggtgg    1920
ggacggacct ttggacttga gtacacggaa acgtccaaga caataagtgt tccatatccg    1980
tgtttactta aggtgacgtc aatatttgtg tgacagtgca atgtaataaa aatatgttaa    2040
ctgttcactg gtttttattg ctttttgggc ggggactcag gtatataagt agaagcagac    2100
ctgtgtggtt agctcatagg agctggcttt catccatgga ggtttgggcc attttggaag    2160
accttaggaa gactaggcaa ctgttagaga acgcttcgga cggagtctcc ggtttttgga    2220
gattctggtt cgctagtgaa ttagctaggg tagtttttag gataaaacag gactataaac    2280
aagaatttga aaagttgttg gtagattgcc caggactttt tgaagctctt aatttgggcc    2340
atcaggttca ctttaaagaa aaagttttat cagttttaga cttttcaacc ccaggtagaa    2400
ctgctgctgc tgtggctttt cttactttta tattagataa atggatcccg cagactcatt    2460
tcagcagggg atacgttttg gatttcatag ccacagcatt gtggagaaca tggaaggttc    2520
gcaagatgag gacaatctta ggttactggc cagtgcagcc tttgggtgta gcgggaatcc    2580
tgaggcatcc accggtcatg ccagcggttc tggaggagga acagcaagag gacaacccga    2640
gagccggcct ggaccctcca gtggaggagg cggagtagct gacttgtctc ctgaactgca    2700
acgggtgctt actggatcta cgtccactgg acgggatagg ggcgttaaga gggagagggc    2760
atctagtggt actgatgcta gatctgagtt ggctttaagt ttaatgagtc gcagacgtcc    2820
tgaaaccatt tggtggcatg aggttcagaa agagggaagg gatgaagttt ctgtattgca    2880
ggagaaatat tcactggaac aggtgaaaac atgttggttg gagcctgagg atgattggga    2940
ggtggccatt aaaaattatg ccaagatagc tttgaggcct gataaacagt ataagattac    3000
tagacggatt aatatccgga atgcttgtta catatctgga aatggggctg aggtggtaat    3060
agatactcaa gacaaggcag ttattagatg ctgcatgatg gatatgtggc ctggggtagt    3120
cggtatggaa gcagtaactt ttgtaaatgt taagtttagg ggagatggtt ataatggaat    3180
```

-continued

```
agtgtttatg gccaatacca aacttatatt gcatggttgt agctttttttg gtttcaacaa   3240
tacctgtgta gatgcctggg gacaggttag tgtacgggga tgtagtttct atgcgtgttg   3300
gattgccaca gctggcagaa ccaagagtca attgtctctg aagaaatgca tatttcaaag   3360
atgtaacctg ggcattctga atgaaggcga agcaagggtc cgccactgcg cttctacaga   3420
tactggatgt tttattttga ttaagggaaa tgccagcgta aagcataaca tgatttgcgg   3480
tgcttccgat gagaggcctt atcaaatgct cacttgtgct ggtgggcatt gtaatatgct   3540
ggctactgtg catattgttt cccatcaacg caaaaaatgg cctgtttttg atcacaatgt   3600
gatgacgaag tgtaccatgc atgcaggtgg gcgtagagga atgtttatgc cttaccagtg   3660
taacatgaat catgtgaaag tgttgttgga accagatgcc ttttccagaa tgagcctaac   3720
aggaattttt gacatgaaca tgcaaatctg gaagatcctg aggtatgatg atacgagatc   3780
gagggtacgc gcatgcgaat gcggaggcaa gcatgccagg ttccagccgg tgtgtgtaga   3840
tgtgactgaa gatctcagac cggatcattt ggttattgcc cgcactggag cagagttcgg   3900
atccagtgga gaagaaactg actaaggtga gtattgggaa aactttgggg tgggattttc   3960
agatggacag attgagtaaa aatttgtttt ttctgtcttg cagctgtcat gagtggaaac   4020
gcttctttta agggggggagt cttcagccct tatctgacag ggcgtctccc atcctgggca   4080
ggagttcgtc agaatgttat gggatctact gtggatggaa gacccgtcca acccgccaat   4140
tcttcaacgc tgacctatgc tactttaagt tcttcacctt tggacgcagc tgcagctgcc   4200
gccgccgctt ctgttgccgc taacactgtg cttggaatgg gttactatgg aagcatcatg   4260
gctaattcca cttcctctaa taacccttct accctgactc aggacaagtt acttgtcctt   4320
ttggcccagc tggaggcttt gacccaacgt ctgggtgaac tttctcagca ggtggtcgag   4380
ttgcgagtac aaactgagtc tgctgtcggc acggcaaagt ctaaataaaa aaatcccaga   4440
atcaatgaat aaataaacaa gcttgttgtt gatttaaaat caagtgtttt tatttcattt   4500
ttcgcgcacg gtatgcccta gaccaccgat ctctatcatt gagaactcgg tggatttttt   4560
ccaggatcct atagaggtgg gattgaatgt ttagatacat gggcattagg ccgtctttgg   4620
ggtggagata gctccattga agggattcat gctccggggt agtgttgtaa atcacccagt   4680
cataacaagg tcgcagtgca tggtgttgca caatatcttt tagaagtagg ctgattgcca   4740
cagataagcc cttggtgtag gtgtttacaa accggttgag ctgggatggg tgcattcggg   4800
gtgaaattat gtgcattttg gattggattt ttaagttggc aatattgccg ccaagatccc   4860
gtcttgggtt catgttatga aggaccacca agacggtgta tccggtacat ttaggaaatt   4920
tatcgtgcag cttggatgga aaagcgtgga aaaatttgga gacacccttg tgtcctccaa   4980
gattttccat gcactcatcc atgataatag caatggggcc gtgggcagcg gcgcgggcaa   5040
acacgttccg tgggtctgac acatcatagt tatgttcctg agttaaatca tcataagcca   5100
ttttaatgaa tttggggcgg agagtaccag attggggtat gaatgttcct tcgggccccg   5160
gagcatagtt cccctcacag atttgcattt cccaagcttt cagttccgag ggtggaatca   5220
tgtccacctg gggggctatg aaaaacaccg tttctggggc gggggtgatt aattgtgatg   5280
atagcaaatt tctgagcaat tgagatttgc cacatccggt ggggccataa atgattccga   5340
ttacgggttg caggtggtag tttagggaac ggcaactgcc gtcttctcga agcaaggggg   5400
ccacctcgtt catcatttcc cttacatgca tattttcccg caccaaatcc attaggaggc   5460
gctctcctcc tagtgataga agttcttgta gtgaggaaaa gtttttcagc ggtttcagac   5520
```

-continued

```
cgtcagccat gggcattttg gagagagttt gctgcaaaag ttctagtctg ttccacagtt   5580
cagtgatgtg ttctatggca tctcgatcca gcagacctcc tcgtttcgcg ggtttggacg   5640
gctcctggaa tagggtatga gacgatgggc gtccagcgct gccagggttc ggtccttcca   5700
gggtctcagt gttcgagtca gggttgtttc cgtcacagtg aaggggtgtg cgcctgcttg   5760
ggcgcttgcc agggtgcgct tcagactcat cctgctggtc gaaaacttct gtcgcttggc   5820
gccctgtatg tcggccaagt agcagtttac catgagttcg tagttgagcg cctcggctgc   5880
gtggcctttg gcgcggagct tacctttgga agttttcttg cataccgggc agtataggca   5940
tttcagcgca tacaacttgg gcgcaaggaa aacggattct ggggagtatg catctgcgcc   6000
gcaggaggcg caaacagttt cacattccac cagccaggtt aaatccggtt cattggggtc   6060
aaaaacaagt tttccgccat attttttgat gcgtttctta cctttggtct ccatgagttc   6120
gtgtcctcgt tgagtgacaa acaggctgtc cgtgtccccg tagactgatt ttacaggcct   6180
cttctccagt ggagtgcctc ggtcttcttc gtacaggaac tctgaccact ctgatacaaa   6240
ggcgcgcgtc caggccagca caaaggaggc tatgtgggag ggtagcgat cgttgtcaac    6300
cagggggtcc accttttcca aagtatgcaa acacatgtca ccctcttcaa catccaggaa   6360
tgtgattggc ttgtaggtgt atttcacgtg acctggggtc cccgctgggg gggtataaaa   6420
gggggcggtt ctttgctctt cctcactgtc ttccggatcg ctgtccagga acgtcagctg   6480
ttggggtagg tattccctct cgaaggcggg catgacctct gcactcaggt tgtcagtttc   6540
taagaacgag gaggatttga tattgacagt gccggttgag atgcctttca tgaggttttc   6600
gtccatttgg tcagaaaaca caattttttt attgtcaagt ttggtggcaa atgatccata   6660
cagggcgttg gataaaagtt tggcaatgga tcgcatggtt tggttctttt ccttgtccgc   6720
gcgctctttg gcggcgatgt tgagttggac atactcgcgt gccaggcact tccattcggg   6780
gaagatagtt gttaattcat ctggcacgat tctcacttgc caccctcgat tatgcaaggt   6840
aattaaatcc acactggtgg ccacctcgcc tcgaaggggt tcattggtcc aacagagcct   6900
acctcctttc ctagaacaga aagggggaag tgggtctagc ataagttcat cgggagggtc   6960
tgcatccatg gtaaagattc ccggaagtaa atccttatca aaatagctga tgggagtggg   7020
gtcatctaag gccatttgcc attctcgagc tgccagtgcg cgctcatatg ggttaagggg   7080
actgccccat ggcatgggat gggtgagtgc agaggcatac atgccacaga tgtcatagac   7140
gtagatggga tcctcaaaga tgcctatgta ggttggatag catcgccccc ctctgatact   7200
tgctcgcaca tagtcatata gttcatgtga tggcgctagc agccccggac ccaagttggt   7260
gcgattgggt tttctgttc tgtagacgat ctggcgaaag atggcgtgag aattggaaga    7320
gatggtgggt ctttgaaaaa tgttgaaatg ggcatgaggt agacctacag agtctctgac   7380
aaagtgggca taagattctt gaagcttggt taccagttcg gcggtgacaa gtacgtctag   7440
ggcgcagtag tcaagtgttt cttgaatgat gtcataacct ggttggtttt tcttttccca   7500
cagttcgcgg ttgagaaggt attcttcgcg atccttccag tactcttcta gcggaaaccc   7560
gtctttgtct gcacggtaag atcctagcat gtagaactga ttaactgcct tgtaagggca   7620
gcagcccttc tctacgggta gagagtatgc ttgagcagct tttcgtagcg aagcgtgagt   7680
aagggcaaag gtgtctctga ccatgacttt gagaaattgg tatttgaagt cgatgtcgtc   7740
acaggctccc tgttcccaga gttggaagtc tacccgtttc ttgtaggcgg ggttgggcaa   7800
agcgaaagta acatcattga agagaatctt accggctctg ggcataaaat tgcgagtgat   7860
gcgaaaaggc tgtggtactt ccgctcgatt gttgatcacc tgggcagcta ggacgatctc   7920
```

-continued

```
gtcgaaaccg ttgatgttgt gtcctacgat gtataattct atgaaacgcg gcgtgcctct   7980
gacgtgaggt agcttactga gctcatcaaa ggttaggtct gtggggtcag ataaggcgta   8040
gtgttcgaga gcccattcgt gcaggtgagg atttgcatgt aggaatgatg accaaagatc   8100
taccgccagt gctgtttgta actggtcccg atactgacga aaatgccggc caattgccat   8160
tttttctgga gtgacacagt agaaggttct ggggtcttgt tgccatcgat cccacttgag   8220
tttaatggct agatcgtggg ccatgttgac gagacgctct tctcctgaga gtttcatgac   8280
cagcatgaaa ggaactagtt gtttgccaaa ggatcccatc caggtgtaag tttccacatc   8340
gtaggtcagg aagagtcttt ctgtgcgagg atgagagccg atcgggaaga actggatttc   8400
ctgccaccag ttggaggatt ggctgttgat gtgatggaag tagaagtttc tgcggcgcgc   8460
cgagcattcg tgtttgtgct tgtacagacg gccgcagtag tcgcagcgtt gcacgggttg   8520
tatctcgtga atgagttgta cctggcttcc cttgacgaga aatttcagtg ggaagccgag   8580
gcctggcgat tgtatctcgt gctcttctat attcgctgta tcggcctgtt catcttctgt   8640
ttcgatggtg gtcatgctga cgagcccccg cgggaggcaa gtccagacct cggcgcggga   8700
ggggcggagc tgaaggacga gagcgcgcag gctggagctg tccagagtcc tgagacgctg   8760
cggactcagg ttagtaggta gggacagaag attaacttgc atgatctttt ccagggcgtg   8820
cgggaggttc agatggtact tgatttccac aggttcgttt gtagagacgt caatggcttg   8880
cagggttccg tgtcctttgg gcgccactac cgtacctttg ttttttcttt tgatcggtgg   8940
tggctctctt gcttcttgca tgctcagaag cggtgacggg gacgcgcgcc gggcggcagc   9000
ggttgttccg gacccgaggg catggctggt agtggcacgt cggcgccgcg cacgggcagg   9060
ttctggtact gcgctctgag aagacttgcg tgcgccacca cgcgtcgatt gacgtcttgt   9120
atctgacgtc tctgggtgaa agctaccggc cccgtgagct tgaacctgaa agagagttca   9180
acagaatcaa tttcggtatc gttaacggca gcttgtctca gtatttcttg tacgtcacca   9240
gagttgtcct ggtaggcgat ctccgccatg aactgctcga tttcttcctc ctgaagatct   9300
ccgcgacccg ctctttcgac ggtggccgcg aggtcattgg agatacggcc catgagttgg   9360
gagaatgcat tcatgcccgc ctcgttccag acgcggctgt aaaccacggc cccctcggag   9420
tctcttgcgc gcatcaccac ctgagcgagg ttaagctcca cgtgtctggt gaagaccgca   9480
tagttgcata ggcgctgaaa aaggtagttg agtgtggtgg caatgtgttc ggcgacgaag   9540
aaatacatga tccatcgtct cagcggcatt tcgctaacat cgcccagagc ttccaagcgc   9600
tccatggcct cgtagaagtc cacggcaaaa ttaaaaaact gggagtttcg cgcggacacg   9660
gtcaattcct cctcgagaag acggatgagt tcggctatgg tggcccgtac ttcgcgttcg   9720
aaggctcccg ggatctcttc ttcctcttct atctcttctt ccactaacat ctcttcttcg   9780
tcttcaggcg gggcggaggg gggcacgcgg cgacgtcgac ggcgcacggg caaacggtcg   9840
atgaatcgtt caatgacctc tccgcggcgg cggcgcatgg tttcagtgac ggcgcggccg   9900
ttctcgcgcg gtcgcagagt aaaaacaccg ccgcgcatct ccttaaagtg gtgactggga   9960
ggttctccgt ttgggaggga gagggcgctg attatacatt ttattaattg gcccgtaggg  10020
actgcacgca gagatctgat cgtgtcaaga tccacgggat ctgaaaacct ttcgacgaaa  10080
gcgtctaacc agtcacagtc acaaggtagg ctgagtacgg cttcttgtgg gcgggggtgg  10140
ttatgtgttc ggtctgggtc ttctgtttct tcttcatctc gggaaggtga gacgatgctg  10200
ctggtgatga aattaaagta ggcagttcta agacggcgga tggtggcgag gagcaccagg  10260
```

-continued tctttgggtc cggcttgctg gatacgcagg cgattggcca ttccccaagc attatcctga 10320
catctagcaa gatctttgta gtagtcttgc atgagccgtt ctacgggcac ttcttcctca 10380
cccgttctgc catgcatacg tgtgagtcca aatccgcgca ttggttgtac cagtgccaag 10440
tcagctacga ctctttcggc gaggatggct tgctgtactt gggtaagggt ggcttgaaag 10500
tcatcaaaat ccacaaagcg gtggtaagct cctgtattaa tggtgtaagc acagttggcc 10560
atgactgacc agttaactgt ctggtgacca gggcgcacga gctcggtgta tttaaggcgc 10620
gaataggcgc gggtgtcaaa gatgtaatcg ttgcaggtgc gcaccagata ctggtaccct 10680
ataagaaaat gcggcggtgg ttggcggtag agaggccatc gttctgtagc tggagcgcca 10740
ggggcgaggt cttccaacat aaggcggtga tagccgtaga tgtacctgga catccaggtg 10800
attcctgcgg cggtagtaga agcccgagga aactcgcgta cgcggttcca aatgttgcgt 10860
agcggcatga agtagttcat tgtaggcacg gtttgaccag tgaggcgcgc gcagtcattg 10920
atgctctata gacacggaga aaatgaaagc gttcagcgac tcgactccgt agcctggagg 10980
aacgtgaacg ggttgggtcg cggtgtaccc cggttcgaga cttgtactcg agccggccgg 11040
agccgcggct aacgtggtat tggcactccc gtctcgaccc agcctacaaa aatccaggat 11100
acggaatcga gtcgttttgc tggtttccga atggcaggga agtgagtcct attttttttt 11160
ttttgccgct cagatgcatc ccgtgctgcg acagatgcgc ccccaacaac agcccccctc 11220
gcagcagcag cagcagcaat cacaaaaggc tgtccctgca actactgcaa ctgccgccgt 11280
gagcggtgcg ggacagcccg cctatgatct ggacttggaa gagggcgaag gactggcacg 11340
tctaggtgcg ccttcacccg agcggcatcc gcgagttcaa ctgaaaaaag attctcgcga 11400
ggcgtatgtg ccccaacaga acctatttag agacagaagc ggcgaggagc cggaggagat 11460
gcgagcttcc cgctttaacg cgggtcgtga gctgcgtcac ggtttggacc gaagacgagt 11520
gttgcgggac gaggatttcg aagttgatga aatgacaggg atcagtcctg ccagggcaca 11580
cgtggctgca gccaaccttg tatcggctta cgagcagaca gtaaaggaag agcgtaactt 11640
ccaaaagtct tttaataatc atgtgcgaac cctgattgcc cgcgaagaag ttacccttgg 11700
tttgatgcat ttgtgggatt tgatggaagc tatcattcag aaccctacta gcaaacctct 11760
gaccgcccag ctgtttctgg tggtgcaaca cagcagagac aatgaggctt tcagagaggc 11820
gctgctgaac atcaccgaac ccgaggggag atggttgtat gatcttatca acattctaca 11880
gagtatcata gtgcaggagc ggagcctggg cctggccgag aaggtggctg ccatcaatta 11940
ctcggttttg agcttgggaa aatattacgc tcgcaaaatc tacaagactc catacgttcc 12000
catagacaag gaggtgaaga tagatgggtt ctacatgcgc atgacgctca aggtcttgac 12060
cctgagcgat gatcttgggg tgtatcgcaa tgacagaatg catcgcgcgg ttagcgccag 12120
caggaggcgc gagttaagcg acagggaact gatgcacagt ttgcaaagag ctctgactgg 12180
agctggaacc gagggtgaga attacttcga catgggagct gacttgcagt ggcagcctag 12240
tcgcagggct ctgagcgccg cgacggcagg atgtgagctt ccttacatag aagaggcgga 12300
tgaaggcgag gaggaagagg gcgagtactt ggaagactga tggcacaacc cgtgtttttt 12360
gctagatgga acagcaagca ccggatcccg caatgcgggc ggcgctgcag agccagccgt 12420
ccggcattaa ctcctcggac gattggaccc aggccatgca acgtatcatg gcgttgacga 12480
ctcgcaaccc cgaagccttt agacagcaac cccaggccaa ccgtctatcg gccatcatgg 12540
aagctgtagt gccttcccgc tctaatccca ctcatgagaa ggtcctggcc atcgtgaacg 12600
cgttggtgga gaacaaagct attcgtccag atgaggccgg actggtatac aacgctctct 12660

-continued

```
tagaacgcgt ggctcgctac aacagtagca atgtgcaaac caatttggac cgtatgataa  12720
cagatgtacg cgaagccgtg tctcagcgcg aaaggttcca gcgtgatgcc aacctgggtt  12780
cgctggtggc gttaaatgct ttcttgagta ctcagcctgc taatgtgccg cgtggtcaac  12840
aggattatac taacttttta agtgctttga gactgatggt atcagaagta cctcagagcg  12900
aagtgtatca gtccggtcct gattacttct ttcagactag cagacagggc ttgcagacgg  12960
taaatctgag ccaagctttt aaaaacctta aaggtttgtg gggagtgcat gccccggtag  13020
gagaaagagc aaccgtgtct agcttgttaa ctccgaactc ccgcctatta ttactgttgg  13080
tagctccttt caccgacagc ggtagcatcg accgtaattc ctatttgggt tacctactaa  13140
acctgtatcg cgaagccata gggcaaagtc aggtggacga gcagacctat caagaaatta  13200
cccaagtcag tcgcgctttg ggacaggaag acactggcag tttggaagcc actctgaact  13260
tcttgcttac caatcggtct caaaagatcc ctcctcaata tgctcttact gcggaggagg  13320
agaggatcct tagatatgtg cagcagagcg tgggattgtt tctgatgcaa gagggggcaa  13380
ctccgactgc agcactggac atgacagcgc gaaatatgga gcccagcatg tatgccagta  13440
accgaccttt cattaacaaa ctgctggact acttgcacag agctgccgct atgaactctg  13500
attatttcac caatgccatc ttaaacccgc actggctgcc cccacctggt ttctacacgg  13560
gcgaatatga catgcccgac cctaatgacg gatttctgtg ggacgacgtg gacagcgatg  13620
ttttttcacc tctttctgat catcgcacgt ggaaaaagga aggcggcgat agaatgcatt  13680
cttctgcatc gctgtccggg gtcatgggtg ctaccgcggc tgagcccgag tctgcaagtc  13740
cttttcctag tctacccttt tctctacaca gtgtacgtag cagcgaagtg ggtagaataa  13800
gtcgcccgag tttaatgggc gaagaggagt atctaaacga ttccttgctc agaccggcaa  13860
gagaaaaaaa tttcccaaac aatggaatag aaagtttggt ggataaaatg agtagatgga  13920
agacttatgc tcaggatcac agagacgagc ctgggatcat ggggattaca agtagagcga  13980
gccgtagacg ccagcgccat gacagacaga ggggtcttgt gtgggacgat gaggattcgg  14040
ccgatgatag cagcgtgctg gacttgggtg ggagaggaag gggcaacccg tttgctcatt  14100
tgcgccctcg cttgggtggt atgttgtaaa aaaaaataaa aaaaaaactc accaaggcca  14160
tggcgacgag cgtacgttcg ttcttcttta ttatctgtgt ctagtataat gaggcgagtc  14220
gtgctaggcg gagcggtggt gtatccggag ggtcctcctc cttcgtacga gagcgtgatg  14280
cagcagcagc aggcgacggc ggtgatgcaa tccccactgg aggctccctt tgtgcctccg  14340
cgatacctgg cacctacgga gggcagaaac agcattcgtt attcggaact ggcacctcag  14400
tacgatacca ccaggttgta tctggtggac aacaagtcgg cggacattgc ttctctgaac  14460
tatcagaatg accacagcaa cttcttgacc acggtggtgc aaaacaatga ctttacccct  14520
acggaagcca gcacccagac cattaacttt gatgaacgat cgcggtgggg cggtcagcta  14580
aagaccatca tgcatactaa catgccaaac gtgaacgagt atatgtttag taacaagttc  14640
aaagcgcgtg tgatggtgtc cagaaaacct cccgacggtg ctgcagttgg ggatacttat  14700
gatcacaagc aggatatttt gaaatatgag tggttcgagt ttactttgcc agaaggcaac  14760
ttttcagtta ctatgactat tgatttgatg aacaatgcca tcatagataa ttacttgaaa  14820
gtgggtagac agaatggagt gcttgaaagt gacattggtg ttaagttcga caccaggaac  14880
ttcaagctgg gatgggatcc cgaaaccaag ttgatcatgc ctggagtgta tacgtatgaa  14940
gccttccatc ctgacattgt cttactgcct ggctgcggag tggattttac cgagagtcgt  15000
```

```
ttgagcaacc ttcttggtat cagaaaaaaa cagccatttc aagagggttt taagattttg  15060
tatgaagatt tagaaggtgg taatattccg gccctcttgg atgtagatgc ctatgagaac  15120
agtaagaaag aacaaaaagc caaaatagaa gctgctacag ctgctgcaga agctaaggca  15180
aacatagttg ccagcgactc tacaagggtt gctaacgctg gagaggtcag aggagacaat  15240
tttgcgccaa cacctgttcc gactgcagaa tcattattgg ccgatgtgtc tgaaggaacg  15300
gacgtgaaac tcactattca acctgtagaa aaagatagta agaatagaag ctataatgtg  15360
ttggaagaca aaatcaacac agcctatcgc agttggtatc tttcgtacaa ttatggcgat  15420
cccgaaaaag gagtgcgttc ctggacattg ctcaccacct cagatgtcac ctgcggagca  15480
gagcaggtct actggtcgct tccagacatg atgaaggatc ctgtcacttt ccgctccact  15540
agacaagtca gtaactaccc tgtggtgggt gcagagctta tgcccgtctt ctcaaagagc  15600
ttctacaacg aacaagctgt gtactcccag cagctccgcc agtccacctc gcttacgcac  15660
gtcttcaacc gctttcctga gaaccagatt ttaatccgtc cgccggcgcc caccattacc  15720
accgtcagtg aaaacgttcc tgctctcaca gatcacggga ccctgccgtt gcgcagcagt  15780
atccggggag tccaacgtgt gaccgttact gacgccagac gccgcacctg tccctacgtg  15840
tacaaggcac tgggcatagt cgcaccgcgc gtcctttcaa gccgcacttt ctaaaaaaaa  15900
aaaaaatgtc cattcttatc tcgcccagta ataacaccgg ttggggtctg cgcgctccaa  15960
gcaagatgta cggaggcgca cgcaaacgtt ctacccaaca tcctgtccgt gttcgcggac  16020
attttcgcgc tccatggggc gccctcaagg gccgcactcg cgttcgaacc accgtcgatg  16080
atgtaatcga tcaggtggtt gccgacgccc gtaattatac tcctactgcg cctacatcta  16140
ctgtggatgc agttattgac agtgtagtgg ctgacgctcg caactatgct cgacgtaaga  16200
gccggcgaag gcgcattgcc agacgccacc gagctaccac tgccatgcga gccgcaagag  16260
ctctgctacg aagagctaga cgcgtggggc gaagagccat gcttagggcg gccagacgtg  16320
cagcttcggg cgccagcgcc ggcaggtccc gcaggcaagc agccgctttc gcagcggcga  16380
ctattgccga catggcccaa tcgcgaagag gcaatgtata ctgggtgcgt gacgctgcca  16440
ccggtcaacg tgtacccgtg cgcacccgtc cccctcgcac ttagaagata ctgagcagtc  16500
tccgatgttg tgtcccagcg gcgaggatgt ccaagcgcaa atacaaggaa gaaatgctgc  16560
aggttatcgc acctgaagtc tacggccaac cgttgaagga tgaaaaaaaa ccccgcaaaa  16620
tcaagcgggt taaaaaggac aaaaaagaag aggaagatgg cgatgatggg ctggcggagt  16680
ttgtgcgcga gtttgcccca cggcgacgcg tgcaatggcg tgggcgcaaa gttcgacatg  16740
tgttgagacc tggaacttcg gtggtcttta cacccggcga gcgttcaagc gctactttta  16800
agcgttccta tgatgaggtg tacggggatg atgatattct tgagcaggcg gctgaccgat  16860
taggcgagtt tgcttatggc aagcgtagta gaataacttc caaggatgag acagtgtcga  16920
tacccttgga tcatggaaat cccacccccta gtcttaaacc ggtcactttg cagcaagtgt  16980
tacccgtaac tccgcgaaca ggtgttaaac gcgaaggtga agatttgtat cccactatgc  17040
aactgatggt acccaaacgc cagaagttgg aggacgtttt ggagaaagta aaagtggatc  17100
cagatattca acctgaggtt aaagtgagac ccattaagca ggtagcgcct ggtctggggg  17160
tacaaactgt agacattaag attcccactg aaagtatgga agtgcaaact gaacccgcaa  17220
agcctactgc cacctccact gaagtgcaaa cggatccatg gatgcccatg cctattacaa  17280
ctgacgccgc cggtcccact cgaagatccc gacgaaagta cggtccagca agtctgttga  17340
tgcccaatta tgttgtacac ccatctatta ttcctactcc tggttaccga ggcactcgct  17400
```

actatcgcag ccgaaacagt acctcccgcc gtcgccgcaa gacacctgca aatcgcagtc 17460
gtcgccgtag acgcacaagc aaaccgactc ccggcgccct ggtgcggcaa gtgtaccgca 17520
atggtagtgc ggaacctttg acactgccgc gtgcgcgtta ccatccgagt atcatcactt 17580
aatcaatgtt gccgctgcct ccttgcagat atggccctca cttgtcgcct tcgcgttccc 17640
atcactggtt accgaggaag aaactcgcgc cgtagaagag ggatgttggg acgcggaatg 17700
cgacgctaca ggcgacggcg tgctatccgc aagcaattgc ggggtggttt tttaccagcc 17760
ttaattccaa ttatcgctgc tgcaattggc gcgataccag gcatagcttc cgtggcggtt 17820
caggcctcgc aacgacattg acattggaaa aaaacgtata aataaaaaaa aaaaaataca 17880
atggactctg acactcctgg tcctgtgact atgttttctt agagatggaa gacatcaatt 17940
tttcatcctt ggctccgcga cacggcacga agccgtacat gggcacctgg agcgacatcg 18000
gcacgagcca actgaacggg ggcgccttca attggagcag tatctggagc gggcttaaaa 18060
attttggctc aaccataaaa acatacggga acaaagcttg gaacagcagt acaggacagg 18120
cgcttagaaa taaacttaaa gaccagaact tccaacaaaa agtagtcgat gggatagctt 18180
ccggcatcaa tggagtggta gatttggcta accaggctgt gcagaaaaag ataaacagtc 18240
gtttggaccc gccgccagca accccaggtg aaatgcaagt ggaggaagaa attcctccgc 18300
cagaaaaacg aggcgacaag cgtccgcgtc ccgatttgga agagacgctg gtgacgcgcg 18360
tagatgaacc gccttcttat gaggaagcaa cgaagcttgg aatgcccacc actagaccga 18420
tagccccaat ggccaccggg gtgatgaaac cttctcagtt gcatcgaccc gtcaccttgg 18480
atttgccccc tcccctgct gctactgctg tacccgcttc taagcctgtc gctgccccga 18540
aaccagtcgc cgtagccagg tcacgtcccg gggcgctcc tcgtccaaat gcgcactggc 18600
aaaatactct gaacagcatc gtgggtctag gcgtgcaaag tgtaaaacgc cgtcgctgct 18660
tttaattaaa tatggagtag cgcttaactt gcctatctgt gtatatgtgt cattacacgc 18720
cgtcacagca gcagaggaaa aaaggaagag gtcgtgcgtc gacgctgagt tactttcaag 18780
atggccaccc catcgatgct gccccaatgg gcatacatgc acatcgccgg acaggatgct 18840
tcggagtacc tgagtccggg tctggtgcag ttcgcccgcg ccacagacac ctacttcaat 18900
ctgggaaata agtttagaaa tcccaccgta gcgccgaccc acgatgtgac caccgaccgt 18960
agccagcggc tcatgttgcg cttcgtgccc gttgaccggg aggacaatac atactcttac 19020
aaagtgcggt acaccctggc cgtgggcgac aacagagtgc tggatatggc cagcacgttc 19080
tttgacatta ggggtgtgtt ggacagaggt cccagtttca aaccctattc tggtacggct 19140
tacaactccc tggctcctaa aggcgctcca aatacatctc agtggattgc agaaggtgta 19200
aaaaatacaa ctggtgagga acacgtaaca gaagaggaaa ccaatactac tacttacact 19260
tttggcaatg ctcctgtaaa agctgaagct gaaattacaa aagaaggact cccagtaggt 19320
ttggaagttt cagatgaaga aagtaaaccg atttatgctg ataaaacata tcagccagaa 19380
cctcagctgg gagatgaaac ttggactgac cttgatggaa aaaccgaaaa gtatggaggc 19440
agggctctca aacccgatac taagatgaaa ccatgctacg ggtcctttgc caaacctact 19500
aatgtgaaag gcggtcaggc aaaacaaaaa acaacggagc agccaaatca gaaagtcgaa 19560
tatgatatcg acatggagtt ttttgatgcg gcatcgcaga aaacaaactt aagtcctaaa 19620
attgtcatgt atgcagaaaa tgtaaatttg gaaactccag acactcatgt agtgtacaaa 19680
cctggaacag aagacacaag ttccgaagct aatttgggac aacaatctat gcccaacaga 19740

```
cccaactaca ttggcttcag agataacttt attggactta tgtactataa cagtactggt  19800
aacatggggg tgctggctgg tcaagcgtct cagttaaatg cagtggttga cttgcaggac  19860
agaaacacag aactttctta ccaactcttg cttgactctc tgggcgacag aaccagatac  19920
tttagcatgt ggaatcaggc tgtggacagt tatgatcctg atgtacgtgt tattgaaaat  19980
catggtgtgg aagatgaact tcccaactac tgttttccac tggacggcat aggtgttcca  20040
acaaccagtt acaaatcaat agttccaaat ggagacaatg cgcctaattg gaaggaacct  20100
gaagtaaatg gaacaagtga gatcggacag ggtaatttgt ttgccatgga aattaacctt  20160
caagccaatc tatggcgaag tttcctttat tccaatgtgg ctctatatct cccagactcg  20220
tacaaataca ccccgtccaa tgtcactctt ccagaaaaca aaaacaccta cgactacatg  20280
aacgggcggg tggtgccgcc atctctagta gacacctatg tgaacattgg tgccaggtgg  20340
tctctggatg ccatggacaa tgtcaaccca ttcaaccacc accgtaacgc tggcttgcgt  20400
taccgatcca tgcttctggg taacggacgt tatgtgcctt tccacataca agtgcctcaa  20460
aaattcttcg ctgttaaaaa cctgctgctt ctcccaggct cctacactta tgagtggaac  20520
tttaggaagg atgtgaacat ggttctacag agttccctcg gtaacgacct gcgggtagat  20580
ggcgccagca tcagtttcac gagcatcaac ctctatgcta ctttttttccc catggctcac  20640
aacaccgctt ccacccttga agccatgctg cggaatgaca ccaatgatca gtcattcaac  20700
gactacctat ctgcagctaa catgctctac cccattcctg ccaatgcaac caatattccc  20760
atttccattc cttctcgcaa ctgggcggct ttcagaggct ggtcatttac cagactgaaa  20820
accaaagaaa ctccctcttt ggggtctgga tttgacccct actttgtcta ttctggttct  20880
attccctacc tggatggtac cttctacctg aaccacactt ttaagaaggt ttccatcatg  20940
tttgactctt cagtgagctg gcctggaaat gacaggttac tatctcctaa cgaatttgaa  21000
ataaagcgca ctgtggatgg cgaaggctac aacgtagccc aatgcaacat gaccaaagac  21060
tggttcttgg tacagatgct cgccaactac aacatcggct atcagggctt ctacattcca  21120
gaaggataca aagatcgcat gtattcattt ttcagaaact tccagcccat gagcaggcag  21180
gtggttgatg aggtcaatta caaagacttc aaggccgtcg ccatacccta ccaacacaac  21240
aactctggct ttgtgggtta catggctccg accatgcgcc aaggtcaacc ctatcccgct  21300
aactatccct atccactcat tggaacaact gccgtaaata gtgttacgca gaaaaagttc  21360
ttgtgtgaca gaaccatgtg gcgcataccg ttctcgagca acttcatgtc tatgggggcc  21420
cttacagact tgggacagaa tatgctctat gccaactcag ctcatgctct ggacatgacc  21480
tttgaggtgg atcccatgga tgagcccacc ctgctttatc ttctcttcga agttttcgac  21540
gtggtcagag tgcatcagcc acaccgcggc atcatcgagg cagtctacct gcgtacaccg  21600
ttctcggccg gtaacgctac cacgtaagaa gcttcttgct tcttgcaaat agcagctgca  21660
accatggcct gcggatccca aaacggctcc agcgagcaag agctcagagc cattgtccaa  21720
gacctgggtt gcggaccccta ttttttggga acctacgata agcgcttccc ggggttcatg  21780
gcccccgata agctcgcctg tgccattgta aatacggccg gacgtgagac gggggggagag  21840
cactggttgg ctttcggttg gaacccacgt tctaacacct gctacctttt tgatcctttt  21900
ggattctcgg atgatcgtct caaacagatt taccagtttg aatatgaggg tctcctgcgc  21960
cgcagcgctc ttgctaccaa ggaccgctgt attacgctgg aaaaatctac ccagaccgtg  22020
cagggtcccc gttctgccgc ctgcggactt ttctgctgca tgttccttca cgcctttgtg  22080
cactggcctg accgtcccat ggacggaaac cccaccatga aattgctaac tggagtgcca  22140
```

```
aacaacatgc ttcattctcc taaagtccag cccaccctgt gtgacaatca aaaagcactc  22200
taccattttc ttaataccca ttcgccttat tttcgctccc atcgtacaca catcgaaagg  22260
gccactgcgt tcgaccgtat ggatgttcaa taatgactca tgtaaacaac gtgttcaata  22320
aacatcactt tatttttta catgtatcaa ggctctgcat tacttattta tttacaagtc  22380
gaatgggttc tgacgagaat cagaatgacc cgcaggcagt gatacgttgc ggaactgata  22440
cttgggttgc cacttgaatt cgggaatcac caacttggga accggtatat cgggcaggat  22500
gtcactccac agctttctgg tcagctgcaa agctccaagc aggtcaggag ccgaaatctt  22560
gaaatcacaa ttaggaccag tgctttgagc gcgagagttg cggtacaccg gattgcagca  22620
ctgaaacacc atcagcgacg gatgtctcac gcttgccagc acggtgggat ctgcaatcat  22680
gcccacatcc agatcttcag cattggcaat gctgaacggg gtcatcttgc aggtctgcct  22740
acccatggcg ggcacccaat taggcttgtg gttgcaatcg cagtgcaggg ggatcagtat  22800
catcttggcc tgatcctgtc tgattcctgg atacacggct ctcatgaaag catcatattg  22860
cttgaaagcc tgctgggctt tactaccctc ggtataaaac atcccgcagg acctgctcga  22920
aaactggtta gctgcacagc cggcatcatt cacacagcag cgggcgtcat tgttagctat  22980
ttgcaccaca cttctgcccc agcggttttg ggtgattttg gttcgctcgg gattctcctt  23040
taaggctcgt tgtccgttct cgctggccac atccatctcg ataatctgct ccttctgaat  23100
cataatattg ccatgcaggc acttcagctt gccctcataa tcattgcagc catgaggcca  23160
caacgcacag cctgtacatt cccaattatg gtgggcgatc tgagaaaaag aatgtatcat  23220
tccctgcaga aatcttccca tcatcgtgct cagtgtcttg tgactagtga aagttaactg  23280
gatgcctcgg tgctcctcgt ttacgtactg gtgacagatg cgcttgtatt gttcgtgttg  23340
ctcaggcatt agtttaaaag aggttctaag ttcgttatcc agcctgtact tctccatcag  23400
cagacacatc acttccatgc ctttctccca agcagacacc aggggcaagc taatcggatt  23460
cttaacagtg caggcagcag ctcctttagc cagagggtca tctttagcga tcttctcaat  23520
gcttcttttg ccatccttct caacgatgcg cacgggcggg tagctgaaac ccactgctac  23580
aagttgcgcc tcttctcttt cttcttcgct gtcttgactg atgtcttgca tggggatatg  23640
tttggtcttc cttggcttct ttttgggggg tatcggagga ggaggactgt cgctccgttc  23700
cggagacagg gaggattgtg acgtttcgct caccattacc aactgactgt cggtagaaga  23760
acctgacccc acacggcgac aggtgtttct cttcgggggc agaggtggag gcgattgcga  23820
agggctgcgg tccgacctgg aaggcggatg actggcagaa cccccttccgc gttcgggggt  23880
gtgctccctg tggcggtcgc ttaactgatt tccttcgcgg ctggccattg tgttctccta  23940
ggcagagaaa caacagacat ggaaactcag ccattgctgt caacatcgcc acgagtgcca  24000
tcacatctcg tcctcagcga cgaggaaaag gagcagagct taagcattcc accgcccagt  24060
cctgccacca cctctaccct agaagataag gaggtcgacg catctcatga catgcagaat  24120
aaaaaagcga aagagtctga gacagacatc gagcaagacc cgggctatgt gacaccggtg  24180
gaacacgagg aagagttgaa acgctttcta gagagagagg atgaaaactg cccaaaacaa  24240
cgagcagata actatcacca agatgctgga aatagggatc agaacaccga ctacctcata  24300
gggcttgacg gggaagacgc gctccttaaa catctagcaa gacagtcgct catagtcaag  24360
gatgcattat tggacagaac tgaagtgccc atcagtgtgg aagagctcag ccgcgcctac  24420
gagcttaacc tcttttcacc tcgtactccc cccaaacgtc agccaaacgg cacctgcgag  24480
```

-continued

```
ccaaatcctc gcttaaactt ttatccagct tttgctgtgc cagaagtact ggctacctat  24540
cacatctttt ttaaaaatca aaaaattcca gtctcctgcc gcgctaatcg cacccgcgcc  24600
gatgccctac tcaatctggg acctggttca cgcttacctg atatagcttc cttggaagag  24660
gttccaaaga tcttcgaggg tctgggcaat aatgagactc gggccgcaaa tgctctgcaa  24720
aagggagaaa atggcatgga tgagcatcac agcgttctgg tggaattgga aggcgataat  24780
gccagactcg cagtactcaa gcgaagcatc gaggtcacac acttcgcata tcccgctgtc  24840
aacctgcccc ctaaagtcat gacggcggtc atggaccagt tactcattaa gcgcgcaagt  24900
ccccctttcag aagacatgca tgacccagat gcctgtgatg agggtaaacc agtggtcagt  24960
gatgagcagc taacccgatg gctgggcacc gactctccca gggatttgga agagcgtcgc  25020
aagcttatga tggccgtggt gctggttacc gtagaactag agtgtctccg acgtttcttt  25080
accgattcag aaaccttgcg caaactcgaa gagaatctgc actacacttt tagacacggc  25140
tttgtgcggc aggcatgcaa gatatctaac gtggaactca ccaacctggt ttcctacatg  25200
ggtattctgc atgagaatcg cctaggacaa agcgtgctgc acagcaccct gaaggggggaa  25260
gcccgccgtg attacatccg cgattgtgtc tatctgtacc tgtgccaaac gtggcaaacc  25320
ggcatgggtg tatggcagca atgtttagaa gaacagaact tgaaagagct tgacaagctc  25380
ttacagaaat ctcttaaggt tctgtggaca gggttcgacg agcgcaccgt cgcttccgac  25440
ctggcagacc tcatcttccc agagcgtctc agggttactt tgcgaaacgg attgcctgac  25500
tttatgagcc agagcatgct taacaatttt cgctctttca tcctggaacg ctccggtatc  25560
ctgcccgcca cctgctgcgc actgccctcc gactttgtgc ctctcaccta ccgcgagtgc  25620
cccccgccgc tatggagtca ctgctacctg ttccgtctgg ccaactatct ctcctaccac  25680
tcggatgtga tcgaggatgt gagcggagac ggcttgctgg agtgtcactg ccgctgcaat  25740
ctgtgcacgc cccaccggtc cctagcttgc aaccccccagt tgatgagcga aacccagata  25800
ataggcacct ttgaattgca aggccccagc agccaaggcg atgggtcttc tcctgggcaa  25860
agtttaaaac tgaccccggg actgtggacc tccgcctact tgcgcaagtt tgctccggaa  25920
gattaccacc cctatgaaat caagttctat gaggaccaat cacagcctcc aaaggccgaa  25980
ctttcggcct gcgtcatcac ccagggggca attctggccc aattgcaagc catccaaaaa  26040
tcccgccaag aatttctact gaaaaagggt aagggggtct accttgaccc ccagaccggc  26100
gaggaactca acacaaggtt ccctcaggat gtcccaacga cgagaaaaca agaagttgaa  26160
ggtgcagccg ccgcccccag aagatatgga ggaagattgg gacagtcagg cagaggaggc  26220
ggaggaggac agtctggagg acagtctgga ggaagacagt ttggaggagg aaaacgagga  26280
ggcagaggag gtggaagaag taaccgccga caaacagtta tcctcggctg cggagacaag  26340
caacagcgct accatctccg ctccgagtcg aggaacccgg cggcgtccca gcagtagatg  26400
ggacgagacc ggacgcttcc cgaacccaac cagcgcttcc aagaccggta agaaggatcg  26460
gcagggatac aagtcctggc gggggcataa gaatgccatc atctcctgct tgcatgagtg  26520
cgggggcaac atatccttca cgcggcgcta cttgctattc caccatgggg tgaactttcc  26580
gcgcaatgtt ttgcattact accgtcacct ccacagcccc tactatagcc agcaaatccc  26640
ggcagtctcg acagataaag acagcggcgg cgacctccaa cagaaaacca gcagcggcag  26700
ttagaaaata cacaacaagt gcagcaacag gaggattaaa gattacagcc aacgagccag  26760
cgcaaacccg agagttaaga aatcggatct ttccaaccct gtatgccatc ttccagcaga  26820
gtcggggtca agagcaggaa ctgaaaataa aaaaccgatc tctgcgttcg ctcaccagaa  26880
```

```
gttgtttgta tcacaagagc gaagatcaac ttcagcgcac tctcgaggac gccgaggctc   26940

tcttcaacaa gtactgcgcg ctgactctta aagagtaggc agcgaccgcg cttattcaaa   27000

aaaggcggga attacatcat cctcgacatg agtaaagaaa ttcccacgcc ttacatgtgg   27060

agttatcaac cccaaatggg attggcggca ggcgcctccc aggactactc cacccgcatg   27120

aattggctca gcgccgggcc ttctatgatt tctcgagtta atgatatacg cgcctaccga   27180

aaccaaatac ttttggaaca gtcagctctt accaccacgc cccgccaaca ccttaatccc   27240

agaaattggc ccgccgccct agtgtaccag gaaagtcccg ctcccaccac tgtattactt   27300

cctcgagacg cccaggccga agtccaaatg actaatgcag gtgcgcagtt agctggcggc   27360

tccaccctat gtcgtcacag gcctcggcat aatataaaac gcctgatgat cagaggccga   27420

ggtatccagc tcaacgacga gtcggtgagc tctccgcttg gtctacgacc agacggaatc   27480

tttcagattg ccggctgcgg gagatcttcc ttcacccctc gtcaggctgt tctgactttg   27540

gaaagttcgt cttcgcaacc ccgctcgggc ggaatcggga ccgttcaatt tgtggaggag   27600

tttactccct ctgtctactt caacccccttc tccggatctc ctgggcatta cccggacgag   27660

ttcataccga acttcgacgc gattagcgag tcagtggacg gctacgattg atgtctggtg   27720

acgcggctga gctatctcgg ctgcgacatc tagaccactg ccgccgcttt cgctgctttg   27780

cccgggaact cattgagttc atctacttcg aactccccaa ggatcaccct caaggtccgg   27840

cccacggagt gcggatttct atcgaaggca aaatagactc tcgcctgcaa cgaattttct   27900

cccagcggcc cgtgctgatc gagcgagacc agggaaacac cacggtttcc atctactgca   27960

tttgtaatca ccccggattg catgaaagcc tttgctgtct tatgtgtact gagtttaata   28020

aaaactgaat taagactctc ctacggactg ccgcttcttc aacccggatt ttacaaccag   28080

aagaacgaaa cttttcctgt cgtccaggac tctgttaact tcacctttcc tactcacaaa   28140

ctagaagctc aacgactaca ccgcttttcc agaagcattt tccctactaa tactactttc   28200

aaaaccggag gtgagctcca aggtcttcct acagaaaacc cttgggtgga agcgggcctt   28260

gtagtgctag gaattcttgc gggtgggctt gtgattattc tttgctacct atacacacct   28320

tgcttcactt tcttagtggt gttgtggtat tggtttaaaa aatatggtga gcaagggcga   28380

ggagctgttc accggggtgg tgcccatcct ggtcgagctg gacggcgacg taaacggcca   28440

caagttcagc gtgtccggcg agggcgaggg cgatgccacc tacggcaagc tgaccctgaa   28500

gttcatctgc accaccggca agctgcccgt gccctggccc accctcgtga ccaccctgac   28560

ctacggcgtg cagtgcttca gccgctaccc cgaccacatg aagcagcacg acttcttcaa   28620

gtccgccatg cccgaaggct acgtccagga gcgcaccatc ttcttcaagg acgacggcaa   28680

ctacaagacc cgcgccgagg tgaagttcga gggcgacacc ctggtgaacc gcatcgagct   28740

gaagggcatc gacttcaagg aggacggcaa catcctgggg cacaagctgg agtacaacta   28800

caacagccac aacgtctata tcatggccga caagcagaag aacggcatca aggtgaactt   28860

caagatccgc cacaacatcg aggacggcag cgtgcagctc gccgaccact accagcagaa   28920

cacccccatc ggcgacggcc ccgtgctgct gcccgacaac cactacctga gcacccagtc   28980

cgccctgagc aaagacccca acgagaagcg cgatcacatg gtcctgctgg agttcgtgac   29040

cgccgccggg atcactctcg gcatggacga gctgtacaag taacctcttt ctgtttacag   29100

acatggcttc tcttacatct ctcatatttg tcagcattgt cactgccgct catggacaaa   29160

cagtcgtctc tatccctcta ggacataatt acactctcat aggaccccca atcacttcag   29220
```

-continued

```
aggtcatctg ggccaaactg ggaagcgttg attactttga tataatctgc aacaaaacaa  29280
aaccaataat agtaacttgc aacatacaaa atcttacatt gattaatgtt agcaaagttt  29340
acagcggtta ctattatggt tatgacagat acagtagtca atatagaaat tacttggttc  29400
gtgttaccca gttgaaaacc acgaaaatgc caaatatggc aaagattcga tccgatgaca  29460
attctctaga aacttttaca tctcccacca cacccgacga aaaaaacatc ccagattcaa  29520
tgattgcaat tgttgcagcg gtggcagtgg tgatggcact aataataata tgcatgcttt  29580
tatatgcttg tcgctacaaa aagtttcatc ctaaaaaaca agatctccta ctaaggctta  29640
acatttaatt tctttttata cagccatggt ttccactacc acattcctta tgcttactag  29700
tctcgcaact ctgacttctg ctcgctcaca cctcactgta actataggct caaactgcac  29760
actaaaagga cctcaaggtg gtcatgtctt ttggtggaga atatatgaca atggatggtt  29820
tacaaaacca tgtgaccaac ctggtagatt tttctgcaac ggcagagacc taaccattat  29880
caacgtgaca gcaaatgaca aaggcttcta ttatggaacc gactataaaa gtagtttaga  29940
ttataacatt attgtactgc catctaccac tccagcaccc cgcacaacta ctttctctag  30000
cagcagtgtc gctaacaata caatttccaa tccaaccttt gccgcgcttt taaaacgcac  30060
tgtgaataat tctacaactt cacatacaac aatttccact tcaacaatca gcattatcgc  30120
tgcagtgaca attggaatat ctattcttgt ttttaccata acctactacg cctgctgcta  30180
tagaaaagac aaacataaag gtgatccatt acttagattt gatatttaat ttgttctttt  30240
tttttttatt tacagtatgg tgaacaccaa tcatggtacc tagaaatttc ttcttcacca  30300
tactcatttg tgcatttaat gtttgcgcta ctttcacagc agtagccaca gcaaccccag  30360
actgtatagg agcatttgct tcctatgcac tttttgcttt tgttacttgc atctgcgtat  30420
gtagcatagt ctgcctggtt attaattttt tccaacttat agactggatc cttgtgcgaa  30480
ttgcctacct gcgccaccat cccgaatacc gcaaccaaaa tatcgcggca cttcttagac  30540
tcatctaaaa ccatgcaggc tatactacca atatttttgc ttctattgct tccctacgct  30600
gtctcaaccc cagctgccta tagtactcca ccagaacacc ttagaaaatg caaattccaa  30660
caaccgtggt catttcttgc ttgctatcga gaaaaatcag aaattccccc aaatttaata  30720
atgattgctg gaataattaa tataatctgt tgcaccataa tttcattttt gatatacccc  30780
ctatttgatt ttggctggaa tgctcccaat gcacatgatc atccacaaga cccagaggaa  30840
cacattcccc tacaaaacat gcaacatcca atagcgctaa tagattacga aagtgaacca  30900
caacccccac tactccctgc tattagttac ttcaacctaa ccggcggaga tgactgaaac  30960
actcaccacc tccaattccg ccgaggatct gctcgatatg gacggccgcg tctcagaaca  31020
gcgactcgcc caactacgca tccgccagca gcaggaacgc gcggccaaag agctcagaga  31080
tgtcatccaa attcaccaat gcaaaaaagg catattctgt ttggtaaaac aagccaagat  31140
atcctacgag atcaccgcta ctgaccatcg cctctcttac gaacttggcc cccaacgaca  31200
aaaatttacc tgcatggtgg gaatcaaccc catagttatc acccagcaaa gtggagatac  31260
taagggttgc attcactgct cctgcgattc catcgagtgc acctacaccc tgctgaagac  31320
cctatgcggc ctaagagacc tgctaccaat gaattaaaaa atgattaata aaaaatcact  31380
tacttgaaat cagcaataag gtctctgttg aaattttctc ccagcagcac ctcacttccc  31440
tcttcccaac tctggtattc taaaccccgt tcagcggcat actttctcca tactttaaag  31500
gggatgtcaa attttagctc ctctcctgta cccacaatct tcatgtcttt cttcccagat  31560
gaccaagaga gtccggctca gtgactcctt caaccctgtc tacccctatg aagatgaaag  31620
```

```
cacctcccaa caccccttta taaacccagg gtttatttcc ccaaatggct tcacacaaag  31680
cccaaacgga gttcttactt taaaatgttt aaccccacta acaaccacag gcggatctct  31740
acagctaaaa gtgggagggg gacttacagt ggatgacacc aacggttttt tgaaagaaaa  31800
cataagtgcc accacaccac tcgttaagac tggtcactct ataggtttac cactaggagc  31860
cggattggga acgaatgaaa ataaactttg tatcaaatta ggacaaggac ttacattcaa  31920
ttcaaacaac atttgcattg atgacaatat taacacctta tggacaggag tcaaccccac  31980
cgaagccaac tgtcaaatca tgaactccag tgaatctaat gattgcaaat taattctaac  32040
actagttaaa actggagcac tagtcactgc atttgtttat gttataggag tatctaacaa  32100
ttttaatatg ctaactacac acagaaatat aaattttact gcagagctgt tttcgattc   32160
tactggtaat ttactaacta gactctcatc cctcaaaact ccacttaatc ataaatcagg  32220
acaaaacatg gctactggtg ccattactaa tgctaaaggt ttcatgccca gcacgactgc  32280
ctatcctttc aatgataatt ctagagaaaa agaaaactac atttacggaa cttgttacta  32340
cacagctagt gatcgcactg cttttcccat tgacatatct gtcatgctta accgaagagc  32400
aataaatgac gagacatcat attgtattcg tataacttgg tcctggaaca caggagatgc  32460
cccagaggtg caaacctctg ctacaaccct agtcacctcc ccatttacct tttactacat  32520
cagagaagac gactgacaaa taaagtttaa cttgtttatt tgaaaatcaa ttcacaaaat  32580
ccgagtagtt attttgcctc cccccttccca tttaacagaa tacaccaatc tctccccacg  32640
cacagcttta aacatttgga taccattaga tatagacatg gttttagatt ccacattcca  32700
aacagtttca gagcgagcca atctggggtc agtgatagat aaaaatccat cgggatagtc  32760
ttttaaagcg ctttcacagt ccaactgctg cggatggact ccggagtctg gatcacggtc  32820
atctggaaga agaacgatgg gaatcataat ccgaaaacgg tatcggacga ttgtgtctca  32880
tcaaacccac aagcagccgc tgtctgcgtc gctccgtgcg actgctgttt atgggatcag  32940
ggtccacagt gtcctgaagc atgattttaa tagcccttaa catcaacttt ctggtgcgat  33000
gcgcgcagca acgcattctg atttcactca aatctttgca gtaggtacaa cacattatta  33060
caatattgtt taataaacca taattaaaag cgctccagcc aaaactcata tctgatataa  33120
tcgcccctgc atgaccatca taccaaagtt taatataaat taaatgacgt tccctcaaaa  33180
acacactacc cacatacatg atctcttttg gcatgtgcat attaacaatc tgtctgtacc  33240
atggacaacg ttggttaatc atgcaaccca atataacctt ccggaaccac actgccaaca  33300
ccgctccccc agccatgcat tgaagtgaac cctgctgatt acaatgacaa tgaagaaccc  33360
aattctctcg accgtgaatc acttgagaat gaaaaatatc tatagtggca caacatagac  33420
ataaatgcat gcatcttctc ataattttta actcctcagg atttagaaac atatcccagg  33480
gaataggaag ctcttgcaga acagtaaagc tggcagaaca aggaagacca cgaacacaac  33540
ttacactatg catagtcata gtatcacaat ctggcaacag cgggtggtct tcagtcatag  33600
aagctcgggt ttcattttcc tcacaacgtg gtaactgggc tctggtgtaa gggtgatgtc  33660
tggcgcatga tgtcgagcgt gcgcgcaacc ttgtcataat ggagttgctt cctgacattc  33720
tcgtattttg tatagcaaaa cgcggccctg gcagaacaca ctcttcttcg ccttctatcc  33780
tgccgcttag cgtgttccgt gtgatagttc aagtacaacc acactcttaa gttggtcaaa  33840
agaatgctgg cttcagttgt aatcaaaact ccatcgcatc taatcgttct gaggaaatca  33900
tccacggtag catatgcaaa tcccaaccaa gcaatgcaac tggattgtgt ttcaagcagg  33960
```

agaggagagg gaagagacgg aagaaccatg ttaattttta ttccaaacga tctcgcagta 34020
cttcaaattg tagatcgcgc agatggcatc tctcgccccc actgtgttgg tgaaaaagca 34080
cagctagatc aaaagaaatg cgattttcaa ggtgctcaac ggtggcttcc agcaaagcct 34140
ccacgcgcac atccaagaac aaaagaatac caaaagaagg agcattttct aactcctcaa 34200
tcatcatatt acattcctgc accattccca gataattttc agctttccag ccttgaatta 34260
ttcgtgtcag ttcttgtggt aaatccaatc cacacattac aaacaggtcc cggagggcgc 34320
cctccaccac cattcttaaa cacaccctca taatgacaaa atatcttgct cctgtgtcac 34380
ctgtagcgaa ttgagaatgg caacatcaat tgacatgccc ttggctctaa gttcttcttt 34440
aagttctagt tgtaaaaact ctctcatatt atcaccaaac tgcttagcca gaagcccccc 34500
gggaacaaga gcaggggacg ctacagtgca gtacaagcgc agacctcccc aattggctcc 34560
agcaaaaaca agattggaat aagcatattg ggaaccgcca gtaatatcat cgaagttgct 34620
ggaaatataa tcaggcagag tttcttgtaa aaattgaata aaagaaaaat ttgccaaaaa 34680
aacattcaaa acctctggga tgcaaatgca ataggttacc gcgctgcgct ccaacattgt 34740
tagttttgaa ttagtctgca aaaataaaaa aaaaaacaag cgtcatatca tagtagcctg 34800
acgaacagat ggataaatca gtctttccat cacaagacaa gccacagggt ctccagctcg 34860
accctcgtaa aacctgtcat catgattaaa caacagcacc gaaagttcct cgcggtgacc 34920
agcatgaata attcttgatg aagcatacaa tccagacatg ttagcatcag ttaacgagaa 34980
aaaacagcca acatagcctt tgggtataat tatgcttaat cgtaagtata gcaaagccac 35040
ccctcgcgga tacaaagtaa aaggcacagg agaataaaaa atataattat ttctctgctg 35100
ctgttcaggc aacgtcgccc ccggtccctc taaatacaca tacaaagcct catcagccat 35160
ggcttaccag acaaagtaca gcgggcacac aaagcacaag ctctaaagtg actctccaac 35220
ctctccacaa tatatatata cacaagccct aaactgacgt aatgggagta aagtgtaaaa 35280
aatcccgcca aacccaacac acaccccgaa actgcgtcac cagggaaaag tacagtttca 35340
cttccgcaat cccaacaggc gtaacttcct ctttctcacg gtacgtgata tcccactaac 35400
ttgcaacgtc attttcccac ggtcgcaccg cccctttttag ccgttaaccc cacagccaat 35460
caccacacga tccacacttt ttaaaatcac ctcatttaca tattggcacc attccatcta 35520
taaggtatat tattgatgat g 35541

<210> SEQ ID NO 11
<211> LENGTH: 35541
<212> TYPE: DNA
<213> ORGANISM: Artificial Sequence
<220> FEATURE:
<223> OTHER INFORMATION: Fully synthetic

<400> SEQUENCE: 11
catcatcaat aatatacctt atagatggaa tggtgccaat atgtaaatga ggtgatttta 60
aaaagtgtgg atcgtgtggt gattggctgt ggggttaacg gctaaaaggg gcggtgcgac 120
cgtgggaaaa tgacgttttg tgggggtgga gttttttttgc aagttgtcgc gggaaatgtg 180
acgcataaaa aggctacaca ggaagtgaca attttcgcgc ggttttaggc ggatgttgta 240
gtaaatttgg gcgtaaccga gtaagatttg gccattttcg cgggaaaact gaataagagg 300
aagtgaaatc tgaataattt tgtgttactc atagcgcgta atatttgtct agggccgcgg 360
ggactttgac cgtttacgtg tgtcaaggag cccaagtcgc ggggaagtgt tgcagggagg 420
cactccggga ggtcccgcgt gcccgtccag ggagcaatgc gtcctcgggt tcgtccccag 480

-continued ccgcgtctac gcgcctccgt cctccccttc acgtccggca ttcgtggtgc ccggagcccg 540
acgccccgcg tccggacctg gaggcagccc tgggtctccg gatcaggcca gcggccaaag 600
ggtcgccgca cgcacctgtt cccagggcct ccacatcatg gcccctccct cgggttaccc 660
cacagcttag gccgattcga cctctctccg ctggggccct cgctggcgtc cctgcaccct 720
gggagcgcga gcggcgcgcg ggcggggaag cgcggcccag acccccgggt ccgcccggag 780
cagctgcgct gtcggggcca ggccgggctc ccagtggatt cgcgggcaca gacgcccagg 840
accgcgcttc ccacgtggcg gagggactgg ggacccgggc acccgtcctg cccccttcacc 900
ttccagctcc gcctcctccg cgcggacccc gccccgtccc gacccctccc gggtccccgg 960
cccagccccc tccgggccct cccagcccct ccccttcctt tccgcggccc cgccctctcc 1020
tcgcggcgcg agtttcaggc agcgctgcgt cctgctgcgc acgtgggaag ccctggcccc 1080
ggccaccccc gcgatgagag atttgcgatt tctgcctcag gaaataatct ctgctgagac 1140
tggaaatgaa atattggagc ttgtggtgca cgccctgatg ggagacgatc cggagccacc 1200
tgtgcagctt tttgagcctc ctacgcttca ggaactgtat gatttagagg tagagggatc 1260
ggaggattct aatgaggaag ctgtaaatgg ctttttttacc gattctatgc ttttagctgc 1320
taatgaaggg ttagaattag atccgccttt ggacactttt gatactccag gggtaattgt 1380
ggaaagcggt acaggtgtaa gaaaattacc tgatttgagt tccgtggact gtgatttgca 1440
ctgctatgaa gacgggtttc ctccgagtga tgaggaggac catgaaaagg agcagtccat 1500
gcagactgca gcgggtgagg gagtgaaggc tgccaatgtt ggttttcagt tggattgccc 1560
ggagcttcct ggacatggct gtaagtcttg tgaatttcac aggaaaaata ctggagtaaa 1620
ggaactgtta tgttcgcttt gttatatgag aacgcactgc cactttattt acagtaagtg 1680
tgtttaagtt aaaatttaaa ggaatatgct gtttttcaca tgtatattga gtgtgagttt 1740
tgtgcttctt attataggtc ctgtgtctga tgctgatgaa tcaccatctc ctgattctac 1800
tacctcacct cctgagattc aagcacctgt tcctgtggac gtgcgcaagc ccattcctgt 1860
gaagcttaag cctgggaaac gtccagcagt ggaaaaactt gaggacttgt tacagggtgg 1920
ggacggacct ttggacttga gtacacggaa acgtccaaga caataagtgt tccatatccg 1980
tgtttactta aggtgacgtc aatatttgtg tgacagtgca atgtaataaa aatatgttaa 2040
ctgttcactg gtttttattg ctttttgggc ggggactcag gtatataagt agaagcagac 2100
ctgtgtggtt agctcatagg agctggcttt catccatgga ggtttgggcc attttggaag 2160
accttaggaa gactaggcaa ctgttagaga acgcttcgga cggagtctcc ggtttttgga 2220
gattctggtt cgctagtgaa ttagctaggg tagtttttag gataaaacag gactataaac 2280
aagaatttga aaagttgttg gtagattgcc caggactttt tgaagctctt aatttgggcc 2340
atcaggttca ctttaaagaa aaagttttat cagttttaga cttttcaacc ccaggtagaa 2400
ctgctgctgc tgtggctttt cttacttttta tattagataa atggatcccg cagactcatt 2460
tcagcagggg atacgttttg gatttcatag ccacagcatt gtggagaaca tggaaggttc 2520
gcaagatgag gacaatctta ggttactggc cagtgcagcc tttgggtgta gcgggaatcc 2580
tgaggcatcc accggtcatg ccagcggttc tggaggagga acagcaagag gacaacccga 2640
gagccggcct ggaccctcca gtggaggagg cggagtagct gacttgtctc ctgaactgca 2700
acgggtgctt actggatcta cgtccactgg acgggatagg ggcgttaaga gggagagggc 2760
atctagtggt actgatgcta gatctgagtt ggctttaagt ttaatgagtc gcagacgtcc 2820

-continued

```
tgaaaccatt tggtggcatg aggttcagaa agagggaagg gatgaagttt ctgtattgca   2880
ggagaaatat tcactggaac aggtgaaaac atgttggttg gagcctgagg atgattggga   2940
ggtggccatt aaaaattatg ccaagatagc tttgaggcct gataaacagt ataagattac   3000
tagacggatt aatatccgga atgcttgtta catatctgga aatggggctg aggtggtaat   3060
agatactcaa gacaaggcag ttattagatg ctgcatgatg gatatgtggc ctggggtagt   3120
cggtatggaa gcagtaactt ttgtaaatgt taagtttagg ggagatggtt ataatggaat   3180
agtgtttatg gccaatacca aacttatatt gcatggttgt agcttttttg gtttcaacaa   3240
tacctgtgta gatgcctggg gacaggttag tgtacgggga tgtagtttct atgcgtgttg   3300
gattgccaca gctggcagaa ccaagagtca attgtctctg aagaaatgca tatttcaaag   3360
atgtaacctg ggcattctga atgaaggcga agcaagggtc cgccactgcg cttctacaga   3420
tactggatgt tttattttga ttaagggaaa tgccagcgta aagcataaca tgatttgcgg   3480
tgcttccgat gagaggcctt atcaaatgct cacttgtgct ggtgggcatt gtaatatgct   3540
ggctactgtg catattgttt cccatcaacg caaaaaatgg cctgtttttg atcacaatgt   3600
gatgacgaag tgtaccatgc atgcaggtgg gcgtagagga atgtttatgc cttaccagtg   3660
taacatgaat catgtgaaag tgttgttgga accagatgcc ttttccagaa tgagcctaac   3720
aggaattttt gacatgaaca tgcaaatctg gaagatcctg aggtatgatg atacgagatc   3780
gagggtacgc gcatgcgaat gcggaggcaa gcatgccagg ttccagccgg tgtgtgtaga   3840
tgtgactgaa gatctcagac cggatcattt ggttattgcc cgcactggag cagagttcgg   3900
atccagtgga gaagaaactg actaaggtga gtattgggaa aactttgggg tgggattttc   3960
agatggacag attgagtaaa aatttgtttt ttctgtcttg cagctgtcat gagtggaaac   4020
gcttctttta aggggggagt cttcagccct tatctgacag ggcgtctccc atcctgggca   4080
ggagttcgtc agaatgttat gggatctact gtggatggaa gacccgtcca acccgccaat   4140
tcttcaacgc tgacctatgc tactttaagt tcttcacctt tggacgcagc tgcagctgcc   4200
gccgccgctt ctgttgccgc taacactgtg cttggaatgg gttactatgg aagcatcatg   4260
gctaattcca cttcctctaa taacccttct accctgactc aggacaagtt acttgtcctt   4320
ttggcccagc tggaggcttt gacccaacgt ctgggtgaac tttctcagca ggtggtcgag   4380
ttgcgagtac aaactgagtc tgctgtcggc acggcaaagt ctaaataaaa aaatcccaga   4440
atcaatgaat aaataaacaa gcttgttgtt gatttaaaat caagtgtttt tatttcattt   4500
ttcgcgcacg gtatgcccta gaccaccgat ctctatcatt gagaactcgg tggatttttt   4560
ccaggatcct atagaggtgg gattgaatgt ttagatacat gggcattagg ccgtctttgg   4620
ggtggagata gctccattga agggattcat gctccggggt agtgttgtaa atcacccagt   4680
cataacaagg tcgcagtgca tggtgttgca caatatcttt tagaagtagg ctgattgcca   4740
cagataagcc cttggtgtag gtgtttacaa accggttgag ctgggatggg tgcattcggg   4800
gtgaaattat gtgcattttg gattggattt ttaagttggc aatattgccg ccaagatccc   4860
gtcttgggtt catgttatga aggaccacca agacggtgta tccggtacat ttaggaaatt   4920
tatcgtgcag cttggatgga aaagcgtgga aaaatttgga gacacccttg tgtcctccaa   4980
gattttccat gcactcatcc atgataatag caatggggcc gtgggcagcg gcgcgggcaa   5040
acacgttccg tgggtctgac acatcatagt tatgttcctg agttaaatca tcataagcca   5100
ttttaatgaa tttggggcgg agagtaccag attggggtat gaatgttcct tcgggccccg   5160
gagcatagtt cccctcacag atttgcattt cccaagcttt cagttccgag ggtggaatca   5220
```

tgtccacctg gggggctatg aaaaacaccg tttctggggc gggggtgatt aattgtgatg 5280
atagcaaatt tctgagcaat tgagatttgc cacatccggt ggggccataa atgattccga 5340
ttacgggttg caggtggtag tttagggaac ggcaactgcc gtcttctcga agcaaggggg 5400
ccacctcgtt catcatttcc cttacatgca tattttcccg caccaaatcc attaggaggc 5460
gctctcctcc tagtgataga agttcttgta gtgaggaaaa gtttttcagc ggtttcagac 5520
cgtcagccat gggcattttg gagagagttt gctgcaaaag ttctagtctg ttccacagtt 5580
cagtgatgtg ttctatggca tctcgatcca gcagacctcc tcgtttcgcg ggtttggacg 5640
gctcctggaa tagggtatga gacgatgggc gtccagcgct gccagggttc ggtccttcca 5700
gggtctcagt gttcgagtca gggttgtttc cgtcacagtg aaggggtgtg cgcctgcttg 5760
ggcgcttgcc agggtgcgct tcagactcat cctgctggtc gaaaacttct gtcgcttggc 5820
gccctgtatg tcggccaagt agcagtttac catgagttcg tagttgagcg cctcggctgc 5880
gtggcctttg gcgcggagct tacctttgga agtttttcttg cataccgggc agtataggca 5940
tttcagcgca tacaacttgg gcgcaaggaa aacggattct ggggagtatg catctgcgcc 6000
gcaggaggcg caaacagttt cacattccac cagccaggtt aaatccggtt cattggggtc 6060
aaaaacaagt tttccgccat attttttgat gcgtttctta cctttggtct ccatgagttc 6120
gtgtcctcgt tgagtgacaa acaggctgtc cgtgtccccg tagactgatt ttacaggcct 6180
cttctccagt ggagtgcctc ggtcttcttc gtacaggaac tctgaccact ctgatacaaa 6240
ggcgcgcgtc caggccagca caaaggaggc tatgtgggag ggtagcgat cgttgtcaac 6300
cagggggtcc accttttcca aagtatgcaa acacatgtca ccctcttcaa catccaggaa 6360
tgtgattggc ttgtaggtgt atttcacgtg acctggggtc cccgctgggg gggtataaaa 6420
gggggcggtt ctttgctctt cctcactgtc ttccggatcg ctgtccagga acgtcagctg 6480
ttggggtagg tattccctct cgaaggcggg catgacctct gcactcaggt tgtcagtttc 6540
taagaacgag gaggatttga tattgacagt gccggttgag atgcctttca tgaggttttc 6600
gtccatttgg tcagaaaaca caattttttt attgtcaagt ttggtggcaa atgatccata 6660
cagggcgttg gataaaagtt tggcaatgga tcgcatggtt tggttctttt ccttgtccgc 6720
gcgctctttg gcggcgatgt tgagttggac atactcgcgt gccaggcact tccattcggg 6780
gaagatagtt gttaattcat ctggcacgat tctcacttgc caccctcgat tatgcaaggt 6840
aattaaatcc acactggtgg ccacctcgcc tcgaaggggt tcattggtcc aacagagcct 6900
acctcctttc ctagaacaga aagggggaag tgggtctagc ataagttcat cgggagggtc 6960
tgcatccatg gtaaagattc ccggaagtaa atccttatca aaatagctga tgggagtggg 7020
gtcatctaag gccatttgcc attctcgagc tgccagtgcg cgctcatatg ggttaagggg 7080
actgccccat ggcatgggat gggtgagtgc agaggcatac atgccacaga tgtcatagac 7140
gtagatggga tcctcaaaga tgcctatgta ggttggatag catcgccccc ctctgatact 7200
tgctcgcaca tagtcatata gttcatgtga tggcgctagc agccccggac ccaagttggt 7260
gcgattgggt ttttctgttc tgtagacgat ctggcgaaag atggcgtgag aattggaaga 7320
gatggtgggt ctttgaaaaa tgttgaaatg ggcatgaggt agacctacag agtctctgac 7380
aaagtgggca taagattctt gaagcttggt taccagttcg gcggtgacaa gtacgtctag 7440
ggcgcagtag tcaagtgttt cttgaatgat gtcataacct ggttggtttt tcttttccca 7500
cagttcgcgg ttgagaaggt attcttcgcg atccttccag tactcttcta gcggaaaccc 7560

-continued

```
gtctttgtct gcacggtaag atcctagcat gtagaactga ttaactgcct tgtaagggca   7620
gcagcccttc tctacgggta gagagtatgc ttgagcagct tttcgtagcg aagcgtgagt   7680
aagggcaaag gtgtctctga ccatgacttt gagaaattgg tatttgaagt cgatgtcgtc   7740
acaggctccc tgttcccaga gttggaagtc tacccgtttc ttgtaggcgg ggttgggcaa   7800
agcgaaagta acatcattga agagaatctt accggctctg ggcataaaat tgcgagtgat   7860
gcgaaaaggc tgtggtactt ccgctcgatt gttgatcacc tgggcagcta ggacgatctc   7920
gtcgaaaccg ttgatgttgt gtcctacgat gtataattct atgaaacgcg gcgtgcctct   7980
gacgtgaggt agcttactga gctcatcaaa ggttaggtct gtggggtcag ataaggcgta   8040
gtgttcgaga gcccattcgt gcaggtgagg atttgcatgt aggaatgatg accaaagatc   8100
taccgccagt gctgtttgta actggtcccg atactgacga aaatgccggc caattgccat   8160
tttttctgga gtgacacagt agaaggttct ggggtcttgt tgccatcgat cccacttgag   8220
tttaatggct agatcgtggg ccatgttgac gagacgctct tctcctgaga gtttcatgac   8280
cagcatgaaa ggaactagtt gtttgccaaa ggatcccatc caggtgtaag tttccacatc   8340
gtaggtcagg aagagtcttt ctgtgcgagg atgagagccg atcgggaaga actggatttc   8400
ctgccaccag ttggaggatt ggctgttgat gtgatggaag tagaagtttc tgcggcgcgc   8460
cgagcattcg tgtttgtgct tgtacagacg gccgcagtag tcgcagcgtt gcacgggttg   8520
tatctcgtga atgagttgta cctggcttcc cttgacgaga aatttcagtg ggaagccgag   8580
gcctggcgat tgtatctcgt gctcttctat attcgctgta tcggcctgtt catcttctgt   8640
ttcgatggtg gtcatgctga cgagcccccg cgggaggcaa gtccagacct cggcgcggga   8700
ggggcggagc tgaaggacga gagcgcgcag gctggagctg tccagagtcc tgagacgctg   8760
cggactcagg ttagtaggta gggacagaag attaacttgc atgatctttt ccagggcgtg   8820
cgggaggttc agatggtact tgatttccac aggttcgttt gtagagacgt caatggcttg   8880
cagggttccg tgtcctttgg gcgccactac cgtacctttg tttttttcttt tgatcggtgg   8940
tggctctctt gcttcttgca tgctcagaag cggtgacggg gacgcgcgcc gggcggcagc   9000
ggttgttccg gacccgaggg catggctggt agtggcacgt cggcgccgcg cacgggcagg   9060
ttctggtact gcgctctgag aagacttgcg tgcgccacca cgcgtcgatt gacgtcttgt   9120
atctgacgtc tctgggtgaa agctaccggc cccgtgagct tgaacctgaa agagagttca   9180
acagaatcaa tttcggtatc gttaacggca gcttgtctca gtatttcttg tacgtcacca   9240
gagttgtcct ggtaggcgat ctccgccatg aactgctcga tttcttcctc ctgaagatct   9300
ccgcgacccg ctctttcgac ggtggccgcg aggtcattgg agatacggcc catgagttgg   9360
gagaatgcat tcatgcccgc ctcgttccag acgcggctgt aaaccacggc cccctcggag   9420
tctcttgcgc gcatcaccac ctgagcgagg ttaagctcca cgtgtctggt gaagaccgca   9480
tagttgcata ggcgctgaaa aaggtagttg agtgtggtgg caatgtgttc ggcgacgaag   9540
aaatacatga tccatcgtct cagcggcatt tcgctaacat cgcccagagc ttccaagcgc   9600
tccatggcct cgtagaagtc cacggcaaaa ttaaaaaact gggagtttcg cgcggacacg   9660
gtcaattcct cctcgagaag acggatgagt tcggctatgg tggcccgtac ttcgcgttcg   9720
aaggctcccg ggatctcttc ttcctcttct atctcttctt ccactaacat ctcttcttcg   9780
tcttcaggcg gggggcggagg gggcacgcgg cgacgtcgac ggcgcacggg caaacggtcg   9840
atgaatcgtt caatgacctc tccgcggcgg cggcgcatgg tttcagtgac ggcgcggccg   9900
ttctcgcgcg gtcgcagagt aaaaacaccg ccgcgcatct ccttaaagtg gtgactggga   9960
```

ggttctccgt ttgggaggga gagggcgctg attatacatt ttattaattg gcccgtaggg 10020
actgcacgca gagatctgat cgtgtcaaga tccacgggat ctgaaaacct ttcgacgaaa 10080
gcgtctaacc agtcacagtc acaaggtagg ctgagtacgg cttcttgtgg gcgggggtgg 10140
ttatgtgttc ggtctgggtc ttctgtttct tcttcatctc gggaaggtga gacgatgctg 10200
ctggtgatga aattaaagta ggcagttcta agacggcgga tggtggcgag gagcaccagg 10260
tctttgggtc cggcttgctg gatacgcagg cgattggcca ttccccaagc attatcctga 10320
catctagcaa gatctttgta gtagtcttgc atgagccgtt ctacgggcac ttcttcctca 10380
cccgttctgc catgcatacg tgtgagtcca aatccgcgca ttggttgtac cagtgccaag 10440
tcagctacga ctctttcggc gaggatggct tgctgtactt gggtaagggt ggcttgaaag 10500
tcatcaaaat ccacaaagcg gtggtaagct cctgtattaa tggtgtaagc acagttggcc 10560
atgactgacc agttaactgt ctggtgacca gggcgcacga gctcggtgta tttaaggcgc 10620
gaataggcgc gggtgtcaaa gatgtaatcg ttgcaggtgc gcaccagata ctggtaccct 10680
ataagaaaat gcggcggtgg ttggcggtag agaggccatc gttctgtagc tggagcgcca 10740
ggggcgaggt cttccaacat aaggcggtga tagccgtaga tgtacctgga catccaggtg 10800
attcctgcgg cggtagtaga agcccgagga aactcgcgta cgcggttcca aatgttgcgt 10860
agcggcatga agtagttcat tgtaggcacg gtttgaccag tgaggcgcgc gcagtcattg 10920
atgctctata gacacggaga aaatgaaagc gttcagcgac tcgactccgt agcctggagg 10980
aacgtgaacg ggttgggtcg cggtgtaccc cggttcgaga cttgtactcg agccggccgg 11040
agccgcggct aacgtggtat tggcactccc gtctcgaccc agcctacaaa aatccaggat 11100
acggaatcga gtcgttttgc tggtttccga atggcaggga agtgagtcct attttttttt 11160
ttttgccgct cagatgcatc ccgtgctgcg acagatgcgc cccaacaac agcccccctc 11220 gcagcagcag cagcagcaat cacaaaaggc tgtccctgca actactgcaa ctgccgccgt 11280
gagcggtgcg ggacagcccg cctatgatct ggacttggaa gagggcgaag gactggcacg 11340
tctaggtgcg ccttcacccg agcggcatcc gcgagttcaa ctgaaaaaag attctcgcga 11400
ggcgtatgtg ccccaacaga acctatttag agacagaagc ggcgaggagc cggaggagat 11460
gcgagcttcc cgctttaacg cgggtcgtga gctgcgtcac ggtttggacc gaagacgagt 11520
gttgcgggac gaggatttcg aagttgatga aatgacaggg atcagtcctg ccagggcaca 11580
cgtggctgca gccaaccttg tatcggctta cgagcagaca gtaaaggaag agcgtaactt 11640
ccaaaagtct tttaataatc atgtgcgaac cctgattgcc cgcgaagaag ttacccttgg 11700
tttgatgcat ttgtgggatt tgatggaagc tatcattcag aaccctacta gcaaacctct 11760
gaccgcccag ctgtttctgg tggtgcaaca cagcagagac aatgaggctt tcagagaggc 11820
gctgctgaac atcaccgaac ccgaggggag atggttgtat gatcttatca acattctaca 11880
gagtatcata gtgcaggagc ggagcctggg cctggccgag aaggtggctg ccatcaatta 11940
ctcggttttg agcttgggaa aatattacgc tcgcaaaatc tacaagactc catacgttcc 12000
catagacaag gaggtgaaga tagatgggtt ctacatgcgc atgacgctca aggtcttgac 12060
cctgagcgat gatcttgggg tgtatcgcaa tgacagaatg catcgcgcgg ttagcgccag 12120
caggaggcgc gagttaagcg acagggaact gatgcacagt ttgcaaagag ctctgactgg 12180
agctggaacc gagggtgaga attacttcga catgggagct gacttgcagt ggcagcctag 12240
tcgcagggct ctgagcgccg cgacggcagg atgtgagctt ccttacatag aagaggcgga 12300

-continued tgaaggcgag gaggaagagg gcgagtactt ggaagactga tggcacaacc cgtgtttttt 12360
gctagatgga acagcaagca ccggatcccg caatgcgggc ggcgctgcag agccagccgt 12420
ccggcattaa ctcctcggac gattggaccc aggccatgca acgtatcatg gcgttgacga 12480
ctcgcaaccc cgaagccttt agacagcaac cccaggccaa ccgtctatcg gccatcatgg 12540
aagctgtagt gccttcccgc tctaatccca ctcatgagaa ggtcctggcc atcgtgaacg 12600
cgttggtgga gaacaaagct attcgtccag atgaggccgg actggtatac aacgctctct 12660
tagaacgcgt ggctcgctac aacagtagca atgtgcaaac caatttggac cgtatgataa 12720
cagatgtacg cgaagccgtg tctcagcgcg aaaggttcca gcgtgatgcc aacctgggtt 12780
cgctggtggc gttaaatgct ttcttgagta ctcagcctgc taatgtgccg cgtggtcaac 12840
aggattatac taacttttta agtgctttga gactgatggt atcagaagta cctcagagcg 12900
aagtgtatca gtccggtcct gattacttct ttcagactag cagacagggc ttgcagacgg 12960
taaatctgag ccaagctttt aaaaacctta aaggtttgtg gggagtgcat gccccggtag 13020
gagaaagagc aaccgtgtct agcttgttaa ctccgaactc ccgcctatta ttactgttgg 13080
tagctccttt caccgacagc ggtagcatcg accgtaattc ctatttgggt tacctactaa 13140
acctgtatcg cgaagccata gggcaaagtc aggtggacga gcagacctat caagaaatta 13200
cccaagtcag tcgcgctttg ggacaggaag acactggcag tttggaagcc actctgaact 13260
tcttgcttac caatcggtct caaaagatcc ctcctcaata tgctcttact gcggaggagg 13320
agaggatcct tagatatgtg cagcagagcg tgggattgtt tctgatgcaa gagggggcaa 13380
ctccgactgc agcactggac atgacagcgc gaaatatgga gcccagcatg tatgccagta 13440
accgaccttt cattaacaaa ctgctggact acttgcacag agctgccgct atgaactctg 13500
attatttcac caatgccatc ttaaacccgc actggctgcc cccacctggt ttctacacgg 13560
gcgaatatga catgcccgac cctaatgacg gatttctgtg ggacgacgtg gacagcgatg 13620
ttttttcacc tctttctgat catcgcacgt ggaaaaagga aggcggcgat agaatgcatt 13680
cttctgcatc gctgtccggg gtcatgggtg ctaccgcggc tgagcccgag tctgcaagtc 13740
cttttcctag tctacccttt tctctacaca gtgtacgtag cagcgaagtg ggtagaataa 13800
gtcgcccgag tttaatgggc gaagaggagt atctaaacga ttccttgctc agaccggcaa 13860
gagaaaaaaa tttcccaaac aatggaatag aaagtttggt ggataaaatg agtagatgga 13920
agacttatgc tcaggatcac agagacgagc ctgggatcat ggggattaca agtagagcga 13980
gccgtagacg ccagcgccat gacagacaga ggggtcttgt gtgggacgat gaggattcgg 14040
ccgatgatag cagcgtgctg gacttgggtg ggagaggaag gggcaacccg tttgctcatt 14100
tgcgccctcg cttgggtggt atgttgtaaa aaaaaataaa aaaaaaactc accaaggcca 14160
tggcgacgag cgtacgttcg ttcttcttta ttatctgtgt ctagtataat gaggcgagtc 14220
gtgctaggcg gagcggtggt gtatccggag ggtcctcctc cttcgtacga gagcgtgatg 14280
cagcagcagc aggcgacggc ggtgatgcaa tccccactgg aggctccctt tgtgcctccg 14340
cgatacctgg cacctacgga gggcagaaac agcattcgtt attcggaact ggcacctcag 14400
tacgatacca ccaggttgta tctggtggac aacaagtcgg cggacattgc ttctctgaac 14460
tatcagaatg accacagcaa cttcttgacc acggtggtgc aaaacaatga ctttacccct 14520
acggaagcca gcacccagac cattaacttt gatgaacgat cgcggtgggg cggtcagcta 14580
aagaccatca tgcatactaa catgccaaac gtgaacgagt atatgtttag taacaagttc 14640
aaagcgcgtg tgatggtgtc cagaaaacct cccgacggtg ctgcagttgg ggatacttat 14700

-continued

```
gatcacaagc aggatatttt gaaatatgag tggttcgagt ttactttgcc agaaggcaac  14760
ttttcagtta ctatgactat tgatttgatg aacaatgcca tcatagataa ttacttgaaa  14820
gtgggtagac agaatggagt gcttgaaagt gacattggtg ttaagttcga caccaggaac  14880
ttcaagctgg gatgggatcc cgaaaccaag ttgatcatgc ctggagtgta tacgtatgaa  14940
gccttccatc ctgacattgt cttactgcct ggctgcggag tggattttac cgagagtcgt  15000
ttgagcaacc ttcttggtat cagaaaaaaa cagccatttc aagagggttt taagattttg  15060
tatgaagatt tagaaggtgg taatattccg gccctcttgg atgtagatgc ctatgagaac  15120
agtaagaaag aacaaaaagc caaaatagaa gctgctacag ctgctgcaga agctaaggca  15180
aacatagttg ccagcgactc tacaagggtt gctaacgctg gagaggtcag aggagacaat  15240
tttgcgccaa cacctgttcc gactgcagaa tcattattgg ccgatgtgtc tgaaggaacg  15300
gacgtgaaac tcactattca acctgtagaa aaagatagta agaatagaag ctataatgtg  15360
ttggaagaca aaatcaacac agcctatcgc agttggtatc tttcgtacaa ttatggcgat  15420
cccgaaaaag gagtgcgttc ctggacattg ctcaccacct cagatgtcac ctgcggagca  15480
gagcaggtct actggtcgct tccagacatg atgaaggatc ctgtcacttt ccgctccact  15540
agacaagtca gtaactaccc tgtggtgggt gcagagctta tgcccgtctt ctcaaagagc  15600
ttctacaacg aacaagctgt gtactcccag cagctccgcc agtccacctc gcttacgcac  15660
gtcttcaacc gctttcctga gaaccagatt ttaatccgtc cgccggcgcc caccattacc  15720
accgtcagtg aaaacgttcc tgctctcaca gatcacggga ccctgccgtt gcgcagcagt  15780
atccggggag tccaacgtgt gaccgttact gacgccagac gccgcacctg tccctacgtg  15840
tacaaggcac tgggcatagt cgcaccgcgc gtcctttcaa gccgcacttt ctaaaaaaaa  15900
aaaaaatgtc cattcttatc tcgcccagta ataacaccgg ttggggtctg cgcgctccaa  15960
gcaagatgta cggaggcgca cgcaaacgtt ctacccaaca tcctgtccgt gttcgcggac  16020
attttcgcgc tccatggggc gccctcaagg gccgcactcg cgttcgaacc accgtcgatg  16080
atgtaatcga tcaggtggtt gccgacgccc gtaattatac tcctactgcg cctacatcta  16140
ctgtggatgc agttattgac agtgtagtgg ctgacgctcg caactatgct cgacgtaaga  16200
gccggcgaag gcgcattgcc agacgccacc gagctaccac tgccatgcga gccgcaagag  16260
ctctgctacg aagagctaga cgcgtggggc gaagagccat gcttagggcg gccagacgtg  16320
cagcttcggg cgccagcgcc ggcaggtccc gcaggcaagc agccgctttc gcagcggcga  16380
ctattgccga catggcccaa tcgcgaagag gcaatgtata ctgggtgcgt gacgctgcca  16440
ccggtcaacg tgtacccgtg cgcacccgtc cccctcgcac ttagaagata ctgagcagtc  16500
tccgatgttg tgtcccagcg gcgaggatgt ccaagcgcaa atacaaggaa gaaatgctgc  16560
aggttatcgc acctgaagtc tacggccaac cgttgaagga tgaaaaaaaa ccccgcaaaa  16620
tcaagcgggt taaaaaggac aaaaaagaag aggaagatgg cgatgatggg ctggcggagt  16680
ttgtgcgcga gtttgcccca cggcgacgcg tgcaatggcg tgggcgcaaa gttcgacatg  16740
tgttgagacc tggaacttcg gtggtcttta cacccggcga gcgttcaagc gctactttta  16800
agcgttccta tgatgaggtg tacggggatg atgatattct tgagcaggcg gctgaccgat  16860
taggcgagtt tgcttatggc aagcgtagta gaataacttc caaggatgag acagtgtcga  16920
tacccttgga tcatggaaat cccaccccta gtcttaaacc ggtcactttg cagcaagtgt  16980
tacccgtaac tccgcgaaca ggtgttaaac gcgaaggtga agatttgtat cccactatgc  17040
```

```
aactgatggt acccaaacgc cagaagttgg aggacgtttt ggagaaagta aaagtggatc  17100
cagatattca acctgaggtt aaagtgagac ccattaagca ggtagcgcct ggtctggggg  17160
tacaaactgt agacattaag attcccactg aaagtatgga agtgcaaact gaacccgcaa  17220
agcctactgc cacctccact gaagtgcaaa cggatccatg gatgcccatg cctattacaa  17280
ctgacgccgc cggtcccact cgaagatccc gacgaaagta cggtccagca agtctgttga  17340
tgcccaatta tgttgtacac ccatctatta ttcctactcc tggttaccga ggcactcgct  17400
actatcgcag ccgaaacagt acctcccgcc gtcgccgcaa gacacctgca aatcgcagtc  17460
gtcgccgtag acgcacaagc aaaccgactc ccggcgccct ggtgcggcaa gtgtaccgca  17520
atggtagtgc ggaacctttg acactgccgc gtgcgcgtta ccatccgagt atcatcactt  17580
aatcaatgtt gccgctgcct ccttgcagat atggccctca cttgtcgcct tcgcgttccc  17640
atcactggtt accgaggaag aaactcgcgc cgtagaagag ggatgttggg acgcggaatg  17700
cgacgctaca ggcgacggcg tgctatccgc aagcaattgc ggggtggttt tttaccagcc  17760
ttaattccaa ttatcgctgc tgcaattggc gcgataccag gcatagcttc cgtggcggtt  17820
caggcctcgc aacgacattg acattggaaa aaaacgtata aataaaaaaa aaaaaataca  17880
atggactctg acactcctgg tcctgtgact atgttttctt agagatggaa gacatcaatt  17940
tttcatcctt ggctccgcga cacggcacga agccgtacat gggcacctgg agcgacatcg  18000
gcacgagcca actgaacggg ggcgccttca attggagcag tatctggagc gggcttaaaa  18060
attttggctc aaccataaaa acatacggga acaaagcttg gaacagcagt acaggacagg  18120
cgcttagaaa taaacttaaa gaccagaact tccaacaaaa agtagtcgat gggatagctt  18180
ccggcatcaa tggagtggta gatttggcta accaggctgt gcagaaaaag ataaacagtc  18240
gtttggaccc gccgccagca accccaggtg aaatgcaagt ggaggaagaa attcctccgc  18300
cagaaaaacg aggcgacaag cgtccgcgtc ccgatttgga agagacgctg gtgacgcgcg  18360
tagatgaacc gccttcttat gaggaagcaa cgaagcttgg aatgcccacc actagaccga  18420
tagccccaat ggccaccggg gtgatgaaac cttctcagtt gcatcgaccc gtcaccttgg  18480
atttgccccc tccccctgct gctactgctg tacccgcttc taagcctgtc gctgccccga  18540
aaccagtcgc cgtagccagg tcacgtcccg gggcgctcc tcgtccaaat gcgcactggc  18600
aaaatactct gaacagcatc gtgggtctag gcgtgcaaag tgtaaaacgc cgtcgctgct  18660
tttaattaaa tatggagtag cgcttaactt gcctatctgt gtatatgtgt cattacacgc  18720
cgtcacagca gcagaggaaa aaaggaagag gtcgtgcgtc gacgctgagt tactttcaag  18780
atggccaccc catcgatgct gccccaatgg gcatacatgc acatcgccgg acaggatgct  18840
tcggagtacc tgagtccggg tctggtgcag ttcgcccgcg ccacagacac ctacttcaat  18900
ctgggaaata agtttagaaa tcccaccgta gcgccgaccc acgatgtgac caccgaccgt  18960
agccagcggc tcatgttgcg cttcgtgccc gttgaccggg aggacaatac atactcttac  19020
aaagtgcggt acaccctggc cgtgggcgac aacagagtgc tggatatggc cagcacgttc  19080
tttgacatta ggggtgtgtt ggacagaggt cccagtttca aaccctattc tggtacggct  19140
tacaactccc tggctcctaa aggcgctcca aatacatctc agtggattgc agaaggtgta  19200
aaaaatacaa ctggtgagga acacgtaaca gaagaggaaa ccaatactac tacttacact  19260
tttggcaatg ctcctgtaaa agctgaagct gaaattacaa aagaaggact cccagtaggt  19320
ttggaagttt cagatgaaga aagtaaaccg atttatgctg ataaaacata tcagccagaa  19380
cctcagctgg gagatgaaac ttggactgac cttgatggaa aaaccgaaaa gtatggaggc  19440
```

agggctctca aacccgatac taagatgaaa ccatgctacg ggtcctttgc caaacctact 19500
aatgtgaaag gcggtcaggc aaaacaaaaa acaacggagc agccaaatca gaaagtcgaa 19560
tatgatatcg acatggagtt ttttgatgcg gcatcgcaga aaacaaactt aagtcctaaa 19620
attgtcatgt atgcagaaaa tgtaaatttg gaaactccag acactcatgt agtgtacaaa 19680
cctggaacag aagacacaag ttccgaagct aatttgggac aacaatctat gcccaacaga 19740
cccaactaca ttggcttcag agataacttt attggactta tgtactataa cagtactggt 19800
aacatggggg tgctggctgg tcaagcgtct cagttaaatg cagtggttga cttgcaggac 19860
agaaacacag aactttctta ccaactcttg cttgactctc tgggcgacag aaccagatac 19920
tttagcatgt ggaatcaggc tgtggacagt tatgatcctg atgtacgtgt tattgaaaat 19980
catggtgtgg aagatgaact tcccaactac tgttttccac tggacggcat aggtgttcca 20040
acaaccagtt acaaatcaat agttccaaat ggagacaatg cgcctaattg gaaggaacct 20100
gaagtaaatg gaacaagtga gatcggacag ggtaatttgt ttgccatgga aattaacctt 20160
caagccaatc tatggcgaag tttcctttat tccaatgtgg ctctatatct cccagactcg 20220
tacaaataca ccccgtccaa tgtcactctt ccagaaaaca aaaacaccta cgactacatg 20280
aacgggcggg tggtgccgcc atctctagta gacacctatg tgaacattgg tgccaggtgg 20340
tctctggatg ccatggacaa tgtcaaccca ttcaaccacc accgtaacgc tggcttgcgt 20400
taccgatcca tgcttctggg taacggacgt tatgtgcctt tccacataca agtgcctcaa 20460
aaattcttcg ctgttaaaaa cctgctgctt ctcccaggct cctacactta tgagtggaac 20520
tttaggaagg atgtgaacat ggttctacag agttccctcg gtaacgacct gcgggtagat 20580
ggcgccagca tcagtttcac gagcatcaac ctctatgcta ctttttttccc catggctcac 20640 aacaccgctt ccacccttga agccatgctg cggaatgaca ccaatgatca gtcattcaac 20700
gactacctat ctgcagctaa catgctctac cccattcctg ccaatgcaac caatattccc 20760
atttccattc cttctcgcaa ctgggcggct ttcagaggct ggtcatttac cagactgaaa 20820
accaaagaaa ctccctcttt ggggtctgga tttgacccct actttgtcta ttctggttct 20880
attccctacc tggatggtac cttctacctg aaccacactt ttaagaaggt ttccatcatg 20940
tttgactctt cagtgagctg gcctggaaat gacaggttac tatctcctaa cgaatttgaa 21000
ataaagcgca ctgtggatgg cgaaggctac aacgtagccc aatgcaacat gaccaaagac 21060
tggttcttgg tacagatgct cgccaactac aacatcggct atcagggctt ctacattcca 21120
gaaggataca aagatcgcat gtattcattt ttcagaaact tccagcccat gagcaggcag 21180
gtggttgatg aggtcaatta caaagacttc aaggccgtcg ccatacccta ccaacacaac 21240
aactctggct ttgtgggtta catggctccg accatgcgcc aaggtcaacc ctatcccgct 21300
aactatccct atccactcat tggaacaact gccgtaaata gtgttacgca gaaaaagttc 21360
ttgtgtgaca gaaccatgtg gcgcataccg ttctcgagca acttcatgtc tatgggggcc 21420
cttacagact tgggacagaa tatgctctat gccaactcag ctcatgctct ggacatgacc 21480
tttgaggtgg atcccatgga tgagcccacc ctgctttatc ttctcttcga agttttcgac 21540
gtggtcagag tgcatcagcc acaccgcggc atcatcgagg cagtctacct gcgtacaccg 21600
ttctcggccg gtaacgctac cacgtaagaa gcttcttgct tcttgcaaat agcagctgca 21660
accatggcct gcggatccca aaacggctcc agcgagcaag agctcagagc cattgtccaa 21720
gacctgggtt gcggacccta ttttttggga acctacgata agcgcttccc ggggttcatg 21780

-continued

```
gcccccgata agctcgcctg tgccattgta aatacggccg gacgtgagac ggggggagag  21840
cactggttgg ctttcggttg gaacccacgt tctaacacct gctacctttt tgatcctttt  21900
ggattctcgg atgatcgtct caaacagatt taccagtttg aatatgaggg tctcctgcgc  21960
cgcagcgctc ttgctaccaa ggaccgctgt attacgctgg aaaaatctac ccagaccgtg  22020
cagggtcccc gttctgccgc ctgcggactt ttctgctgca tgttccttca cgcctttgtg  22080
cactggcctg accgtcccat ggacggaaac cccaccatga aattgctaac tggagtgcca  22140
aacaacatgc ttcattctcc taaagtccag cccaccctgt gtgacaatca aaaagcactc  22200
taccatttc ttaataccca ttcgccttat tttcgctccc atcgtacaca catcgaaagg  22260
gccactgcgt tcgaccgtat ggatgttcaa taatgactca tgtaaacaac gtgttcaata  22320
aacatcactt tattttttta catgtatcaa ggctctgcat tacttattta tttacaagtc  22380
gaatgggttc tgacgagaat cagaatgacc cgcaggcagt gatacgttgc ggaactgata  22440
cttgggttgc cacttgaatt cgggaatcac caacttggga accggtatat cgggcaggat  22500
gtcactccac agctttctgg tcagctgcaa agctccaagc aggtcaggag ccgaaatctt  22560
gaaatcacaa ttaggaccag tgctttgagc gcgagagttg cggtacaccg gattgcagca  22620
ctgaaacacc atcagcgacg gatgtctcac gcttgccagc acggtgggat ctgcaatcat  22680
gcccacatcc agatcttcag cattggcaat gctgaacggg gtcatcttgc aggtctgcct  22740
acccatggcg ggcacccaat taggcttgtg gttgcaatcg cagtgcaggg ggatcagtat  22800
catcttggcc tgatcctgtc tgattcctgg atacacggct ctcatgaaag catcatattg  22860
cttgaaagcc tgctgggctt tactaccctc ggtataaaac atcccgcagg acctgctcga  22920
aaactggtta gctgcacagc cggcatcatt cacacagcag cgggcgtcat tgttagctat  22980
ttgcaccaca cttctgcccc agcggttttg ggtgattttg gttcgctcgg gattctcctt  23040
taaggctcgt tgtccgttct cgctggccac atccatctcg ataatctgct ccttctgaat  23100
cataatattg ccatgcaggc acttcagctt gccctcataa tcattgcagc catgaggcca  23160
caacgcacag cctgtacatt cccaattatg gtgggcgatc tgagaaaaag aatgtatcat  23220
tccctgcaga aatcttccca tcatcgtgct cagtgtcttg tgactagtga aagttaactg  23280
gatgcctcgg tgctcctcgt ttacgtactg gtgacagatg cgcttgtatt gttcgtgttg  23340
ctcaggcatt agtttaaaag aggttctaag ttcgttatcc agcctgtact tctccatcag  23400
cagacacatc acttccatgc ctttctccca agcagacacc aggggcaagc taatcggatt  23460
cttaacagtg caggcagcag ctcctttagc cagagggtca tctttagcga tcttctcaat  23520
gcttcttttg ccatccttct caacgatgcg cacgggcggg tagctgaaac ccactgctac  23580
aagttgcgcc tcttctcttt cttcttcgct gtcttgactg atgtcttgca tggggatatg  23640
tttggtcttc cttggcttct ttttgggggg tatcggagga ggaggactgt cgctccgttc  23700
cggagacagg gaggattgtg acgtttcgct caccattacc aactgactgt cggtagaaga  23760
acctgacccc acacggcgac aggtgtttct cttcgggggc agaggtggag gcgattgcga  23820
agggctgcgg tccgacctgg aaggcggatg actggcagaa ccccttccgc gttcgggggt  23880
gtgctccctg tggcggtcgc ttaactgatt tccttcgcgg ctggccattg tgttctccta  23940
ggcagagaaa caacagacat ggaaactcag ccattgctgt caacatcgcc acgagtgcca  24000
tcacatctcg tcctcagcga cgaggaaaag gagcagagct taagcattcc accgcccagt  24060
cctgccacca cctctaccct agaagataag gaggtcgacg catctcatga catgcagaat  24120
aaaaaagcga aagagtctga gacagacatc gagcaagacc cgggctatgt gacaccggtg  24180
```

gaacacgagg aagagttgaa acgctttcta gagagagagg atgaaaactg cccaaaacaa 24240
cgagcagata actatcacca agatgctgga aatagggatc agaacaccga ctacctcata 24300
gggcttgacg gggaagacgc gctccttaaa catctagcaa gacagtcgct catagtcaag 24360
gatgcattat tggacagaac tgaagtgccc atcagtgtgg aagagctcag ccgcgcctac 24420
gagcttaacc tcttttcacc tcgtactccc cccaaacgtc agccaaacgg cacctgcgag 24480
ccaaatcctc gcttaaactt ttatccagct tttgctgtgc cagaagtact ggctacctat 24540
cacatctttt ttaaaaatca aaaaattcca gtctcctgcc gcgctaatcg cacccgcgcc 24600
gatgccctac tcaatctggg acctggttca cgcttacctg atatagcttc cttggaagag 24660
gttccaaaga tcttcgaggg tctgggcaat aatgagactc gggccgcaaa tgctctgcaa 24720
aagggagaaa atggcatgga tgagcatcac agcgttctgg tggaattgga aggcgataat 24780
gccagactcg cagtactcaa gcgaagcatc gaggtcacac acttcgcata tcccgctgtc 24840
aacctgcccc ctaaagtcat gacggcggtc atggaccagt tactcattaa gcgcgcaagt 24900 ccccttcag aagacatgca tgacccagat gcctgtgatg agggtaaacc agtggtcagt 24960
gatgagcagc taacccgatg gctgggcacc gactctccca gggatttgga agagcgtcgc 25020
aagcttatga tggccgtggt gctggttacc gtagaactag agtgtctccg acgtttcttt 25080
accgattcag aaaccttgcg caaactcgaa gagaatctgc actacacttt tagacacggc 25140
tttgtgcggc aggcatgcaa gatatctaac gtggaactca ccaacctggt ttcctacatg 25200
ggtattctgc atgagaatcg cctaggacaa agcgtgctgc acagcaccct gaaggggaa 25260 gcccgccgtg attacatccg cgattgtgtc tatctgtacc tgtgccaaac gtggcaaacc 25320
ggcatgggtg tatggcagca atgtttagaa gaacagaact tgaaagagct tgacaagctc 25380
ttacagaaat ctcttaaggt tctgtggaca gggttcgacg agcgcaccgt cgcttccgac 25440
ctggcagacc tcatcttccc agagcgtctc agggttactt tgcgaaacgg attgcctgac 25500
tttatgagcc agagcatgct taacaatttt cgctctttca tcctggaacg ctccggtatc 25560
ctgcccgcca cctgctgcgc actgccctcc gactttgtgc ctctcaccta ccgcgagtgc 25620
cccccgccgc tatggagtca ctgctacctg ttccgtctgg ccaactatct ctcctaccac 25680
tcggatgtga tcgaggatgt gagcggagac ggcttgctgg agtgtcactg ccgctgcaat 25740
ctgtgcacgc cccaccggtc cctagcttgc aacccccagt tgatgagcga aacccagata 25800
ataggcacct ttgaattgca aggccccagc agccaaggcg atgggtcttc tcctgggcaa 25860
agtttaaaac tgaccccggg actgtggacc tccgcctact tgcgcaagtt tgctccggaa 25920
gattaccacc cctatgaaat caagttctat gaggaccaat cacagcctcc aaaggccgaa 25980
ctttcggcct gcgtcatcac ccagggggca attctggccc aattgcaagc catccaaaaa 26040
tcccgccaag aatttctact gaaaaagggt aagggggtct accttgaccc ccagaccggc 26100
gaggaactca acacaaggtt ccctcaggat gtcccaacga cgagaaaaca agaagttgaa 26160
ggtgcagccg ccgcccccag aagatatgga ggaagattgg gacagtcagg cagaggaggc 26220
ggaggaggac agtctggagg acagtctgga ggaagacagt ttggaggagg aaaacgagga 26280
ggcagaggag gtggaagaag taaccgccga caaacagtta tcctcggctg cggagacaag 26340
caacagcgct accatctccg ctccgagtcg aggaacccgg cggcgtccca gcagtagatg 26400
ggacgagacc ggacgcttcc cgaacccaac cagcgcttcc aagaccggta agaaggatcg 26460
gcagggatac aagtcctggc gggggcataa gaatgccatc atctcctgct tgcatgagtg 26520

-continued cgggggcaac atatccttca cgcggcgcta cttgctattc caccatgggg tgaactttcc 26580
gcgcaatgtt ttgcattact accgtcacct ccacagcccc tactatagcc agcaaatccc 26640
ggcagtctcg acagataaag acagcggcgg cgacctccaa cagaaaacca gcagcggcag 26700
ttagaaaata cacaacaagt gcagcaacag gaggattaaa gattacagcc aacgagccag 26760
cgcaaacccg agagttaaga aatcggatct ttccaaccct gtatgccatc ttccagcaga 26820
gtcggggtca agagcaggaa ctgaaaataa aaaaccgatc tctgcgttcg ctcaccagaa 26880
gttgtttgta tcacaagagc gaagatcaac ttcagcgcac tctcgaggac gccgaggctc 26940
tcttcaacaa gtactgcgcg ctgactctta aagagtaggc agcgaccgcg cttattcaaa 27000
aaaggcggga attacatcat cctcgacatg agtaaagaaa ttcccacgcc ttacatgtgg 27060
agttatcaac cccaaatggg attggcggca ggcgcctccc aggactactc cacccgcatg 27120
aattggctca gcgccgggcc ttctatgatt tctcgagtta atgatatacg cgcctaccga 27180
aaccaaatac ttttggaaca gtcagctctt accaccacgc cccgccaaca ccttaatccc 27240
agaaattggc ccgccgccct agtgtaccag gaaagtcccg ctcccaccac tgtattactt 27300
cctcgagacg cccaggccga agtccaaatg actaatgcag gtgcgcagtt agctggcggc 27360
tccaccctat gtcgtcacag gcctcggcat aatataaaac gcctgatgat cagaggccga 27420
ggtatccagc tcaacgacga gtcggtgagc tctccgcttg gtctacgacc agacggaatc 27480
tttcagattg ccggctgcgg gagatcttcc ttcacccctc gtcaggctgt tctgactttg 27540
gaaagttcgt cttcgcaacc ccgctcgggc ggaatcggga ccgttcaatt tgtggaggag 27600
tttactccct ctgtctactt caaccccttc tccggatctc ctgggcatta cccggacgag 27660
ttcataccga acttcgacgc gattagcgag tcagtggacg gctacgattg atgtctggtg 27720
acgcggctga gctatctcgg ctgcgacatc tagaccactg ccgccgcttt cgctgctttg 27780
cccgggaact cattgagttc atctacttcg aactccccaa ggatcaccct caaggtccgg 27840
cccacggagt gcggatttct atcgaaggca aaatagactc tcgcctgcaa cgaattttct 27900
cccagcggcc cgtgctgatc gagcgagacc agggaaacac cacggtttcc atctactgca 27960
tttgtaatca ccccggattg catgaaagcc tttgctgtct tatgtgtact gagtttaata 28020
aaaactgaat taagactctc ctacggactg ccgcttcttc aacccggatt ttacaaccag 28080
aagaacgaaa cttttcctgt cgtccaggac tctgttaact tcacctttcc tactcacaaa 28140
ctagaagctc aacgactaca ccgcttttcc agaagcattt tccctactaa tactactttc 28200
aaaaccggag gtgagctcca aggtcttcct acagaaaacc cttgggtgga agcgggcctt 28260
gtagtgctag gaattcttgc gggtgggctt gtgattattc tttgctacct atacacacct 28320
tgcttcactt tcttagtggt gttgtggtat tggtttaaaa aatatggtga gcaagggcga 28380
ggagctgttc accggggtgg tgcccatcct ggtcgagctg gacggcgacg taaacggcca 28440
caagttcagc gtgtccggcg agggcgaggg cgatgccacc tacggcaagc tgaccctgaa 28500
gttcatctgc accaccggca agctgcccgt gccctggccc accctcgtga ccaccctgac 28560
ctacggcgtg cagtgcttca gccgctaccc cgaccacatg aagcagcacg acttcttcaa 28620
gtccgccatg cccgaaggct acgtccagga gcgcaccatc ttcttcaagg acgacggcaa 28680
ctacaagacc cgcgccgagg tgaagttcga gggcgacacc ctggtgaacc gcatcgagct 28740
gaagggcatc gacttcaagg aggacggcaa catcctgggg cacaagctgg agtacaacta 28800
caacagccac aacgtctata tcatggccga caagcagaag aacggcatca aggtgaactt 28860
caagatccgc cacaacatcg aggacggcag cgtgcagctc gccgaccact accagcagaa 28920

```
caccccccatc ggcgacggcc ccgtgctgct gcccgacaac cactacctga gcacccagtc  28980
cgccctgagc aaagacccca acgagaagcg cgatcacatg gtcctgctgg agttcgtgac  29040
cgccgccggg atcactctcg gcatggacga gctgtacaag taacctcttt ctgtttacag  29100
acatggcttc tcttacatct ctcatatttg tcagcattgt cactgccgct catggacaaa  29160
cagtcgtctc tatccctcta ggacataatt acactctcat aggacccccca atcacttcag  29220
aggtcatctg ggccaaactg ggaagcgttg attactttga tataatctgc aacaaaaacaa  29280
aaccaataat agtaacttgc aacatacaaa atcttacatt gattaatgtt agcaaagttt  29340
acagcggtta ctattatggt tatgacagat acagtagtca atatagaaat tacttggttc  29400
gtgttaccca gttgaaaacc acgaaaatgc caaatatggc aaagattcga tccgatgaca  29460
attctctaga aacttttaca tctcccacca cacccgacga aaaaaacatc ccagattcaa  29520
tgattgcaat tgttgcagcg gtggcagtgg tgatggcact aataataata tgcatgcttt  29580
tatatgcttg tcgctacaaa aagtttcatc ctaaaaaaca agatctccta ctaaggctta  29640
acatttaatt tctttttata cagccatggt ttccactacc acattcctta tgcttactag  29700
tctcgcaact ctgacttctg ctcgctcaca cctcactgta actataggct caaactgcac  29760
actaaaagga cctcaaggtg gtcatgtctt ttggtggaga atatatgaca atggatggtt  29820
tacaaaaacca tgtgaccaac ctggtagatt tttctgcaac ggcagagacc taaccattat  29880
caacgtgaca gcaaatgaca aaggcttcta ttatggaacc gactataaaa gtagtttaga  29940
ttataacatt attgtactgc catctaccac tccagcaccc cgcacaacta ctttctctag  30000
cagcagtgtc gctaacaata caatttccaa tccaaccttt gccgcgcttt taaaacgcac  30060
tgtgaataat tctacaactt cacatacaac aatttccact tcaacaatca gcattatcgc  30120
tgcagtgaca attggaatat ctattcttgt tttaccata acctactacg cctgctgcta  30180
tagaaaagac aaacataaag gtgatccatt acttagattt gatatttaat ttgttctttt  30240
tttttttatt tacagtatgg tgaacaccaa tcatggtacc tagaaatttc ttcttcacca  30300
tactcatttg tgcatttaat gtttgcgcta ctttcacagc agtagccaca gcaaccccag  30360
actgtatagg agcatttgct tcctatgcac tttttgcttt tgttacttgc atctgcgtat  30420
gtagcatagt ctgcctggtt attaattttt tccaacttat agactggatc cttgtgcgaa  30480
ttgcctacct gcgccaccat cccgaatacc gcaaccaaaa tatcgcggca cttcttagac  30540
tcatctaaaa ccatgcaggc tatactacca atattttttgc ttctattgct tccctacgct  30600
gtctcaaccc cagctgccta tagtactcca ccagaacacc ttagaaaatg caaattccaa  30660
caaccgtggt catttcttgc ttgctatcga gaaaaatcag aaattccccc aaatttaata  30720
atgattgctg gaataattaa tataatctgt tgcaccataa tttcattttt gatataccccc  30780
ctatttgatt ttggctggaa tgctcccaat gcacatgatc atccacaaga cccagaggaa  30840
cacattcccc tacaaaacat gcaacatcca atagcgctaa tagattacga aagtgaacca  30900
caacccccac tactccctgc tattagttac ttcaacctaa ccggcggaga tgactgaaac  30960
actcaccacc tccaattccg ccgaggatct gctcgatatg gacggccgcg tctcagaaca  31020
gcgactcgcc caactacgca tccgccagca gcaggaacgc gcggccaaag agctcagaga  31080
tgtcatccaa attcaccaat gcaaaaaagg catattctgt ttggtaaaac aagccaagat  31140
atcctacgag atcaccgcta ctgaccatcg cctctcttac gaacttggcc cccaacgaca  31200
aaaatttacc tgcatggtgg gaatcaaccc catagttatc acccagcaaa gtggagatac  31260
```

-continued

```
taagggttgc attcactgct cctgcgattc catcgagtgc acctacaccc tgctgaagac  31320
cctatgcggc ctaagagacc tgctaccaat gaattaaaaa atgattaata aaaaatcact  31380
tacttgaaat cagcaataag gtctctgttg aaattttctc ccagcagcac ctcacttccc  31440
tcttcccaac tctggtattc taaaccccgt tcagcggcat actttctcca tactttaaag  31500
gggatgtcaa attttagctc ctctcctgta cccacaatct tcatgtcttt cttcccagat  31560
gaccaagaga gtccggctca gtgactcctt caaccctgtc tacccctatg aagatgaaag  31620
cacctcccaa caccccttta taaacccagg gtttatttcc ccaaatggct tcacacaaag  31680
cccaaacgga gttcttactt taaaatgttt aaccccacta acaaccacag gcggatctct  31740
acagctaaaa gtgggagggg gacttacagt ggatgacacc aacggttttt tgaaagaaaa  31800
cataagtgcc accacaccac tcgttaagac tggtcactct ataggtttac cactaggagc  31860
cggattggga acgaatgaaa ataaactttg tatcaaatta ggacaaggac ttacattcaa  31920
ttcaaacaac atttgcattg atgacaatat taacacctta tggacaggag tcaaccccac  31980
cgaagccaac tgtcaaatca tgaactccag tgaatctaat gattgcaaat taattctaac  32040
actagttaaa actggagcac tagtcactgc atttgtttat gttataggag tatctaacaa  32100
ttttaatatg ctaactacac acagaaatat aaattttact gcagagctgt ttttcgattc  32160
tactggtaat ttactaacta gactctcatc cctcaaaact ccacttaatc ataaatcagg  32220
acaaaacatg gctactggtg ccattactaa tgctaaaggt ttcatgccca gcacgactgc  32280
ctatcctttc aatgataatt ctagagaaaa agaaaactac atttacggaa cttgttacta  32340
cacagctagt gatcgcactg cttttcccat tgacatatct gtcatgctta accgaagagc  32400
aataaatgac gagacatcat attgtattcg tataacttgg tcctggaaca caggagatgc  32460
cccagaggtg caaacctctg ctacaaccct agtcacctcc ccatttacct tttactacat  32520
cagagaagac gactgacaaa taaagtttaa cttgtttatt tgaaaatcaa ttcacaaaat  32580
ccgagtagtt attttgcctc ccccttccca tttaacagaa tacaccaatc tctccccacg  32640
cacagcttta aacatttgga taccattaga tatagacatg gttttagatt ccacattcca  32700
aacagtttca gagcgagcca atctggggtc agtgatagat aaaaatccat cgggatagtc  32760
ttttaaagcg ctttcacagt ccaactgctg cggatggact ccggagtctg gatcacggtc  32820
atctggaaga agaacgatgg gaatcataat ccgaaaacgg tatcggacga ttgtgtctca  32880
tcaaacccac aagcagccgc tgtctgcgtc gctccgtgcg actgctgttt atgggatcag  32940
ggtccacagt gtcctgaagc atgattttaa tagcccttaa catcaacttt ctggtgcgat  33000
gcgcgcagca acgcattctg atttcactca aatctttgca gtaggtacaa cacattatta  33060
caatattgtt taataaacca taattaaaag cgctccagcc aaaactcata tctgatataa  33120
tcgcccctgc atgaccatca taccaaagtt taatataaat taaatgacgt tccctcaaaa  33180
acacactacc cacatacatg atctcttttg gcatgtgcat attaacaatc tgtctgtacc  33240
atggacaacg ttggttaatc atgcaaccca atataacctt ccggaaccac actgccaaca  33300
ccgctccccc agccatgcat tgaagtgaac cctgctgatt acaatgacaa tgaagaaccc  33360
aattctctcg accgtgaatc acttgagaat gaaaaatatc tatagtggca caacatagac  33420
ataaatgcat gcatcttctc ataattttta actcctcagg atttagaaac atatcccagg  33480
gaataggaag ctcttgcaga acagtaaagc tggcagaaca aggaagacca cgaacacaac  33540
ttacactatg catagtcata gtatcacaat ctggcaacag cgggtggtct tcagtcatag  33600
aagctcgggt ttcattttcc tcacaacgtg gtaactgggc tctggtgtaa gggtgatgtc  33660
```

tggcgcatga tgtcgagcgt gcgcgcaacc ttgtcataat ggagttgctt cctgacattc 33720
tcgtattttg tatagcaaaa cgcggccctg gcagaacaca ctcttcttcg ccttctatcc 33780
tgccgcttag cgtgttccgt gtgatagttc aagtacaacc acactcttaa gttggtcaaa 33840
agaatgctgg cttcagttgt aatcaaaact ccatcgcatc taatcgttct gaggaaatca 33900
tccacggtag catatgcaaa tcccaaccaa gcaatgcaac tggattgtgt ttcaagcagg 33960
agaggagagg gaagagacgg aagaaccatg ttaattttta ttccaaacga tctcgcagta 34020
cttcaaattg tagatcgcgc agatggcatc tctcgccccc actgtgttgg tgaaaaagca 34080
cagctagatc aaaagaaatg cgattttcaa ggtgctcaac ggtggcttcc agcaaagcct 34140
ccacgcgcac atccaagaac aaaagaatac caaaagaagg agcattttct aactcctcaa 34200
tcatcatatt acattcctgc accattccca gataattttc agctttccag ccttgaatta 34260
ttcgtgtcag ttcttgtggt aaatccaatc cacacattac aaacaggtcc cggagggcgc 34320
cctccaccac cattcttaaa cacaccctca taatgacaaa atatcttgct cctgtgtcac 34380
ctgtagcgaa ttgagaatgg caacatcaat tgacatgccc ttggctctaa gttcttcttt 34440
aagttctagt tgtaaaaact ctctcatatt atcaccaaac tgcttagcca gaagcccccc 34500
gggaacaaga gcaggggacg ctacagtgca gtacaagcgc agacctcccc aattggctcc 34560
agcaaaaaca agattggaat aagcatattg ggaaccgcca gtaatatcat cgaagttgct 34620
ggaaatataa tcaggcagag tttcttgtaa aaattgaata aaagaaaaat ttgccaaaaa 34680
aacattcaaa acctctggga tgcaaatgca ataggttacc gcgctgcgct ccaacattgt 34740
tagttttgaa ttagtctgca aaaataaaaa aaaaaacaag cgtcatatca tagtagcctg 34800
acgaacagat ggataaatca gtctttccat cacaagacaa gccacagggt ctccagctcg 34860
accctcgtaa aacctgtcat catgattaaa caacagcacc gaaagttcct cgcggtgacc 34920
agcatgaata attcttgatg aagcatacaa tccagacatg ttagcatcag ttaacgagaa 34980
aaaacagcca acatagcctt tgggtataat tatgcttaat cgtaagtata gcaaagccac 35040
ccctcgcgga tacaaagtaa aaggcacagg agaataaaaa atataattat ttctctgctg 35100
ctgttcaggc aacgtcgccc ccggtccctc taaatacaca tacaaagcct catcagccat 35160
ggcttaccag acaaagtaca gcgggcacac aaagcacaag ctctaaagtg actctccaac 35220
ctctccacaa tatatatata cacaagccct aaactgacgt aatgggagta aagtgtaaaa 35280
aatcccgcca aacccaacac acaccccgaa actgcgtcac cagggaaaag tacagtttca 35340
cttccgcaat cccaacaggc gtaacttcct ctttctcacg gtacgtgata tcccactaac 35400
ttgcaacgtc attttcccac ggtcgcaccg cccctttttag ccgttaaccc cacagccaat 35460
caccacacga tccacacttt ttaaaatcac ctcatttaca tattggcacc attccatcta 35520
taaggtatat tattgatgat g 35541

<210> SEQ ID NO 12
<211> LENGTH: 1900
<212> TYPE: DNA
<213> ORGANISM: Artificial Sequence
<220> FEATURE:
<223> OTHER INFORMATION: Fully synthetic

<400> SEQUENCE: 12
atacctgtga cggaagatca cttcgcagaa taaataaatc ctggtgtccc tgttgatacc 60
gggaagccct gggccaactt ttggcgaaaa tgagacgttg atcggcacgt aagaggttcc 120
aactttcacc ataatgaaat aagatcacta ccgggcgtat tttttgagtt atcgagattt 180
tcaggagcta aggaagctaa aatggagaaa aaaatcactg gatataccac cgttgatata 240
tcccaatggc atcgtaaaga acattttgag gcatttcagt cagttgctca atgtacctat 300
aaccagaccg ttcagctgga tattacggcc tttttaaaga ccgtaaagaa aaataagcac 360
aagttttatc cggcctttat tcacattctt gcccgcctga tgaatgctca tccggaattc 420
cgtatggcaa tgaaagacgg tgagctggtg atatgggata gtgttcaccc ttgttacacc 480
gttttccatg agcaaactga aacgttttca tcgctctgga gtgaatacca cgacgatttc 540
cggcagtttc tacacatata ttcgcaagat gtggcgtgtt acggtgaaaa cctggcctat 600
ttccctaaag ggtttattga gaatatgttt ttcgtctcag ccaatccctg ggtgagtttc 660
accagttttg atttaaacgt ggccaatatg gacaacttct tcgcccccgt tttcaccatg 720
ggcaaatatt atacgcaagg cgacaaggtg ctgatgccgc tggcgattca ggttcatcat 780
gccgtctgtg atggcttcca tgtcggcaga atgcttaatg aattacaaca gtactgcgat 840
gagtggcagg gcggggcgta atttttttaa ggcagttatt ggtggcctta aacgcctatt 900
taaattacgt agcgatcgct tagactcgag cggccgcggt ccgtttaaac tgtcagacca 960
agtttactca tatatacttt agattgattt aaaacttcat ttttaattta aaaggatcta 1020
ggtgaagatc ctttttgata atctcatgac caaaatccct taacgtgagt tttcgttcca 1080
ctgagcgtca gaccccgtag aaaagaccaa aggatcttct tgagatcctt tttttctgcg 1140
cgtaatctgc tgcttgcaaa caaaaaaacc accgctacca gcggtggttt gtttgccgga 1200
tcaagagcta ccaactcttt ttccgaaggt aactggcttc agcagagcgc agataccaaa 1260
tactgtcctt ctagtgtagc cgtagttggg ccaccacttc aagaactctg tagcaccgcc 1320
tacatacctc gctctgctaa tcctgttacc agtggctgct gccagtggcg ataagtcgtg 1380
tcttaccggg ttggactcaa gacgatagtt accggataag gcgcagcggt cgggctgaac 1440
ggggggttcg tgcacacagc ccagcttgga gcgaacgacc tacaccgaac tgagatacct 1500
acagcgtgag ctatgagaaa gcgccacgct tcccgaaggg agaaaggcgg acaggtatcc 1560
ggtaagcggc agggtcggaa caggagagcg cacgaaggag cttccagggg gaaacgcctg 1620
gtatctttat agtcctgtcg ggtttcgcca cctctgactt gagcgtcgat ttttgtgatg 1680
ctcgtcaggg gggcggagcc tatggaaaaa cgccagcaac gcggcctttt tacggttcct 1740
ggccttttgc tggccttttg ctcacatgtt ccttcctgcg ttatcccctg attctgtgga 1800
taaccgtatt accgcctttg agtgagctga taccgctcgc cgcaggttta aacagatctg 1860
tcgacgcccg ggcaagctgg ccggccgata tcatttaaat 1900

<210> SEQ ID NO 13
<211> LENGTH: 2056
<212> TYPE: DNA
<213> ORGANISM: Artificial Sequence
<220> FEATURE:
<223> OTHER INFORMATION: Fully synthetic

<400> SEQUENCE: 13
atacctgtga cggaagatca cttcgcagaa taaataaatc ctggtgtccc tgttgatacc 60
gggaagccct gggccaactt ttggcgaaaa tgagacgttg atcggcacgt aagaggttcc 120
aactttcacc ataatgaaat aagatcacta ccgggcgtat tttttgagtt atcgagattt 180
tcaggagcta aggaagctaa aatgagccat attcaacggg aaacgtcttg ctctaggccg 240
cgattaaatt ccaacatgga tgctgattta tatgggtata aatgggctcg cgataatgtc 300

```
gggcaatcag gtgcgacaat ctatcgattg tatgggaagc ccgatgcgcc agagttgttt    360
ctgaaacatg gcaaaggtag cgttgccaat gatgttacag atgagatggt cagactaaac    420
tggctgacgg aatttatgcc tcttccgacc atcaagcatt ttatccgtac tcctgatgat    480
gcatggttac tcaccactgc gatccccggg aaaacagcat tccaggtatt agaagaatat    540
cctgattcag gtgaaaacat tgttgatgcg ctggcagtgt tcctgcgccg gttgcattcg    600
attcctgttt gtaattgtcc ttttaacagc gatcgcgtat ttcgtctcgc tcaggcgcaa    660
tcacgaatga ataacggttt ggttgatgcg agtgattttg atgacgagcg taatggctgg    720
cctgttgaac aagtctggaa agaaatgcat aaacttttgc cattctcacc ggattcagtc    780
gtcactcatg gtgatttctc acttgataac cttatttttg acgaggggaa attaataggt    840
tgtattgatg ttggacgagt cggaatcgca gaccgatacc aggatcttgc catcctatgg    900
aactgcctcg gtgagttttc tccttcatta cagaaacggc tttttcaaaa atatggtatt    960
gataatcctg atatgaataa attgcagttt catttgatgc tcgatgagtt tttctaattt   1020
ttttaaggca gttattggtg gccttaaacg cctatttaaa ttacgtagcg atcgcttaga   1080
ctcgagcggc cgcggtccgt ttaaactgtc agaccaagtt tactcatata tactttagat   1140
tgatttaaaa cttcattttt aatttaaaag gatctaggtg aagatccttt ttgataatct   1200
catgaccaaa atcccttaac gtgagttttc gttccactga gcgtcagacc ccgtagaaaa   1260
gaccaaagga tcttcttgag atcctttttt tctgcgcgta atctgctgct tgcaaacaaa   1320
aaaaccaccg ctaccagcgg tggtttgttt gccggatcaa gagctaccaa ctctttttcc   1380
gaaggtaact ggcttcagca gagcgcagat accaaatact gtccttctag tgtagccgta   1440
gttgggccac cacttcaaga actctgtagc accgcctaca tacctcgctc tgctaatcct   1500
gttaccagtg gctgctgcca gtggcgataa gtcgtgtctt accgggttgg actcaagacg   1560
atagttaccg gataaggcgc agcggtcggg ctgaacgggg ggttcgtgca cacagcccag   1620
cttggagcga acgacctaca ccgaactgag atacctacag cgtgagctat gagaaagcgc   1680
cacgcttccc gaagggagaa aggcggacag gtatccggta agcggcaggg tcggaacagg   1740
agagcgcacg aaggagcttc caggggggaaa cgcctggtat ctttatagtc ctgtcgggtt  1800
tcgccacctc tgacttgagc gtcgattttt gtgatgctcg tcaggggggc ggagcctatg   1860
gaaaaacgcc agcaacgcgg cctttttacg gttcctggcc ttttgctggc cttttgctca   1920
catgttcctt cctgcgttat cccctgattc tgtggataac cgtattaccg cctttgagtg   1980
agctgatacc gctcgccgca ggtttaaaca gatctgtcga cgcccgggca agctggccgg   2040
ccgatatcat ttaaat                                                   2056
```

<210> SEQ ID NO 14
<211> LENGTH: 4361
<212> TYPE: DNA
<213> ORGANISM: Artificial Sequence
<220> FEATURE:
<223> OTHER INFORMATION: Fully synthetic

<400> SEQUENCE: 14

```
ttctcatgtt tgacagctta tcatcgataa gctttaatgc ggtagtttat cacagttaaa     60
ttgctaacgc agtcaggcac cgtgtatgaa atctaacaat gcgctcatcg tcatcctcgg    120
caccgtcacc ctggatgctg taggcatagg cttggttatg ccggtactgc cgggcctctt    180
gcgggatatc gtccattccg acagcatcgc cagtcactat ggcgtgctgc tagcgctata    240
```

-continued

```
tgcgttgatg caatttctat gcgcacccgt tctcggagca ctgtccgacc gctttggccg    300
ccgcccagtc ctgctcgctt cgctacttgg agccactatc gactacgcga tcatggcgac    360
cacacccgtc ctgtggatcc tctacgccgg acgcatcgtg gccggcatca ccggcgccac    420
aggtgcggtt gctggcgcct atatcgccga catcaccgat ggggaagatc gggctcgcca    480
cttcgggctc atgagcgctt gtttcggcgt gggtatggtg gcaggccccg tggccggggg    540
actgttgggc gccatctcct tgcatgcacc attccttgcg gcggcggtgc tcaacggcct    600
caacctacta ctgggctgct tcctaatgca ggagtcgcat aagggagagc gtcgaccgat    660
gcccttgaga gccttcaacc cagtcagctc cttccggtgg gcgcggggca tgactatcgt    720
cgccgcactt atgactgtct tctttatcat gcaactcgta ggacaggtgc cggcagcgct    780
ctgggtcatt ttcggcgagg accgctttcg ctggagcgcg acgatgatcg gcctgtcgct    840
tgcggtattc ggaatcttgc acgccctcgc tcaagccttc gtcactggtc ccgccaccaa    900
acgtttcggc gagaagcagg ccattatcgc cggcatggcg gccgacgcgc tgggctacgt    960
cttgctggcg ttcgcgacgc gaggctggat ggccttcccc attatgattc ttctcgcttc   1020
cggcggcatc gggatgcccg cgttgcaggc catgctgtcc aggcaggtag atgacgacca   1080
tcagggacag cttcaaggat cgctcgcggc tcttaccagc ctaacttcga tcactggacc   1140
gctgatcgtc acggcgattt atgccgcctc ggcgagcaca tggaacgggt tggcatggat   1200
tgtaggcgcc gccctatacc ttgtctgcct ccccgcgttg cgtcgcggtg catggagccg   1260
ggccacctcg acctgaatgg aagccggcgg cacctcgcta acggattcac cactccaaga   1320
attggagcca atcaattctt gcggagaact gtgaatgcgc aaaccaaccc ttggcagaac   1380
atatccatcg cgtccgccat ctccagcagc cgcacgcggc gcatctcggg cagcgttggg   1440
tcctggccac gggtgcgcat gatcgtgctc ctgtcgttga ggacccggct aggctggcgg   1500
ggttgcctta ctggttagca gaatgaatca ccgatacgcg agcgaacgtg aagcgactgc   1560
tgctgcaaaa cgtctgcgac ctgagcaaca acatgaatgg tcttcggttt ccgtgtttcg   1620
taaagtctgg aaacgcggaa gtcagcgccc tgcaccatta tgttccggat ctgcatcgca   1680
ggatgctgct ggctaccctg tggaacacct acatctgtat taacgaagcg ctggcattga   1740
ccctgagtga tttttctctg gtcccgccgc atccataccg ccagttgttt accctcacaa   1800
cgttccagta accgggcatg ttcatcatca gtaacccgta tcgtgagcat cctctctcgt   1860
ttcatcggta tcattacccc catgaacaga aatccccctt acacggaggc atcagtgacc   1920
aaacaggaaa aaaccgccct taacatggcc cgctttatca gaagccagac attaacgctt   1980
ctggagaaac tcaacgagct ggacgcggat gaacaggcag acatctgtga atcgcttcac   2040
gaccacgctg atgagcttta ccgcagctgc ctcgcgcgtt tcggtgatga cggtgaaaac   2100
ctctgacaca tgcagctccc ggagacggtc acagcttgtc tgtaagcgga tgccgggagc   2160
agacaagccc gtcagggcgc gtcagcgggt gttggcgggt gtcggggcgc agccatgacc   2220
cagtcacgta gcgatagcgg agtgtatact ggcttaacta tgcggcatca gagcagattg   2280
tactgagagt gcaccatatg cggtgtgaaa taccgcacag atgcgtaagg agaaaatacc   2340
gcatcaggcg ctcttccgct tcctcgctca ctgactcgct gcgctcggtc gttcggctgc   2400
ggcgagcggt atcagctcac tcaaaggcgg taatacggtt atccacagaa tcaggggata   2460
acgcaggaaa gaacatgtga gcaaaaggcc agcaaaaggc caggaaccgt aaaaaggccg   2520
cgttgctggc gtttttccat aggctccgcc cccctgacga gcatcacaaa aatcgacgct   2580
caagtcagag gtggcgaaac ccgacaggac tataaagata ccaggcgttt ccccctggaa   2640
```

-continued gctccctcgt gcgctctcct gttccgaccc tgccgcttac cggatacctg tccgcctttc 2700
tcccttcggg aagcgtggcg ctttctcata gctcacgctg taggtatctc agttcggtgt 2760
aggtcgttcg ctccaagctg ggctgtgtgc acgaaccccc cgttcagccc gaccgctgcg 2820
ccttatccgg taactatcgt cttgagtcca acccggtaag acacgactta tcgccactgg 2880
cagcagccac tggtaacagg attagcagag cgaggtatgt aggcggtgct acagagttct 2940
tgaagtggtg gcctaactac ggctacacta gaaggacagt atttggtatc tgcgctctgc 3000
tgaagccagt taccttcgga aaaagagttg gtagctcttg atccggcaaa caaaccaccg 3060
ctggtagcgg tggttttttt gtttgcaagc agcagattac gcgcagaaaa aaaggatctc 3120
aagaagatcc tttgatcttt tctacggggt ctgacgctca gtggaacgaa aactcacgtt 3180
aagggatttt ggtcatgaga ttatcaaaaa ggatcttcac ctagatcctt ttaaattaaa 3240
aatgaagttt taaatcaatc taaagtatat atgagtaaac ttggtctgac agttaccaat 3300
gcttaatcag tgaggcacct atctcagcga tctgtctatt tcgttcatcc atagttgcct 3360
gactccccgt cgtgtagata actacgatac gggagggctt accatctggc cccagtgctg 3420
caatgatacc gcgagaccca cgctcaccgg ctccagattt atcagcaata aaccagccag 3480
ccggaagggc cgagcgcaga agtggtcctg caactttatc cgcctccatc cagtctatta 3540
attgttgccg ggaagctaga gtaagtagtt cgccagttaa tagtttgcgc aacgttgttg 3600
ccattgctgc aggcatcgtg gtgtcacgct cgtcgtttgg tatggcttca ttcagctccg 3660
gttcccaacg atcaaggcga gttacatgat cccccatgtt gtgcaaaaaa gcggttagct 3720
ccttcggtcc tccgatcgtt gtcagaagta agttggccgc agtgttatca ctcatggtta 3780
tggcagcact gcataattct cttactgtca tgccatccgt aagatgcttt tctgtgactg 3840
gtgagtactc aaccaagtca ttctgagaat agtgtatgcg gcgaccgagt tgctcttgcc 3900
cggcgtcaac acgggataat accgcgccac atagcagaac tttaaaagtg ctcatcattg 3960
gaaaacgttc ttcggggcga aaactctcaa ggatcttacc gctgttgaga tccagttcga 4020
tgtaacccac tcgtgcaccc aactgatctt cagcatcttt tactttcacc agcgtttctg 4080
ggtgagcaaa aacaggaagg caaaatgccg caaaaaaggg aataagggcg acacggaaat 4140
gttgaatact catactcttc ctttttcaat attattgaag catttatcag ggttattgtc 4200
tcatgagcgg atacatattt gaatgtattt agaaaaataa acaaataggg gttccgcgca 4260
catttccccg aaaagtgcca cctgacgtct aagaaaccat tattatcatg acattaacct 4320
ataaaaatag gcgtatcacg aggccctttc gtcttcaaga a 4361

<210> SEQ ID NO 15
<211> LENGTH: 2686
<212> TYPE: DNA
<213> ORGANISM: Artificial Sequence
<220> FEATURE:
<223> OTHER INFORMATION: Fully synthetic

<400> SEQUENCE: 15
gcgcccaata cgcaaaccgc ctctccccgc gcgttggccg attcattaat gcagctggca 60
cgacaggttt cccgactgga aagcgggcag tgagcgcaac gcaattaatg tgagttagct 120
cactcattag gcaccccagg ctttacactt tatgcttccg gctcgtatgt tgtgtggaat 180
tgtgagcgga taacaatttc acacaggaaa cagctatgac catgattacg aattcgagct 240
cggtacccgg ggatcctcta gagtcgacct gcaggcatgc aagcttggca ctggccgtcg 300

-continued

```
ttttacaacg tcgtgactgg gaaaaccctg gcgttaccca acttaatcgc cttgcagcac    360
atcccccttt cgccagctgg cgtaatagcg aagaggcccg caccgatcgc ccttcccaac    420
agttgcgcag cctgaatggc gaatggcgcc tgatgcggta ttttctcctt acgcatctgt    480
gcggtatttc acaccgcata tggtgcactc tcagtacaat ctgctctgat gccgcatagt    540
taagccagcc ccgacacccg ccaacacccg ctgacgcgcc ctgacgggct tgtctgctcc    600
cggcatccgc ttacagacaa gctgtgaccg tctccgggag ctgcatgtgt cagaggtttt    660
caccgtcatc accgaaacgc gcgagacgaa agggcctcgt gatacgccta tttttatagg    720
ttaatgtcat gataataatg gtttcttaga cgtcaggtgg cacttttcgg ggaaatgtgc    780
gcggaacccc tatttgttta tttttctaaa tacattcaaa tatgtatccg ctcatgagac    840
aataaccctg ataaatgctt caataatatt gaaaaaggaa gagtatgagt attcaacatt    900
tccgtgtcgc ccttattccc ttttttgcgg cattttgcct tcctgttttt gctcacccag    960
aaacgctggt gaaagtaaaa gatgctgaag atcagttggg tgcacgagtg ggttacatcg   1020
aactggatct caacagcggt aagatccttg agagttttcg ccccgaagaa cgttttccaa   1080
tgatgagcac ttttaaagtt ctgctatgtg gcgcggtatt atcccgtatt gacgccgggc   1140
aagagcaact cggtcgccgc atacactatt ctcagaatga cttggttgag tactcaccag   1200
tcacagaaaa gcatcttacg gatggcatga cagtaagaga attatgcagt gctgccataa   1260
ccatgagtga taacactgcg gccaacttac ttctgacaac gatcggagga ccgaaggagc   1320
taaccgcttt tttgcacaac atgggggatc atgtaactcg ccttgatcgt tgggaaccgg   1380
agctgaatga agccatacca aacgacgagc gtgacaccac gatgcctgta gcaatggcaa   1440
caacgttgcg caaactatta actggcgaac tacttactct agcttcccgg caacaattaa   1500
tagactggat ggaggcggat aaagttgcag gaccacttct gcgctcggcc cttccggctg   1560
gctggtttat tgctgataaa tctggagccg gtgagcgtgg gtctcgcggt atcattgcag   1620
cactggggcc agatggtaag ccctcccgta tcgtagttat ctacacgacg gggagtcagg   1680
caactatgga tgaacgaaat agacagatcg ctgagatagg tgcctcactg attaagcatt   1740
ggtaactgtc agaccaagtt tactcatata tactttagat tgatttaaaa cttcattttt   1800
aatttaaaag gatctaggtg aagatccttt ttgataatct catgaccaaa atcccttaac   1860
gtgagttttc gttccactga gcgtcagacc ccgtagaaaa gatcaaagga tcttcttgag   1920
atcctttttt tctgcgcgta atctgctgct tgcaaacaaa aaaaccaccg ctaccagcgg   1980
tggtttgttt gccggatcaa gagctaccaa ctctttttcc gaaggtaact ggcttcagca   2040
gagcgcagat accaaatact gtccttctag tgtagccgta gttaggccac cacttcaaga   2100
actctgtagc accgcctaca tacctcgctc tgctaatcct gttaccagtg gctgctgcca   2160
gtggcgataa gtcgtgtctt accgggttgg actcaagacg atagttaccg gataaggcgc   2220
agcggtcggg ctgaacgggg ggttcgtgca cacagcccag cttggagcga acgacctaca   2280
ccgaactgag atacctacag cgtgagctat gagaaagcgc cacgcttccc gaagggagaa   2340
aggcggacag gtatccggta agcggcaggg tcggaacagg agagcgcacg agggagcttc   2400
caggggggaaa cgcctggtat ctttatagtc ctgtcgggtt tcgccacctc tgacttgagc   2460
gtcgattttt gtgatgctcg tcaggggggc ggagcctatg gaaaaacgcc agcaacgcgg   2520
cctttttacg gttcctggcc ttttgctggc cttttgctca catgttcttt cctgcgttat   2580
cccctgattc tgtggataac cgtattaccg cctttgagtg agctgatacc gctcgccgca   2640
gccgaacgac cgagcgcagc gagtcagtga gcgaggaagc ggaaga                  2686
```

<210> SEQ ID NO 16
<211> LENGTH: 3697
<212> TYPE: DNA
<213> ORGANISM: Artificial Sequence
<220> FEATURE:
<223> OTHER INFORMATION: Fully synthetic

<400> SEQUENCE: 16
atacctgtga cggaagatca cttcgcagaa taaataaatc ctggtgtccc tgttgatacc 60
gggaagccct gggccaactt ttggcgaaaa tgagacgttg atcggcacgt aagaggttcc 120
aactttcacc ataatgaaat aagatcacta ccgggcgtat tttttgagtt atcgagattt 180
tcaggagcta aggaagctaa aatggagaaa aaaatcactg gatataccac cgttgatata 240
tcccaatggc atcgtaaaga acattttgag gcatttcagt cagttgctca atgtacctat 300
aaccagaccg ttcagctgga tattacggcc tttttaaaga ccgtaaagaa aaataagcac 360
aagttttatc cggcctttat tcacattctt gcccgcctga tgaatgctca tccggaattc 420
cgtatggcaa tgaaagacgg tgagctggtg atatgggata gtgttcaccc ttgttacacc 480
gttttccatg agcaaactga aacgttttca tcgctctgga gtgaatacca cgacgatttc 540
cggcagtttc tacacatata ttcgcaagat gtggcgtgtt acggtgaaaa cctggcctat 600
ttccctaaag ggtttattga gaatatgttt ttcgtctcag ccaatccctg ggtgagtttc 660
accagttttg atttaaacgt ggccaatatg gacaacttct tcgcccccgt tttcaccatg 720
ggcaaatatt atacgcaagg cgacaaggtg ctgatgccgc tggcgattca ggttcatcat 780
gccgtctgtg atggcttcca tgtcggcaga atgcttaatg aattacaaca gtactgcgat 840
gagtggcagg gcggggcgta attttttttaa ggcagttatt ggtggcctta aacgcctatt 900
taaattacgt cattttccca cggtcgcacc gccccttttta gccgttaacc ccacagccaa 960
tcaccacacg atccacactt tttaaaatca cctcatttac atattggcac cattccatct 1020
ataaggtata ttattgatga tgcatcatca ataatatacc ttatagatgg aatggtgcca 1080
atatgtaaat gaggtgattt taaaaagtgt ggatcgtgtg gtgattggct gtggggttaa 1140
cggctaaaag gggcggtgcg accgtgggaa aatgacgttt tgtgggggtg gagttttttt 1200
gcaagttgtc gcgggaaatg tgacgcataa aaaggctgta gcgatcgctt agactcgagc 1260
ggccgcggtc cgtttaaact gtcagaccaa gtttactcat atatacttta gattgattta 1320
aaacttcatt tttaatttaa aaggatctag gtgaagatcc tttttgataa tctcatgacc 1380
aaaatccctt aacgtgagtt ttcgttccac tgagcgtcag accccgtaga aaagaccaaa 1440
ggatcttctt gagatccttt ttttctgcgc gtaatctgct gcttgcaaac aaaaaaacca 1500
ccgctaccag cggtggtttg tttgccggat caagagctac caactctttt tccgaaggta 1560
actggcttca gcagagcgca gataccaaat actgtccttc tagtgtagcc gtagttgggc 1620
caccacttca agaactctgt agcaccgcct acatacctcg ctctgctaat cctgttacca 1680
gtggctgctg ccagtggcga taagtcgtgt cttaccgggt tggactcaag acgatagtta 1740
ccggataagg cgcagcggtc gggctgaacg gggggttcgt gcacacagcc cagcttggag 1800
cgaacgacct acaccgaact gagataccta cagcgtgagc tatgagaaag cgccacgctt 1860
cccgaaggga gaaaggcgga caggtatccg gtaagcggca gggtcggaac aggagagcgc 1920
acgaaggagc ttccaggggg aaacgcctgg tatctttata gtcctgtcgg gtttcgccac 1980
ctctgacttg agcgtcgatt tttgtgatgc tcgtcagggg ggcggagcct atggaaaaac 2040

```
gccagcaacg cggccttttt acggttcctg gccttttgct ggccttttgc tcacatgttc   2100

cttcctgcgt tatcccctga ttctgtggat aaccgtatta ccgcctttga gtgagctgat   2160

accgctcgcc gcaggtttaa acagatctgt cgacgcccgg gcaagctggc cggccgatac   2220

acaggaagtg acaattttcg cgcggtttta ggcggatgtt gtagtaaatt tgggcgtaac   2280

cgagtaagat ttggccattt tcgcgggaaa actgaataag aggaagtgaa atctgaataa   2340

ttttgtgtta ctcatagcgc gtaatatttg tctagggccg cggggacttt gaccgtttac   2400

gttctagagt gtcaaggagc ccaagtcgcg gggaagtgtt gcagggaggc actccgggag   2460

gtcccgcgtg cccgtccagg gagcaatgcg tcctcgggtt cgtccccagc cgcgtctacg   2520

cgcctccgtc ctccccttca cgtccggcat tcgtggtgcc cggagcccga cgccccgcgt   2580

ccggacctgg aggcagccct gggtctccgg atcaggccag cggccaaagg gtcgccgcac   2640

gcacctgttc ccagggcctc cacatcatgg cccctccctc gggttacccc acagcttagg   2700

ccgattcgac ctctctccgc tggggccctc gctggcgtcc ctgcaccctg ggagcgcgag   2760

cggcgcgcgg gcggggaagc gcggcccaga cccccgggtc cgcccggagc agctgcgctg   2820

tcggggccag gccgggctcc cagtggattc gcgggcacag acgcccagga ccgcgcttcc   2880

cacgtggcgg agggactggg gacccgggca cccgtcctgc cccttcacct tccagctccg   2940

cctcctccgc gcggaccccg ccccgtcccg acccctcccg ggtccccggc ccagcccccct   3000

ccgggccctc ccagcccctc cccttccttt ccgcggcccc gccctctcct cgcggcgcga   3060

gtttcaggca gcgctgcgtc ctgctgcgca cgtgggaagc cctggccccg gccacccccg   3120

cgccatggat gagagatttg cgatttctgc ctcaggaaat aatctctgct gagactggaa   3180

atgaaatatt ggagcttgtg gtgcacgccc tgatgggaga cgatccggag ccacctgtgc   3240

agctttttga gcctcctacg cttcaggaac tgtatgattt agaggtagag ggatcggagg   3300

attctaatga ggaagctgta aatggctttt ttaccgattc tatgctttta gctgctaatg   3360

aagggttaga attagatccg cctttggaca cttttgatac tccaggggta attgtggaaa   3420

gcggtacagg tgtaagaaaa ttacctgatt tgagttccgt ggactgtgat ttgcactgct   3480

atgaagacgg gtttcctccg agtgatgagg aggaccatga aaaggagcag tccatgcaga   3540

ctgcagcggg tgagggagtg aaggctgcca atgttggttt tcagttggat tgcccggagc   3600

ttcctggaca tggctgtaag tcttgtgaat ttcacaggaa aaatactgga gtaaaggaac   3660

tgttatgttc gctttgttat atgagaatca tttaaat                           3697
```

<210> SEQ ID NO 17
<211> LENGTH: 3903
<212> TYPE: DNA
<213> ORGANISM: Artificial Sequence
<220> FEATURE:
<223> OTHER INFORMATION: Fully synthetic

<400> SEQUENCE: 17

```
atacctgtga cggaagatca cttcgcagaa taaataaatc ctggtgtccc tgttgatacc     60

gggaagccct gggccaactt ttggcgaaaa tgagacgttg atcggcacgt aagaggttcc    120

aactttcacc ataatgaaat aagatcacta ccgggcgtat tttttgagtt atcgagattt    180

tcaggagcta aggaagctaa aatgagccat attcaacggg aaacgtcttg ctctaggccg    240

cgattaaatt ccaacatgga tgctgattta tatgggtata aatgggctcg cgataatgtc    300

gggcaatcag gtgcgacaat ctatcgattg tatgggaagc ccgatgcgcc agagttgttt    360

ctgaaacatg gcaaaggtag cgttgccaat gatgttacag atgagatggt cagactaaac    420
```

-continued

```
tggctgacgg aatttatgcc tcttccgacc atcaagcatt ttatccgtac tcctgatgat    480
gcatggttac tcaccactgc gatccccggg aaaacagcat tccaggtatt agaagaatat    540
cctgattcag gtgaaaacat tgttgatgcg ctggcagtgt tcctgcgccg gttgcattcg    600
attcctgttt gtaattgtcc ttttaacagc gatcgcgtat ttcgtctcgc tcaggcgcaa    660
tcacgaatga ataacggttt ggttgatgcg agtgattttg atgacgagcg taatggctgg    720
cctgttgaac aagtctggaa agaaatgcat aaacttttgc cattctcacc ggattcagtc    780
gtcactcatg gtgatttctc acttgataac cttatttttg acgaggggaa attaataggt    840
tgtattgatg ttggacgagt cggaatcgca gaccgatacc aggatcttgc catcctatgg    900
aactgcctcg gtgagttttc tccttcatta cagaaacggc tttttcaaaa atatggtatt    960
gataatcctg atatgaataa attgcagttt catttgatgc tcgatgagtt tttctaattt   1020
ttttaaggca gttattggtg gccttaaacg cctatttaaa ttacccctca aggtccggcc   1080
cacggagtgc ggatttctat cgaaggcaaa atagactctc gcctgcaacg aattttctcc   1140
cagcggcccg tgctgatcga gcgagaccag ggaaacacca cggtttccat ctactgcatt   1200
tgtaatcacc ccggattgca tgaaagcctt tgctgtctta tgtgtactga gtttaataaa   1260
aactgaatta agactctcct acggactgcc gcttcttcaa cccggatttt acaaccagaa   1320
gaacgaaact tttcctgtcg tccaggactc tgttaacttc acctttccta ctcacaaact   1380
agaagctcaa cgactacacc gcttttccag aagcattttc cctactaata ctactttcaa   1440
aaccggaggt gagctccaag gtcttcctac agaaaaccct tgggtggaag cgggccttgt   1500
agtgctagga attcttgcgg gtgggcttgt gattattctt tgctacctat acacaccttg   1560
cttcactttc ttagtggtgt tgtggtattg gtttaaaaaa tccatggatg gtgagcaagg   1620
gcgaggagct gttcaccggg gtggtgccca tcctggtcga gctggacggc gacgtaaacg   1680
gccacaagtt cagcgtgtcc ggcgagggcg agggcgatgc cacctacggc aagctgaccc   1740
tgaagttcat ctgcaccacc ggcaagctgc ccgtgccctg gcccaccctc gtgaccaccc   1800
tgacctacgg cgtgcagtgc ttcagccgct accccgacca catgaagcag cacgacttct   1860
tcaagtccgc catgcccgaa ggctacgtcc aggagcgcac catcttcttc aaggacgacg   1920
gcaactacaa gacccgcgcc gaggtgaagt tcgagggcga caccctggtg aaccgcatcg   1980
agctgaaggg catcgacttc aaggaggacg gcaacatcct ggggcacaag ctggagtaca   2040
actacaacag ccacaacgtc tatatcatgg ccgacaagca gaagaacggc atcaaggtga   2100
acttcaagat ccgccacaac atcgaggacg gcagcgtgca gctcgccgac cactaccagc   2160
agaacacccc catcggcgac ggccccgtgc tgctgcccga caaccactac ctgagcaccc   2220
agtccgccct gagcaaagac cccaacgaga agcgcgatca catggtcctg ctggagttcg   2280
tgaccgccgc cgggatcact ctcggcatgg acgagctgta caagtaagta gcgatcgctt   2340
agactcgagc ggccgcggtc cgtttaaact gtcagaccaa gtttactcat atatacttta   2400
gattgattta aaacttcatt tttaatttaa aaggatctag gtgaagatcc tttttgataa   2460
tctcatgacc aaaatccctt aacgtgagtt ttcgttccac tgagcgtcag accccgtaga   2520
aaagaccaaa ggatcttctt gagatccttt ttttctgcgc gtaatctgct gcttgcaaac   2580
aaaaaaacca ccgctaccag cggtggtttg tttgccggat caagagctac caactctttt   2640
tccgaaggta actggcttca gcagagcgca gataccaaat actgtccttc tagtgtagcc   2700
gtagttgggc caccacttca agaactctgt agcaccgcct acatacctcg ctctgctaat   2760
```

-continued

| | |
|---|---|
| cctgttacca gtggctgctg ccagtggcga taagtcgtgt cttaccgggt tggactcaag | 2820 |
| acgatagtta ccggataagg cgcagcggtc gggctgaacg gggggttcgt gcacacagcc | 2880 |
| cagcttggag cgaacgacct acaccgaact gagataccta cagcgtgagc tatgagaaag | 2940 |
| cgccacgctt cccgaaggga gaaaggcgga caggtatccg gtaagcggca gggtcggaac | 3000 |
| aggagagcgc acgaaggagc ttccaggggg aaacgcctgg tatctttata gtcctgtcgg | 3060 |
| gtttcgccac ctctgacttg agcgtcgatt tttgtgatgc tcgtcagggg ggcggagcct | 3120 |
| atggaaaaac gccagcaacg cggccttttt acggttcctg gccttttgct ggccttttgc | 3180 |
| tcacatgttc cttcctgcgt tatcccctga ttctgtggat aaccgtatta ccgcctttga | 3240 |
| gtgagctgat accgctcgcc gcaggtttaa acagatctgt cgacgcccgg gcaagctggc | 3300 |
| cggccgatcc tctttctgtt tacagacatg gcttctctta catctctcat atttgtcagc | 3360 |
| attgtcactg ccgctcatgg acaaacagtc gtctctatcc ctctaggaca taattacact | 3420 |
| ctcataggac ccccaatcac ttcagaggtc atctgggcca aactgggaag cgttgattac | 3480 |
| tttgatataa tctgcaacaa aacaaaacca ataatagtaa cttgcaacat acaaaatctt | 3540 |
| acattgatta atgttagcaa agtttacagc ggttactatt atggttatga cagatacagt | 3600 |
| agtcaatata gaaattactt ggttcgtgtt acccagttga aaaccacgaa aatgccaaat | 3660 |
| atggcaaaga ttcgatccga tgacaattct ctagaaactt ttacatctcc caccacaccc | 3720 |
| gacgaaaaaa acatcccaga ttcaatgatt gcaattgttg cagcggtggc agtggtgatg | 3780 |
| gcactaataa taatatgcat gcttttatat gcttgtcgct acaaaaagtt tcatcctaaa | 3840 |
| aaacaagatc tcctactaag gcttaacatt taatttcttt ttatacagcc atatcattta | 3900 |
| aat | 3903 |